United States Patent
Hopkins et al.

(10) Patent No.: US 10,874,639 B2
(45) Date of Patent: *Dec. 29, 2020

(54) NONRACEMIC MIXTURES AND USES THEREOF

(71) Applicant: Sunovion Pharmaceuticals Inc., Marlborough, MA (US)

(72) Inventors: Seth Cabot Hopkins, Northborough, MA (US); Kenneth Stephen Koblan, Sudbury, MA (US); John R. Snoonian, Bolton, MA (US); Harold Scott Wilkinson, Westborough, MA (US)

(73) Assignee: Sunovion Pharmaceuticals Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/846,905

(22) Filed: Apr. 13, 2020

(65) Prior Publication Data

US 2020/0237719 A1 Jul. 30, 2020

Related U.S. Application Data

(63) Continuation of application No. 16/738,261, filed on Jan. 9, 2020, now Pat. No. 10,660,875, which is a continuation of application No. 16/452,880, filed on Jun. 26, 2019, now Pat. No. 10,576,058, which is a continuation of application No. 16/209,412, filed on Dec. 4, 2018, now Pat. No. 10,369,134.

(60) Provisional application No. 62/716,804, filed on Aug. 9, 2018, provisional application No. 62/650,613, filed on Mar. 30, 2018, provisional application No. 62/594,883, filed on Dec. 5, 2017.

(51) Int. Cl.
*A61K 31/40* (2006.01)
*A61P 25/24* (2006.01)

(52) U.S. Cl.
CPC .............. *A61K 31/40* (2013.01); *A61P 25/24* (2018.01)

(58) Field of Classification Search
CPC ................................ A61K 31/40; A61P 25/24
See application file for complete search history.

(56) References Cited

U.S. PATENT DOCUMENTS

| | | | |
|---|---|---|---|
| 4,294,828 A | 10/1981 | Thominet et al. | |
| 5,955,500 A | 9/1999 | Logstreth et al. | |
| 6,069,165 A | 5/2000 | Andrieu et al. | |
| 6,169,094 B1 | 1/2001 | Perrault et al. | |
| 6,187,807 B1 | 2/2001 | Perrault et al. | |
| 6,210,712 B1 | 4/2001 | Edgren et al. | |
| 6,861,072 B1 | 3/2005 | Alaux et al. | |
| 6,897,242 B1 | 5/2005 | Somerville et al. | |
| 7,815,936 B2 | 10/2010 | Hasenzahl et al. | |
| 7,825,156 B2 | 11/2010 | Azorin | |
| 7,976,871 B2 | 7/2011 | Vaya et al. | |
| 7,985,422 B2 | 7/2011 | Vaya et al. | |
| 8,066,661 B2 | 11/2011 | Boyd et al. | |
| 8,138,169 B2 | 3/2012 | Oronsky et al. | |
| 8,216,609 B2 | 7/2012 | Vaya et al. | |
| 8,263,125 B2 | 9/2012 | Vaya et al. | |
| 8,268,352 B2 | 9/2012 | Vaya et al. | |
| 8,304,431 B2 | 11/2012 | Buntinx | |
| 8,377,994 B2 | 2/2013 | Gray et al. | |
| 8,394,790 B2 | 3/2013 | Portnoy et al. | |
| 8,480,631 B2 | 7/2013 | Wooton et al. | |
| 8,575,172 B2 | 11/2013 | Wilding et al. | |
| 8,579,865 B2 | 11/2013 | Wooton et al. | |
| 8,697,127 B2 | 4/2014 | Sah | |
| 8,876,758 B2 | 11/2014 | Boyd et al. | |
| 8,906,847 B2 | 12/2014 | Cleemann et al. | |
| 8,945,063 B2 | 2/2015 | Wooton et al. | |
| 9,050,343 B2 | 6/2015 | Peters et al. | |
| 9,156,829 B2 | 10/2015 | Fieldhoue et al. | |
| 9,173,953 B2 | 11/2015 | Rau et al. | |
| 9,186,461 B2 | 11/2015 | Boyd et al. | |
| 9,283,192 B2 | 3/2016 | Mullen et al. | |
| 9,421,333 B2 | 8/2016 | Wooton et al. | |
| 9,474,719 B2 | 10/2016 | Mullen et al. | |
| 9,750,881 B2 | 9/2017 | Wooton et al. | |
| 9,827,315 B2 | 11/2017 | Patel et al. | |
| 10,011,588 B2 | 7/2018 | Fieldhouse et al. | |
| 10,137,091 B2 | 11/2018 | Mullen et al. | |

(Continued)

FOREIGN PATENT DOCUMENTS

| AT | 264666 B | 9/1968 |
|---|---|---|
| CA | 2646779 | 5/2010 |

(Continued)

OTHER PUBLICATIONS

Abbas et al., "Amisulpride is a potent 5-HT7 antagonist: relevance for antidepressant actions in vivo," Psychopharmacology, Jul. 2009, 205(1)119-128.

(Continued)

*Primary Examiner* — Barbara P Badio

(74) *Attorney, Agent, or Firm* — Fish & Richardson P.C.

(57) ABSTRACT

Provided are compositions comprising unequal mixtures of (R)-amisulpride and (S)-amisulpride, or pharmaceutically acceptable salts thereof, where the amount of (R)-amisulpride is greater than the amount of (S)-amisulpride, compositions and medicaments comprising the same used for the treatment of various diseases and disorders, and methods of using same for the treatment of various diseases and disorders, including, but not limited to, dosage regimens. In addition, provided are various formulations thereof, including, but not limited to, formulations employing polymorphs of enantiomeric amisulpride.

30 Claims, 34 Drawing Sheets

(56) References Cited

U.S. PATENT DOCUMENTS

| | | |
|---|---|---|
| 10,369,134 B2 | 8/2019 | Hopkins et al. |
| 10,377,708 B2 | 8/2019 | Snoonian et al. |
| 10,576,058 B2 | 3/2020 | Hopkins et al. |
| 10,577,317 B2 | 3/2020 | Snoonian et al. |
| 10,660,875 B1 | 5/2020 | Hopkins et al. |
| 2003/0096264 A1 | 5/2003 | Altar et al. |
| 2003/0130334 A1 | 7/2003 | Muller |
| 2005/0085463 A1 | 4/2005 | Weiner et al. |
| 2005/0171086 A1 | 8/2005 | Brodney et al. |
| 2005/0181049 A1 | 8/2005 | Dong et al. |
| 2005/0250767 A1 | 11/2005 | Weiner et al. |
| 2005/0281752 A1 | 12/2005 | Dugger, III |
| 2006/0150989 A1 | 7/2006 | Migaly |
| 2006/0153916 A1 | 7/2006 | Vaya et al. |
| 2006/0153925 A1 | 7/2006 | Andre et al. |
| 2006/0167068 A1 | 7/2006 | Feuerstein et al. |
| 2006/0167074 A1 | 7/2006 | Muller |
| 2008/0188464 A1 | 8/2008 | Green et al. |
| 2008/0188537 A1 | 8/2008 | Azorin |
| 2008/0280886 A1 | 11/2008 | Grant et al. |
| 2008/0319041 A1 | 12/2008 | Digenis et al. |
| 2009/0053329 A1 | 2/2009 | Peters et al. |
| 2009/0082342 A1 | 3/2009 | Uldam et al. |
| 2009/0208979 A1 | 8/2009 | Silver et al. |
| 2009/0269770 A1 | 10/2009 | Silver et al. |
| 2010/0069356 A1 | 3/2010 | Gant et al. |
| 2010/0069399 A1 | 3/2010 | Gant et al. |
| 2010/0074973 A1 | 3/2010 | Gant et al. |
| 2010/0119622 A1 | 5/2010 | Gant et al. |
| 2010/0119624 A1 | 5/2010 | Gant et al. |
| 2010/0143507 A1 | 6/2010 | Gant et al. |
| 2010/0159033 A1 | 6/2010 | Gant et al. |
| 2010/0168085 A1 | 7/2010 | Eisenbach-Schwartz et al. |
| 2010/0234288 A1 | 9/2010 | Jain et al. |
| 2010/0266711 A1 | 10/2010 | Gant et al. |
| 2011/0130390 A1 | 6/2011 | Muller |
| 2011/0136742 A1 | 6/2011 | Mickle et al. |
| 2011/0136865 A1 | 6/2011 | Buntinx |
| 2011/0207776 A1 | 8/2011 | Buntinx |
| 2012/0231092 A1 | 9/2012 | Oronsky et al. |
| 2013/0096319 A1 | 4/2013 | Paghdar et al. |
| 2013/0218086 A1 | 8/2013 | Woonton et al. |
| 2013/0281410 A1 | 10/2013 | Renshaw |
| 2014/0031372 A1 | 1/2014 | Fong et al. |
| 2014/0044786 A1 | 2/2014 | Wilding et al. |
| 2014/0113912 A1 | 4/2014 | Loebel et al. |
| 2014/0154328 A1 | 6/2014 | Sovic Brkicic et al. |
| 2015/0018360 A1 | 1/2015 | Halse et al. |
| 2015/0057221 A1 | 2/2015 | Cleemann et al. |
| 2015/0099741 A1 | 4/2015 | Li et al. |
| 2015/0231126 A1 | 8/2015 | Peters et al. |
| 2015/0272946 A1 | 10/2015 | Sato et al. |
| 2016/0032390 A1 | 2/2016 | Hakonarson et al. |
| 2016/0060702 A1 | 3/2016 | Li et al. |
| 2016/0081987 A1 | 3/2016 | Lawton et al. |
| 2016/0193151 A1 | 7/2016 | Noriega Escobar et al. |
| 2016/0348101 A1 | 12/2016 | Chen et al. |
| 2017/0027958 A1 | 2/2017 | Patel et al. |
| 2017/0100490 A1 | 4/2017 | Cleeman et al. |
| 2017/0258787 A1 | 9/2017 | Sato et al. |
| 2017/0361021 A1 | 12/2017 | Woonton et al. |
| 2018/0071390 A1 | 3/2018 | Patel et al. |
| 2018/0111891 A1 | 4/2018 | Tsai et al. |
| 2018/0282309 A1 | 10/2018 | Fieldhouse et al. |
| 2018/0346400 A9 | 12/2018 | Tsai et al. |
| 2019/0070124 A1 | 3/2019 | Anavi-Goffer |
| 2019/0083407 A1 | 3/2019 | Hanna |
| 2019/0167635 A1 | 6/2019 | Hopkins et al. |
| 2019/0169123 A1 | 6/2019 | Hopkins et al. |
| 2019/0314331 A1 | 10/2019 | Hopkins et al. |
| 2019/0315686 A1 | 10/2019 | Snoonian et al. |
| 2020/0165200 A1 | 5/2020 | Snoonian et al. |

FOREIGN PATENT DOCUMENTS

| | | |
|---|---|---|
| CN | 1018988991 | 12/2010 |
| CN | 102600132 | 5/2014 |
| CN | 104725292 | 6/2015 |
| CN | 106995397 | 8/2017 |
| CN | 107049981 | 8/2017 |
| CN | 107126422 | 9/2017 |
| CN | 109010300 | 12/2018 |
| EP | 1547650 | 6/2005 |
| EP | 1646379 | 4/2006 |
| EP | 1944295 | 7/2008 |
| EP | 1946777 | 7/2008 |
| EP | 2030619 | 3/2009 |
| EP | 2959895 | 3/2009 |
| EP | 2272514 | 1/2011 |
| EP | 2508174 | 10/2012 |
| EP | 2596805 | 5/2013 |
| EP | 2676691 | 12/2013 |
| EP | 3058972 | 8/2016 |
| GB | 2456183 | 7/2009 |
| GE | P20115310 | 10/2011 |
| IN | 1013/MUM/2005 | 6/2007 |
| IN | 201641042385 | 6/2018 |
| WO | WO 1998047506 | 10/1998 |
| WO | WO 9929297 | 6/1999 |
| WO | WO 200023045 | 4/2000 |
| WO | WO 2000032558 | 6/2000 |
| WO | WO 2002053140 | 7/2002 |
| WO | WO 2002102297 | 12/2002 |
| WO | WO 3037379 | 5/2003 |
| WO | WO 2003042654 | 5/2003 |
| WO | WO 2004012699 | 2/2004 |
| WO | WO 2004012700 | 2/2004 |
| WO | WO 2004103262 | 12/2004 |
| WO | WO 2005004860 | 1/2005 |
| WO | WO 2005/053796 | 6/2005 |
| WO | WO 2005051358 | 6/2005 |
| WO | WO 2005053796 | 6/2005 |
| WO | WO 2005084654 | 9/2005 |
| WO | WO 2005092392 | 10/2005 |
| WO | WO 2006079547 | 8/2006 |
| WO | WO 2006106425 | 10/2006 |
| WO | WO 2007061896 | 5/2007 |
| WO | WO 2007110878 | 10/2007 |
| WO | WO 2007128349 | 11/2007 |
| WO | WO 2007133802 | 11/2007 |
| WO | WO 2007137224 | 11/2007 |
| WO | WO 2008038003 | 4/2008 |
| WO | WO 2008050341 | 5/2008 |
| WO | WO 2008065500 | 6/2008 |
| WO | WO 2008070296 | 6/2008 |
| WO | WO 2008116024 | 9/2008 |
| WO | WO 2008155357 | 12/2008 |
| WO | WO 2009017453 | 2/2009 |
| WO | WO 2009035473 | 3/2009 |
| WO | WO 2009036056 | 3/2009 |
| WO | WO 2009039461 | 3/2009 |
| WO | WO 2009095479 | 8/2009 |
| WO | WO 2009126931 | 10/2009 |
| WO | WO 2010020642 | 2/2010 |
| WO | WO 2010023690 | 3/2010 |
| WO | WO 2010056065 | 5/2010 |
| WO | WO 2010058314 | 5/2010 |
| WO | WO 2010075275 | 7/2010 |
| WO | WO 2010085452 | 7/2010 |
| WO | WO 2010108116 | 9/2010 |
| WO | WO 2011012722 | 2/2011 |
| WO | WO 2011057199 | 5/2011 |
| WO | WO 2011060363 | 5/2011 |
| WO | WO 2011082337 | 5/2011 |
| WO | WO 2011107749 | 9/2011 |
| WO | WO 2011107750 | 9/2011 |
| WO | WO 2011107755 | 9/2011 |
| WO | WO 2011110854 | 9/2011 |
| WO | WO 2012002583 | 1/2012 |
| WO | WO 2012006959 | 1/2012 |
| WO | WO 2012016646 | 2/2012 |
| WO | WO 2012065102 | 5/2012 |

(56) References Cited

FOREIGN PATENT DOCUMENTS

| | | |
|---|---|---|
| WO | WO 2012065110 | 5/2012 |
| WO | WO 2012088441 | 6/2012 |
| WO | WO 2012118562 | 9/2012 |
| WO | WO 2012136816 | 10/2012 |
| WO | WO 2012158492 | 11/2012 |
| WO | WO 2013003586 | 1/2013 |
| WO | WO 2013016727 | 1/2013 |
| WO | WO 2013040164 | 3/2013 |
| WO | WO 2013122554 | 8/2013 |
| WO | WO 2014065437 | 5/2014 |
| WO | WO 2014178065 | 11/2014 |
| WO | WO 2015085004 | 6/2015 |
| WO | WO 2015/124932 | 8/2015 |
| WO | WO 2015154025 | 10/2015 |
| WO | WO 2015154030 | 10/2015 |
| WO | WO 2016020573 | 2/2016 |
| WO | WO 2016/111725 | 7/2016 |
| WO | WO 2016109359 | 7/2016 |
| WO | WO 2016162695 | 10/2016 |
| WO | WO 2016166679 | 10/2016 |
| WO | WO 2016186968 | 11/2016 |
| WO | WO 2017/049294 | 3/2017 |
| WO | WO 2017/149387 | 9/2017 |
| WO | WO 2017/149392 | 9/2017 |
| WO | WO 2018/015915 | 1/2018 |
| WO | WO 2012037457 | 5/2018 |
| WO | WO 2018077157 | 5/2018 |
| WO | WO 2018/200381 | 11/2018 |
| WO | WO 2019113079 | 6/2019 |
| WO | WO 2019113084 | 6/2019 |

OTHER PUBLICATIONS

Babichev, "Interaction between regions of the hypothalamus regulating hypophyseal gonadotropic function in female rats," Neurosci Behav Physiol., Jul.-Sep. 1972, 5(3):195-199.

Bard et al., "Cloning of a novel human serotonin receptor (5-HT7) positively linked to adenylate cyclase," J Biol Chem, Nov. 5, 1993, 268(31):23422-23426.

BioOrganics, "R-Amisulpride," [retrieved on Mar. 22, 2018], retrieved from: <www.bioorganics.biz/product_details.php?id=BO%ADA67%AD009#1/2>, 2 pages.

No Author, "Dementia and Mental Illness: Findings on Dementia Detailed by Investigators at Department of Medicine (Antipsychotic Drug Use and the Risk of Seizures: Follow-up Study with a nested Case-Control Analysis)," Biotech Week; Atlanta, ProQuest document ID 1715999653, Sep. 30, 2015, 3 pages.

Bonaventure et al., "Translational evaluation of JNJ-18038683, a 5-hydroxytryptamine type 7 receptor antagonist, on rapid eye movement sleep and in major depressive disorder.," Aug. 2012, J Pharmacol Exp Ther., 342(2):429-440.

Bonaventure et al., "Selective blockade of 5-hydroxytryptamine (5-HT)7 receptors enhances 5-HT transmission, antidepressant-like behavior, and rapid eye movement sleep suppression induced by citalopram in rodents.," J Pharmacol Exp Ther., May 2007, 321(2):690-698.

Boulu, "Behavioral and neurochemical methods in research on new psychotropics," Ann Pharm Fr, 1998, 56(2):54-59.

Cassano et al., "Efficacy and safety of amisulpride 50 mg versus paroxetine 20 mg in major depression: a randomized, double-blind, parallel group study," Int Clin Psychopharmacol., Jan. 2002, 17(1):27-32.

Carta et al., "An Open Label Follow-up Study on Amisulpride in the add-on Treatment of Bipolar 1 Patients," Clinical Practive and Epidemiology in Mental Health, Aug. 24, 2006, 2:19.

Castelli et al., "(−)S amisulpride binds with high affinity to cloned dopamine D(3) and D(2) receptors," Euro Journal of Pharma., Nov. 5, 2001, 432:143-147.

Cates et al., "Effects of lurasidone in behavioral models of depression. Role of the 5-HT$_7$ receptor subtype," Neuropharmacology, Jul. 2013, 70:211-217.

Chaggar et al., "Effect of antipsychotic medications on glucose and lipid levels," J Clin Pharmacol, May 2011, 51(5):631-638.

Chen et al., "Second-generation antipsychotics in major depressive disorder: update and clinical perspective," Curr Opin Psychiatry., Jan. 2011, 24(1):10-17.

Clinicaltrials.gov, Search Results, Jul. 25, 2018, 25 pages.

Clinicaltrials.gov, "A Four-week Clinical Trial Investigating Efficacy and Safety of Cannabidiol as a Treatment for Acutely Ill Schizophrenic Patients," NCT02088060, Mar. 8, 2018, [retrieved on Dec. 4, 2018] retrieved from URL<https://clinicaltrials.gov/ct2/show/NCT02088060>, 8 pages.

Clinicaltrials.gov, "A Randomized, Double-blind, Comparison of the Efficacy and Safety of Amisulpride Versus Low-dose Amisulpride Plus Low-dose Sulpiride in the Treatment of Schizophrenia," NCT01615185, Mar. 1, 2016, [retrieved on Dec. 3, 2018] retrieved from URL<https://clinicaltrials.gov/ct2/show/NCT01615185>, 8 pages.

Clinicaltrials.gov, "Amisulpride Augmentation in Clozapine-unresponsive Schizophrenia (AMICUS)," NCT01246232, Apr. 1, 2015, [retrieved on Dec. 3, 2018] retrieved from URL<https://clinicaltrials.gov/ct2/show/NCT01246232>, 8 pages.

Clinicaltrials.gov, "Amisulpride Augmentation Therapy for Clozapine-resistant Schizophrenic Patients (M1106)," NCT01105481, Apr. 16, 2010, [retrieved on Dec. 3, 2018] retrieved from URL<https://clinicaltrials.gov/ct2/show/NCT01105481>, 7 pages.

Clinicaltrials.gov, "Amisulpride in Schizophrenic Patients," NCT00331981, Apr. 10, 2008, [retrieved on Dec. 3, 2018] retrieved from URL<https://clinicaltrials.gov/ct2/show/NCT00331981>, 5 pages.

Clinicaltrials.gov, "Amisulpride in Schizophrenic Acute Phase Patients (ASAP)," NCT00436371, Sep. 5, 2008, [retrieved on Dec. 3, 2018] retrieved from URL<https://clinicaltrials.gov/ct2/show/NCT00436371>, 5 pages.

Clinicaltrials.gov, "An Investigation of Early life Stress and Depression", NCT 017101258, Dec. 28, 2016, [retrieved on Jul. 22, 2017] retrieved from URL<https://clinicaltrials.gov/ct2/show/NCT01701258?term=amisulpride&draw=1>, 6 pages.

Clinicaltrials.gov, "An Observational Drug Utilization Study of Asenapine in the United Kingdom (P08308)," NCT01498770, Jun. 7, 2017, [retrieved on Jul. 22, 2017] retrieved from URL<https://clinicaltrials.gov/ct2/show/NCT01498770?term=amisulpride&draw=1>, 6 pages.

Clinicaltrials.gov, "An Observational Study on Atypical Antipsychotics Long-term Treatment Patients With Schizophrenia," NCT02640911, Aug. 1, 2017, [retrieved on Dec. 4, 2018] retrieved from URL<https://clinicaltrials.gov/ct2/show/NCT02640911>, 6 pages.

Clinicaltrials.gov, "An Observational Study on Metabolic Syndrome Parameters in Schizophrenia Patients Treated With Atypical Antipsychotics (MESSAGE)," NCT00448630, Jul. 7, 2010, [retrieved Dec. 4, 2018] retrieved from URL<https://clinicaltrials.gov/ct2/show/NCT00448630>, 8 pages.

Clinicaltrials.gov, "Antipsychotic Induced Structural and Functional Brain Changes (APIC)," NCT02435095, Dec. 22, 2017, [retrieved on Dec. 4, 2018] retrieved from URL<https://clinicaltrials.gov/ct2/show/NCT02435095>, 10 pages.

Clinicaltrials.gov, "Association of Amisulpride Response in Schizophrenia With Brain Image (ARB)," NCT02095938, Mar. 26, 2014, [retrieved Dec. 3, 2018] retrieved from URL<https://clinicaltrials.gov/ct2/show/NCT02095938>, 9 pages.

Clinicaltrials.gov, "Benzamide Derivates as Treatment of Clozapine-induced Hypersalivation (CIH)," NCT00534573, Jul. 26, 2012, Jul. 26, 2012, [retrieved on Dec. 3, 2018] retrieved from URL<https://clinicaltrials.gov/ct2/show/NCT00534573>, 6 pages.

Clinicaltrials.gov, "Bergen Psychosis Project 2—The Best Intro Study (BP2)," NCT01446328, Jan. 30, 2018, [retrieved on Dec. 4, 2018] retrieved from URL<https://clinicaltrials.gov/ct2/show/NCT01446328>, 7 pages.

Clinicaltrials.gov, "Cannabidiol as a Different Type of an Antipsychotic: Drug Delivery and Interaction Study (CBD-IS)," NCT02051387, Mar. 8, 2018, [retrieved on Dec. 4, 2018] retrieved from URL<https://clinicaltrials.gov/ct2/show/NCT02051387>, 7 pages.

Clinicaltrials.gov, "Clinical Trial to Evaluate the Efficacy of Treatment vs Discontinuation in a First Episode of Non-affective Psy-

(56) References Cited

OTHER PUBLICATIONS chosis (NONSTOP)," NCT01765829, Dec. 5, 2014, [retrieved on Dec. 4, 2018] retrieved from URL<https://clinicaltrials.gov/ct2/show/NCT01765829>, 10 pages.

Clinicaltrials.gov, "Clozapine Versus Amisulpride in Treatment-resistant Schizophrenia Patients (ClozAmi)," NCT01448499, Dec. 9, 2015, [retrieved on Dec. 3, 2018] retrieved from URL<https://clinicaltrials.gov/ct2/show/NCT01448499>, 7 pages.

Clinicaltrials.gov, "Characterize the Modulatory Effects of Dopamine D2/D3 Receptor Agonist and Antagonist Drugs on Compulsive Behaviors," NCT00471588, Sep. 15, 2014, [retrieved on Dec. 4, 2018] retrieved from URL<https://clinicaltrials.gov/ct2/showNCT00471588>, 7 pages.

Clinicaltrials.gov, "Comparison of Antipsychotic Combination Treatment of Olanzapine and Amisulpride to Monotherapy," NCT01609153, Jan. 23, 2017, [retrieved on Jul. 22, 2017] retrieved from URL<https://clinicaltrials.gov/ct2/show/NCT01609153?term=amisulpride&draw=1>, 7 pages.

Clinicaltrials.gov, "Comparison of Valproate-Amisulpride and Valproate-Haloperidol in Bipolar I Patients," NCT00126009, Apr. 8, 2008, [retireved on Jul. 22, 2017] retrieved from URL<https://clinicaltrials.gov/ct2/show/NCT00126009?term=amisulpride&draw=1>, 5 pages.

Clinicaltrials.gov, "Dopamine and Opioid Receptor Antagonists Reduce Cue-induced Reward Responding and Reward Impulsivity," NCT02557984, Sep. 23, 2015, [retrieved on Dec. 4, 2018] retrieved from URL<https://clinicaltrials.gov/ct2/show/NCT02557984>, 8 pages.

Clinicaltrials.gov, "Early Pharmacological and Psychological Intervention for Late Prodromal States of Psychosis," NCT00204061, Dec. 24, 2014, [retrieved on Dec. 4, 2018] retrieved from URL<https://clinicaltrials.gov/ct2/show/NCT00204061>, 7 pages.

Clinicaltrials.gov, "Effect of Atypical Antipsychotic Drugs Olanzapine and Amisulpride on Glucose Metabolism," NCT01160991, Aug. 3, 2010, [retrieved on Dec. 3, 2018] retrieved from URL https://clinicaltrials.gov/ct2/show/NCT01160991>, 7 pages.

Clinicaltrials.gov, "Effectiveness and Safety of Amisulpride in Chinese Patients With Schizophrenia (ESCAPE)," NCT01795183, Jan. 22, 2015, [retrieved on Dec. 3, 2018] retrieved from URL<https://clinicaltrials.gov/ct2/show/NCT01795183>, 6 pages.

Clinicaltrials.gov, "Efficacy of an Early Antipsychotic Switch in Case of Poor Initial Response to the Treatment of Schizophrenia," NCT01029769, May 27, 2015, [retrieved on Jul. 22, 2018], retrieved from URL<https://clinicaltrials.gov/ct2/show/NCT01029769?term=amisulpride&draw=1>, 4 pages.

Clinicaltrials.gov, "Efficacy Study on Cognitive Functions in Schizophrenic Patients (AMIMIND)," NCT00761670, Dec. 9, 2010, [retrieved on Dec. 3, 2018] retrieved from URL<https://clinicaltrials.gov/ct2/show/NCT00761670>, 7 pages.

Clinicaltrials.gov, "Enhancing Recovery in Early Schizophrenia," NCT02926859, Mar. 8, 2018, [retrieved on Dec. 4, 2018] retrieved from URL<https://clinicaltrials.gov/ct2/show/NCT02926859>, 9 pages.

Clinicaltrials.gov, "European Phase III Study of APD421 in PONV," NCT01991821, Jan. 12, 2015, [retrieved on Dec. 4, 2018] retrieved from URL<https://clinicaltrials.gov/ct2/show/NCT01991821>, 5 pages.

Clinicaltrials.gov, "Evaluation of the Antipsychotic Efficacy of Cannabidiol in Acute Schizophrenic Psychosis (CBD-CT1)," NCT00628290, Mar. 18, 2008, [retrieved on Dec. 4, 2018] retrieved from URL<https://clinicaltrials.gov/ct2/show/NCT00628290>, 6 pages.

Clinicaltrials.gov, "Evaluation of Negative Symptoms and Cognitive Function After Administration of Antipsychotics in Healthy Volunteer," NCT01185418, Aug. 20, 2010, [retrieved on Dec. 4, 2018] retrieved from URL<https://clinicaltrials.gov/ct2/show/NCT01185418>, 6 pages.

Clinicaltrials.gov,"Evaluation of the Necessity of Long-term Pharmacological Treatment with Antipsychotics in Schizophrenic Patients," NCT02307396, Feb. 29, 2016, [retreived on Jul. 22, 2017] retrieved from URL<https://clinicaltrials.gov/ct2/show/NCT02307396?term=amisulpride&draw=1>, 5 pages.

Clinicaltrials.gov, "Identification and Treatment Response Prediction of Antipsychotic-Related Metabolic Syndrome," NCT00956189, Jan. 3, 2013, [retrieved on Dec. 3, 2018] retrieved from URL<https://clinicaltrials.gov/ct2/show/NCT00956189>, 6 pages.

Clinicaltrials.gov, "Investigation of the Safety, Tolerability and Potential Therapeutic Effects of JNJ-40411813 in Patients With Schizophrenia," NCT01323205, May 30, 2014, [retrieved on Dec. 4, 2018] retrieved from URL<https://clinicaltrials.gov/ct2/show/NCT01323205>, 8 pages.

Clinicaltrials.gov, "Metabolic Side-effects for Second-generation Antipsychotics," NCT01280396, Jan. 28, 2011, [retrieved on Jul. 22, 2017] retrieved from URL<https://clinicaltrials.gov/ct2/show/NCT01280396?term=amisulpride&draw=1>, 4 pages.

Clinicaltrials.gov, "Metoclopramide as Treatment of Clozapine-induced Hypersalivation," NCT02222220, Aug. 21, 2014, [retrieved on Dec. 4, 2018] retrieved from URL<https://clinicaltrials.gov/ct2/show/NCT02222220>, 7 pages.

Clinicaltrials.gov, "Modulation of Regional Brain Activation in Schizophrenic Patients by Pharmacological Therapy," NCT00419653, Sep. 16, 2008, [retrieved on Dec. 4, 2018] retrieved from URL<https://clinicaltrials.gov/ct2/show/NCT00419653>, 6 pages.

Clinicaltrials.gov, "Optimisation of Antipsychotic Drug Use in Older People," NC01454453, Oct. 19, 2011, [retrieved on Dec. 4, 2018] retrieved from URL<https://clinicaltrials.gov/ct2/show/NCT01454453>, 6 pages.

Clinicaltrials.gov, "Optimization of Treatment and Management of Schizophrenia in Europe (OPTIMISE): Substudy Site Copenhagen," NCT0155814, Oct. 25, 2016, [retrieved Jul. 22, 2017] retrieved from URL<https://clinicaltrials.gov/ct2/show/NCT01555814?term=amisulpride&draw=1>, 5 pages.

Clinicaltrials.gov, "Optimization of Treatment and Management of Schizophrenia in Europe (OPTIMISE)," NCT01248195, Nov. 3, 2016, [retrieved Jul. 22, 2017] retrieved from URL<https://clinicaltrials.gov/ct2/show/NCT01248195?term=amisulpride&draw=1>, 6 pages.

Clinicaltrials.gov, "Pan European Collaboration on Antipsychotic Naive Schizophrenia (PECANS) (PECANS)," NCT01154829, May 26, 2016, [retrieved on Dec. 4, 2018] retrieved from URL<https://clinicaltrials.gov/ct2/show/NCT01154829>, 7 pages.

Clinicaltrials.gov, "Pharmacovigilance in Gerontopsychiatric Patients (GAP)," NCT02374567, Feb. 23, 2017, [retrieved on Jul. 22, 2017] retrieved from URL<https://clinicaltrials.gov/ct2/show/NCT02374567?term=amisulpride&draw=1>, 8 pages.

Clinicaltrials.gov, "Phase IIIb Study of APD421 in Combination as PONV Prophylaxis," NCT02337062, Aug. 4, 2017, [retrieved on Dec. 4, 2018] retrieved from URL<https://clinicaltrials.gov/ct2/show/NCT02337062>, 7 pages.

Clinicaltrials.gov. "Safety and Efficacy of Aripiprazole and Ziprasidone Among Schizophrenic Patients With Metabolic Syndrome," NCT01714011, Nov. 27, 2012, [retrieved on Dec. 4, 2018] retrieved from URL<https://clinicaltrials.gov/ct2/show/NCT01714011>, 8 pages.

Clinicaltrials.gov, "SOLIACS: Solian Solution in the Acute Setting," NCT00245674, Apr. 10, 2008, [retrieved on Dec. 3, 2018] retrieved from URL<https://clinicaltrials.gov/ct2/show/NCT00245674>, 5 pages.

Clinicaltrials.gov, "SOLMANIA—Comparison of Valproate-Amisulpride and Valproate-Haloperidol in Bipolar I Patients," NCT00126009, Apr. 10, 2008, [retrieved on Dec. 3, 2018] retrieved from URL<https://clinicaltrials.gov/ct2/show/NCT00126009>, 7 pages.

Clinicaltrials.gov, "Study Assessing SEP-363856 in Male and Female Volunteers With High or Low Schizotype Characteristics," NCT01972711, Feb. 23, 2016, [retrieved Dec. 4, 2018] retrieved from URL<https://clinicaltrials.gov/ct2/show/NCT01972711>, 9 pages.

Clinicaltrials.gov, "Study of APD421 as PONV Treatment (Prior Prophylaxis)," NCT02646566, Jan. 24, 2017, [retrieved Dec. 4, 2018] retrieved from URL<https://clinicaltrials.gov/ct2/show/NCT02646566>, 7 pages.

Clinicaltrials.gov, "Study of APD421 as PONV Treatment (no Prior Prophylaxis)," NCT024492914, Aug. 5, 2016, [retrieved Dec. 4, 2018] retrieved from URL<https://clinicaltrials.gov/ct2/show/NCT02449291>, 6pages.

Clinicaltrials.gov, "SWitching to Abilify Trial (SWAT)," NCT00304616, Dec. 17, 2009, [retrieved on Dec. 4, 2018] retireved from URL<https://clinicaltrials.gov/ct2/show/NCT00304616>, 6 pages.

(56) References Cited

OTHER PUBLICATIONS

Clinicaltrials.gov, "Tardive Dyskinesia and Cognitive Function (TD)," NCT00926965, Jun. 24, 2009, [retrieved on Dec. 4, 2018] retrieved from URL<https://clinicaltrials.gov/ct2/show/NCT00926965>, 6 pages.
Clinicaltrials.gov, "The Effects of Dopamine on Reward Processing," NCT01253421, Dec. 27, 2016, [retrieved on Jul. 22, 2017] retrieved from URL<https://clinicaltrials.gov/ct2/show/NCT01253421?term=amisulpride&draw=1>, 5 pages.
Clinicaltrials.gov, "Thorough QT Study of Intravenous Amisulpride," NCT02661594, Nov. 29, 2018, [retrieved on Dec. 3, 2018] retrieved from URL<https://clinicaltrials.gov/ct2/show/NCT02661594>, 11 pages.
Clinicaltrials.gov, "US Phase III Study of APD421 in PONV," NCT01991860, Sep. 6, 2018, [retrieved on Dec. 4, 2018] retrieved from URL<https://clinicaltrials.gov/ct2/show/NCT01991860>, 5 pages.
Clinicaltrials.gov, "[18 Fluorine(F)]DOPA Determinants and Predictors of Treatment Response in Psychosis (DPTP)," NCT02880995, Aug. 26, 2016, [retrieved on Dec. 4, 2018] retrieved from URL<https://clinicaltrials.gov/ct2/show/NCT02880995>, 8 pages.
Coukell et al., "A Review of its Pharmacodynamic and Pharmacokinetic Properties and Therapeutic Efficacy in the Management of Schizophrenia," Drug Evaluation, Sep. 1996, 6(3):237-256.
Coulouvrat et al., "Safety of amisulpride (Solian): a review of 11 clinical studies," International Clinical Psychopharmacology, Jul. 1999, 14(4):209-218.
DeVane et al., "Clinical Pharmacokinetics of Quetiapine," Drug Disposition, 2001, 40(7):509-522.
Donahue, "Amisulpride is a potent 5-HT7 antagonist: relevance for antidepressant actions in vivo," Psychopharmacology, Jul. 2009, 205(1):119-128.
Donahue, Characterization of the Decriminative Stimulus Properties of the Atypical Antipsychotic Amisulpride in C57BL/6 Mice:, Thesis or the degree of Doctor of Philosophy, Virginia Commonwealth University, Department of Psychology, Nov. 2014, 141 pages.
Donahue, "Discriminative stimulus properties of he atypical antipsychotic amisulpride: comparison to its isomers and to other benzamide derivatives, antipsychotic, antidepressant, and antianxiety drugs in C57BL/6 mice," Psychopharmacology, Dec. 2017, 234(23-24):3507-3520.
Donahue et al., "(S)-amisulpride as a discriminative stimulus in C57BL/6 mice and its comparison to the stimulus effects of typical and atypical antipsychotics," Eur J Pharmacolo., Jul. 5, 2014, 734(1):15-22.
Farde et al., "Positron emission tomographic analysis of central D1 and D2 dopamine receptor occupancy in patients treated with classical neuroleptics and clozapine. Relation to extrapyramidal side effects," Arch Gen Psychiatry., Jul. 1992, 49:538-544.
Gao et al., "Efficacy of typical and atypical antipsychotics for primary and comorbid anxiety symptoms or disorders: a review," J Clin Psychiatry, Sep. 2006, 67(9):13727-1340.
Grunder et al., "The 'atypicality' of antipsychotics: a concept re-examined and re-defined," Nat Rev Drug Discov., Mar. 2009, 8(3):197-202.
Guscott et al., "Genetic knockout and pharmacological blockade studies of the 5-HT7 receptor suggest therapeutic potential in depression," Neuropharmacology, Mar. 2005, 48(4):492-502.
Hardoy et al., "Adjunctive amisulpride to fluvoxamine in major depression: Early ssri onset of action," European psychiatry, 2000, 15:s325.
Harvey et al., "Effect of lurasidone on neurocognitive performance in patients with schizophrenia: a short-term placebo- and active-controlled study followed by a 6-month double-blind extension," Eur Neuropsychopharmocol., Nov. 2013, 23(11):1373-1382.
Harvey et al., "Effect of lurasidone dose on cognition in patients with schizophrenia: post-hoc analysis of a long-term, double-blind continuation study," Schizophr Res., Aug. 2015, 166(1-3):334-338.
Hedlund et al., "The 5-HT7 receptor and disorders of the nervous system: an overview," Psycopharmacology, Oct. 2009, 206(3):345-354.
Hedlund et al., "5-HT7 receptor inhibition and inactivation induce antidepressantlike behavior and sleep pattern," Biol Psychiatry., Nov. 15, 2005, 58(10):831-837.
International Search Report and Written Opinion in International Application No. PCT/US2018/63865, dated Mar. 25, 2019, 13 pages.
International Search Report and Written Opinion in International Application No. PCT/US2018/63859, dated Mar. 26, 2019, 23 pages.
Jakovcevska-Kujundziska et al., "Amisulpride in combination with maprotiline in the treatment of psychotic depression—a clinical experience," European NeuroPsychopharmacology, Oct. 2003, 13:s193.
Kapur et al., "Clinical and Theoretical Implications of 5-HT2 and D2 Receptor Occupancy of Clozapine, Risperidone, and Olanzapine in Schizophrenia," Am J Psychiatry, Feb. 1999, 156:2.
Kapur et al., "A Positron Emission Tomography Study of Quetiapine in Schizophrenia," Arch Gen Psychiatry, Jun. 2000, 57:553-559.
Kaul et al., "Comparative evaluation of amisulpride and escitalopram on Hamilton Depression Rating Scale among depression patients in a tertiary care teaching hospital in Nepal," Int J Med Sci Public Health., 2015, 4(5):642-646.
Keshipeddy et al., "Nonracemic Antifolates Stereoselectively Recruit Alternate Cofactors and Overcome Resistance in S. aureus", Journal of the American Chemical Society, Jun. 22, 2015, 137:8983-8990.
Komossa et al., "Second-generation antipsychotics for major depressive disorder and dysthymia," Cochrane Database Syst Rev., Dec. 8, 2010, (12):CD008121.
La Fougere et al., "D2 receptor occupancy during high- and low-dose therapy with the atypical antipsychotic amisulpride: a 123I-iodobenzamide SPECT study.," J Nucl Med., Jun. 2005, 46(6):1028-1033.
Lecrubier et al., "Amisulpride versus imipramine and placebo in dysthymia and major depression. Amisulpride Study Group," J Affect Disord., Apr. 1997, 43(2):95-103.
Leopoldo et al., "Serotonin 5-HT7 receptor agents: Structure-activity relationships and potential therapeutic applications in central nervous system disorders," Pharmacol Ther., Feb. 2011, 129(2):120-148.
Leucht et al., "Comparative efficacy and tolerability of 15 antipsychotic drugs in schizophrenia: a multiple-treatments meta-analysis," Lancet, Sep. 14, 2013, 382(9896):951-962.
Lopez-Monoz et al., "Bipolar disorder as an emerging pathology in the scientific literature: a bibliometric approach," J Affect Disorder, Jun. 2006, 92(2-3):161-170.
Lovenberg et al., "A novel adenylyl cyclase-activating serotonin receptor (5-HT7) implicated in the regulation of mammalian circadian rhythms," Neuron, Sep. 1993, 11(3):449-458.
Mamo et al., "Quetiapine Extended-Release Versus Immediate-Release Formulation: A Positron Emission Tomography Study," J Clin PsyChiatry, Jan. 2008, 69(1):81-86.
Marchese et al., "Effect of the Amisulpride Isomers on Rat Catalepsy," European Journal of Pharmacology, May 24, 2002, 444(1-2):69-74.
Moller et al., "Antipsychotic and antidepressive effects of second generation antipsychotics," Eur Arch Psychiatry Clin Neurosci., Jun. 2005, 255(3):190-201.
Montgomery, "Dopaminergic deficit and the role of amisulpride in the treatment of mood disorders," Int Clin Psychopharmacol., Dec. 2002, 17 Suppl 4:S9-15.
Morgan et al., "Characterization of the Antiociceptive Effects of the Individual Isomers of Methadone After Acute and Chronic Administrations," Behav Pharmacol., Sep. 2011, 22(5-6):548-557.
Morita et al., "HTR7 Mediates Seratonergic Acute and Chronic Itch," Neuron, Jul. 1, 2015, 87(1):124-138.
Nelson et al., "Atypical antipsychotic augmentation in major depressive disorder: a meta-analysis of placebo-controlled randomized trials," Am J Psychiatry, Sep. 2009, 166(9):980-991.
Nikiforuk, "Targeting the Serotonin 5-HT7 Receptor in the Search for Treatments for CNS Disorders: Rationale and Progress to Date," CNS Drugs, Apr. 2015, 29(4):265-275.
Nikiforuk et al., "Effects of the selective 5-HT7 receptor antagonist SB-269970 and amisulpride on ketamine-induced schizophrenia-like deficits in rats," PLoS One., Jun. 11, 2013, 8(6):e66695.

(56) References Cited

OTHER PUBLICATIONS

Nyberg et al., "Suggested Minimal Effective Dose of Risperidone Based on PET-Measured D2 5-HT2A Receptor Occupancy in Schizophrenic Patients," Am J Psychiatry., Jun. 1999, 156:873-875.
Office Action (Final) in U.S. Appl. No. 14/344,665, dated Oct. 28, 2016, 32 pages.
Palovics et al., "Separation of the Mixtures of Chiral Compounds by Crystallization," Advances in Crystallization Processes, Apr. 27, 2012, retrieved from URL <https://www.intechopen.com/books/advances-in-crystallization-processes/separation-of-the-mixtures-of-chiral-compounds-by-crystallization>, pp. 1-38.
Papp and Wieronska, "Antidepressant-like activity of amisulpride in two animal models of depression," Journal of Psychopharmacology, 2000, 14(1):46-52.
Pawar et al., "Evaluation of antidepressant like property of amisulpride per se and its comparison with fluoxetine and olanzapine using forced swimming test in albino mice," Acta Pol Pharma., May-Jun. 2009, 66(3):327-331.
Popovic et al., "Number needed to treat analyses of drugs used for maintenance treatment of bipolar disorder,", Psychopharmacology, Feb. 2011, 213(4):657-667.
Barrett, "Aspects of cognitive function in healthy volunteers administered antipsychotic drugs and in patients with bipolar disorder," Queen's University Belfast (United Kingdom), ProQuest Dissertations Publishing, 2001. U151775. (Abstract only).
Roix et al., "Effect of the antipsychotic agent amisulpride on clucose lowering and insulin secretion," Diabetes, Obesity and Metabolism, Apr. 2012, 14(4):329-334.
Rybakowski et al., "Treatment of depression in first episode of schizophrenia: results from EUFEST," Eur Neuropsychopharmacol., Dec. 2012, 22(12):875-882.
Sarkisyan et al., "The 5-HT(7) receptor as a mediator and modulator of antidepressant-like behavior," Behave Brain Res., May 1, 2010, 209(1):99-108.
Smeraldi, "Amisulpride versus fluoxetine in patients with dysthymia or major depression in partial remission: a double-blind, comparative study," J Affect Disord., Feb. 1998, 48(1):47-56.
Spina et al., "Metabolic drug interactions with newer antipsychotics: a comparative review," Basic Clin Pharmacol Toxicol, Jan. 2007, 100(1):4-22.
Suppes et al., "Lurasidone for the Treatment of Major Depressive Disorder With Mixed Features: A Randomized, Double-Blind, Placebo-Controlled Study," Am J Psychiatry., Apr. 1, 2016, 174(4):400-407.
Taubel et al., "Thorough QT study of the effect of intravenous amisulpride on QTc Interval in Caucasian and Japanese healthy subjects," British Journal of Clinical Pharmacology, Feb. 2017, 83(2):339-348.
Toronto Research Chemicals, "R-Amisulpride," 2017, [retrieved on Mar. 20, 2017], retrieved from: URL<https://www.trc-canada.com/product-detail/?CatNum=A633255&CAS=71675-90-6&Chemical_Name=R-Amisulpride&Mol_Formula=$C_{17}H_{27}N_3O_4S$>, 2 pages.
Thomas et al., "Amisulpride Plus Valproate vs Haloperidol Plus Valproate in the Treatment of Acute Mania of Bipolar I Patients: A Multicenter, Open-label Randomized, Comparative Trial," Original Research, 2008, 4(3):675-686.
Thomas et al., "SB-656104-A, A Novel Selective 5-HT7 Receptor Antagonist, Modulates REM Sleep in Rats," British Journal of Pharmacology, Jun. 2003, 139(4):705-714.
Vanelle et al., "Metabolic control in patients with comorbidschizophrenia and depression treated with amisulpride or olanzapine," European Neuropsychopharmacology, Oct. 2004, 14(3):S284.
Vernaleken et al., "High striatal occupancy of D2-like dopamine receptors by amisulpride in the brain of patients with schizophrenia," Int J Neuropsychopharmacol., Dec. 2004, 7(4):421-430.
Vieta et al. "An open-label study of amisulpride in the treatment of mania," The Journal of Clinical Psychiatry, May 2005, 66(5):575-8.
Wesolowska et al., "Enhancement of the anti-immobility action of antidepressants by a selective 5-HT7 receptor antagonist in the forced swimming test in mice," Eur J Pharmacol., Jan. 19, 2007, 555(1):43-47.
Willner et al., "Dopaminergic mechanism of antidepressant action in depressed patients," J Affect Disord., May 2005, 86(1):37-45.
Winter et al., "Structure of the Neuropeptic Drug 4-Amino-N-1-[(1-ethyl-2-pyrrolidinyl)methyl]-5-(ethylsulfonyl)-2-methoxybenzamide (Amisulpride)," Acta Cryst., Feb. 15, 1990, 46(2):313-317.
Yatham et al., "Canadian Network for Mood and Anxiety Treatments (CANMAT) and International Society for Bipolar Disorders (ISBD) collaborative update of CANMAT guidelines for the management of patients with bipolar disorder: update 2009," Bipolar Disord., May 2009, 11(3):225-255.
Zhang et al., "Crystal Structures and physicochemical properties of amisulpride polymorphs," Journal of Pharmacautical and Biomedicinal Analysis, Jun. 5, 2017, 140:252-257.
Zhou et al., "Atypical Antipsychotic Augmentation for Treatment-Resistant Depression: A Systematic Review and Network Meta-Analysis," Int J Neuropsychopharmacol, May 25, 2015, 18(11):pyv060.
Al-Khatib et al., "What Clinicians Should Know About the QT Interval," JAMA, 2003, 289(16):2120-2127.
Asada, T., et al., "An Innovative Method for the Preparation of High API-Loaded Hollow Spherical Granules for Use in Controlled-Release Formulation", International Journal of Pharmaceutics, 523:167-175 (2017).
Asada, T., et al., "Formulation of a Poorly Water-Soluble Drug in Sustained-Release Hollow Granules with a High Viscosity Water-Soluble Polymer Using a Fluidized Bed Rotor Granulator", International Journal of Pharmaceutics, 541:246-252 (2018).
Asada, T., et al., "Mechanism of the Formation of Hollow Spherical Granules Using a High Shear Granulator", European Journal of Pharmaceutical Sciences, 117:371-378 (2018).
Berge et al., "Pharmaceutical Salts," J. Pharmaceutical Sciences, 1977, 66:1-19.
Canal, M., et al., "Lack of Effect of Amisulpride on the Pharmacokinetics and Safety of Lithium", International Journal of Neuropsychopharmacology, 6:103-109 (2003).
Chhabra, V. and Bhatia, M.S., "Amisulpride: A Brief Review", Delhi Psychiatry Journal, 10(2):140-143 (2007).
Colonna, L., et al., "Long-Term Safety and Efficacy of Amisulpride in Subchronic or Chronic Schizophrenia", International Clinical Psychopharmacology, 15:13-22 (2000).
Davey, "How to correct the QT interval for the effects of heart rate in clinical studies," J. Pharmacol. Toxicol. Methods, 2002, 48:3-9.
Dos Santos Pereira, J.N., et al., "The Poorly Membrane Permable Antipsychotic Drugs Amisulpride and Sulpiride are Substrates of the Organic Cation Transporters from the SLC22 Family", The AAPS Journal, 16(6):1247-1258 (2014).
El Ela, A.A., et al., "Identification of P-Glycoprotein Substrates and Inhibitors Among Psychoactive Compounds—Implications for Pharmacokinetics of Selected Substrates", Journal of Pharmacy and Pharmacology, 56:967-975 (2004).
Fox, G.M., et al., "Intravenous Amisulpride Does Not Meaningfully Prolong the QTc Interval at Doses Effective for the Management of Postoperative Nausea and Vomiting", Anasthetic Clinical Pharmacology, ahead of print issue:10 pages (2019).
Grandy, D.K., et al., "Cloning of the cDNA and Gene for a Human D2 Dopamine Receptor", Proc Natl Acad Sci USA, 86:9762-9766 (1989).
Hayes, G., et al., "Structural Subtypes of the Dopamine D2 Receptor are Functionally Distinct: Expression of the Cloned D2A and D2B Subtypes in a Heterlogous Cell Line", Molecular Endocrinology, 6:920-926 (1992).
Hillgren, K.M., et al., "Emerging Transporters of Clinical Importance: An Update from the International Transporter Consortium", Nature, 94(1):52-63 (2013).
Hu et al., "Mixed Specifier for Bipolar Mania and Depression: Highlights of DSM-5 Changes and Implications for Diagnosis and Treatment in Primary Care," Prim. Care Companion CNS Disord., 2014, 16(2):PCC.13r01599.
Hartter, S., et al., "How Does the Benzamide Antipsychotic Amisulpride get into the Brain?—An In Vitro Approach Comparing Amisulpride with Clozapine", Neuropsychopharmacology, 28:1916-1922 (2003).

(56) References Cited

OTHER PUBLICATIONS

Isbister, G.K., et al., "Amisulpride Deliberate Self-Poisoning Causing Severe Cardiac Toxicity Including QT Prolongation and Torsades de Pointes", Med J Aust., 184:354-356 (2006).
Kim, E., et al., "Predicting Brain Occupancy from Plasma Levels Using PET: Superiority of Combining Pharmacokinetics with Pharmacodynamics While Modeling the Relationship", Journal of Cerebral Blood Flow & Metabolism, 32:759-768 (2012).
Krause, M., et al., "Anitpsychotic Drugs for Patients with Schizophrenia and Predominant Prominent Negative Symptoms: A Systematic Review and Meta-Analysis", Eur Arch Psychiatry Clin Neurosci., 268(7):625-639 (2018).
Le Foll, B., et al., "Occupancy of Dopamine D3 and D2 Receptors by Buspirone: a[11C]-(+)-PHNO PET Study in Humans", Neuropsychopharmacology, 41:529-537 (2016).
Li,J-X, "Imidaoline 12, Receptors: An Update", Pharmacol Ther, 178:48-56 (2017).
Macrae et al., "Mercury: visualization and analysis of crystal structures," J. Appl. Cryst., 2006, 39:453-457.
Mortimer, A., et al., "A Double-Blind, Randomized Comparative Trial of Amisulpride Versus Olanzapine for 6 Months in the Treatment of Schizophrenia", Int Clin Psychopharmacol, 19:63-69 (2004).
Panicker et al., "Intra- and interreader variability in QT interval measurement by tangent and threshold methods in a central electrocardiogram laboratory," J. Electrocardiol., 2009, 42:348-52.
Porsolt, R.D., et al., "Behavioural Despair in Rats: A New Model Sensitive to Antidepressant Treatment", Eur J Pharmacol., 47:379-391 (1978).
Reeves et al., "Therapeutic window of dopamine D2/3 receptor occupancy to treat psychosis in Alzheimer's disease," Brain, 2017, 140(4):1117-1127.
Reeves, S., et al., :Therapeutic Window of Dopamine D2/3 Receptor Occupancy to Treat Psychosis in Alzheimer's Disease, Brain A Journal of Neurology, pp. 1118-1127 (2017).
Rein, w., et al., "Safety Profile of Amisulpride in Short- and Long-Term Use", Acta Pschiatr. Scan. Suppl., 400:23-27 (2000).
Rosenzweig, P., et al., "A Review of the Pharmacokinetics, Tolerability and Pharmacodynamics of Amisulpride in Healthy Volunteers", Human Psychopharmacology, 17:1-13 (2002).
Roth, B.L., et atl., "Binding of Typical and Atypical Antipsychotic Agents to 5-Hydroxytryptamine-6 and 5-Hydroxytryptamine-7 Receptors", The Journal of Pharmacology and Experimental Therapeutics, 268(3):1403-1410 (1994).
Rothman, R.B., et al., "Evidence for Possible Involvement of 5-HT(2B) Receptors in the Cardiac Valvulopathy Associated with Fenfluramine and Other Serotonergic Medications", Circulation, 102:2836-2847 (2000).
Sechter, D., et al., "Amisulpride vs. Risperidone in Chronic Schizophrenia: Results of a 6-Month Double-Blind Study", Neuropsychopharmacology, 27:1071-1081 (2002).
Shapiro, D.A., et al., "Aripiprazole, a Novel Atypical Antipsychotic Drug with a Unique and Robust Pharmacology", Neuropsychopharmacology, 28(8):1400-1411 (2003).
Shen, Y., et al., "Molecular Cloning and Expression of a 5-Hyderoxytryptamine7 Serotonin Receptor Subtype", The Journal of Biological Chemistry, 268(24):18200-18204 (1993).
Silveira da Mota Neto, J.I., et al., Amisulpride for Schizophrenia (Review), The Cochrane Library, Chochran Database of Systematic Reviews, Issue 2, Article No. CD001357 (2013).
Solian® Tablets and Solution, Product Information, 13 pages, Jun. 28, 2012.
Tauscher, J., et al., "Significant Dissociation of Brain and Plasma Kinetics with Antipsychotics", Molecular Psychiatry, 7:317-321 (2002).
Uchida et al., "Therapeutic Window for Striatal Dopamine D2/3 Receptor Occupancy in Older Patients With Schizophrenia: A Pilot PET Study," The American J. of Geriatric Psychiatry, 2014, 22(1):1007-1016.
Vanhauwe, J.F., et al., "Comparison of the Ligand Binding and Signaling Properties of Human Dopamine D(2) and D(3) Receptors in Chinese Hamster Ovary Cells", J Pharmacol Exp Ther., 290(2):908-916 (1999).
Zamek-Gliszczynski, M.J., et al., "ITC Recommendations for Transporter Kinetic Parameter Estimation and Translational Modeling of Transport-Mediated PK and DDIs in Humans", Nature, 94(1):64-79 (2013).

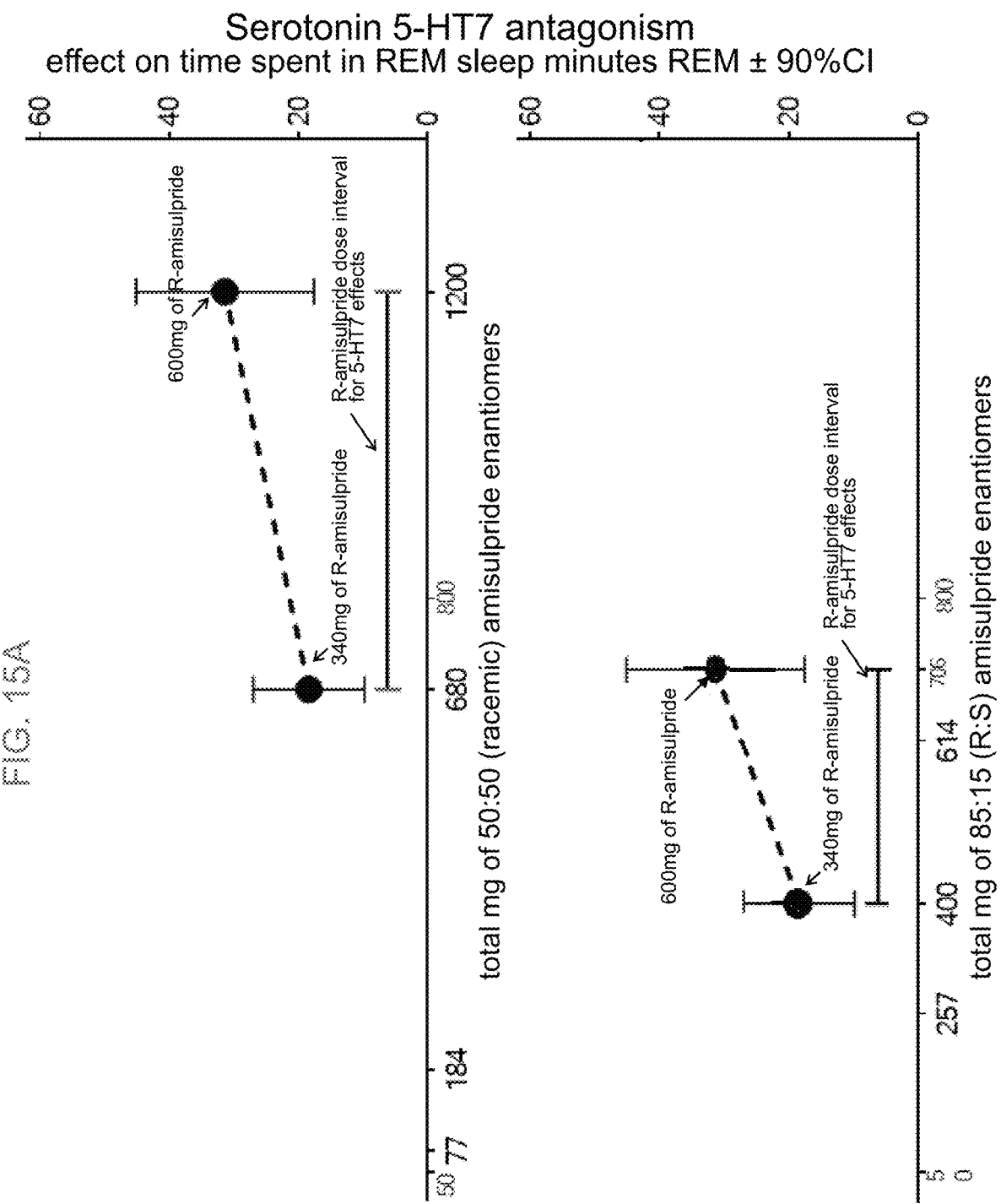

NONRACEMIC MIXTURES AND USES THEREOF

FIELD OF THE INVENTION

The present inventions relate to pharmaceutical compositions of non-racemic amisulpride and methods and uses thereof.

BACKGROUND

Amisulpride is a member of the chemical class benzamide, and has the chemical name 4-amino-N-[(1-ethylpyrrolidin-2-yl)methyl]-5-ethylsulfonyl-2-methoxy-benzamide. The chemical structure of amisulpride is as follows:

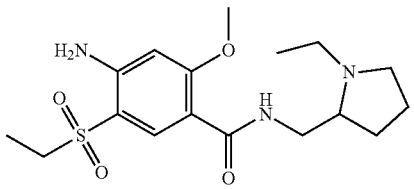 [SMILES: CCN1CCC[C@@H]1CNC(=O)c1cc(S(=O)(=O)CC)c(N)cc1OC]

There is a need for better treatments of psychiatric and mood disorders, including bipolar disorder and in particular depression associated with bipolar disorder. For example, psychiatrists indicate that about 25% of patients across all bipolar disorders are refractory during a manic episode, while about 70% are refractory during a depressive episode. Thus, there is a need for drugs that remit depressive symptoms in bipolar patients.

Dopamine receptor antagonists are one class of drugs used to treat psychiatric disorders, however efficacious $D_2$ occupancy levels are also related to deleterious side effects. A need also therefore exists for central nervous system drugs (CNS) and in particular psychiatric drugs for the treatment of depression and diseases and disorders with a depressive component, that provide a therapeutic effect with no or reduced side effects and in particular side effects associated with dopamine $D_2$ receptor occupancy.

Racemic amisulpride is sold under the tradename SOLIAN® as 400 mg tablet and as a solution for the treatment of acute and chronic schizophrenic disorders, in which positive symptoms (such as delusions, hallucinations, thought disorders) and/or negative symptoms (such as blunted affect, emotional and social withdrawal) are prominent, including patients characterized by predominant negative symptoms, with a recommend total daily dose of 400-800 mg. However, movement related adverse events including tremor, rigidity, hypokinesia, hypersalivation, akathisia, dyskinesia are listed as "very common" in the label for racemic amisulpride in the 400-800 mg/day dosage range. Such as extrapyramidal symptoms are commonly associated with antipsychotic drugs employing dopamine receptor blockade. Typically, extrapyramidal symptoms are observed at high dopamine receptor occupancy, e.g., at about 70-75% occupancy. Other side effects associated with racemic amisulpride include prolongation of the QT interval and increase in prolactin which may lead to galactorrhoea, amenorrhoea, gynaecomastia, breast pain, erectile dysfunction. Therefore, there is need for better psychiatric drugs with reduced side effects.

A need exists for an amisulpride composition which has reduced adverse events and a greater safety profile. A further need exists for an amisulpride composition which can effectively treat bipolar symptoms accompanied with depression more effectively than current formulations. A still further need exists for an amisulpride formulation which is optimized to antagonize the $D_2$ dopamine receptor associated with bipolar symptoms and separately optimized to antagonize the 5-$HT_7$ serotonin receptor associated with symptoms of depression.

SUMMARY

These and other objectives of the present invention make use of the unexpected discovery by the inventors that the R and S amisulpride isomers have different properties that were unexpected. The R isomer is a selective serotonin antagonist. In contrast the S isomer is a highly selective $D_2$ dopamine antagonist. The present inventors provide amisulpride compositions tailored to provide specific antagonism effects against the $D_2$ dopamine receptors and the 5-$HT_7$ receptors independent of one another. In various aspects and embodiments, the amisulpride compositions provide the ability to adjust the $D_2$ dopamine and 5-$HT_7$ receptors antagonism activity and reduce the adverse effects associated with racemic amisulpride of comparable total dosage amounts. Adverse effects associated with racemic amisulpride include, but are not limited to, Extrapyramidal Symptoms (EPS), akathisia, sedation, metabolic parameters such as weight gain, glucose and lipids, prolactin related events, sexual dysfunction and manic depression. In various aspects and embodiments, the degree of reduction is determined by the ratio of R to S amisulpride in the composition and total dosage amount.

The inventors of the present application have discovered that (R)-amisulpride is associated with serotonin 5-$HT_7$ receptors where the serotonergic activity of (R)-amisulpride has an antidepressant effect. Dopamine D2 antagonism resides primarily in the (S)-amisulpride and D2 antagonism can help control the positive symptoms that may arise as a result of treating depression. The inventors have discovered enrichment of serotonin mood disorder benefits while minimizing D2 mediated side effects by using a non-racemic ratio of (R)-amisulpride and (S)-amisulpride to treat patients with bipolar disorder and in particular depression associated with bipolar disorder. The inventors have discovered that non-racemic ratios of R:S amisulpride can provide sufficient 5-HT7 antagonist activity while reducing the level of D2 antagonism to the level associated with antidepressant benefit, thus achieving serotonergic efficacy while limiting D2-associated undesirable side effects. Administration of a composition having a greater amount of R than S amisulpride provides novel pharmacology which confers significant antidepressant benefits with reduced D2-related side effects in patients with bipolar disorder.

It has been unexpectedly discovered that benefits can be obtained from unequal mixtures of the (R)-(+)-amisulpride and (S)-(−)-amisulpride, or pharmaceutically acceptable salts thereof, where the amount of (R)-(+)-amisulpride is greater than the amount of (S)-(−)-amisulpride. It has been discovered that the serotonergic activity of (R)-(+)-amisulpride has an antidepressant effect. It has also been discovered that amisulpride enantiomers have different stereoselectivities between dopamine $D_2$ and serotonin 5-$HT_7$ receptors, such that the relative potencies of mixtures of amisulpride enantiomers can be changed to increase serotonin 5-HT7 potency relative to dopamine D2 receptor potency, and concomitantly provide efficacious compositions, methods of treatment, methods of receptor inhibition, and medicaments whilst decreasing undesirable side effects associated with one or both of the enantiomers.

It has been discovered that certain unequal mixtures of the (R)-(+)-amisulpride and (S)-(−)-amisulpride, or pharmaceutically acceptable salts thereof, where the amount of (R)-(+)-amisulpride is greater than the amount of (S)-(−)-amisulpride can provide an approach to the treatment of mood disorders, psychiatric disorders and/or mixed mood/psychotic disorders by increasing the proportion of 5-HT7 antagonism provided by (R)-amisulpride in relation to D2 blockade provided by (S)-amisulpride in order to more effectively target mood and cognitive symptoms while still maintaining the anxiolytic and antipsychotic benefits of D2 blockade and concomitantly reducing dopamine-related extrapyramidal side effects.

The present inventors have demonstrated that the R-enantiomer is highly stereoselective for serotonin 5-HT7 receptors, such that the 5-HT7 antagonism seen with amisulpride can be attributed almost exclusively to the R-enantiomer. In addition, the present inventors have conducted preclinical polysomnography (PSG) studies in rats that demonstrate rapid eye movement (REM) suppression with R-amisulpride, with results consistent with the effects reported for selective 5-HT7 antagonists. Also, the present inventors have shown in healthy human volunteers that R-amisulpride demonstrates clinically meaningful and statistically significant suppression of REM sleep, similar to what has been observed with other 5-HT7 selective antagonists in human studies.

The present inventors have demonstrated that the S-enantiomer is highly stereoselective for dopamine D2 receptors with in vivo non-human primate PET imaging experiments. Also, the present inventors have shown in healthy human volunteers that S-amisulpride demonstrates clinically meaningful dose-dependent D2 receptor occupancy.

In various aspects and embodiments, provided are various compositions, formulations, methods and medicaments comprising and/or employing unequal mixtures of the (R)-(+)-amisulpride and (S)-(−)-amisulpride, or pharmaceutically acceptable salts thereof, where the amount of (R)-(+)-amisulpride is greater than the amount of (S)-(−)-amisulpride, that can provide the discovered antidepressant activity of (R)-(+)-amisulpride while maintaining the mood stabilization activity of (S)-(−)-amisulpride and minimizing the undesirable side effects associated with higher levels of dopamine D2 receptor blockade associated with (S)-(−)-amisulpride.

It has been discovered by the inventors that, in various aspects and embodiments of the present inventions, a fixed-dose combination of amisulpride enantiomers, defined in various embodiments by the contribution of 5-HT$_7$ occupancy relative to D$_2$ occupancy exhibits clinical benefit by allowing physicians to treat subjects with a dominant 5-HT$_7$ pharmacodynamics while still maintaining a dose-responsive underlying dopamine D$_2$ activity for a combined, and in various embodiments improved, clinical benefit in depressive disorders.

Since the R and S isomer are separately prepared it is possible to customize formulations to provide the desired D$_2$ antagonism separately from the 5-HT7 antagonism by changing the ratio of the R and S isomers in the formulation. This customization is not possible with racemic amisulpride. The present inventions in various aspects and embodiments allow for formulations which can avoid the problems traditionally associated with the racemic mixture.

BRIEF DESCRIPTION OF THE DRAWINGS

FIG. 1A presents data on the % inhibition of dopamine D2 receptor binding; FIG. 1B presents data on the % inhibition of serotonin 5-HT7 receptor binding; and FIG. 1C presents data on relative receptor affinity (5-HT7: D$_2$) for various mixtures of (R)-amisulpride and (S)-amisulpride.

FIG. 3A presenting data comparing vehicle to 10 mg/kg and 100 mg/kg of (R)-amisulpride, and FIG. 3B presenting data comparing vehicle to 10 mg/kg, 30 mg/kg and 100 mg/kg of (R)-amisulpride.

FIG. 3C presents data comparing vehicle to 30 mg/kg and 100 mg/kg of 85:15 ratio (R:S-amisulpride) and racemic amisulpride in REM sleep time (min). FIG. 3D presents data comparing vehicle to 30 mg/kg and 100 mg/kg of 85:15 ratio (R:S-amisulpride) and racemic amisulpride in NREM sleep time (min). FIG. 3E presents data comparing vehicle to 30 mg/kg and 100 mg/kg of 85:15 ratio (R:S-amisulpride) and racemic amisulpride in WAKE time (min).

FIG. 6A presents data from human clinical studies on the binding to dopamine D2 receptors of an 85:15 ratio by weight percentage (w/w %) of (R)-amisulpride to (S)-amisulpride, FIG. 6B illustrates data on a racemic (50:50 ratio by weight percentage mixture of (R)-amisulpride to (S)-amisulpride), and FIG. 6C illustrates the substantial overlap of the 5-HT$_7$ effect with 30% to 50% D$_2$ receptor occupancy that may be achieved with administration of an 85:15 ratio by weight percentage (w/w %) mixture of (R)-amisulpride to (S)-amisulpride. In FIG. 6B the mg designations within the field of the graph indicate the amount of the indicted enantiomer in the racemic mixture. In FIG. 6C the grey shaded circles are the data for (S)-amisulpride from FIG. 6B plotted on the FIG. 6C x-axis as the total mg amount required to deliver the indicated amount of (S)-amisulpride in the (R)-amisulpride:(S)-amisulpride (85:15) mixture, the dark shaded circles are the data for (R)-amisulpride from FIG. 6B plotted on the FIG. 6C x-axis as the total mg amount required to deliver the indicated amount of (R)-amisulpride in the (R)-amisulpride:(S)-amisulpride (85:15) mixture, and the white diamond symbols are data for administration of an 85:15 ratio by weight percentage (w/w %) mixture of (R)-amisulpride to (S)-amisulpride.

FIG. 7A presents a DSC thermogram; FIG. 7B a XRPD pattern; and FIG. 7C a micrograph image.

FIG. 8A presents a DSC thermogram; FIG. 8B a XRPD pattern; FIG. 8C a micrograph image; and FIG. 8D a DVS water sorption isotherm.

FIGS. 15A, 15B, and 15C present analytical data on the effects of mixtures of amisulpride.

FIG. 15A presents data from human clinical studies on the effects of (R)-amisulpride (dark circles) on 5-HT$_7$ shown by suppression of REM sleep from Example 5, where the x-axis in the top graph is 50:50 racemic amisulpride, and the x-axis in the bottom graph is 85:15 ratio by weight percentage (w/w %) of R:S-amisulpride.

FIG. 15B presents data from human clinical studies on the binding to dopamine D2 receptors of (S)-amisulpride and an 85:15 ratio by weight percentage (w/w %) of (R)-amisulpride to (S)-amisulpride. The x-axis in the top graph is 50:50 racemic amisulpride. The top graph shows the amount of (S)-amisulpride (grey circles) has on D2 occupancy based on data from Example 4. The x-axis in the bottom graph is 85:15 ratio of (R)-amisulpride to (S)-amisulpride, showing the amount of (S)-amisulpride (grey circles) and 85:15 ratio (white diamonds) have on D2 occupancy based on data from Example 4 and Example 6, respectively.

FIG. 15C illustrates the substantial overlap of the 5-HT$_7$ effect with 30% to 50% D$_2$ receptor occupancy that may be achieved with administration of an 85:15 ratio by weight percentage (w/w %) mixture of (R)-amisulpride to (S)-amisulpride. The x-axis in the top graph is the total amount of racemic amisulpride. The mg designations indicate the amount of the indicted enantiomer in the racemic mixture. The grey shaded circles are the data for (S)-amisulpride from Example 4, showing the effect of (S)-amisulpride has on D2 occupancy. The dark circles are the data for (R)-amisulpride from Example 5, showing the effect of (R)-amisulpride has on 5-HT$_7$. The x-axis in the bottom graph is the total amount of 85:15 ratio R:S amisulpride. The mg designations indicate the amount of the indicted enantiomer in the 85:15 ratio mixture. The grey shaded circles are the data for (S)-amisulpride from Example 4, showing the effect of (S)-amisulpride has on D2 occupancy. The dark circles are the data for (R)-amisulpride from Example 5, showing the effect of (R)-amisulpride has on 5-HT$_7$. The white diamonds are data for the 85:15 ratio R:S amisulpride from Example 6 (D2 occupancy).

DETAILED DESCRIPTION

Figures 1A, 1B:
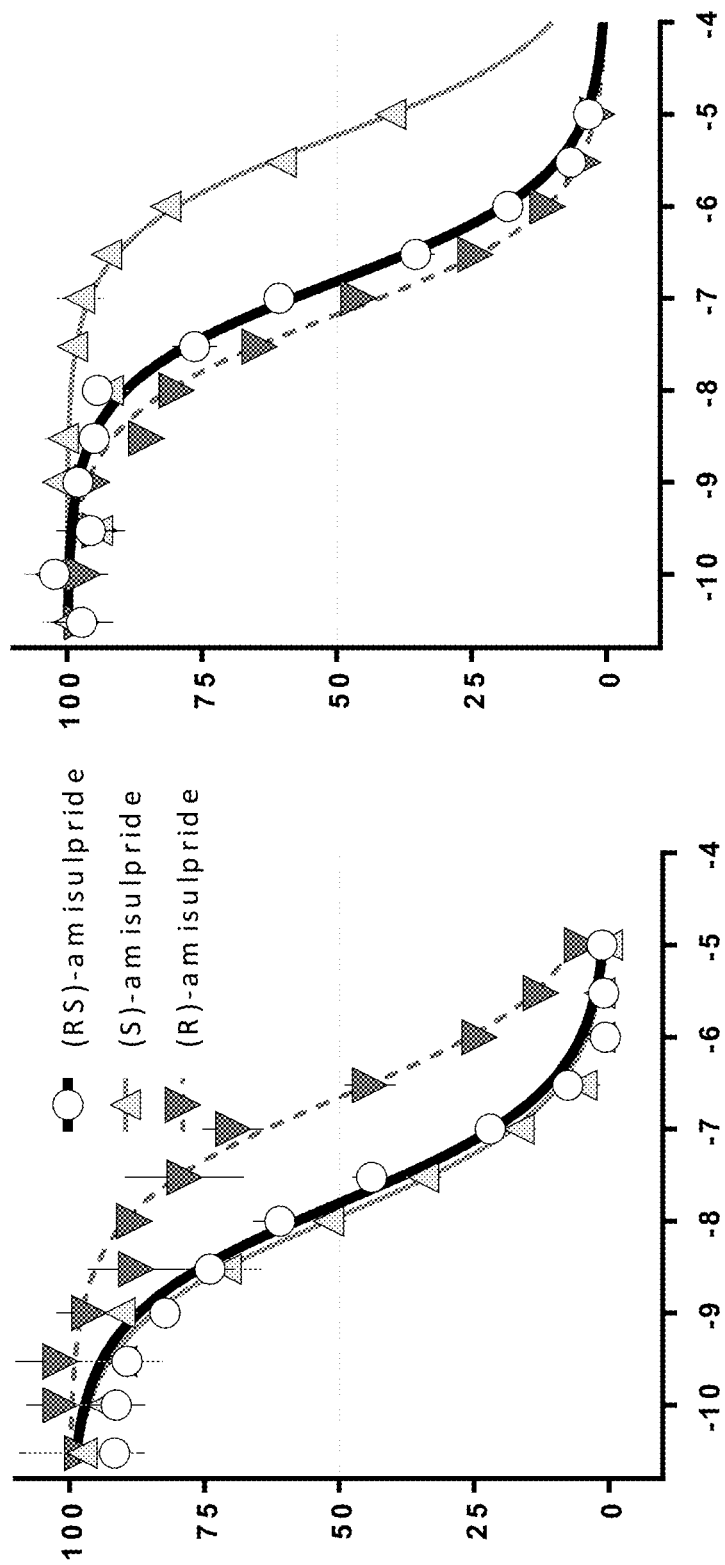
FIGS. 1A-1C present various analytical in vitro data for the inhibition of radioligand binding activity by racemic amisulpride, (R)-amisulpride, and (S)-amisulpride, and various mixtures of (R)-amisulpride and (S)-amisulpride; where

The present inventions relate to pharmaceutical compositions comprising unequal mixtures of amisulpride enantiomers, medicaments for the treatment of a disorder comprising unequal mixtures of amisulpride enantiomers, methods of treating a disorder in a subject with a pharmaceutical compositions comprising unequal mixtures of amisulpride enantiomers, methods of inhibiting dopamine D$_2$ activity and serotonin 5-HT7 activity in a subject with a pharmaceutical compositions comprising unequal mixtures of amisulpride enantiomers.

In various aspects, the disorder which the medicaments and methods of the present inventions treat comprise one or more of a: psychiatric disorder; mood disorder; depressive disorder; as an adjunctive treatment of major depressive disorder; bipolar disorder; bipolar depression; schizophrenia; negative symptoms of schizophrenia; treatment resistant depression (TRD); schizoaffective disorder; anxiety disorder; obsessive-compulsive disorder; behavior disturbances associated with a neurocognitive disorder; conduct disorder; neurological disorder; medication-induced movement disorder; and motor disorder.

Amisulpride has a single asymmetric center and as a result exists in two enantiomeric forms: R-4-Amino-N-[(1-ethyl-2-pyrrolidinyl)methyl]-5-(ethylsulfonyl)-2-methoxybenzamide (also referred to as: (R)-(+)-4-amino-N-[(1-ethylpyrrolidin-2-yl)methyl]-5-(ethylsulfonyl)-2-methoxybenzamide, and under the IUPAC name as 4-amino-5-(ethanesulfonyl)-N-{[(2R)-1-ethylpyrrolidin-2-yl]methyl}-2-methoxybenzamide), abbreviated herein as (R)-(+)-amisulpride or (R)-amisulpride; and S-4-Amino-N-[(1-ethyl-2-pyrrolidinyl)methyl]-5-(ethylsulfonyl)-2-methoxybenzamide (also referred to as: (S)-(−)-4-amino-N-[(1-ethylpyrrolidin-2-yl)methyl]-5-(ethylsulfonyl)-2-methoxybenzamide, and under the IUPAC name as 4-amino-5-(ethanesulfonyl)-N-{[(2S)-1-ethylpyrrolidin-2-yl]methyl}-2-methoxybenzamide), abbreviated herein as (S)-(−)-amisulpride or (S)-amisulpride. These two enantiomeric forms have the following chemical structures:

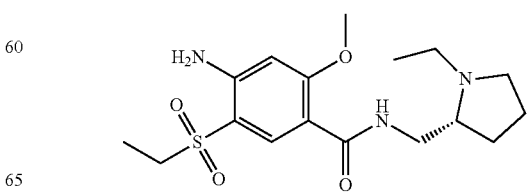

R-4-Amino-N-[(1-ethyl-2-pyrrolidinyl)methyl]-5-(ethyl sulfonyl)-2-methoxybenzamide, (R)-amisulpride

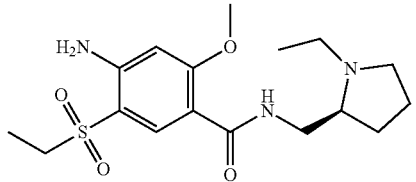 [SMILES: CCN1CCC[C@H]1CNC(=O)c1cc(S(=O)(=O)CC)c(N)cc1OC]

S-4-Amino-N-[(1-ethyl-2-pyrrolidinyl)methyl]-5-(ethylsulfonyl)-2-methoxybenzamide (S)-amisulpride Dopamine D2-related side effects are well-known from clinical experience, it has been observed that the incidence of extrapyramidal side effects increases when occupancy exceeds the 80% threshold and studies have shown that extrapyramidal side effects occur even at about 70-75% occupancy (G. Grunder, et al., Nature, 8, 198-202, (2009); Nyberg, et al., Am. J. Psychiatry, 156, 873-875 (1999); Farde, et al. Arch. Gen. Psychiatry, 49, 538-544 (1992)). However, it is believed that very high D2/3 receptor occupancy is not only associated with but generally required for effectiveness against the positive symptoms of schizophrenia and that the antipsychotic effects of dopamine receptor antagonists occur within a therapeutic window between 60 and 80% striatal D2/3 receptor occupancy. (G. Grunder, et al., Nature, 8, 198-202, (2009)).

Dopamine D2-related side effects are also known from clinical experience with racemic amisulpride and include Extrapyramidal Symptoms (EPS), Tardive Dyskinesia (TD), and Akathisia. (C. Coulouvrat et al., International Clinical Psychopharmacology, Vol 14, No. 4, 209-218 (1999)). It has been determined that in general D2 occupancy greater than about 67% results in side-effects that limit the ability of the underlying 5-HT7 pharmacodynamics to contribute to clinical benefit as a function of dose. (Farde, et al. Arch. Gen. Psychiatry, 49, 538-544 (1992). The impact of $D_2$ occupancy is associated with age with EPS events being noted in older patients with Alzheimer's at occupancies of about 60%; clinically meaningful responses were seen at occupancies of 43%. (Reeves et al., Brain, 140, 1117-1127). Similar results were also obtained with older patients in general. (Uchida et al., The American J. of Geriatic Pyschiatry, 22 (1) 1007-1016).

Selective serotonin 5-HT7 antagonists are known to modulate rapid eye movement (REM) sleep in rodents and humans (Bonaventure et al, 2012). In general, REM suppression is understood to be a translational biomarker of serotonergic antidepressant-like activity appropriate for selecting human doses. The 5-HT7 receptor has been shown, through various pharmacological tools (receptor-specific agonists and antagonists) and through the use of knockout models, to be involved in the central regulation of sleep and circadian rhythms, mood, and cognition. These same three domains are often critically impaired in mood disorders such as major depressive disorder and bipolar disorder, as well as in psychotic disorders.

In the course of several experiments, the present inventors have unexpectedly discovered that a benefit can be obtained from unequal mixtures of the (R)-(+)-amisulpride and (S)-(−)-amisulpride, or pharmaceutically acceptable salts thereof, where the amount of (R)-(+)-amisulpride is greater than the amount of (S)-(−)-amisulpride. It has been discovered that the serotonergic activity of (R)-(+)-amisulpride has an antidepressant effect. It has also been discovered that amisulpride enantiomers have different stereoselectivities between dopamine D2 and serotonin 5-HT7 receptors, such that the relative potencies of mixtures of amisulpride enantiomers can be changed to increase serotonin 5-HT7 potency relative to dopamine D2 receptor potency, and concomitantly provide efficacious compositions, methods of treatment, methods of receptor inhibition, and medicaments whilst decreasing undesirable side effects associated with one or more of the enantiomers.

It has been discovered that certain unequal mixtures of the (R)-(+)-amisulpride and (S)-(−)-amisulpride, or pharmaceutically acceptable salts thereof, where the amount of (R)-(+)-amisulpride is greater than the amount of (S)-(−)-amisulpride can provide an approach to the treatment of mood disorders, psychiatric disorders and/or mixed mood/psychotic disorders by increasing the proportion of 5-HT7 antagonism provided by (R)-amisulpride in relation to D2 blockade provided by (S)-amisulpride in order to more effectively target mood and cognitive symptoms while still maintaining the anxiolytic and antipsychotic benefits of D2 blockade whilst concomitantly reducing dopamine-related extrapyramidal side effects.

The present inventors have demonstrated that the R-enantiomer is highly stereoselective for serotonin 5-HT7 receptors, such that the 5-HT7 antagonism seen with amisulpride can be attributed almost exclusively to the R-enantiomer. In addition, the present inventors have conducted preclinical polysomnography (PSG) studies in rats that demonstrate REM suppression with R-amisulpride, with results consistent with the effects reported for selective 5-HT7 antagonists. Also, the present inventors have shown in healthy human volunteers that R-amisulpride demonstrates clinically meaningful and statistically significant suppression of REM sleep, similar to what has been observed with other 5-HT7 selective antagonists in human studies.

The present inventors have demonstrated that the S-enantiomer is highly stereoselective for dopamine D2 receptors with in vivo non-human primate PET imaging experiments. Also, the present inventors have shown in healthy human volunteers that S-amisulpride demonstrates clinically meaningful dose-dependent D2 receptor occupancy.

In various aspects and embodiments, provided are various compositions, formulations, methods and medicaments comprising and/or employing unequal mixtures of the (R)-(+)-amisulpride and (S)-(−)-amisulpride, or pharmaceutically acceptable salts thereof, where the amount of (R)-(+)-amisulpride is greater than the amount of (S)-(−)-amisulpride, that can provide the discovered antidepressant activity of (R)-(+)-amisulpride while maintaining the mood stabilization activity of (S)-(−)-amisulpride while minimizing the undesirable side effects associated with higher levels of dopamine D2 receptor blockade associated with (S)-(−)-amisulpride.

It has been discovered by the inventors that, in various aspects and embodiments of the present inventions, a fixed-dose combination of amisulpride enantiomers, defined in various embodiments by the contribution of 5-HT7 occupancy relative to D2 occupancy exhibits clinical benefit by allowing physicians to treat subjects with a dominant 5-HT7 pharmacodynamics while still maintaining a dose-responsive underlying dopamine D2 activity for a combined, and in various embodiments improved, clinical benefit in depressive disorders.

The present compositions comprise an unequal mixture of (R)-(+)-amisulpride and (S)-(−)-amisulpride, or pharmaceutically acceptable salts thereof, where the amount of (R)-(+)-amisulpride is greater than the amount of (S)-(−)-amisulpride, and the ratio of (R)-(+)-amisulpride to (S)-(−)-amisulpride, or pharmaceutically acceptable salts thereof, is in a ratio effective to provide in a subject after administration: an occupancy of dopamine D2 receptors between about 20% and about 60%; and a suppression of time in rapid eye movement (REM) sleep is characterized, for example, by one or more of: (a) a decrease in REM sleep by an amount greater than about 10 minutes; (b) a latency to REM sleep by an amount greater than about 20 minutes, or (c) a decrease in total REM sleep time relative to total sleep time by an amount greater than about 5%. In various embodiments, the combined amount of (R)-(+)-amisulpride and (S)-(−)-amisulpride is between about 50 mg and about 1000 mg, in various embodiments between about 200 mg and about 700 mg, and in various embodiments between about 350 mg and about 700 mg. In various embodiments, the combined amount of (R)-(+)-amisulpride and (S)-(−)-amisulpride is between about 100 mg and about 800 mg. In various embodiments, the combined amount of (R)-(+)-amisulpride and (S)-(−)-amisulpride is between about 100 mg and about 600 mg. In various embodiments, the combined amount of (R)-(+)-amisulpride and (S)-(−)-amisulpride is about 100 mg. In various embodiments, the combined amount of (R)-(+)-amisulpride and (S)-(−)-amisulpride is about 200 mg. In various embodiments, the combined amount of (R)-(+)-amisulpride and (S)-(−)-amisulpride is about 300 mg. In various embodiments, the combined amount of (R)-(+)-amisulpride and (S)-(−)-amisulpride is about 400 mg. In various embodiments, the combined amount of (R)-(+)-amisulpride and (S)-(−)-amisulpride is about 500 mg. In various embodiments, the combined amount of (R)-(+)-amisulpride and (S)-(−)-amisulpride is about 600 mg. In various embodiments, the combined amount of (R)-(+)-amisulpride and (S)-(−)-amisulpride is about 700 mg.

The relative amounts of R and S amisulpride in the composition are chosen such that the $D_2$ occupancy is about 20% to about 60%. Occupancies above about 65% are associated with adverse events. Considering adverse events, in some embodiments, the amount of S isomer in the composition should not exceed the amount necessary to achieve about 60% or about 50% $D_2$ occupancy. In some embodiments, the minimum S isomer should be sufficient to achieve about 20% to about 25% $D_2$ occupancy. In some embodiments, the minimum S isomer is sufficient to achieve about 30% $D_2$ occupancy.

The amount R-amisulpride administered should be sufficient to achieve a reduction on the time a patient spends in REM sleep time of at least about 10 minutes to about 45 minutes, about 15 minutes to 30 minutes, or about 18 minutes to about 31 minutes.

In some embodiments, the relative ratios of R:S isomers in an amisulpride composition is about 63:37 to about 95:5 by weight of free base. In some embodiments, the ratio of R:S is about 77:23 to about 93:7 by weight of free base. In some embodiments, the ratio of R:S is about 74:26 to about 92:8 by weight of free base. In some embodiments, the ratio of R:S is about 65:35 to about 88:12 by weight of free base. In some embodiments, the ratio of R:S is about 75:25 to about 88:12 by weight of free base. In some embodiments, the ratio of R:S is about 80:20 to about 88:12 by weight of free base. In some embodiments, the ratio of R:S is about 80:20 to about 90:10 by weight of free base. In various embodiments the ratio of R:S is about 85:15 by weight of free base.

In various aspects, the compositions of the present inventions comprise an unequal mixture of (R)-(+)-amisulpride and (S)-(−)-amisulpride, or pharmaceutically acceptable salts thereof, where the amount of (R)-(+)-amisulpride is greater than the amount of (S)-(−)-amisulpride, and the ratio of (R)-(+)-amisulpride to (S)-(−)-amisulpride, or pharmaceutically acceptable salts thereof, is in a ratio effective to provide in a subject after administration inhibition of dopamine D2 activity and serotonin 5-HT7 activity in said subject such that the ratio of the serotonin 5-HT7 receptor inhibitory constant to the dopamine D2 receptor inhibitory constant is in the range between about 2 to about 6. In various embodiments, the ratio of the serotonin 5-HT7 receptor inhibitory constant to the dopamine D2 receptor inhibitory constant is in the range between about 3 to about 5; and in various embodiments, the ratio of the serotonin 5-HT7 receptor inhibitory constant to the dopamine D2 receptor inhibitory constant is about 4. In various embodiments, the dopamine D2 receptor inhibitory constant is in the range between about 11 nM to about 20 nM and the serotonin 5-HT7 receptor inhibitory constant is in a range between about 40 nM to about 85 nM. In various embodiments, the dopamine D2 receptor inhibitory constant is in the range between about 15 nM to about 20 nM and the serotonin 5-HT7 receptor inhibitory constant is in a range between about 50 nM to about 80 nM. In various embodiments, the dopamine D2 receptor inhibitory constant is about 17 nM and the serotonin 5-HT7 receptor inhibitory constant is about 66 nM. In various embodiments, the combined amount of (R)-(+)-amisulpride and (S)-(−)-amisulpride is between about 50 mg and about 1000 mg, in various embodiments between about 200 mg and about 700 mg, and in various embodiments preferably between about 350 mg and about 700 mg. In various embodiments, the combined amount of (R)-(+)-amisulpride and (S)-(−)-amisulpride is between about 100 mg and about 800 mg. In various embodiments, the combined amount of (R)-(+)-amisulpride and (S)-(−)-amisulpride is between about 100 mg and about 600 mg. In various embodiments, the combined amount of (R)-(+)-amisulpride and (S)-(−)-amisulpride is about 100 mg. In various embodiments, the combined amount of (R)-(+)-amisulpride and (S)-(−)-amisulpride is about 200 mg. In various embodiments, the combined amount of (R)-(+)-amisulpride and (S)-(−)-amisulpride is about 300 mg. In various embodiments, the combined amount of (R)-(+)-amisulpride and (S)-(−)-amisulpride is about 400 mg. In various embodiments, the combined amount of (R)-(+)-amisulpride and (S)-(−)-amisulpride is about 500 mg. In various embodiments, the combined amount of (R)-(+)-amisulpride and (S)-(−)-amisulpride is about 600 mg. In various embodiments, the combined amount of (R)-(+)-amisulpride and (S)-(−)-amisulpride is about 700 mg. In various embodiments, such compositions comprise a ratio of (R)-(+)-amisulpride to (S)-(−)-amisulpride, or pharmaceutically acceptable salts thereof, that is in the range between about 80:20 to about 90:10 by weight of free base; and preferably in various embodiments the ratio is about 85:15 by weight of free base.

In various aspects, the compositions of the present inventions comprise a ratio of (R)-(+)-amisulpride to (S)-(−)-amisulpride, or pharmaceutically acceptable salts thereof, that is in the range between about 80:20 to about 90:10 by weight of free base. In various embodiments, the compositions comprise a ratio of (R)-(+)-amisulpride to (S)-(−)-amisulpride, or pharmaceutically acceptable salts thereof, that is about 85:15 by weight of free base. In various embodiments, the compositions comprise a ratio of (R)-(+)-amisulpride to (S)-(−)-amisulpride, or pharmaceutically acceptable salts thereof, that is in the range between about 63:37 to about 95:5 by weight of free base. In various embodiments, the compositions comprise a ratio of (R)-(+)-amisulpride to (S)-(−)-amisulpride, or pharmaceutically acceptable salts thereof, that is in the range between about 77:23 to about 93:7 by weight of free base. In various embodiments, the compositions comprise a ratio of (R)-(+)-amisulpride to (S)-(−)-amisulpride, or pharmaceutically acceptable salts thereof, that is in the range between about 74:26 to about 92:8 by weight of free base. In various embodiments, the compositions comprise a ratio of (R)-(+)-amisulpride to (S)-(−)-amisulpride, or pharmaceutically acceptable salts thereof, that is in the range between about 65:35 to about 88:12 by weight of free base. In various embodiments, the compositions comprise a ratio of (R)-(+)-amisulpride to (S)-(−)-amisulpride, or pharmaceutically acceptable salts thereof, that is in the range between about 75:25 to about 88:12 by weight of free base. In various embodiments, the compositions comprise a ratio of (R)-(+)-amisulpride to (S)-(−)-amisulpride, or pharmaceutically acceptable salts thereof, that is in the range between about 80:20 to about 88:12 by weight of free base. In various embodiments, the compositions comprise a ratio of (R)-(+)-amisulpride to (S)-(−)-amisulpride, or pharmaceutically acceptable salts thereof, that is in the range between about 80:20 to about 90:10 by weight of free base.

In various embodiments, the combined amount of (R)-(+)-amisulpride and (S)-(−)-amisulpride is between about 50 mg and about 1000 mg, in various embodiments between about 200 mg and about 700 mg, and in various embodiments preferably between about 350 mg and about 700 mg. In various embodiments, the combined amount of (R)-(+)-amisulpride and (S)-(−)-amisulpride is between about 100 mg and about 800 mg. In various embodiments, the combined amount of (R)-(+)-amisulpride and (S)-(−)-amisulpride is between about 100 mg and about 600 mg. In various embodiments, the combined amount of (R)-(+)-amisulpride and (S)-(−)-amisulpride is about 100 mg. In various embodiments, the combined amount of (R)-(+)-amisulpride and (S)-(−)-amisulpride is about 200 mg. In various embodiments, the combined amount of (R)-(+)-amisulpride and (S)-(−)-amisulpride is about 300 mg. In various embodiments, the combined amount of (R)-(+)-amisulpride and (S)-(−)-amisulpride is about 400 mg. In various embodiments, the combined amount of (R)-(+)-amisulpride and (S)-(−)-amisulpride is about 500 mg. In various embodiments, the combined amount of (R)-(+)-amisulpride and (S)-(−)-amisulpride is about 600 mg. In various embodiments, the combined amount of (R)-(+)-amisulpride and (S)-(−)-amisulpride is about 700 mg.

It is to be understood that when an amisulpride enantiomer is said to be present in a certain weight amount, and such enantiomeric amisulpride is provided as a pharmaceutically acceptable salt thereof, that the weight amount refers to the amisulpride enantiomer portion exclusive of the salt portion, that is as the free base. Accordingly, it is to be understood that when a weight ratio of (R)-(+)-amisulpride to (S)-(−)-amisulpride is recited, it is the weight ratios only of the amisulpride portions exclusive of any salt portion especially if only one of the amisulpride enantiomers is present as a pharmaceutically acceptable salt thereof or the amisulpride enantiomers are present as different pharmaceutically acceptable salts.

It is to be understood, that in various aspects, the present inventions provide compositions comprising unequal mixtures of amisulpride enantiomers (or a pharmaceutically acceptable salt of one or more of the enantiomers) and one or more pharmaceutically acceptable excipient, carrier, adjuvant, or vehicle. In various embodiments, a composition of the present inventions is formulated for administration to a subject in need of such composition. In various embodiments, a composition of the inventions is formulated for oral administration to a subject; and that in various embodiments the compositions are provided in a solid oral dosage form.

In various embodiments, wherein the compositions comprising unequal mixtures of amisulpride enantiomers (or a pharmaceutically acceptable salt of one or more of the enantiomers) and one or more pharmaceutically acceptable excipient, carrier, adjuvant, or vehicle, the combined amount of (R)-(+)-amisulpride and (S)-(−)-amisulpride is between about 50 mg and about 1000 mg, in various embodiments between about 200 mg and about 700 mg, and in various embodiments preferably between about 350 mg and about 700 mg. In various embodiments, the combined amount of (R)-(+)-amisulpride and (S)-(−)-amisulpride is between about 100 mg and about 800 mg. In various embodiments, the combined amount of (R)-(+)-amisulpride and (S)-(−)-amisulpride is between about 100 mg and about 600 mg. In various embodiments, the combined amount of (R)-(+)-amisulpride and (S)-(−)-amisulpride is about 100 mg. In various embodiments, the combined amount of (R)-(+)-amisulpride and (S)-(−)-amisulpride is about 200 mg. In various embodiments, the combined amount of (R)-(+)-amisulpride and (S)-(−)-amisulpride is about 300 mg. In various embodiments, the combined amount of (R)-(+)-amisulpride and (S)-(−)-amisulpride is about 400 mg. In various embodiments, the combined amount of (R)-(+)-amisulpride and (S)-(−)-amisulpride is about 500 mg. In various embodiments, the combined amount of (R)-(+)-amisulpride and (S)-(−)-amisulpride is about 600 mg. In various embodiments, the combined amount of (R)-(+)-amisulpride and (S)-(−)-amisulpride is about 700 mg. In various embodiments, such compositions comprise a ratio of (R)-(+)-amisulpride to (S)-(−)-amisulpride, or pharmaceutically acceptable salts thereof, that is in the range between about 80:20 to about 90:10 by weight; and in various embodiments the ratio is about 85:15 by weight.

Dosing of (S)-(−)-amisulpride should be sufficient to achieve a D2 occupancy level of between about 20% and about 60% to achieve the desired therapeutic effect with reduced adverse events. At levels above about 70% to about 75% the adverse events occur at an increasing frequency and severity. Higher dosing levels to achieve a greater D2 occupancy can be used if the patient does not experience an unacceptable level of adverse events. Typical daily doses of (S)-(−)-amisulpride are from about 5 mg to about 150 mg, about 10 mg to about 150 mg, or about 15 mg to about 100 mg. All doses are as the free base.

Typical daily doses of (R)-(+)-amisulpride free base are from about 50 mg to about 1000 mg, preferably from about 100 mg to about 600 mg, still more preferably from 150 mg to about 600 mg, yet another preferred daily dose is from 170 mg to about 340 mg. The doses may be administered in a single daily dose or in divided doses.

If the (R)-(+)-amisulpride and (S)-(−)-amisulpride are combined into a single dosage form, the relative amounts of each should be about 77:23-93:7 by weight of free base as the free base, from about 80:20 to about 90:10, or about 85:15. The ratio of (R)-(+)-amisulpride and (S)-(−)-amisulpride may be determined by the relative amounts of each necessary to achieve the desired therapeutic effect.

In various aspects, the present inventions provide medicaments for and provide methods of treating one or more of a neurological disorder and a psychiatric disorder in a subject, comprising administering a pharmaceutical composition comprising an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride.

To aid in conciseness of explanation, the term "R dominant amisulpride mixture" shall be used to mean: an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride.

In various aspects, the present inventions provide a method of treating a psychiatric disorder in a subject comprising administering a composition comprising a R dominant amisulpride mixture where the mixture is administered in a therapeutically effective amount to provide in a subject after administration: an occupancy of dopamine D2 receptors between about 20% and about 60%; and a suppression of time in rapid eye movement (REM) sleep is characterized, for example, by one or more of: (a) a decrease in REM sleep by an amount greater than about 10 minutes; (b) a latency to REM sleep by an amount greater than about 20 minutes, or (c) a decrease in total REM sleep time relative to total sleep time by an amount greater than about 5%. In various embodiments, such compositions comprise a ratio of (R)-(+)-amisulpride to (S)-(−)-amisulpride, or pharmaceutically acceptable salts thereof, that is in the range between about 80:20 to about 90:10 by weight; and preferably in various embodiments the ratio is about 85:15 by weight. In various embodiments, the combined amount of (R)-(+)-amisulpride and (S)-(−)-amisulpride is between about 50 mg and about 1000 mg, in various embodiments between about 200 mg and about 700 mg, and in various embodiments preferably between about 350 mg and about 700 mg. In various embodiments, the combined amount of (R)-(+)-amisulpride and (S)-(−)-amisulpride is between about 100 mg and about 800 mg. In various embodiments, the combined amount of (R)-(+)-amisulpride and (S)-(−)-amisulpride is between about 100 mg and about 600 mg. In various embodiments, the combined amount of (R)-(+)-amisulpride and (S)-(−)-amisulpride is about 100 mg. In various embodiments, the combined amount of (R)-(+)-amisulpride and (S)-(−)-amisulpride is about 200 mg. In various embodiments, the combined amount of (R)-(+)-amisulpride and (S)-(−)-amisulpride is about 300 mg. In various embodiments, the combined amount of (R)-(+)-amisulpride and (S)-(−)-amisulpride is about 400 mg. In various embodiments, the combined amount of (R)-(+)-amisulpride and (S)-(−)-amisulpride is about 500 mg. In various embodiments, the combined amount of (R)-(+)-amisulpride and (S)-(−)-amisulpride is about 600 mg. In various embodiments, the combined amount of (R)-(+)-amisulpride and (S)-(−)-amisulpride is about 700 mg.

In various aspects, the present inventions provide a method of treating a psychiatric disorder in a subject comprising administering a composition comprising a R dominant amisulpride mixture where the mixture is administered in a therapeutically effective amount to provide in a subject after administration: inhibition of dopamine D2 activity and serotonin 5-HT7 activity in said subject such that the ratio of the serotonin 5-HT7 receptor inhibitory constant to the dopamine D2 receptor inhibitory constant is in the range between about 2 to about 6. In various embodiments, the ratio of the serotonin 5-HT7 receptor inhibitory constant to the dopamine D2 receptor inhibitory constant is in the range between about 3 to about 5; and in various embodiments, the ratio of the serotonin 5-HT7 receptor inhibitory constant to the dopamine D2 receptor inhibitory constant is about 4. In various embodiments, the dopamine D2 receptor inhibitory constant is in the range between about 11 nM to about 20 nM and the serotonin 5-HT7 receptor inhibitory constant is in a range between about 40 nM to about 85 nM. In various embodiments, the dopamine D2 receptor inhibitory constant is in the range between about 15 nM to about 20 nM and the serotonin 5-HT7 receptor inhibitory constant is in a range between about 50 nM to about 80 nM. In various embodiments, the dopamine D2 receptor inhibitory constant is about 17 nM and the serotonin 5-HT7 receptor inhibitory constant is about 66 nM. In various embodiments, such compositions comprise a ratio of (R)-(+)-amisulpride to (S)-(−)-amisulpride, or pharmaceutically acceptable salts thereof, that is in the range between about 80:20 to about 90:10 by weight; and preferably in various embodiments the ratio is about 85:15 by weight. In various embodiments, the combined amount of (R)-(+)-amisulpride and (S)-(−)-amisulpride is between about 50 mg and about 1000 mg, in various embodiments between about 200 mg and about 700 mg, and in various embodiments preferably between about 350 mg and about 700 mg.

In various aspects, the present inventions provide a method of treating a psychiatric disorder in a subject comprising administering a pharmaceutical composition comprising one or more pharmaceutically excipient, carrier, adjuvant, or vehicle, and a combined amount of (R)-(+)-amisulpride and (S)-(−)-amisulpride between about 50 mg and about 1000 mg, in various embodiments between about 200 mg and about 700 mg, and in various embodiments preferably between about 350 mg and about 700 mg. In various embodiments, the combined amount of (R)-(+)-amisulpride and (S)-(−)-amisulpride is between about 100 mg and about 800 mg. In various embodiments, the combined amount of (R)-(+)-amisulpride and (S)-(−)-amisulpride is between about 100 mg and about 600 mg. In various embodiments, the combined amount of (R)-(+)-amisulpride and (S)-(−)-amisulpride is about 100 mg. In various embodiments, the combined amount of (R)-(+)-amisulpride and (S)-(−)-amisulpride is about 200 mg. In various embodiments, the combined amount of (R)-(+)-amisulpride and (S)-(−)-amisulpride is about 300 mg. In various embodiments, the combined amount of (R)-(+)-amisulpride and (S)-(−)-amisulpride is about 400 mg. In various embodiments, the combined amount of (R)-(+)-amisulpride and (S)-(−)-amisulpride is about 500 mg. In various embodiments, the combined amount of (R)-(+)-amisulpride and (S)-(−)-amisulpride is about 600 mg. In various embodiments, the combined amount of (R)-(+)-amisulpride and (S)-(−)-amisulpride is about 700 mg. In various embodiments, such composition comprises a ratio of (R)-(+)-amisulpride to (S)-(−)-amisulpride, or pharmaceutically acceptable salts thereof, that is in the range between about 80:20 to about 90:10 by weight; and preferably in various embodiments the ratio is about 85:15 by weight.

In various aspects, the present inventions provide medicaments for and provide methods of treating a psychiatric disorder in a human subject, comprising administering on a treatment cycle an amount of (R)-(+)-amisulpride, or a pharmaceutically acceptable salt thereof, and an amount of (S)-(−)-amisulpride, or a pharmaceutically acceptable salt thereof, in a combined amount between about 50 mg and about 1000 mg, in various embodiments between about 200 mg and about 700 mg, and in various embodiments preferably between about 350 mg and about 700 mg per treatment cycle to a human subject in need thereof, wherein the amount of (R)-(+)-amisulpride is greater than the amount of (S)-(−)-amisulpride during the treatment cycle. In various embodiments, the combined amount of (R)-(+)-amisulpride and (S)-(−)-amisulpride is between about 100 mg and about 800 mg. In various embodiments, the combined amount of (R)-(+)-amisulpride and (S)-(−)-amisulpride is between about 100 mg and about 600 mg. In various embodiments, the combined amount of (R)-(+)-amisulpride and (S)-(−)-amisulpride is about 100 mg. In various embodiments, the combined amount of (R)-(+)-amisulpride and (S)-(−)-amisulpride is about 200 mg. In various embodiments, the combined amount of (R)-(+)-amisulpride and (S)-(−)-amisulpride is about 300 mg. In various embodiments, the combined amount of (R)-(+)-amisulpride and (S)-(−)-amisulpride is about 400 mg. In various embodiments, the combined amount of (R)-(+)-amisulpride and (S)-(−)-amisulpride is about 500 mg. In various embodiments, the combined amount of (R)-(+)-amisulpride and (S)-(−)-amisulpride is about 600 mg. In various embodiments, the combined amount of (R)-(+)-amisulpride and (S)-(−)-amisulpride is about 700 mg. In various embodiments, the enantiomeric ratio of (R)-(+)-amisulpride to (S)-(−)-amisulpride over a treatment cycle of the combined amount is in the range between about 80:20 to about 90:10 by weight; and preferably in various embodiments the ratio is about 85:15 by weight. In various embodiments, the (R)-amisulpride, or a pharmaceutically acceptable salt thereof, and the (S)-amisulpride, or a pharmaceutically acceptable salt thereof, are given separately during a treatment cycle. In various embodiments, the enantiomeric ratio of (R)-(+)-amisulpride to (S)-(−)-amisulpride over a treatment cycle is about 85:15 by weight, the treatment cycle is daily and the total amount of (R)-(+)-amisulpride and (S)-(−)-amisulpride is about 200 mg over the treatment cycle. In various embodiments, the enantiomeric ratio of (R)-(+)-amisulpride to (S)-(−)-amisulpride over a treatment cycle is about 85:15 by weight, the treatment cycle is daily and the total amount of (R)-(+)-amisulpride and (S)-(−)-amisulpride is about 400 mg over the treatment cycle. In various embodiments, of the aspects and embodiments of treating a psychiatric disorder in a subject, or both a neurological disorder and a psychiatric disorder, the disorder is one or more of a mood disorder, bipolar disorder (BPD), depression, bipolar depression, major depressive disorder (MDD), as an adjunctive treatment of major depressive disorder, major depressive disorder with mixed features (MDD-MF), treatment resistant depression (TRD), schizophrenia, negative symptoms of schizophrenia, and schizoaffective disorder. In various embodiments, the provided are medicaments and methods for treatment of major depressive episodes associated with bipolar I disorder.

In various aspects, the present inventions provide medicaments for and provide methods of inhibiting dopamine D2 activity and serotonin 5-HT7 activity in a subject comprising administering to a subject an effective amount of an unequal mixture of (R)-(+)-amisulpride, or a pharmaceutically acceptable salt thereof, and (S)-(−)-amisulpride, or a pharmaceutically acceptable salt thereof. In various embodiments, the inhibition of dopamine D2 activity and the inhibition serotonin 5-HT7 activity comprises: an occupancy of dopamine D2 receptors between about 20% and about 60%; and a suppression of the time in rapid eye movement (REM) sleep as characterized by one or more of: (a) a decrease in REM sleep by an amount greater than about 10 minutes, (b) a latency to REM sleep by an amount greater than about 20 minutes, or (c) a decrease in total REM sleep time relative to total sleep time by an amount greater than about 5%.

In various embodiments of the methods of inhibiting dopamine D2 activity and serotonin 5-HT7 activity in a subject, the unequal mixture of (R)-(+)-amisulpride, or a pharmaceutically acceptable salt thereof, and (S)-(−)-amisulpride, or a pharmaceutically acceptable salt thereof, comprises an amount of (R)-(+)-amisulpride that is greater than the amount of (S)-(−)-amisulpride, and in various embodiments, the ratio of (R)-amisulpride to (S)-amisulpride, or pharmaceutically acceptable salts thereof, is in the range between about 80:20 to about 90:10 by weight; and preferably in various embodiments the ratio is about 85:15 by weight.

In various embodiments of the methods of inhibiting dopamine D2 activity and serotonin 5-HT7 activity in a subject, the unequal mixture of (R)-(+)-amisulpride, or a pharmaceutically acceptable salt thereof, and (S)-(−)-amisulpride, or a pharmaceutically acceptable salt thereof, the of (R)-amisulpride, or a pharmaceutically acceptable salt thereof, and (S)-amisulpride, or a pharmaceutically acceptable salt thereof, in are present in a combined amount between about 50 mg and about 1000 mg and the amount of (R)-(+)-amisulpride is greater than the amount of (S)-(−)-amisulpride. In various embodiments, the ratio of (R)-amisulpride to (S)-amisulpride, or pharmaceutically acceptable salts thereof, is in the range between about 80:20 to about 90:10 by weight; and preferably in various embodiments the ratio is about 85:15 by weight.

In various embodiments of the methods of inhibiting dopamine D2 activity and serotonin 5-HT7 activity in a subject, the unequal mixture of (R)-(+)-amisulpride, or a pharmaceutically acceptable salt thereof, and (S)-(−)-amisulpride, or a pharmaceutically acceptable salt thereof, the of (R)-amisulpride, or a pharmaceutically acceptable salt thereof, and (S)-amisulpride, or a pharmaceutically acceptable salt thereof, in are present in a combined amount between about 50 mg and about 1000 mg, in various embodiments between about 200 mg and about 700 mg; and in various embodiments the combined amount is preferably between about 350 mg and about 700 mg; and the amount of (R)-(+)-amisulpride is greater than the amount of (S)-(−)-amisulpride. In various embodiments, the ratio of (R)-amisulpride to (S)-amisulpride, or pharmaceutically acceptable salts thereof, is in the range between about 80:20 to about 90:10 by weight; and preferably in various embodiments the ratio is about 85:15 by weight. In various embodiments, the combined amount of (R)-(+)-amisulpride and (S)-(−)-amisulpride is between about 100 mg and about 800 mg. In various embodiments, the combined amount of (R)-(+)-amisulpride and (S)-(−)-amisulpride is between about 100 mg and about 600 mg. In various embodiments, the combined amount of (R)-(+)-amisulpride and (S)-(−)-amisulpride is about 100 mg. In various embodiments, the combined amount of (R)-(+)-amisulpride and (S)-(−)-amisulpride is about 200 mg. In various embodiments, the combined amount of (R)-(+)-amisulpride and (S)-(−)-amisulpride is about 300 mg. In various embodiments, the combined amount of (R)-(+)-amisulpride and (S)-(−)-amisulpride is about 400 mg. In various embodiments, the combined amount of (R)-(+)-amisulpride and (S)-(−)-amisulpride is about 500 mg. In various embodiments, the combined amount of (R)-(+)-amisulpride and (S)-(−)-amisulpride is about 600 mg. In various embodiments, the combined amount of (R)-(+)-amisulpride and (S)-(−)-amisulpride is about 700 mg.

In various embodiments of the methods of inhibiting dopamine D2 activity and serotonin 5-HT7 activity in a subject, the inhibition takes place in a subject suffering from one or more psychiatric disorders, a neurological disorder or a combination thereof. In various embodiments, the disorder is one or more of a mood disorder, bipolar disorder (BPD), depression, bipolar depression, major depressive episodes associated with bipolar I disorder, major depressive disorder (MDD), as an adjunctive treatment of major depressive disorder, major depressive disorder with mixed features (MDD-MF), treatment resistant depression (TRD), schizophrenia, negative symptoms of schizophrenia, and schizoaffective disorder.

In various embodiments of the methods of inhibiting dopamine D2 activity and serotonin 5-HT7 activity in a subject, the inhibition takes place in a subject suffering from one or more psychiatric disorders, the unequal mixture of (R)-(+)-amisulpride, or a salt thereof, and (S)-(−)-amisulpride, or a pharmaceutically acceptable salt thereof is present in a therapeutically effective amount. In various embodiments of the methods of inhibiting dopamine D2 activity and serotonin 5-HT7 activity in a subject, the inhibition takes place in a subject suffering from one or more psychiatric disorders, the unequal mixture of (R)-(+)-amisulpride, or a salt thereof, and (S)-(−)-amisulpride, or a pharmaceutically acceptable salt thereof is administered to said subject in a therapeutically effective amount.

It is to be understood, that in various aspects and embodiments of the various compositions, formulations, methods and medicaments of the present inventions, the compositions comprising unequal mixtures of amisulpride enantiomers (or a pharmaceutically acceptable salt of one or more of the enantiomers) further comprise one or more pharmaceutically acceptable excipient, carrier, adjuvant, or vehicle. In various embodiments, such compositions are formulated for formulated for oral administration to a subject; and that in various embodiments the compositions are provided in an oral dosage form. In various embodiments, the oral dosage form is in the form of a powder, tablet, caplet, capsule, oral solution, or oral suspension. In various embodiments, the oral dosage form is a solid oral dosage form. In various embodiments the solid oral dosage form comprises a tablet, and in various embodiments the solid oral dosage form comprises a capsule.

It is to be understood, that in various embodiments that one or both of the enantiomeric amisulprides used in the various compositions, formulations, methods and medicaments of the present inventions is a crystalline form of the free base of the enantiomeric amisulpride of crystalline Forms A and Form A' as described in FIGS. 7 A-C and 8 A-D. In various embodiments, the (R)-(+)-amisulpride is crystalline (R)-(+)-amisulpride of crystal Form A; the (S)-(−)-amisulpride is crystalline (S)-(−)-amisulpride of crystal Form A', or both. In various embodiments, the (R)-(+)-amisulpride is crystalline (R)-(+)-amisulpride of crystal Form A and has greater than about 95% chemical purity; the (S)-(−)-amisulpride is crystalline (S)-(−)-amisulpride of crystal Form A' and has greater than about 95% chemical purity, or the (R)-(+)-amisulpride is crystalline (R)-(+)-amisulpride of crystal Form A having a greater than about 95% chemical purity and the (S)-(−)-amisulpride is crystalline (S)-(−)-amisulpride of crystal Form A' having greater than about 95% chemical purity.

In various embodiments, crystalline forms of the present inventions have several advantageous physical properties. For example, in contrast to (S)-amisulpride D-tartrate crystalline forms, the (R)-amisulpride Form A and (S)-amisulpride Form A' crystalline forms are substantially non-hygroscopic, exhibiting less than a 0.5% maximum mass change in water sorption isotherms, at 25° C. scanned over 0 to 95% relative humidity, as measured by dynamic vapor sorption (DVS), whereas crystalline (S)-amisulpride D-tartrate was found to be highly hygroscopic, exhibiting a 52±9% (n=4, σ=18.25) maximum mass change in water sorption isotherms, at 25° C. scanned over 0 to 95% relative humidity, as measured by DVS.

The abbreviation "DSC" refers to differential scanning calorimetry; the abbreviation XRPD refers to x-ray powder diffraction, the abbreviation NMR refers to nuclear magnetic resonance, the abbreviation DVS refers to, dynamic vapor sorption, the abbreviation HPLC refers to high performance liquid chromatography, and the abbreviation GC refers to gas chromatography. The abbreviations (R)-(+)-amisulpride and (R)-amisulpride refer to R-4-Amino-N-[(1-ethyl-2-pyrrolidinyl)methyl]-5-(ethylsulfonyl)-2-methoxybenzamide. The abbreviations (S)-(−)-amisulpride and (S)-amisulpride refer to S-4-Amino-N-[(1-ethyl-2-pyrrolidinyl)methyl]-5-(ethylsulfonyl)-2-methoxybenzamide. Other abbreviations not explicitly described herein have their normal meanings in the art.

These and other objects, features, and advantages of the inventions will become apparent from the following detailed description of the various aspects and embodiments of the inventions taken in conjunction with the accompanying tables and drawings.

All published documents cited herein are hereby incorporated herein by reference in their entirety.

To facilitate the understanding of the present inventions, the following definitions are provided. It is to be understood that, in general, terms not otherwise defined are to be given their meaning or meanings as generally accepted in the art. The terminology used herein is for the purpose of describing particular embodiments only and is not intended to limit the scope of the present inventions which will be limited only by the appended claims.

Reference in the specification to "one embodiment," "an embodiment," "one aspect," or "an aspect" means that a particular, feature, structure or characteristic described in connection with the embodiment or aspect is included in at least one embodiment or aspect of the teachings.

As used herein, the recitation of "amisulpride," unless expressly further limited, includes pharmaceutically acceptable salts of amisulpride. As used herein, the term "racemic amisulpride" refers to a 50:50 mixture by weight of (R)-amisulpride and (S)-amisulpride.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences,* 1977, 66, 1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Although pharmaceutically acceptable counter ions will be preferred for preparing pharmaceutical formulations, other anions are quite acceptable as synthetic intermediates. Thus X may be pharmaceutically undesirable anions, such as iodide, oxalate, trifluoromethanesulfonate and the like, when such salts are chemical intermediates.

In various aspects, the present inventions provide a compositions comprising unequal mixtures of amisulpride enantiomers (or a pharmaceutically acceptable salt of one or more of the enantiomers) and one or more pharmaceutically acceptable excipient, carrier, adjuvant, or vehicle. In various embodiments, a composition of the present inventions is formulated for administration to a subject in need of such composition. In various embodiments, a composition of the inventions is formulated for oral administration to a subject.

As used herein, the term "subject," to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

Compositions of the present inventions may be administered orally, parenterally, by inhalation, topically, rectally, nasally, buccally, sublingually, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of the present inventions may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, such as, for example, as a solution in 1,3-butanediol. Among the acceptable vehicles and solvents that may be employed, include but are not limited to, water, Ringer's solution and isotonic sodium chloride solution. In addition, sterile, fixed oils are conventionally employed as a solvent or suspending medium. Pharmaceutically acceptable compositions of this invention may be orally administered in any orally acceptable dosage form including capsules, tablets, aqueous suspensions or solutions.

Unless otherwise specified, the word "includes" (or any variation thereon, e.g., "include", "including", etc.) is intended to be open-ended. For example, "A includes 1, 2 and 3" means that A includes but is not limited to 1, 2 and 3.

As used herein, the terms "treatment," "treat," and "treating" refer to reversing, alleviating, delaying the onset of, or inhibiting the progress of a disease or disorder, or one or more symptoms thereof, as described herein. In various embodiments, treatment may be administered after one or more symptoms have developed. In other embodiments, treatment may be administered in the absence of symptoms. For example, treatment may be administered to a subject prior to the onset of symptoms (e.g., in light of a history of symptoms and/or in light of genetic or other susceptibility factors). Treatment may also be continued after symptoms have resolved, for example to prevent or delay their recurrence.

As used herein, the phrase "on a free base basis" indicates that the amount of amisulpride (R and S-amisulpride) is measured based on the molecular weight of amisulpride free base. Unless specified otherwise, the weight amount described herein for amisulpride (e.g., racemic, R, S, or unequal mixtures of amisulpride) refers to the free base. For example, in a mixture of 85:15 ratio of R:S-amisulpride by weight, the amount of amisulpride is measured based on the molecular weight of R and S-amisulpride free base unless stated otherwise. In some embodiments, when referring to the combined amount of (R)-amisulpride and (S)-amisulpride, e.g., between about 50 mg and about 1000 mg, the amount is based on the weight of the free base unless specified otherwise.

The compounds disclosed herein can include isotopes. Isotopes include those atoms having the same atomic number but different mass numbers. For example, isotopes of hydrogen include tritium and deuterium. In some embodiments, one or more atoms of the compounds can be replaced or substituted with isotopes of the atoms in natural or non-natural abundance. In some embodiments, one or more hydrogen atoms in a compound of the present disclosure can be replaced or substituted by deuterium.

As used herein, and unless otherwise specified, the term "about", when used in connection with a numeric value or range of values may vary by 5%, 4%, 3%, 2%, 1%, 0.9%, 0.8%, 0.7%, 0.6%, 0.5%, 0.4%, 0.3%, 0.2% or 0.1% of the recited value or range of values. In some embodiments, the numeric value or range of values vary by 5%.

The unequal mixtures of amisulpride enantiomers (or a pharmaceutically acceptable salt of one or more of the enantiomers) of the present inventions are, in various embodiments, combined with carrier materials to produce a composition in a single dosage form can be varied depending upon a variety of factors, including the subject treated and the particular mode of administration. It should also be understood that a specific dosage and treatment regimen for any particular subject will depend upon a variety of factors, including the age, body weight, general health, sex, and diet of the subject, the time of administration, rate of excretion, drug combination, and the judgment of the treating physician and the severity of the particular disease or disorder being treated.

In various aspects and embodiments, the present inventions provide pharmaceutical compositions comprising:
a pharmaceutically acceptable excipient; and
a combined amount of (R)-(+)-amisulpride, or a pharmaceutically acceptable salt thereof, and (S)-(−)-amisulpride, or a pharmaceutically acceptable salt thereof, in the enantiomeric ratio of (R)-(+)-amisulpride to (S)-(−)-amisulpride of about 85:15 by weight of free base. In some embodiments, the ratio of R:S is about 63:37 to about 95:5 by weight of free base. In some embodiments, the ratio of R:S is about 77:23 to about 93:7 by weight of free base. In some embodiments, the ratio of R:S is about 74:26 to about 92:8 by weight of free base. In some embodiments, the ratio of R:S is about 65:35 to about 88:12 by weight of free base. In some embodiments, the ratio of R:S is about 75:25 to about 88:12 by weight of free base. In some embodiments, the ratio of R:S is about 80:20 to about 88:12 by weight of free base. In some embodiments, the ratio of R:S is about 80:20 to about 90:10 by weight of free base.

In various aspects and embodiments, the present inventions provide compositions comprising an unequal mixture of (R)-(+)-amisulpride and (S)-(−)-amisulpride, or pharmaceutically acceptable salts thereof, where the amount of (R)-(+)-amisulpride is greater than the amount of (S)-(−)-amisulpride, and the ratio of (R)-(+)-amisulpride to (S)-(−)-amisulpride, or pharmaceutically acceptable salts thereof. In various embodiments, the amount of (S)-amisulpride is selected to achieve a dopamine D2 receptor occupancy level of between about 20% to about 60%, and in various embodiments preferably between about 30% and about. 50%; and the amount of (R)-amisulpride is selected to achieve one or more of: (a) a suppression of rapid eye movement (REM) sleep by greater than about 10 minutes, in various embodiments preferably greater than about 20 minutes or more, and in various embodiments preferably between about 15 minutes and about 45 minutes; (b) suppression of rapid eye movement (REM) sleep by increasing the latency to REM sleep by an amount greater than about 10 minutes, in various embodiments greater than about 20 minutes, and in various embodiments greater than about 30 minutes; and (c) a decrease in total REM sleep time relative to total sleep time by an amount greater than about 5%.

Dopamine $D_2$ receptor occupancy can be measured, for example, by D2 Positron Emission Tomography (PET) in human brain through the average occupancy observed in a group of humans of sufficient number to provide statistical significance of the result. Suppression of REM sleep can be measured, for example, by polysomnography (PSG) in human subjects through the average inhibition observed in a group of humans of sufficient number to provide statistical significance of the result.

In various aspects, the compositions of the present inventions comprise an unequal mixture of (R)-(+)-amisulpride and (S)-(−)-amisulpride, or pharmaceutically acceptable salts thereof, where the amount of (R)-(+)-amisulpride is greater than the amount of (S)-(−)-amisulpride, and the ratio of (R)-(+)-amisulpride to (S)-(−)-amisulpride, or pharmaceutically acceptable salts thereof, is in a ratio effective to provide in a subject after administration: an occupancy of dopamine D2 receptors between about 20% and about 60%; and a suppression of time in rapid eye movement (REM) sleep is characterized, for example, by one or more of: (a) a decrease in REM sleep by an amount greater than about 10 minutes; (b) a latency to REM sleep by an amount greater than about 10 minutes, and (c) a decrease in total REM sleep time relative to total sleep time by an amount greater than about 5%.

In various embodiments, the ratio of (R)-amisulpride to (S)-amisulpride, or pharmaceutically acceptable salts thereof, is in a ratio effective to provide an occupancy of dopamine D2 receptors between about 30% and about 50%.

In various embodiments, the ratio of (R)-amisulpride to (S)-amisulpride, or pharmaceutically acceptable salts thereof, is in a ratio effective to provide one or more of: (i) a decrease in REM sleep by an amount greater than about 10 minutes; (ii) a decrease in REM sleep by an amount greater than about 20 minutes; (iii) a decrease in REM sleep by an amount between about 15 minutes and about 45 minutes; and (iv) a decrease in REM sleep by an amount between about 15 minutes and about 30 minutes.

In various embodiments, the ratio of (R)-amisulpride to (S)-amisulpride, or pharmaceutically acceptable salts thereof, is in a ratio effective to provide one or more of: (i) a latency to REM sleep by an amount greater than about 10 minutes; (ii) a latency to REM sleep by an amount greater than about 20 minutes; and (iii) a latency to REM sleep by an amount greater than about 30 minutes.

In various embodiments, the ratio of (R)-amisulpride to (S)-amisulpride, or pharmaceutically acceptable salts thereof, is in a ratio effective to provide one or more of: (i) a decrease in total REM sleep time relative to total sleep time by an amount greater than about 5%; (ii) a decrease in total REM sleep time relative to total sleep time by an amount greater than about 6.5%; and (iii) a decrease in total REM sleep time relative to total sleep time by an amount greater than about 8%.

In various embodiments of the present inventions comprising an unequal mixture of (R)-(+)-amisulpride and (S)-(−)-amisulpride, or pharmaceutically acceptable salts thereof, where the amount of (R)-(+)-amisulpride is greater than the amount of (S)-(−)-amisulpride, the combined amount of (R)-amisulpride and (S)-amisulpride is between about 50 mg and about 1000 mg, in various embodiments between about 200 mg and about 700 mg, and in various embodiments preferably between about 350 mg and about 700 mg. In various embodiments, the combined amount of (R)-amisulpride and (S)-amisulpride is about: 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, or 1000 mg.

In various embodiments of the present inventions comprising an unequal mixture of (R)-(+)-amisulpride and (S)-(−)-amisulpride, or pharmaceutically acceptable salts thereof, where the amount of (R)-(+)-amisulpride is greater than the amount of (S)-(−)-amisulpride, the ratio of (R)-amisulpride to (S)-amisulpride, or pharmaceutically acceptable salts thereof, is in the range between about 80:20 to about 90:10 by weight. In various embodiments, the ratio of (R)-amisulpride to (S)-amisulpride, or pharmaceutically acceptable salts thereof, by weight is about: 80:20, 81:19, 82:18, 83:17, 84:16, 85:15, 86:14, 87:13, 88:12, 89:11, or 90:10. Preferably in various embodiments the ratio of (R)-amisulpride to (S)-amisulpride, or pharmaceutically acceptable salts thereof, is 85:15 by weight.

In various embodiments of the present inventions comprising an unequal mixture of (R)-(+)-amisulpride and (S)-(−)-amisulpride, or pharmaceutically acceptable salts thereof, where the amount of (R)-(+)-amisulpride is greater than the amount of (S)-(−)-amisulpride, the combined amount of (R)-amisulpride and (S)-amisulpride is between about 50 mg and about 1000 mg, in various embodiments between about 200 mg and about 700 mg, and in various embodiments preferably between about 350 mg and about 700 mg. In various embodiments, the combined amount of (R)-amisulpride and (S)-amisulpride is about: 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, or 1000 mg; and the ratio of (R)-amisulpride to (S)-amisulpride, or pharmaceutically acceptable salts thereof, by weight is about: 80:20, 81:19, 82:18, 83:17, 84:16, 85:15, 86:14, 87:13, 88:12, 89:11, or 90:10; and preferably 85:15 by weight. In various embodiments, the combined amount of (R)-(+)-amisulpride and (S)-(−)-amisulpride is between about 100 mg and about 800 mg. In various embodiments, the combined amount of (R)-(+)-amisulpride and (S)-(−)-amisulpride is between about 100 mg and about 600 mg. In various embodiments, the combined amount of (R)-(+)-amisulpride and (S)-(−)-amisulpride is about 100 mg. In various embodiments, the combined amount of (R)-(+)-amisulpride and (S)-(−)-amisulpride is about 200 mg. In various embodiments, the combined amount of (R)-(+)-amisulpride and (S)-(−)-amisulpride is about 300 mg. In various embodiments, the combined amount of (R)-(+)-amisulpride and (S)-(−)-amisulpride is about 400 mg. In various embodiments, the combined amount of (R)-(+)-amisulpride and (S)-(−)-amisulpride is about 500 mg. In various embodiments, the combined amount of (R)-(+)-amisulpride and (S)-(−)-amisulpride is about 600 mg. In various embodiments, the combined amount of (R)-(+)-amisulpride and (S)-(−)-amisulpride is about 700 mg. In various embodiments, the (R)-(+)-amisulpride is present in an amount between about 170 mg to about 600 mg, and in various embodiments preferably between about 300 mg to about 600 mg, and the (S)-(−)-amisulpride is present in an amount between about 30 mg to about 105 mg, and in various embodiments preferably between about 40 mg to about 105 mg.

In various embodiments, the combined amount of (R)-amisulpride and (S)-amisulpride is about 100 mg and the amount of (R)-amisulpride is about 85 mg and the amount of (S)-amisulpride is about 15 mg; in various embodiments, the combined amount of (R)-amisulpride and (S)-amisulpride is about 200 mg and the amount of (R)-amisulpride is about 170 mg and the amount of (S)-amisulpride is about 30 mg; in various embodiments, the combined amount of (R)-amisulpride and (S)-amisulpride is about 300 mg and the amount of (R)-amisulpride is about 255 mg and the amount of (S)-amisulpride is about 45 mg; in various embodiments, the combined amount of (R)-amisulpride and (S)-amisulpride is about 400 mg and the amount of (R)-amisulpride is about 340 mg and the amount of (S)-amisulpride is about 60 mg; in various embodiments, the combined amount of (R)-amisulpride and (S)-amisulpride is about 500 mg and the amount of (R)-amisulpride is about 425 mg and the amount of (S)-amisulpride is about 75 mg; in various embodiments, the combined amount of (R)-amisulpride and (S)-amisulpride is about 600 mg and the amount of (R)-amisulpride is about 510 mg and the amount of (S)-amisulpride is about 90 mg; in various embodiments, the combined amount of (R)-amisulpride and (S)-amisulpride is about 700 mg and the amount of (R)-amisulpride is about 595 mg and the amount of (S)-amisulpride is about 105 mg.

In various aspects, the compositions of the present inventions comprise an unequal mixture of (R)-(+)-amisulpride, or a pharmaceutically acceptable salt thereof, and (S)-(−)-amisulpride, or a pharmaceutically acceptable salt thereof, in a combined amount between about 50 mg and about 1000 mg, in various embodiments between about 350 mg and about 700 mg; and one or more of where: (a) the enantiomeric ratio of (R)-amisulpride to (S)-amisulpride is about 85:15 by weight; and (b) the combined amount of (R)-amisulpride and (S)-amisulpride is present an amount effective to provide in a subject after administration an occupancy of dopamine D2 receptors between about 20% and about 60%; and a suppression of time in rapid eye movement (REM) sleep is characterized, for example, by one or more of: (i) a decrease in REM sleep by an amount greater than about 10 minutes, (ii) a decrease in REM sleep by an amount greater than about 20 minutes; and (iii) a decrease in REM sleep by an amount between about 15 minutes and about 45 minutes. In various embodiments, the combined amount of (R)-(+)-amisulpride and (S)-(−)-amisulpride is between about 100 mg and about 800 mg. In various embodiments, the combined amount of (R)-(+)-amisulpride and (S)-(−)-amisulpride is between about 100 mg and about 600 mg. In various embodiments, the combined amount of (R)-(+)-amisulpride and (S)-(−)-amisulpride is about 100 mg. In various embodiments, the combined amount of (R)-(+)-amisulpride and (S)-(−)-amisulpride is about 200 mg. In various embodiments, the combined amount of (R)-(+)-amisulpride and (S)-(−)-amisulpride is about 300 mg. In various embodiments, the combined amount of (R)-(+)-amisulpride and (S)-(−)-amisulpride is about 400 mg. In various embodiments, the combined amount of (R)-(+)-amisulpride and (S)-(−)-amisulpride is about 500 mg. In various embodiments, the combined amount of (R)-(+)-amisulpride and (S)-(−)-amisulpride is about 600 mg. In various embodiments, the combined amount of (R)-(+)-amisulpride and (S)-(−)-amisulpride is about 700 mg.

In various embodiments of aspects of the present inventions, where the combined amount of (R)-amisulpride and (S)-amisulpride is between about 50 mg and about 1000 mg, in various embodiments between about 200 mg and about 700 mg, and in various embodiments preferably between about 400 mg and about 700 mg; the combined amount of (R)-amisulpride and (S)-amisulpride is about: 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, or 1000 mg.

In various embodiments of aspects of the present inventions, where the combined amount of (R)-amisulpride and (S)-amisulpride is between about 50 mg and about 1000 mg, in various embodiments between about 200 mg and about 700 mg, and in various embodiments preferably between about 350 mg and about 700 mg, and the combined amount of (R)-amisulpride and (S)-amisulpride is present an amount effective to provide in a subject after administration an occupancy of dopamine D2 receptors between about 20% and about 60%; and a suppression of time in rapid eye movement (REM) sleep is characterized, for example, by one or more of: (a) a decrease in REM sleep by an amount greater than about 10 minutes; the ratio of (R)-amisulpride to (S)-amisulpride, or pharmaceutically acceptable salts thereof, by weight of free base is about: 80:20, 81:19, 82:18, 83:17, 84:16, 85:15, 86:14, 87:13, 88:12, 89:11, or 90:10; and preferably 85:15 by weight of free base. In various embodiments, the ratio of (R)-amisulpride to (S)-amisulpride, or pharmaceutically acceptable salts thereof, by weight of free base is about: 63:37, 65:35, 74:26, 75:35, 77:23, 80:20, 88:12, 95:5, 93:7, or 92:8. In various embodiments, the ratio of (R)-amisulpride to (S)-amisulpride, or pharmaceutically acceptable salts thereof, by weight of free base is about: 63:37-95:5, 65:35-88:12, 74:26-92:8, 75:35-88:12, 77:23-93:7, or 80:20-88:12. In various embodiments, the combined amount of (R)-(+)-amisulpride and (S)-(−)- amisulpride is between about 100 mg and about 800 mg. In various embodiments, the combined amount of (R)-(+)-amisulpride and (S)-(−)-amisulpride is between about 100 mg and about 600 mg. In various embodiments, the combined amount of (R)-(+)-amisulpride and (S)-(−)-amisulpride is about 100 mg. In various embodiments, the combined amount of (R)-(+)-amisulpride and (S)-(−)-amisulpride is about 200 mg. In various embodiments, the combined amount of (R)-(+)-amisulpride and (S)-(−)-amisulpride is about 300 mg. In various embodiments, the combined amount of (R)-(+)-amisulpride and (S)-(−)-amisulpride is about 400 mg. In various embodiments, the combined amount of (R)-(+)-amisulpride and (S)-(−)-amisulpride is about 500 mg. In various embodiments, the combined amount of (R)-(+)-amisulpride and (S)-(−)-amisulpride is about 600 mg. In various embodiments, the combined amount of (R)-(+)-amisulpride and (S)-(−)-amisulpride is about 700 mg.

In various aspects, the compositions of the present inventions comprise an unequal mixture of (R)-(+)-amisulpride and (S)-(−)-amisulpride, or pharmaceutically acceptable salts thereof, where the amount of (R)-(+)-amisulpride is greater than the amount of (S)-(−)-amisulpride, and the ratio of (R)-(+)-amisulpride to (S)-(−)-amisulpride, or pharmaceutically acceptable salts thereof, is in a ratio effective to provide in a subject after administration inhibition of dopamine D2 activity and serotonin 5-HT7 activity in said subject such that the ratio of the serotonin 5-HT7 receptor inhibitory constant to the dopamine D2 receptor inhibitory constant is in the range between about 2 to about 6. In various embodiments, the ratio of the serotonin 5-HT7 receptor inhibitory constant to the dopamine D2 receptor inhibitory constant is in the range between about 3 to about 5. In various embodiments, the ratio of the serotonin 5-HT7 receptor inhibitory constant to the dopamine D2 receptor inhibitory constant is about 4.

In various embodiments of aspects of the present inventions, where the ratio of (R)-amisulpride to (S)-amisulpride, or pharmaceutically acceptable salts thereof, is in a ratio effective to provide in a subject after administration inhibition of dopamine D2 activity and serotonin 5-HT7 activity in said subject such that the ratio of the serotonin 5-HT7 receptor inhibitory constant to the dopamine D2 receptor inhibitory constant is in the range between about 2 to about 6, and in various embodiments between about 3 to about 5; the combined amount of (R)-amisulpride and (S)-amisulpride is between about 50 mg and about 1000 mg, in various embodiments between about 200 mg and about 700 mg, and in various embodiments preferably between about 350 mg and about 700 mg, and in various embodiments, the combined amount of (R)-amisulpride and (S)-amisulpride is about: 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, or 1000 mg. In various embodiments, the combined amount of (R)-(+)-amisulpride and (S)-(−)-amisulpride is between about 100 mg and about 800 mg. In various embodiments, the combined amount of (R)-(+)-amisulpride and (S)-(−)-amisulpride is between about 100 mg and about 600 mg. In various embodiments, the combined amount of (R)-(+)-amisulpride and (S)-(−)-amisulpride is about 100 mg. In various embodiments, the combined amount of (R)-(+)-amisulpride and (S)-(−)-amisulpride is about 200 mg. In various embodiments, the combined amount of (R)-(+)-amisulpride and (S)-(−)-amisulpride is about 300 mg. In various embodiments, the combined amount of (R)-(+)-amisulpride and (S)-(−)-amisulpride is about 400 mg. In various embodiments, the combined amount of (R)-(+)-amisulpride and (S)-(−)-amisulpride is about 500 mg. In various embodiments, the combined amount of (R)-(+)-amisulpride and (S)-(−)-amisulpride is about 600 mg. In various embodiments, the combined amount of (R)-(+)-amisulpride and (S)-(−)-amisulpride is about 700 mg.

In various embodiments of aspects of the present inventions, where the ratio of (R)-amisulpride to (S)-amisulpride, or pharmaceutically acceptable salts thereof, is in a ratio effective to provide in a subject after administration inhibition of dopamine D2 activity and serotonin 5-HT7 activity in said subject such that the ratio of the serotonin 5-HT7 receptor inhibitory constant to the dopamine D2 receptor inhibitory constant is in the range between about 2 to about 6, and in various embodiments between about 3 to about 5; the ratio of (R)-amisulpride to (S)-amisulpride, or pharmaceutically acceptable salts thereof, by weight is about: 80:20, 81:19, 82:18, 83:17, 84:16, 85:15, 86:14, 87:13, 88:12, 89:11, or 90:10; and preferably 85:15 by weight of free base.

In various embodiments of aspects of the present inventions, where the ratio of (R)-amisulpride to (S)-amisulpride, or pharmaceutically acceptable salts thereof, is in a ratio effective to provide in a subject after administration inhibition of dopamine D2 activity and serotonin 5-HT7 activity in said subject such that the ratio of the serotonin 5-HT7 receptor inhibitory constant to the dopamine D2 receptor inhibitory constant is in the range between about 2 to about 6, and in various embodiments between about 3 to about 5; the combined amount of (R)-amisulpride and (S)-amisulpride is between about 50 mg and about 1000 mg, in various embodiments between about 200 mg and about 700 mg, and in various embodiments preferably between about 350 mg and about 700 mg, and in various embodiments, the combined amount of (R)-amisulpride and (S)-amisulpride is about: 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, or 1000 mg; and the ratio of (R)-amisulpride to (S)-amisulpride, or pharmaceutically acceptable salts thereof, by weight is about: 80:20, 81:19, 82:18, 83:17, 84:16, 85:15, 86:14, 87:13, 88:12, 89:11, or 90:10; and preferably 85:15 by weight. In various embodiments, the combined amount of (R)-(+)-amisulpride and (S)-(−)-amisulpride is between about 100 mg and about 800 mg. In various embodiments, the combined amount of (R)-(+)-amisulpride and (S)-(−)-amisulpride is between about 100 mg and about 600 mg. In various embodiments, the combined amount of (R)-(+)-amisulpride and (S)-(−)-amisulpride is about 100 mg. In various embodiments, the combined amount of (R)-(+)-amisulpride and (S)-(−)-amisulpride is about 200 mg. In various embodiments, the combined amount of (R)-(+)-amisulpride and (S)-(−)-amisulpride is about 300 mg. In various embodiments, the combined amount of (R)-(+)-amisulpride and (S)-(−)-amisulpride is about 400 mg. In various embodiments, the combined amount of (R)-(+)-amisulpride and (S)-(−)-amisulpride is about 500 mg. In various embodiments, the combined amount of (R)-(+)-amisulpride and (S)-(−)-amisulpride is about 600 mg. In various embodiments, the combined amount of (R)-(+)-amisulpride and (S)-(−)-amisulpride is about 700 mg. In various embodiments, the (R)-amisulpride is present in an amount between about 300 mg to about 600 mg, and the (S)-amisulpride is present in an amount between about 40 mg to about 105 mg.

It is to be understood, that in various aspects and embodiments, the various embodiments of the medicaments and compositions of the present inventions can be used to treat a psychiatric disorder in a subject, a neurological disorder in a subject, or both a neurological disorder and a psychiatric disorder, the disorder including, but not limited to, one or more of a mood disorder, bipolar disorder (BPD), depression, bipolar depression, major depressive episodes associated with bipolar I disorder, major depressive disorder (MDD), as an adjunctive treatment of major depressive disorder; major depressive disorder with mixed features (MDD-MF), treatment resistant depression (TRD), schizophrenia, negative symptoms of schizophrenia, and schizoaffective disorder.

In various aspects, the present inventions provide a method of treating a psychiatric disorder in a subject comprising administering a composition comprising a R dominant amisulpride mixture where the mixture is administered in a therapeutically effective amount to provide in a subject after administration: an occupancy of dopamine D2 receptors between about 20% and about 60%; and a suppression of time in rapid eye movement (REM) sleep is characterized, for example, by one or more of: (a) a decrease in REM sleep by an amount greater than about 10 minutes, in various embodiments preferably greater than about 20 minutes or more, and in various embodiments preferably between about 15 minutes and about 45 minutes; (b) suppression of rapid eye movement (REM) sleep by increasing the latency to REM sleep by an amount greater than about 10 minutes, in various embodiments greater than about 20 minutes, and in various embodiments greater than about 30 minutes; and (c) a decrease in total REM sleep time relative to total sleep time by an amount greater than about 5%.

In various embodiments, the ratio of (R)-amisulpride to (S)-amisulpride, or pharmaceutically acceptable salts thereof, is in a ratio effective to provide an occupancy of dopamine D2 receptors between about 30% and about 50%.

Dopamine $D_2$ receptor occupancy can be measured, for example, by D2 Positron Emission Tomography (PET) in human brain through the average occupancy observed in a group of humans of sufficient number to provide statistical significance of the result. Suppression of REM sleep can be measured, for example, by polysomnography (PSG) in human subjects through the average inhibition observed in a group of humans of sufficient number to provide statistical significance of the result.

In various aspects, the present inventions provide a method of treating a psychiatric disorder in a subject comprising administering a composition comprising a R dominant amisulpride mixture where the mixture is administered in a therapeutically effective amount to provide in a subject after administration: inhibition of dopamine D2 activity and serotonin 5-HT7 activity in said subject such that the ratio of the serotonin 5-HT7 receptor inhibitory constant to the dopamine D2 receptor inhibitory constant is in the range between about 2 to about 6. In various embodiments, the ratio of the serotonin 5-HT7 receptor inhibitory constant to the dopamine D2 receptor inhibitory constant is in the range between about 3 to about 5, and in various embodiments, the ratio of the serotonin 5-HT7 receptor inhibitory constant to the dopamine D2 receptor inhibitory constant is about 4.

In various embodiments, of aspects and embodiments of the present inventions for treating a psychiatric disorder in subject comprising administering a R dominant amisulpride mixture, the mixture comprises a ratio of (R)-(+)-amisulpride to (S)-(−)-amisulpride, or pharmaceutically acceptable salts thereof, that is in the range between about 80:20 to about 90:10 by weight. In various embodiments, the ratio of (R)-amisulpride to (S)-amisulpride, or pharmaceutically acceptable salts thereof, by weight is about: 80:20, 81:19, 82:18, 83:17, 84:16, 85:15, 86:14, 87:13, 88:12, 89:11, or 90:10. Preferably in various embodiments the ratio of (R)-amisulpride to (S)-amisulpride, or pharmaceutically acceptable salts thereof, is 85:15 by weight.

In various embodiments, of aspects and embodiments of the present inventions for treating a psychiatric disorder in subject comprising administering a R dominant amisulpride mixture, the mixture comprises a total combined amount of (R)-(+)-amisulpride and (S)-(−)-amisulpride is between about 50 mg and about 1000 mg, in various embodiments between about 200 mg and about 700 mg, and in various embodiments preferably between about 350 mg and about 700 mg. In various embodiments, the combined amount of (R)-amisulpride and (S)-amisulpride is about: 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, or 1000 mg. In various embodiments, the combined amount of (R)-(+)-amisulpride and (S)-(−)-amisulpride is between about 100 mg and about 800 mg. In various embodiments, the combined amount of (R)-(+)-amisulpride and (S)-(−)-amisulpride is between about 100 mg and about 600 mg. In various embodiments, the combined amount of (R)-(+)-amisulpride and (S)-(−)-amisulpride is about 100 mg. In various embodiments, the combined amount of (R)-(+)-amisulpride and (S)-(−)-amisulpride is about 200 mg. In various embodiments, the combined amount of (R)-(+)-amisulpride and (S)-(−)-amisulpride is about 300 mg. In various embodiments, the combined amount of (R)-(+)-amisulpride and (S)-(−)-amisulpride is about 400 mg. In various embodiments, the combined amount of (R)-(+)-amisulpride and (S)-(−)-amisulpride is about 500 mg. In various embodiments, the combined amount of (R)-(+)-amisulpride and (S)-(−)-amisulpride is about 600 mg. In various embodiments, the combined amount of (R)-(+)-amisulpride and (S)-(−)-amisulpride is about 700 mg.

In various embodiments, of aspects and embodiments of the present inventions for treating a psychiatric disorder in subject comprising administering a R dominant amisulpride mixture, the mixture comprises a total combined amount of (R)-(+)-amisulpride and (S)-(−)-amisulpride is between about 50 mg and about 1000 mg, in various embodiments between about 200 mg and about 700 mg, and in various embodiments preferably between about 350 mg and about 700 mg. In various aspects, the present inventions provide a method of treating a psychiatric disorder in a subject comprising administering a pharmaceutical composition comprising one or more pharmaceutically excipient, carrier, adjuvant, or vehicle, and a combined amount of (R)-(+)-amisulpride and (S)-(−)-amisulpride between about 50 mg and about 1000 mg, in various embodiments between about 200 mg and about 700 mg, and in various embodiments preferably between about 350 mg and about 700 mg. In various embodiments, such composition comprises a ratio of (R)-(+)-amisulpride to (S)-(−)-amisulpride, or pharmaceutically acceptable salts thereof, that is in the range between about 80:20 to about 90:10 by weight; and preferably in various embodiments the ratio is about 85:15 by weight. In various embodiments, the combined amount of (R)-amisulpride and (S)-amisulpride is about: 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, or 1000 mg; and the ratio of (R)-amisulpride to (S)-amisulpride, or pharmaceutically acceptable salts thereof, by weight is about: 80:20, 81:19, 82:18, 83:17, 84:16, 85:15, 86:14, 87:13, 88:12, 89:11, or 90:10; and preferably 85:15 by weight. In various embodiments, the combined amount of (R)-(+)-amisulpride and (S)-(−)-amisulpride is between about 100 mg and about 800 mg. In various embodiments, the combined amount of (R)-(+)-amisulpride and (S)-(−)-amisulpride is between about 100 mg and about 600 mg. In various embodiments, the combined amount of (R)-(+)-amisulpride and (S)-(−)-amisulpride is about 100 mg. In various embodiments, the combined amount of (R)-(+)-amisulpride and (S)-(−)-amisulpride is about 200 mg. In various embodiments, the combined amount of (R)-(+)-amisulpride and (S)-(−)-amisulpride is about 300 mg. In various embodiments, the combined amount of (R)-(+)-amisulpride and (S)-(−)-amisulpride is about 400 mg. In various embodiments, the combined amount of (R)-(+)-amisulpride and (S)-(−)-amisulpride is about 500 mg. In various embodiments, the combined amount of (R)-(+)-amisulpride and (S)-(−)-amisulpride is about 600 mg. In various embodiments, the combined amount of (R)-(+)-amisulpride and (S)-(−)-amisulpride is about 700 mg. In various embodiments, the (R)-(+)-amisulpride is present in an amount between about 300 mg to about 600 mg, and the (S)-(−)-amisulpride is present in an amount between about 40 mg to about 105 mg.

In various aspects, the present inventions provide medicaments for and provide methods of treating a psychiatric disorder in a human subject, comprising administering on a treatment cycle an amount of (R)-(+)-amisulpride, or a pharmaceutically acceptable salt thereof, and an amount of (S)-(−)-amisulpride, or a pharmaceutically acceptable salt thereof, in a combined amount between about 50 mg and about 1000 mg, in various embodiments between about 200 mg and about 700 mg, and in various embodiments preferably between about 350 mg and about 700 mg per treatment cycle to a human subject in need thereof, wherein the amount of (R)-(+)-amisulpride is greater than the amount of (S)-(−)-amisulpride during the treatment cycle. In various embodiments, the enantiomeric ratio of (R)-(+)-amisulpride to (S)-(−)-amisulpride over a treatment cycle of the combined amount is in the range between about 80:20 to about 90:10 by weight of free base. In various embodiments, the ratio of R:S is in the range between about: 65:35-88:12, 75:25-88:12, or 80:20-88:12 by weight of free base. In various embodiments, the combined amount of (R)-(+)-amisulpride and (S)-(−)-amisulpride is between about 100 mg and about 800 mg. In various embodiments, the combined amount of (R)-(+)-amisulpride and (S)-(−)-amisulpride is between about 100 mg and about 600 mg. In various embodiments, the combined amount of (R)-(+)-amisulpride and (S)-(−)-amisulpride is about 100 mg. In various embodiments, the combined amount of (R)-(+)-amisulpride and (S)-(−)-amisulpride is about 200 mg. In various embodiments, the combined amount of (R)-(+)-amisulpride and (S)-(−)-amisulpride is about 300 mg. In various embodiments, the combined amount of (R)-(+)-amisulpride and (S)-(−)-amisulpride is about 400 mg. In various embodiments, the combined amount of (R)-(+)-amisulpride and (S)-(−)-amisulpride is about 500 mg. In various embodiments, the combined amount of (R)-(+)-amisulpride and (S)-(−)-amisulpride is about 600 mg. In various embodiments, the combined amount of (R)-(+)-amisulpride and (S)-(−)-amisulpride is about 700 mg.

In various embodiments, the combined amount of (R)-amisulpride and (S)-amisulpride per treatment cycle is about: 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, or 1000 mg; and the enantiomeric ratio of (R)-amisulpride to (S)-amisulpride, or pharmaceutically acceptable salts thereof, over a treatment cycle of the combined amount is, by weight, about: 80:20, 81:19, 82:18, 83:17, 84:16, 85:15, 86:14, 87:13, 88:12, 89:11, or 90:10; and preferably 85:15 by weight.

In various aspects, the present inventions provide medicaments for and provide methods of inhibiting dopamine D2 activity and serotonin 5-HT7 activity in a subject comprising administering to a subject an effective amount of an unequal mixture of (R)-(+)-amisulpride, or a pharmaceutically acceptable salt thereof, and (S)-(−)-amisulpride, or a pharmaceutically acceptable salt thereof. In various embodiments, the inhibition of dopamine D2 activity and the inhibition serotonin 5-HT7 activity comprises: an occupancy of dopamine D2 receptors between about 20% to about 60%, and in various embodiments preferably between about 30% and about. 50%; and a suppression of the time in rapid eye movement (REM) sleep as characterized by one or more of: (a) a decrease in REM sleep by an amount greater than about 10 minutes, in various embodiments preferably greater than about 20 minutes or more, and in various embodiments preferably between about 15 minutes and about 45 minutes, (b) a latency to REM sleep by an amount greater than about 10 minutes, in various embodiments greater than about 20 minutes, and in various embodiments greater than about 30 minutes; or (c) a decrease in total REM sleep time relative to total sleep time by an amount greater than about 5%.

In various embodiments of the methods of inhibiting dopamine D2 activity and serotonin 5-HT7 activity in a subject, the unequal mixture of (R)-(+)-amisulpride, or a pharmaceutically acceptable salt thereof, and (S)-(−)-amisulpride, or a pharmaceutically acceptable salt thereof, comprises an amount of (R)-(+)-amisulpride that is greater than the amount of (S)-(−)-amisulpride, and in various embodiments, the ratio of (R)-amisulpride to (S)-amisulpride, or pharmaceutically acceptable salts thereof, by weight is about: 80:20, 81:19, 82:18, 83:17, 84:16, 85:15, 86:14, 87:13, 88:12, 89:11, or 90:10; and preferably 85:15 by weight.

In various embodiments of the methods of inhibiting dopamine D2 activity and serotonin 5-HT7 activity in a subject, the unequal mixture of (R)-(+)-amisulpride, or a pharmaceutically acceptable salt thereof, and (S)-(−)-amisulpride, or a pharmaceutically acceptable salt thereof, the of (R)-amisulpride, or a pharmaceutically acceptable salt thereof, and (S)-amisulpride, or a pharmaceutically acceptable salt thereof, in are present in a combined amount between about 50 mg and about 1000 mg, in various embodiments between about 200 mg and about 700 mg, and in various embodiments preferably between about 350 mg and about 700 mg and the amount of (R)-(+)-amisulpride is greater than the amount of (S)-(−)-amisulpride. In various embodiments, the combined amount of (R)-amisulpride and (S)-amisulpride is about: 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, or 1000 mg. In various embodiments, the combined amount of (R)-(+)-amisulpride and (S)-(−)-amisulpride is between about 100 mg and about 800 mg. In various embodiments, the combined amount of (R)-(+)-amisulpride and (S)-(−)-amisulpride is between about 100 mg and about 600 mg. In various embodiments, the combined amount of (R)-(+)-amisulpride and (S)-(−)-amisulpride is about 100 mg. In various embodiments, the combined amount of (R)-(+)-amisulpride and (S)-(−)-amisulpride is about 200 mg. In various embodiments, the combined amount of (R)-(+)-amisulpride and (S)-(−)-amisulpride is about 300 mg. In various embodiments, the combined amount of (R)-(+)-amisulpride and (S)-(−)-amisulpride is about 400 mg. In various embodiments, the combined amount of (R)-(+)-amisulpride and (S)-(−)-amisulpride is about 500 mg. In various embodiments, the combined amount of (R)-(+)-amisulpride and (S)-(−)-amisulpride is about 600 mg. In various embodiments, the combined amount of (R)-(+)-amisulpride and (S)-(−)-amisulpride is about 700 mg.

In various embodiments of the methods of inhibiting dopamine D2 activity and serotonin 5-HT7 activity in a subject, the unequal mixture of (R)-(+)-amisulpride, or a pharmaceutically acceptable salt thereof, and (S)-(−)-amisulpride, or a pharmaceutically acceptable salt thereof, the of (R)-amisulpride, or a pharmaceutically acceptable salt thereof, and (S)-amisulpride, or a pharmaceutically acceptable salt thereof, in are present in a combined amount between about 50 mg and about 1000 mg, in various embodiments between about 200 mg and about 700 mg, and in various embodiments preferably between about 350 mg and about 700 mg and the amount of (R)-(+)-amisulpride is greater than the amount of (S)-(−)-amisulpride. In various embodiments, the combined amount of (R)-amisulpride and (S)-amisulpride is about: 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, or 1000 mg; and the ratio of (R)-amisulpride to (S)-amisulpride, or pharmaceutically acceptable salts thereof, by weight is about: 80:20, 81:19, 82:18, 83:17, 84:16, 85:15, 86:14, 87:13, 88:12, 89:11, or 90:10; and preferably 85:15 by weight. In various embodiments, the combined amount of (R)-(+)-amisulpride and (S)-(−)-amisulpride is between about 100 mg and about 800 mg. In various embodiments, the combined amount of (R)-(+)-amisulpride and (S)-(−)-amisulpride is between about 100 mg and about 600 mg. In various embodiments, the combined amount of (R)-(+)-amisulpride and (S)-(−)-amisulpride is about 100 mg. In various embodiments, the combined amount of (R)-(+)-amisulpride and (S)-(−)-amisulpride is about 200 mg. In various embodiments, the combined amount of (R)-(+)-amisulpride and (S)-(−)-amisulpride is about 300 mg. In various embodiments, the combined amount of (R)-(+)-amisulpride and (S)-(−)-amisulpride is about 400 mg. In various embodiments, the combined amount of (R)-(+)-amisulpride and (S)-(−)-amisulpride is about 500 mg. In various embodiments, the combined amount of (R)-(+)-amisulpride and (S)-(−)-amisulpride is about 600 mg. In various embodiments, the combined amount of (R)-(+)-amisulpride and (S)-(−)-amisulpride is about 700 mg. In various embodiments, the (R)-(+)-amisulpride is present in an amount between about 300 mg to about 600 mg, and the (S)-(−)-amisulpride is present in an amount between about 40 mg to about 105 mg.

It is to be understood, that in various aspects and embodiments, the various embodiments of the compositions of the present inventions can be used to treat, and used to manufacture a medicament to treat, a psychiatric disorder, a neurological disorder, or both a neurological disorder and a psychiatric disorder, the disorder including, but not limited to, one or more of a mood disorder, bipolar disorder (BPD), depression, bipolar depression, major depressive episodes associated with bipolar I disorder, major depressive disorder (MDD), as an adjunctive treatment of major depressive disorder; major depressive disorder with mixed features (MDD-MF), treatment resistant depression (TRD), schizophrenia, negative symptoms of schizophrenia, and schizoaffective disorder.

In various aspects, the present inventions provide compositions and medicaments comprising a R dominant amisulpride mixture used for the treatment of a psychiatric disorder, a neurological disorder, or both, comprise a R dominant amisulpride mixture where the ratio of the serotonin 5-HT7 receptor inhibitory constant measured in vitro to the dopamine D2 receptor inhibitory constant measured in vitro is in the range between about 2 to about 6. In various embodiments, in vitro the ratio of the serotonin 5-HT7 receptor inhibitory constant to the dopamine D2 receptor inhibitory constant is in the range between about 3 to about 5, and in various embodiments, the in vitro ratio of the serotonin 5-HT7 receptor inhibitory constant to the dopamine D2 receptor inhibitory constant is about 4.

In various embodiments, of aspects and embodiments of the present inventions compositions and medicaments comprising a R dominant amisulpride mixture, used for the treatment of a psychiatric disorder, a neurological disorder, or both, the amisulpride mixture comprises a ratio of (R)-(+)-amisulpride to (S)-(−)-amisulpride, or pharmaceutically acceptable salts thereof, that is in the range between about 80:20 to about 90:10 by weight. In various embodiments, the ratio of (R)-amisulpride to (S)-amisulpride, or pharmaceutically acceptable salts thereof, by weight is about: 80:20, 81:19, 82:18, 83:17, 84:16, 85:15, 86:14, 87:13, 88:12, 89:11, or 90:10. Preferably in various embodiments the ratio of (R)-amisulpride to (S)-amisulpride, or pharmaceutically acceptable salts thereof, is 85:15 by weight.

In various embodiments, of aspects and embodiments of the present inventions compositions and medicaments comprising a R dominant amisulpride mixture one or more pharmaceutically excipient, carrier, adjuvant, or vehicle, used for the treatment of a psychiatric disorder, a neurological disorder, or both, the amisulpride mixture comprises a total combined amount of (R)-(+)-amisulpride and (S)-(−)-amisulpride is between about 50 mg and about 1000 mg, in various embodiments between about 200 mg and about 700 mg, and in various embodiments preferably between about 350 mg and about 700 mg. In various embodiments, the combined amount of (R)-amisulpride and (S)-amisulpride is about: 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, or 1000 mg. In various embodiments, the combined amount of (R)-(+)-amisulpride and (S)-(−)-amisulpride is between about 100 mg and about 800 mg. In various embodiments, the combined amount of (R)-(+)-amisulpride and (S)-(−)-amisulpride is between about 100 mg and about 600 mg. In various embodiments, the combined amount of (R)-(+)-amisulpride and (S)-(−)-amisulpride is about 100 mg. In various embodiments, the combined amount of (R)-(+)-amisulpride and (S)-(−)-amisulpride is about 200 mg. In various embodiments, the combined amount of (R)-(+)-amisulpride and (S)-(−)-amisulpride is about 300 mg. In various embodiments, the combined amount of (R)-(+)-amisulpride and (S)-(−)-amisulpride is about 400 mg. In various embodiments, the combined amount of (R)-(+)-amisulpride and (S)-(−)-amisulpride is about 500 mg. In various embodiments, the combined amount of (R)-(+)-amisulpride and (S)-(−)-amisulpride is about 600 mg. In various embodiments, the combined amount of (R)-(+)-amisulpride and (S)-(−)-amisulpride is about 700 mg.

In various embodiments, of aspects and embodiments of the present inventions compositions and medicaments comprising a R dominant amisulpride mixture, used for the treatment of a psychiatric disorder, a neurological disorder, or both, the amisulpride mixture comprises a total combined amount of (R)-(+)-amisulpride and (S)-(−)-amisulpride is between about 50 mg and about 1000 mg, in various embodiments between about 200 mg and about 700 mg, and in various embodiments preferably between about 350 mg and about 700 mg.

In various aspects, the present inventions provide compositions and medicaments comprising a R dominant amisulpride mixture, used for the treatment of a psychiatric disorder, a neurological disorder, or both, the composition or medicament comprises one or more pharmaceutically excipient, carrier, adjuvant, or vehicle, and a combined amount of (R)-(+)-amisulpride and (S)-(−)-amisulpride is between about 50 mg and about 1000 mg, in various embodiments between about 200 mg and about 700 mg, and in various embodiments preferably between about 350 mg and about 700 mg. In various embodiments, such compositions and medicaments comprise a ratio of (R)-(+)-amisulpride to (S)-(−)-amisulpride, or pharmaceutically acceptable salts thereof, that is in the range between about 80:20 to about 90:10 by weight; and preferably in various embodiments the ratio is about 85:15 by weight. In various embodiments, the combined amount of (R)-amisulpride and (S)-amisulpride is about: 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, or 1000 mg; and the ratio of (R)-amisulpride to (S)-amisulpride, or pharmaceutically acceptable salts thereof, by weight is about: 80:20, 81:19, 82:18, 83:17, 84:16, 85:15, 86:14, 87:13, 88:12, 89:11, or 90:10; and preferably 85:15 by weight. In various embodiments, the combined amount of (R)-(+)-amisulpride and (S)-(−)-amisulpride is between about 100 mg and about 800 mg. In various embodiments, the combined amount of (R)-(+)-amisulpride and (S)-(−)-amisulpride is between about 100 mg and about 600 mg. In various embodiments, the combined amount of (R)-(+)-amisulpride and (S)-(−)-amisulpride is about 100 mg. In various embodiments, the combined amount of (R)-(+)-amisulpride and (S)-(−)-amisulpride is about 200 mg. In various embodiments, the combined amount of (R)-(+)-amisulpride and (S)-(−)-amisulpride is about 300 mg. In various embodiments, the combined amount of (R)-(+)-amisulpride and (S)-(−)-amisulpride is about 400 mg. In various embodiments, the combined amount of (R)-(+)-amisulpride and (S)-(−)-amisulpride is about 500 mg. In various embodiments, the combined amount of (R)-(+)-amisulpride and (S)-(−)-amisulpride is about 600 mg. In various embodiments, the combined amount of (R)-(+)-amisulpride and (S)-(−)-amisulpride is about 700 mg. In various embodiments, the (R)-(+)-amisulpride is present in an amount between about 300 mg to about 600 mg, and the (S)-(−)-amisulpride is present in an amount between about 40 mg to about 105 mg.

In various embodiments of the methods of inhibiting dopamine D2 activity and serotonin 5-HT7 activity in a subject, the inhibition takes place in a subject suffering from one or more psychiatric disorders, the unequal mixture of (R)-(+)-amisulpride, or a salt thereof, and (S)-(−)-amisulpride, or a pharmaceutically acceptable salt thereof is present in a therapeutically effective amount.

The compositions of the present inventions are preferably formulated in dosage unit form for ease of administration and uniformity of dosage. The expression "dosage unit form" as used herein refers to a physically discrete unit of agent appropriate for the subject to be treated. It will be understood, however, that the total daily usage of the compositions of the present inventions will be decided by the attending physician within the scope of sound medical judgment.

In various aspects, the present inventions provide medicaments for and provide methods of treating a psychiatric disorder in a human subject, comprising administering on a treatment cycle an amount of (R)-(+)-amisulpride, or a pharmaceutically acceptable salt thereof, and an amount of (S)-(−)-amisulpride, or a pharmaceutically acceptable salt thereof, in a combined amount between about 50 mg and about 1000 mg, in various embodiments between about 200 mg and about 700 mg, and in various embodiments preferably between about 350 mg and about 700 mg per treatment cycle to a human subject in need thereof, wherein the amount of (R)-(+)-amisulpride is greater than the amount of (S)-(−)-amisulpride during the treatment cycle. In various embodiments, the combined amount of (R)-(+)-amisulpride and (S)-(−)-amisulpride is between about 100 mg and about 800 mg. In various embodiments, the combined amount of (R)-(+)-amisulpride and (S)-(−)-amisulpride is between about 100 mg and about 600 mg. In various embodiments, the combined amount of (R)-(+)-amisulpride and (S)-(−)-amisulpride is about 100 mg. In various embodiments, the combined amount of (R)-(+)-amisulpride and (S)-(−)-amisulpride is about 200 mg. In various embodiments, the combined amount of (R)-(+)-amisulpride and (S)-(−)-amisulpride is about 300 mg. In various embodiments, the combined amount of (R)-(+)-amisulpride and (S)-(−)-amisulpride is about 400 mg. In various embodiments, the combined amount of (R)-(+)-amisulpride and (S)-(−)-amisulpride is about 500 mg. In various embodiments, the combined amount of (R)-(+)-amisulpride and (S)-(−)-amisulpride is about 600 mg. In various embodiments, the combined amount of (R)-(+)-amisulpride and (S)-(−)-amisulpride is about 700 mg. In various embodiments, the enantiomeric ratio of (R)-(+)-amisulpride to (S)-(−)-amisulpride over a treatment cycle of the combined amount is in the range between about 80:20 to about 90:10 by weight of free base; and preferably in various embodiments the ratio is about 85:15 by weight of free base. In various embodiments, the ratio of R:S is in the range between about: 65:35-88:12, 75:25-88:12, or 80:20-88:12 by weight of free base. In various embodiments, the (R)-amisulpride, or a pharmaceutically acceptable salt thereof, and the (S)-amisulpride, or a pharmaceutically acceptable salt thereof, are given separately during a treatment cycle.

It is to be understood that the composition can be administered over a treatment cycle as a single dosage unit form, comprising both (R)-amisulpride and the (S)-amisulpride enantiomers, in separate dosage unit forms comprising only one of the amisulpride enantiomers, or a combination thereof. For example, in various embodiments, the (R)-amisulpride, or a pharmaceutically acceptable salt thereof, and the (S)-amisulpride, or a pharmaceutically acceptable salt thereof, are given separately during a treatment cycle.

In addition, it is to be understood that the administration of an amount of the composition over a treatment cycle may be provided in a multiple dosage regimen. For example, in various embodiments, a multiple dosage regimen comprises dosage with two or more dosage unit forms substantially simultaneously; dosage with two or more dosage unit forms sequentially; dosage with two or more dosage unit forms within a period of time from one another, preferably in various embodiments within 4 to 48 hours from one another; and combinations thereof.

For example, in various embodiments, the treatment cycle is two days, where the total S-enantiomer dosage amount is given once per treatment cycle (to, for example, maintain D2 occupancy at therapeutic levels) and the total R-enantiomer dosage amount is given up to three times per day (e.g. up to six times per treatment cycle at roughly equally spaced intervals), in various preferred embodiments in roughly equal dosage amounts per dose (to, for example, maintain desired plasma levels and have 5-HT7 effects throughout the day).

In various embodiments of the present inventions, the treatment cycle is daily and the administration occurs: (a) once per day; (b) twice per day; (c) thrice per day; or (d) four times per day. In various embodiments of the present inventions, the treatment cycle is every two days.

In various embodiments, the enantiomeric ratio of (R)-(+)-amisulpride to (S)-(−)-amisulpride over a treatment cycle is about 85:15 by weight of free base, the treatment cycle is daily and the total amount of (R)-(+)-amisulpride and (S)-(−)-amisulpride is about 200 mg over the treatment cycle. In various embodiments, the enantiomeric ratio of (R)-(+)-amisulpride to (S)-(−)-amisulpride over a treatment cycle is about 85:15 by weight of free base, the treatment cycle is daily and the total amount of (R)-(+)-amisulpride and (S)-(−)-amisulpride is about 400 mg over the treatment cycle.

The Diagnostic and Statistical Manual of Mental Disorders, Fifth Ed., hereinafter, the "DSM-5"), published by the American Psychiatric Association in 2013, and is incorporated herein by reference, provides a standard diagnostic system upon which persons of skill rely for diagnosis of various diseases and disorders.

In various aspects, the disease or disorder which the medicaments and methods of the present inventions treat comprises one or more of a psychiatric disorder; mood disorder; depressive disorder; bipolar disorder; bipolar depression (e.g. major depressive episodes associated with bipolar I disorder), schizophrenia; schizoaffective disorder; anxiety disorder; obsessive-compulsive disorder; behavior disturbances associated with a neurocognitive disorder; conduct disorder; neurological disorder; medication-induced movement disorder; and motor disorder.

In various embodiments, the neurological or psychiatric disease or disorder is one or more of a mood disorder, bipolar disorder (BPD), depression, bipolar depression, major depressive episodes associated with bipolar I disorder, major depressive disorder (MDD), as an adjunctive treatment of major depressive disorder, major depressive disorder with mixed features (MDD-MF), treatment resistant depression (TRD), schizophrenia, negative symptoms of schizophrenia, treatment resistant depression (TRD) and schizoaffective disorder.

In various embodiments, the neurological or psychiatric disease or disorder is selected from a psychosis, including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (e.g., phencyclidine, ketamine and other dissociative anesthetics, amphetamine and other psychostimulants and cocaine) psychotic disorder, psychosis disorder, psychosis associated with affective disorders, brief reactive psychosis, schizoaffective psychosis, "schizophrenia-spectrum" disorders such as schizoid or schizotypal personality disorders, or illnesses with associated psychosis (such as major depression, manic depressive (bipolar) disorder, Alzheimer's disease and post-traumatic stress syndrome), including both positive, negative, and cognitive symptoms of schizophrenia and other psychoses; anxiety disorders including acute stress disorder, agoraphobia, generalized anxiety disorder, obsessive-compulsive disorder and related disorders including body dysmorphic disorder, hoarding disorder, trichotillomania, and excoriation disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); eating disorders such as obesity, bulimia nervosa, pica and compulsive eating disorders; bipolar disorders, including, bipolar depression, bipolar I disorder, bipolar II disorder, cyclothymic disorder, substance/medication-induced bipolar and related disorders, bipolar and related disorder due to another medical condition, other specified bipolar and related disorder, and unspecified bipolar and related disorders, depressive disorders including, but not limited to, unipolar depression, seasonal depression and post-partum depression, atypical depression, catatonic depression, elderly depression, endogenous depression, melancholic depression, perinatal depression, situational depression, chronic depression, bipolar depression, major depressive disorder (MDD), as an adjunctive treatment MDD, major depressive disorder with anxious distress, MDD with mixed features (MDD-MF), MDD with melancholic features, MDD with atypical features, MDD with mood-congruent psychotic features, MDD with mood-incongruent psychotic features, MDD with catatonia, with peripartum onset, MDD with seasonal pattern, treatment resistant depression (TRD), and persistent depressive disorder (dysthymia), and are associated with depressed mood (sadness), poor concentration, insomnia, fatigue, appetite disturbances, excessive guilt and thoughts of suicide, premenstrual syndrome (PMS) and premenstrual dysphoric disorder (PDD), mood disorders due to a general medical condition, and substance-induced mood disorders; and sleep disorders including insomnia, disturbed sleep, jet lag, hypersomnia, cataplexy, sleep apnea, obstructive sleep apnea, REM sleep behavior disorder, Restless Leg Syndrome, periodic limb movement disorder, circadian rhythm sleep disorders, delayed sleep phase disorder, sleepwalking, night terrors, bed wetting, rapid eye movement sleep behavior disorder, shift work sleep disorder, excessive daytime sleepiness, non-24-hour sleep-wake disorder, sleep paralysis and narcolepsy.

Psychiatric disorders are pathological conditions of the brain characterized by identifiable symptoms that result in abnormalities in cognition, emotion or mood, or the highest integrative aspects of behavior. These disorders may vary in severity of symptoms, duration, and functional impairment. Psychiatric disorders afflict millions of people worldwide resulting in tremendous human suffering and economic burden due to lost productivity. Mood disorders are a type of psychiatric disorder often defined as a group of heterogeneous, typically recurrent illnesses including unipolar (depressive) and bipolar (manic-depressive) disorders characterized by pervasive mood disturbances, psychomotor dysfunction, and vegetative symptoms. Suicide, the most serious complication in patients with mood disorders, is the cause of death in 15 to 25% of untreated patients with mood disorders; unrecognized or inadequately treated depression contributes to 50 to 70% of all completed suicides.

The term "mood disorder" as used herein includes depression, major depression, major depressive disorder, mild depression, severe depression without psychosis, severe depression with psychosis, melancholia (formerly endogenous depression), atypical depression, dysthymic disorder, manic depression, bipolar disorder, bipolar depression (e.g. major depressive episodes associated with bipolar I disorder), bipolar I disorder, bipolar II disorder, bipolar III disorder, cyclothymic disorder, and chronic hypomania.

In various embodiments, the neurological or psychiatric disease or disorder is a bipolar disorder. Bipolar disorders (including both bipolar I and bipolar II) are serious psychiatric disorders that have a prevalence of approximately 2% of the population, and affects both genders alike. It is a relapsing-remitting condition characterized by cycling between elevated (i.e., manic) and depressed moods, which distinguishes it from other disorders such as major depressive disorder and schizophrenia. Bipolar I is defined by the occurrence of a full manic episode, although most individuals experience significant depression. Symptoms of mania include elevated or irritable mood, hyperactivity, grandiosity, decreased need for sleep, racing thoughts and in some cases, psychosis. The depressive episodes are characterized by anhedonia, sad mood, hopelessness, poor self-esteem, diminished concentration and lethargy. Bipolar II is defined as the occurrence of a major depressive episode and hypomanic (less severe mania) episode although patients spend considerable more time in the depressive state. Other related conditions include cyclothymic disorder.

In bipolar I disorder, full-fledged manic and major depressive episodes alternate. Bipolar I disorder commonly begins with depression and is characterized by at least one manic or excited period during its course. The depressive phase can be an immediate prelude or aftermath of mania, or depression and mania can be separated by months or years.

In bipolar II disorder, depressive episodes alternate with hypomanias (relatively mild, nonpsychotic periods of usually <1 week). During the hypomanic period, mood brightens, the need for sleep decreases, and psychomotor activity accelerates beyond the patient's usual level. Often, the switch is induced by circadian factors (e.g., going to bed depressed and waking early in the morning in a hypomanic state). Hypersomnia and overeating are characteristic and may recur seasonally (e.g., in autumn or winter); insomnia and poor appetite occur during the depressive phase. For some persons, hypomanic periods are adaptive because they are associated with high energy, confidence, and supernormal social functioning. Many patients who experience pleasant elevation of mood, usually at the end of a depression, do not report it unless specifically questioned.

Patients with major depressive episodes and a family history of bipolar disorders often exhibit subtle hypomanic tendencies; their temperament is termed hyperthymic (i.e., driven, ambitious, and achievement-oriented).

In cyclothymic disorder, less severe hypomanic and mini-depressive periods follow an irregular course, with each period lasting a few days. Cyclothymic disorder is commonly a precursor of bipolar II disorder. But it can also occur as extreme moodiness without being complicated by major mood disorders. In such cases, brief cycles of retarded depression accompanied by low self-confidence and increased sleep alternate with elation or increased enthusiasm and shortened sleep. In another form, low-grade depressive features predominate; the bipolar tendency is shown primarily by how easily elation or irritability is induced by antidepressants. In chronic hypomania, a form rarely seen clinically, elated periods predominate, with habitual reduction of sleep to <6 hours. Persons with this form are constantly overcheerful, self-assured, overenergetic, full of plans, improvident, overinvolved, and meddlesome; they rush off with restless impulses and accost people.

Accordingly, in various embodiments, the neurological or psychiatric disease or disorder is one or more of bipolar I disorder, bipolar II disorder, cyclothymic disorder, other specified bipolar and related disorder, or unspecified bipolar and related disorder, and bipolar I disorder or bipolar II disorder with the specifiers of anxious distress, with mixed features, with rapid cycling, with melancholic features, with atypical features, with mood-congruent psychotic features, with mood incongruent psychotic features, with catatonia, with peripartum onset, and/or with seasonal pattern. A relatively recent article by Hu et al [*Prim Care Companion CNS Disord.* 2014; 16(2): PCC.13r01599] highlights that bipolar disorder, while commonly encountered in the primary care setting, is often misdiagnosed or undiagnosed. The DSM-5 attempts to capture the large proportion of patients with subsyndromal mixed symptoms with the inclusion of the mixed specifier.

In various embodiments, the neurological or psychiatric disease or disorder is a depressive disorder. Depressive disorders include, but are not limited to, depressive disorders including, but not limited to, unipolar depression, seasonal depression and post-partum depression, atypical depression, catatonic depression, elderly depression, endogenous depression, melancholic depression, perinatal depression, situational depression, chronic depression, bipolar depression (e.g., major depressive episodes associated with bipolar I disorder), major depressive disorder (MDD), major depressive disorder with mixed features (MDD-MF), treatment resistant depression (TRD), and dysthymia, and are associated with depressed mood (sadness), poor concentration, insomnia, fatigue, appetite disturbances, excessive guilt and thoughts of suicide, premenstrual syndrome (PMS) and premenstrual dysphoric disorder (PDD), mood disorders due to a general medical condition, and substance-induced mood disorders.

Depression is an affective disorder, the pathogenesis of which cannot be explained by any single cause or theory. Unfortunately, treatment options for depressed patients who have suboptimal clinical responses to therapy with an antidepressant are limited. Approximately thirty percent (30%)

of patients initiating antidepressant therapy show suboptimal or delayed clinical responses to the first-line antidepressant agents that are commonly used to treat depression.

Typically, if a patient exhibits suboptimal or delayed clinical response after several weeks of therapy with an antidepressant, the clinician's initial approach is to increase the dose of the antidepressant. If the patient's response remains unsatisfactory after increasing the dose, the most common approaches that many clinicians will pursue are: a) switching to another antidepressant; or b) adding a second antidepressant; or c) attempting an augmentation therapy by administering agents such as lithium carbonate, thyroid hormone (triiodothyronine), psychostimulants, modafinil, atypical antipsychotics, buspirone, or pindolol.

In its full syndromal expression, clinical depression manifests as major depressive disorder, with episodic course and varying degrees of residual manifestations between episodes. The mood is typically depressed, irritable, and/or anxious. The patient may appear miserable, with furrowed brows, downturned corners of the mouth, slumped posture, poor eye contact, and monosyllabic (or absent) speech. The morbid mood may be accompanied by preoccupation with guilt, self-denigrating ideas, decreased ability to concentrate, indecisiveness, diminished interest in usual activities, social withdrawal, helplessness, hopelessness, and recurrent thoughts of death and suicide. Sleep disorders are common. In some, the morbid mood is so deep that tears dry up; the patient complains of an inability to experience usual emotions—including grief, joy, and pleasure—and of a feeling that the world has become colorless, lifeless, and dead.

Melancholia (formerly endogenous depression) is characterized by marked psychomotor slowing (of thinking and activity) or agitation (e.g., restlessness, wringing of the hands, pressure of speech), weight loss, irrational guilt, and loss of the capacity to experience pleasure. Mood and activity vary diurnally, with a nadir in the morning. Most melancholic patients complain of difficulty falling asleep, multiple arousals, and insomnia in the middle of the night or early morning. Sexual desire is often diminished or lost. Amenorrhea can occur. Anorexia and weight loss may lead to emaciation and secondary disturbances in electrolyte balance.

In atypical depression, reverse vegetative features dominate the clinical presentation; they include anxious-phobic symptoms, evening worsening, initial insomnia, hypersomnia that often extends into the day, and hyperphagia with weight gain. Unlike patients with melancholia, those with atypical depression show mood brightening to potentially positive events but often crash into a paralyzing depression with the slightest adversity. Atypical depressive and bipolar II disorders overlap considerably.

In dysthymic disorder, depressive symptoms typically begin insidiously in childhood or adolescence and pursue an intermittent or low-grade course over many years or decades; major depressive episodes may complicate it (double depression). In pure dysthymia, depressive manifestations occur at a subthreshold level and overlap considerably with those of a depressive temperament: habitually gloomy, pessimistic, humorless, or incapable of fun; passive and lethargic; introverted; skeptical, hypercritical, or complaining; self-critical, self-reproaching, and self-derogatory; and preoccupied with inadequacy, failure, and negative events.

Thorough evaluation of many persons with depression reveals bipolar traits, and as many as one in five patients with a depressive disorder also develops frank hypomania or mania. Most switches from unipolar to bipolar disorder occur within 5 years of the onset of depressive manifestations. Predictors of a switch include early onset of depression (<25 years old), postpartum depression, frequent episodes of depression, quick brightening of mood with somatic treatments (e.g., antidepressants, phototherapy, sleep deprivation, electroconvulsive therapy), and a family history of mood disorders for three consecutive generations.

Between episodes, patients with bipolar disorder exhibit depressive moodiness and sometimes high-energy activity; disruption in developmental and social functioning in bipolar depression is more common than in unipolar disorder. In bipolar disorder, depression episodes are shorter (3 to 6 months), age of onset is younger, onset of episodes is more abrupt, and cycles (time from onset of one episode to that of the next) are shorter than in unipolar disorder. Cyclicity is particularly accentuated in rapid-cycling forms of bipolar disorder (usually defined as >=4 episodes/year). In addition depressive episodes in bipolar disorder are a difficult component of BPD to treat. For example, psychiatrists indicate that about 25% of patients across all bipolar disorders are refractory during a manic episode, while about 70% are refractory during a depressive episode.

Accordingly, in various embodiments, the neurological or psychiatric disease or disorder is one or more of bipolar depression, major depressive episodes associated with bipolar I disorder, major depressive disorder (MDD), persistent depressive disorder (Dysthymia), premenstrual dysphoric disorder (PMDD), major depressive disorder with mixed features (MDD-MF), depressive disorder due to another medical condition, other specified depressive disorder, unspecified depressive disorder, or treatment resistant depression (TRD), and MDD with the specifiers of anxious distress, with mixed features, with melancholic features, with atypical features, with mood-congruent psychotic features, with mood-incongruent psychotic features, with catatonia, with peripartum onset, and/or with seasonal pattern, and seasonal affective disorder.

It is to be understood that TRD is a term used in clinical psychiatry to describe cases of major depressive disorder (MDD) that do not respond adequately to appropriate courses of adequate dose and duration of at least two antidepressants.

In various embodiments, a depressive disorder is associated with acute suicidality or suicide ideation. The United States Food and Drug Administration has adopted a "black box" label warning indicating that antidepressants may increase the risk of suicidal thinking and behavior in some children, adolescents and young adults (up to age 24) with a depressive disorder such as MDD. In various embodiments, it is believed that the compositions and methods of the present inventions do not increase the risk of suicidal thinking and/or behavior in children, adolescents and/or young adults with a depressive disorder, e.g., with MDD. In various embodiments, the present inventions provide medicaments for and provide methods of treating one or more symptoms of a depressive disorder (e.g., MDD) in children, adolescents and/or young adults without increasing the risk of suicidal thinking and/or behavior.

In various embodiments, the neurological or psychiatric disease or disorder is schizophrenia. Schizophrenia is a disorder of unknown origin, which usually appears for the first time in early adulthood and is marked by characteristics such as psychotic symptoms, phasic progression and development, and/or deterioration in social behavior and professional capability. Characteristic psychotic symptoms are disorders of thought content (e.g., multiple, fragmentary, incoherent, implausible or simply delusional contents, or ideas of persecution) and of mentality (e.g., loss of association, flight of imagination, incoherence up to incomprehensibility), as well as disorders of perceptibility (e.g., hallucinations), emotions (e.g., superficial or inadequate emotions), self-perceptions, intentions, impulses, and/or inter-human relationships, and psychomotoric disorders (e.g., catatonia). Other symptoms are also associated with this disorder. Schizophrenia is classified into subgroups: the paranoid type, characterized by delusions and hallucinations and absence of thought disorder, disorganized behavior, and affective flattening; the disorganized type, also named "hebephrenic schizophrenia," in which thought disorder and flat affect are present together; the catatonic type, in which prominent psychomotor disturbances are evident, and symptoms may include catatonic stupor and waxy flexibility; and the undifferentiated type, in which psychotic symptoms are present but the criteria for paranoid, disorganized, or catatonic types have not been met. The symptoms of schizophrenia normally manifest themselves in three broad categories: positive, negative and cognitive symptoms. Positive symptoms are those which represent an "excess" of normal experiences, such as hallucinations and delusions. Negative symptoms are those where the patient suffers from a lack of normal experiences, such as anhedonia and lack of social interaction. The cognitive symptoms relate to cognitive impairment in schizophrenics, such as lack of sustained attention and deficits in decision making.

Accordingly, in various embodiments, the neurological or psychiatric disease or disorder is one or more of schizotypal (personality) disorder, delusional disorder, brief psychotic disorder, schizophreniform disorder, schizophrenia, schizoaffective disorder, substance/medication-induced psychotic disorder, psychotic disorder due to another medical condition, other specified schizophrenia spectrum and other psychotic disorder, unspecified schizophrenia spectrum, and other psychotic disorder.

It is to be understood that schizoaffective disorder includes a condition that includes aspects of both schizophrenia and a mood disorder, such as, for example, a major depressive disorder, a bipolar disorder, major depressive episodes associated with a bipolar disorder, etc.

In various embodiments, the neurological or psychiatric disease or disorder is anxiety disorder. Anxiety disorders are characterized by fear, worry, and uneasiness, usually generalized and unfocused as an overreaction to a situation. Anxiety disorders differ in the situations or types of objects that induce fear, anxiety, or avoidance behavior, and the associated cognitive ideation. Anxiety differs from fear in that anxiety is an emotional response to a perceived future threat while fear is associated with a perceived or real immediate threat. They also differ in the content of the associated thoughts or beliefs. Examples of anxiety disorders include separation anxiety disorder, selective mutism, specific phobia, social anxiety disorder (social phobia), panic disorder, panic attack specifier, agoraphobia, generalized anxiety disorder, substance/medication-induced anxiety disorder, anxiety disorder due to another medical condition, illness anxiety disorder, social (pragmatic) communication disorder, other specified anxiety disorder, and unspecified anxiety disorder; stressor-related disorders, including reactive attachment disorder, disinhibited social engagement disorder, posttraumatic stress disorder (PTSD), acute stress disorder, and adjustment disorders.

In various embodiments, the neurological or psychiatric disease or disorder is a sleep disorder including those sleep disorders which are produced by psychiatric conditions, including, but not limited to, insomnia, disturbed sleep, jet lag, hypersomnia, cataplexy, sleep related disorder (e.g., sleep apnea, insomnia, narcolepsy, cataplexy), obstructive sleep apnea, REM sleep behavior disorder, Restless Leg Syndrome, periodic limb movement disorder, circadian rhythm sleep disorders, delayed sleep phase disorder, sleepwalking, night terrors, bed wetting, rapid eye movement sleep behavior disorder, shift work sleep disorder, excessive daytime sleepiness, non-24-hour sleep-wake disorder, sleep paralysis and narcolepsy.

In various embodiments, the present inventions provide medicaments for and provide methods of suppressing rapid eye movement (REM) during both sleep and daytime equivalent.

In various embodiments, the present inventions provide medicaments for and provide methods of suppressing or eliminating pathological or excessive REM during the night or daytime equivalent.

In various embodiments, the neurological and/or psychiatric disease or disorders are obsessive-compulsive disorder and related disorders (e.g., body dysmorphic disorder, hoarding disorder, trichotillomania, excoriation disorder).

In various embodiments, the neurological and/or psychiatric diseases or disorders are disruptive, impulse-control, and conduct disorders including oppositional defiant disorder, intermittent explosive disorder, conduct disorder, antisocial personality disorder, pyromania, kleptomania, other specified disruptive, impulse-control, and conduct disorder, unspecified disruptive, impulse-control, and conduct disorder.

In various embodiments, the compositions, formulations, methods and medicaments of the present inventions may be used in combination with other therapies. Suitable therapies include, but are not limited to, psychotherapy, cognitive behavioral therapy, electroconvulsive therapy, transcranial magnetic stimulation, vagus nerve stimulation, and deep-brain stimulation.

In various aspects, the present inventions provide formulations and compositions comprising unequal mixtures of amisulpride enantiomers (or a pharmaceutically acceptable salt of one or more of the enantiomers) and one or more pharmaceutically acceptable excipient, carrier, adjuvant, or vehicle.

It is to be understood, that in various embodiments the pharmaceutical compositions of the present inventions comprise one or more pharmaceutically acceptable excipients, including, but not limited to, one or more binders, bulking agents, buffers, stabilizing agents, surfactants, wetting agents, lubricating agents, diluents, viscosity enhancing or reducing agents, emulsifiers, suspending agents, preservatives, antioxidants, opaquing agents, glidants, processing aids, colorants, sweeteners, taste-masking agents, perfuming agents, flavoring agents, diluents and other known additives to provide an elegant presentation of the drug or aid in the manufacturing of a medicament or pharmaceutical product comprising a composition of the present inventions. Examples of carriers and excipients well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005.

In various embodiments, the compositions are formulated with one or more pharmaceutically acceptable excipients in accordance with known and established practice. Thus, in various embodiments the composition are formulated as, for example, a liquid, powder, granules, elixir, injectable solution, or suspension. Formulations for oral use are preferred and may be provided, for instance, as tablets, caplets, or capsules, wherein the pharmacologically active ingredients are mixed with an inert solid diluent. Tablets may also include granulating and disintegrating agents, and may be coated or uncoated. Formulations for topical use may be provided, for example as topical solutions, lotions, creams, ointments, gels, foams, patches, powders, solids, sponges, tapes, vapors, pastes or tinctures.

In various embodiments, the present inventions comprise compositions comprising unequal mixtures of amisulpride enantiomers (or a pharmaceutically acceptable salt of one or more of the enantiomers) and one or more pharmaceutically acceptable excipient, carrier, adjuvant, or vehicle, where the combined amount of (R)-(+)-amisulpride and (S)-(−)-amisulpride is between about 25 mg and about 1000 mg, in various embodiments between about 50 mg and about 750 mg, in various embodiments between about 50 mg and about 300 mg and in various embodiments preferably between about 100 mg and about 300 mg. In various embodiments, such compositions comprise a ratio of (R)-(+)-amisulpride to (S)-(−)-amisulpride, or pharmaceutically acceptable salts thereof, that is in the range between about 80:20 to about 90:10 by weight of free base; and preferably in various embodiments the ratio is about 85:15 by weight of free base.

In various embodiments, compositions comprising unequal mixtures of amisulpride enantiomers formulated as a solid oral dosage form. It is to be understood that the total amount of a composition of the comprising an unequal mixture of (R)-(+)-amisulpride and (S)-(−)-amisulpride, or pharmaceutically acceptable salts thereof, need not be provided in a single dosage unit forms, e.g. a single tablet, capsule, etc. In various embodiments, it is preferred that the compositions be provided in dosage unit forms such that, for example, the administration of two of the dosage unit forms will result in administration of the desired combined amount of (R)-amisulpride and (S)-amisulpride.

For example, in various embodiments provided are dosage unit forms comprising a total combined amount of (R)-amisulpride and (S)-amisulpride of about 100 mg (a 100 mg tablet/capsule), comprising about 85 mg (R)-amisulpride and about 15 mg (S)-amisulpride. Accordingly, administration of three of these 100 mg tablets/capsules would result in administration of a total combined amount of (R)-amisulpride and (S)-amisulpride of about 300 mg; whilst administration of four of these 100 mg tablets/capsules would result in administration of a total combined amount of (R)-amisulpride and (S)-amisulpride of about 400 mg.

For example, in various embodiments provided are dosage unit forms comprising a total combined amount of (R)-amisulpride and (S)-amisulpride of about 200 mg (a 200 mg tablet/capsule), comprising about 170 mg (R)-amisulpride and about 30 mg (S)-amisulpride. Accordingly, administration of two of these 200 mg tablets/capsules would result in administration of a total combined amount of (R)-amisulpride and (S)-amisulpride of about 400 mg; whilst administration of three of these 200 mg tablets/capsules would result in administration of a total combined amount of (R)-amisulpride and (S)-amisulpride of about 600 mg.

In various embodiments comprising an oral dosage form the dosage form is a liquid suspension or solution. For example, in various embodiments, the oral dosage form comprises an unequal mixture of (R)-(+)-amisulpride and (S)-(−)-amisulpride, or pharmaceutically acceptable salts thereof, dissolved or suspended in a liquid with one or more pharmaceutically acceptable excipients. In various embodiments, a liquid dosage form comprises the total combined active ingredients ((R)-amisulpride and (S)-amisulpride) suspended or dissolved in 20 mL solution with a citrate buffer.

In various embodiments, the present inventions provide liquid oral dosage forms comprising a solution substantially in accord with that set forth in Table 1, where in Table 1 the "API mg per mL (R:S 85:15)" column indicates the total combined amount of (R)-amisulpride and (S)-amisulpride (where the ratio of (R)-amisulpride to (S)-amisulpride is 85:15 by weight) per mL of aqueous solution, the pH column indicates the buffered pH range, and the percentages are weight percent.

TABLE 1

| API per mL (R:S 85:15) | pH | Sweetener(s) | Buffer(s) | Preservative(s) |
|---|---|---|---|---|
| 100 mg | 3 to 5 | 50% glycerin 0.5% sucralose | 10 mM citric acid | 0.2% sodium benzoate |
| 33.3 mg | 3 to 5 | 16.7% glycerin 0.167% sucralose | 10 mM citric acid | 0.2% sodium benzoate |
| 10 mg | 3 to 5 | 5% glycerin 0.05% sucralose | 10 mM citric acid | 0.2% sodium benzoate |

In various embodiments, formulations of the present inventions suitable for oral administration are provided as capsules, cachets or tablets each containing a predetermined amount of the active pharmaceutical ingredients ((R)-amisulpride and (S)-amisulpride and pharmaceutically acceptable salts thereof) as a powder, granules or both, and one more pharmaceutically acceptable excipients.

In various embodiments, solid oral dosage forms of the present inventions are in the form of a tablet comprising a core having: (a) a total combined amount of (R)-amisulpride and (S)-amisulpride representing between about 20% to about 40% of the total weight, where the tablet ratio of (R)-amisulpride to (S)-amisulpride is about 85:15 by weight of free base, (b) between about 30% and about 55% of a filler (e.g., one or more of mannitol, lactose monohydrate), and (c) between about 15% and about 30% of disintegrant (e.g. a pregelatinized starch, croscarmellose sodium). In various embodiments, the core further comprises: (i) between about 1% and about 5% of a binder (e.g. a polyvinyl alcohol, including but not limited to partially hydrolyzed polyvinyl alcohols); and (ii) between about 0.75% and about 3% of a lubricant (e.g. magnesium stearate).

In various embodiments, the present inventions provide solid oral dosage forms comprising a tablet having a core substantially in accord with that set forth in Table 2. In various embodiments, the present inventions provide solid oral dosage forms comprising a tablet having a core substantially in accord with that set forth in Table 2 and a coating substantially in accord with that set forth in Table 3, where in Tables 2 and 3 the abbreviation q.s. means quantum sufficiat (as much as necessary) and where it is to be understood that the purified water was and is to be removed during processing.

TABLE 2

Core Composition

| Core Component | Function | 100 mg Tablet | | 200 mg Tablet | |
| --- | --- | --- | --- | --- | --- |
| | | mg/tab | % w/w | mg/tab | % w/w |
| (R)-amisulpride | Drug substance | 85 | 17.0 | 170 | 34.0 |
| (S)-amisulpride | Drug substance | 15 | 3.0 | 30 | 6.0 |
| D-mannitol | Filler | 267.5 | 53.5 | 167.5 | 33.5 |
| Pregelatinized starch | Filler | 100 | 20.0 | 100 | 20.0 |
| Polyvinyl alcohol | Binder | 10 | 2.0 | 10 | 2.0 |
| Croscarmellose sodium | Disintegrant | 15 | 3.0 | 15 | 3.0 |
| Magnesium stearate | Lubricant | 7.5 | 1.5 | 7.5 | 1.5 |
| Purified water | Granulation solvent | q.s. | — | q.s. | — |
| Subtotal (core) | | 500 | 100 | 500 | 100 |

TABLE 3

Film-Coat Composition

| Film-coat Component | Function | Quantity (mg/tab) |
| --- | --- | --- |
| Hydroxypropyl methylcellulose | Coating agent | 3.78 |
| Macrogol 400 | Coating agent | 0.38 |
| Titanium dioxide | Coating agent | 1.89 |
| Talc | Coating agent | 1.36 |
| Iron (III) oxide yellow | Coloring agent | 0.11 |
| Iron (III) oxide red | Coloring agent | 0.05 |
| Carnauba wax | Polishing agent | 0.01 |
| Purified water | Coating solvent | q.s. |
| Subtotal (film) | | 7.58 |

In various embodiments, a tablet having a core substantially in accord with Table 2 and a coating substantially in accord with Table 3 is provided. In various preferred embodiments, all excipients comply with the respective The United States Pharmacopeia (USP), The Japanese Pharmacopeia (JP), Japanese Pharmaceutical Excipients (JPE), The European Pharmacopoeia (Ph. Eur.), and/or The National Formulary (NF) monograph.

In various embodiments, the active pharmaceutical ingredients ((R)-amisulpride and (S)-amisulpride and pharmaceutically acceptable salts thereof) are provided as a dry powder blended with the pharmaceutically acceptable excipients. In various embodiments, the active pharmaceutical ingredients ((R)-amisulpride and (S)-amisulpride and pharmaceutically acceptable salts thereof) are granules. In various embodiments, one or both of the active pharmaceutical ingredients (R)-amisulpride and (S)-amisulpride are crystalline compounds, respectively, of Form A and Form A'.

In various embodiments of granulated active pharmaceutical ingredients, the granules are disposed in a capsule together with one more pharmaceutically acceptable excipients. In various embodiments, provided are capsules comprising granulated active pharmaceutical ingredients together with pharmaceutically acceptable excipients in amounts and proportions substantially in accord with those of Table 2. In various embodiments of granulated active pharmaceutical ingredients the granules are coated with a coating substantially in accord with the coatings of Table 3.

In various embodiments, the pharmaceutical compositions and oral dosage forms are immediate release pharmaceutical compositions. In various embodiments, the immediate release pharmaceutical compositions are formulated (for example, with respect to active ingredient amounts) to be administered once, twice, three times or four times daily. In various embodiments, the enantiomeric ratio of (R)-(+)-amisulpride to (S)-(−)-amisulpride, or pharmaceutically acceptable salts thereof, of the composition is in the range between about 80:20 to about 90:10 by weight. In various embodiments, the ratio of (R)-amisulpride to (S)-amisulpride, or pharmaceutically acceptable salts thereof, by weight is about: 80:20, 81:19, 82:18, 83:17, 84:16, 85:15, 86:14, 87:13, 88:12, 89:11, or 90:10. Preferably in various embodiments the ratio of (R)-amisulpride to (S)-amisulpride, or pharmaceutically acceptable salts thereof, is 85:15 by weight. In various embodiments, the total combined amount of (R)-amisulpride and (S)-amisulpride in an immediate release pharmaceutical composition is about 50 mg, 75 mg, 100 mg, 150 mg, 200 mg, 300 mg, 400 mg, 500 mg, 600 mg, 700 mg, 750 mg, 800 mg, 900 mg, or 1000 mg. In various embodiments, once administered, or as administered over a treatment cycle, the total combined amount of (R)-(+)-amisulpride and (S)-(−)-amisulpride ranges from about 50-1000 mg. In various embodiments, once administered, or as administered over a treatment cycle, the total combined amount of (R)-(+)-amisulpride and (S)-(−)-amisulpride ranges from about 200-750 mg.

In various embodiments, the enantiomeric ratio of (R)-(+)-amisulpride to (S)-(−)-amisulpride over a treatment cycle is about 85:15 by weight, the treatment cycle is daily and the total amount of (R)-(+)-amisulpride and (S)-(−)-amisulpride is 200 mg over the treatment cycle. In various embodiments, the enantiomeric ratio of (R)-(+)-amisulpride to (S)-(−)-amisulpride over a treatment cycle is about 85:15 by weight, the treatment cycle is daily and the total amount of (R)-(+)-amisulpride and (S)-(−)-amisulpride is 400 mg over the treatment cycle.

In various the total combined amount of (R)-amisulpride and (S)-amisulpride in an immediate release pharmaceutical composition, once administered to a subject, or as administered to a subject over a treatment cycle, is sufficient to provide an occupancy of dopamine D2 receptors between about 20% and about 60%; and a suppression of time in rapid eye movement (REM) sleep characterized, for example, by one or more of: (a) a decrease in REM sleep by an amount greater than about 10 minutes; (b) a latency to REM sleep by an amount greater than about 15 minutes, or (c) a decrease in total REM sleep time relative to total sleep time by an amount greater than about 5%. In various embodiments of an immediate release composition, the total combined amount of (R)-amisulpride and (S)-amisulpride is sufficient to cause a suppression of the time in rapid eye movement (REM) sleep by an amount between about 15 minutes and about 60 minutes.

In various embodiments of an immediate release pharmaceutical composition of the present invention, the immediate release pharmaceutical composition further contains a carrier system that includes one or more excipients, including, but not limited to, a binder, a bulking agent, a buffer, a stabilizing agent, a surfactant, a disintegrant, a wetting agent, a lubricating agent, a diluent, a viscosity enhancing or reducing agent, an emulsifier, a suspending agent, a preservatives, an opaquing agent, a glidant, a processing aid, a colorant, a sweetener, a taste-masking agent, a perfuming agent, or a flavoring agent. The amounts of any such excipient ingredients can be determined by those of ordinary skill in the art to maximize delivery of the (R)-amisulpride, the (S)-amisulpride, or both, to the site of interest.

In various embodiments, the oral dosage forms of the present inventions make use of a distinct polymorph of (R)-(+)-amisulpride, (S)-(−)-amisulpride referred to as Form A for the free base crystalline form of (R)-amisulpride, and Form A' for the free base crystalline form of (S)-amisulpride, and described in further detail herein. In various embodiments the enantiomeric amisulpride is provided in one or more of high polymorph purity, chiral purity, and chemical purity.

In some embodiments, the present disclosure provides a pharmaceutical composition comprising:

an amount between about 85 mg and about 600 mg of (R)-(+)-amisulpride, or a pharmaceutically acceptable salt thereof, by weight of free base; and an amount between about 15 mg and about 100 mg (S)-(−)-amisulpride, or a pharmaceutically acceptable salt thereof, by weight of free base;

in the enantiomeric ratio of (R)-(+)-amisulpride to (S)-(−)-amisulpride between about 65:35 and about 88:12 by weight of free base.

In some embodiments, the ratio of (R)-(+)-amisulpride to (S)-(−)-amisulpride is between about 75:25 to about 88:12 by weight of free base. In some embodiments, the ratio of (R)-(+)-amisulpride to (S)-(−)-amisulpride is between about 80:20 to about 88:12 by weight of free base. In some embodiments, the ratio of (R)-(+)-amisulpride to (S)-(−)-amisulpride is between about 85:15 by weight of free base.

In some embodiments, the pharmaceutical composition comprises:

an amount between about 170 mg and about 340 mg of (R)-(+)-amisulpride, or a pharmaceutically acceptable salt thereof, by weight of free base; and an amount between about 30 mg and about 60 mg (S)-(−)-amisulpride, or a pharmaceutically acceptable salt thereof, by weight of free base.

In some embodiments, the pharmaceutical composition comprises:

an amount about 170 mg of (R)-(+)-amisulpride, or a pharmaceutically acceptable salt thereof, by weight of free base; and an amount about 30 mg of (S)-(−)-amisulpride, or a pharmaceutically acceptable salt thereof, by weight of free base.

In some embodiments, the pharmaceutical composition comprises:

an amount about 340 mg of (R)-(+)-amisulpride, or a pharmaceutically acceptable salt thereof, by weight of free base; and an amount about 60 mg of (S)-(−)-amisulpride, or a pharmaceutically acceptable salt thereof, by weight of free base.

In some embodiments, the combined amount of (R)-(+)-amisulpride, or a pharmaceutically acceptable salt thereof, and (S)-(−)-amisulpride, or a pharmaceutically acceptable salt thereof, is about 100 mg, 200 mg, 300 mg, 400 mg, 500 mg, 600 mg or 700 mg by weight of free base. In some embodiments, the combined amount of (R)-(+)-amisulpride, or a pharmaceutically acceptable salt thereof, and (S)-(−)-amisulpride, or a pharmaceutically acceptable salt thereof, is between about 200 mg and about 600 mg by weight of free base. In some embodiments, the combined amount of (R)-(+)-amisulpride, or a pharmaceutically acceptable salt thereof, and (S)-(−)-amisulpride, or a pharmaceutically acceptable salt thereof, is between about 200 mg and about 400 mg by weight of free base. In some embodiments, the combined amount of (R)-(+)-amisulpride, or a pharmaceutically acceptable salt thereof, and (S)-(−)-amisulpride, or a pharmaceutically acceptable salt thereof, is about 200 mg by weight of free base. In some embodiments, the combined amount of (R)-(+)-amisulpride, or a pharmaceutically acceptable salt thereof, and (S)-(−)-amisulpride, or a pharmaceutically acceptable salt thereof, is about 400 mg by weight of free base.

In some embodiments, the (R)-(+)-amisulpride is crystalline (R)-(+)-amisulpride of crystal Form A; and the (S)-(−)-amisulpride is crystalline (S)-(−)-amisulpride of crystal Form A'.

In some embodiments, the combined amount of (R)-(+)-amisulpride and (S)-(−)-amisulpride, or pharmaceutically acceptable salts thereof, is effective to provide in the subject after administration an occupancy of dopamine D2 receptors between about 20% and about 60%. In some embodiments, the combined amount of (R)-(+)-amisulpride and (S)-(−)-amisulpride, or pharmaceutically acceptable salts thereof, is effective to provide in the subject after administration an occupancy of dopamine D2 receptors between about 30% and about 50%.

In some embodiments, the combined amount of (R)-(+)-amisulpride and (S)-(−)-amisulpride, or pharmaceutically acceptable salts thereof, is effective to provide in the subject after administration a suppression of the time in rapid eye movement (REM) sleep as characterized by a decrease in REM sleep by an amount greater than about 10 minutes. In some embodiments, the combined amount of (R)-(+)-amisulpride and (S)-(−)-amisulpride, or pharmaceutically acceptable salts thereof, is effective to provide in the subject after administration a suppression of the time in rapid eye movement (REM) sleep as characterized by a decrease in REM sleep by an amount between about 15 minutes and about 45 minutes. In some embodiments, the combined amount of (R)-(+)-amisulpride and (S)-(−)-amisulpride, or pharmaceutically acceptable salts thereof, is effective to provide in the subject after administration a suppression of the time in rapid eye movement (REM) sleep as characterized by a decrease in REM sleep by an amount between about 15 minutes and about 30 minutes. In some embodiments, the combined amount of (R)-(+)-amisulpride and (S)-(−)-amisulpride, or pharmaceutically acceptable salts thereof, is effective to provide in the subject after administration a suppression of the time in rapid eye movement (REM) sleep as characterized by a latency to REM sleep by an amount greater than about 20 minutes. In some embodiments, the combined amount of (R)-(+)-amisulpride and (S)-(−)-amisulpride, or pharmaceutically acceptable salts thereof, is effective to provide in the subject after administration a suppression of the time in rapid eye movement (REM) sleep as characterized by a latency to REM sleep by an amount greater than about 30 minutes.

In some embodiments, the combined amount of (R)-(+)-amisulpride and (S)-(−)-amisulpride, or pharmaceutically acceptable salts thereof, effective to provide in the subject after administration a suppression of the time in rapid eye movement (REM) sleep as characterized by a decrease in total REM sleep time relative to total sleep time by an amount greater than about 5%. In some embodiments, the combined amount of (R)-(+)-amisulpride and (S)-(−)-amisulpride, or pharmaceutically acceptable salts thereof, effective to provide in the subject after administration a suppression of the time in rapid eye movement (REM) sleep as characterized by a decrease in total REM sleep time relative to total sleep time by an amount greater than about 6.5%.

In some embodiments, the combined amount of (R)-(+)-amisulpride and (S)-(−)-amisulpride, or pharmaceutically acceptable salts thereof, effective to provide in the subject after administration:
an occupancy of dopamine D2 receptors between about 30% and about 50%; and a suppression of the time in rapid eye movement (REM) sleep by an amount between about 15 minutes and about 45 minutes.

In some embodiments, provided herein is a pharmaceutical composition comprising an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride, and wherein the amount of (R)-(+)-amisulpride and (S)-(−)-amisulpride in the composition is effective to provide in a subject after administration:
an occupancy of dopamine D2 receptors between about 20% and about 60%; and
a suppression of time in rapid eye movement (REM) sleep as characterized by one or more of:
a decrease in REM sleep by an amount greater than about 10 minutes,
a latency to REM sleep by an amount greater than about 20 minutes, or
a decrease in total REM sleep time relative to total sleep time by an amount greater than about 5%.

In some embodiments, the occupancy of dopamine D2 receptors is between about 30% and about 50%. In some embodiments, the decrease in REM sleep is between about 15 minutes and about 45 minutes. In some embodiments, the latency to REM sleep is by an amount greater than about 30 minutes. In some embodiments, the decrease in total REM sleep time relative to total sleep time is by an amount greater than about 6.5%. In some embodiments, the ratio of (R)-(+)-amisulpride to (S)-(−)-amisulpride is between about 85:15 by weight of free base. In some embodiments, the combined amount of (R)-(+)-amisulpride, or a pharmaceutically acceptable salt thereof, and (S)-(−)-amisulpride, or a pharmaceutically acceptable salt thereof, is between about 100 mg and about 700 mg by weight of free base.

In some embodiments, provided herein is a pharmaceutical composition comprising an unequal mixture of (R)-(+)-amisulpride and (S)-(−)-amisulpride, or pharmaceutically acceptable salts thereof, wherein the amount of (R)-(+)-amisulpride is greater than the amount of(S)-(−)-amisulpride, in amounts effective to provide in a subject after administration:
inhibition of dopamine D2 activity and serotonin 5-HT7 activity in said subject such that the ratio of the serotonin 5-HT7 receptor inhibitory constant to the dopamine D2 receptor inhibitory constant is in the range between about 2 to about 6.

In some embodiments, the ratio of the serotonin 5-HT7 receptor inhibitory constant to the dopamine D2 receptor inhibitory constant is in the range between about 3 to about 5. In some embodiments, the ratio of the serotonin 5-HT7 receptor inhibitory constant to the dopamine D2 receptor inhibitory constant is about 4. In some embodiments, the dopamine D2 receptor inhibitory constant is in the range between about 11 nM to about 20 nM and the serotonin 5-HT7 receptor inhibitory constant is in the range between about 40 nM to about 85 nM. In some embodiments, the dopamine D2 receptor inhibitory constant is about 17 nM and the serotonin 5-HT7 receptor inhibitory constant is about 66 nM.

In some embodiments, the composition is provided in a solid oral dosage form comprising one or more pharmaceutically acceptable excipients. In some embodiments, the total combined amount of (R)-amisulpride and (S)-amisulpride comprises between about 20% to about 40% of the total weight of the pharmaceutical composition; and the one or more pharmaceutically acceptable excipients comprise:
a filler comprising between about 30% and about 55% of the total weight of the pharmaceutical composition; and
a disintegrant comprising between about 15% and about 30% of the total weight of the pharmaceutical composition.

In some embodiments provided herein is a liquid pharmaceutical composition comprising:
one or more pharmaceutically acceptable excipients; and
an aqueous solution comprising an unequal mixture of (R)-(+)-amisulpride, or a pharmaceutically acceptable salt thereof, and (S)-(−)-amisulpride, or a pharmaceutically acceptable salt thereof, with a combined amount between about 5 mg/mL and about 200 mg/mL, wherein the ratio of (R)-(+)-amisulpride to (S)-(−)-amisulpride is in the range between about 65:35 to about 88:12 by weight of free base.

In some embodiments, this disclosure provides a method of treating a psychiatric disorder in a subject comprising administering a pharmaceutical composition provided herein. In some embodiments, the psychiatric disorder is a depressive disorder. In some embodiments, the psychiatric disorder is major depressive disorder (MDD). In some embodiments, the psychiatric disorder is major depressive disorder with mixed features (MDD-MF). In some embodiments, the psychiatric disorder is treatment resistant depression (TRD). In some embodiments, the psychiatric disorder is one or more of schizophrenia and negative symptoms of schizophrenia. In some embodiments, the psychiatric disorder is schizoaffective disorder. In some embodiments, the psychiatric disorder is bipolar disorder. In some embodiments, the psychiatric disorder is bipolar depression. In some embodiments, the method of treatment treats two or more of schizophrenia, negative symptoms of schizophrenia, treatment resistant depression, bipolar disorder and depression.

In some embodiments, the composition provided herein is administered once daily.

In some embodiments, provided herein is a method of inhibiting dopamine D2 activity and serotonin 5-HT7 activity in a subject, comprising administering to a subject an effective amount of an unequal mixture of (R)-(+)-amisulpride, or a pharmaceutically acceptable salt thereof, and (S)-(−)-amisulpride, or a pharmaceutically acceptable salt thereof.

In various embodiments, provided herein is a method of treating bipolar disorder comprising administering to a subject in need thereof an effective amount of a composition comprising: an amount between about 85 mg and about 600 mg of (R)-(+)-amisulpride, or a pharmaceutically acceptable salt thereof, by weight of free base; and an amount between about 15 mg and about 100 mg (S)-(−)-amisulpride, or a pharmaceutically acceptable salt thereof, by weight of free base; wherein the enantiomeric ratio of (R)-(+)-amisulpride to (S)-(−)-amisulpride in the composition is more than 50:50 by weight of free base.

In some embodiments, provided herein is a method of treating bipolar disorder comprising administering to a subject in need thereof an effective amount of a composition comprising:
an amount between about 85 mg and about 600 mg of (R)-(+)-amisulpride, or a pharmaceutically acceptable salt thereof, by weight of free base; and an amount between about 15 mg and about 100 mg (S)-(−)-amisulpride, or a pharmaceutically acceptable salt thereof, by weight of free base;

wherein the enantiomeric ratio of (R)-(+)-amisulpride to (S)-(−)-amisulpride in the composition is between about 65:35 and about 88:12 by weight of free base.

In some embodiments, the bipolar disorder is bipolar depression.

In some embodiments, provided herein is a method of treating bipolar depression comprising administering once daily to a subject in need thereof an effective amount of a composition comprising:

an amount about 170 mg of (R)-(+)-amisulpride, or a pharmaceutically acceptable salt thereof, by weight of free base; and an amount about 30 mg of (S)-(−)-amisulpride, or a pharmaceutically acceptable salt thereof, by weight of free base.

In some embodiments, provided herein is a method of treating bipolar depression comprising administering once daily to a subject in need thereof an effective amount of a composition comprising:

an amount about 340 mg of (R)-(+)-amisulpride, or a pharmaceutically acceptable salt thereof, by weight of free base; and an amount about 60 mg of (S)-(−)-amisulpride, or a pharmaceutically acceptable salt thereof, by weight of free base.

The present disclosure also provides the following embodiments:

Embodiment 1

A pharmaceutical composition comprising an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride, wherein said unequal mixture is effective to provide in a subject after administration:
- an occupancy of dopamine D2 receptors between about 20% and about 60%; and
- a suppression of time in rapid eye movement (REM) sleep as characterized by one or more of:
- a decrease in REM sleep by an amount greater than about 10 minutes,
- a latency to REM sleep by an amount greater than about 20 minutes, or
- a decrease in total REM sleep time relative to total sleep time by an amount greater than about 5%.

Embodiment 2

The pharmaceutical composition of embodiment 1, wherein the occupancy of dopamine D2 receptors is between about 30% and about 50%.

Embodiment 3

The pharmaceutical composition of embodiment 1, wherein the decrease in REM sleep is between about 15 minutes and about 45 minutes.

Embodiment 4

The pharmaceutical composition of embodiment 1, wherein the latency to REM sleep is by an amount greater than about 30 minutes.

Embodiment 5

The pharmaceutical composition of embodiment 1, wherein the decrease in total REM sleep time relative to total sleep time is by an amount greater than about 6.5%.

Embodiment 6

The pharmaceutical composition of embodiment 1, wherein the ratio of (R)-(+)-amisulpride to (S)-(−)-amisulpride is in the range between about 80:20 to about 90:10 by weight.

Embodiment 7

The pharmaceutical composition of embodiment 6, wherein the ratio of (R)-(+)-amisulpride to (S)-(−)-amisulpride is 85:15 by weight.

Embodiment 8

The pharmaceutical composition of embodiment 1, wherein the (R)-(+)-amisulpride is crystalline (R)-(+)-amisulpride of crystal Form A; and the (S)-(−)-amisulpride is crystalline (S)-(−)-amisulpride of crystal Form A'.

Embodiment 9

The pharmaceutical composition of embodiment 1, wherein the combined amount of (R)-(+)-amisulpride and (S)-(−)-amisulpride is between about 50 mg and about 1000 mg.

Embodiment 10

The pharmaceutical composition of embodiment 1, wherein the combined amount of (R)-(+)-amisulpride and (S)-(−)-amisulpride is between about 200 mg and about 700 mg.

Embodiment 11

The pharmaceutical composition of embodiment 1, wherein the combined amount of (R)-(+)-amisulpride and (S)-(−)-amisulpride is about 400 mg.

Embodiment 12

The pharmaceutical composition of embodiment 1, wherein the combined amount of (R)-(+)-amisulpride and (S)-(−)-amisulpride is about 500 mg.

Embodiment 13

The pharmaceutical composition of embodiment 1, wherein the combined amount of (R)-(+)-amisulpride and (S)-(−)-amisulpride is about 600 mg.

Embodiment 14

The pharmaceutical composition of embodiment 1, wherein the combined amount of (R)-(+)-amisulpride and (S)-(−)-amisulpride is about 700 mg.

Embodiment 15

The pharmaceutical composition of embodiment 1, wherein the composition is provided in a solid oral dosage form comprising one or more pharmaceutically acceptable excipients.

Embodiment 16

A pharmaceutical composition comprising an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride, in amounts effective to provide in a subject after administration:
  inhibition of dopamine D2 activity and serotonin 5-HT7 activity in said subject such that the ratio of the serotonin 5-HT7 receptor inhibitory constant to the dopamine D2 receptor inhibitory constant is in the range between about 2 to about 6.

Embodiment 17

The pharmaceutical composition of embodiment 16, wherein the ratio of the serotonin 5-HT7 receptor inhibitory constant to the dopamine D2 receptor inhibitory constant is in the range between about 3 to about 5.

Embodiment 18

The pharmaceutical composition of embodiment 17, wherein the ratio of the serotonin 5-HT7 receptor inhibitory constant to the dopamine D2 receptor inhibitory constant is about 4.

Embodiment 19

The pharmaceutical composition of embodiment 16, wherein the dopamine D2 receptor inhibitory constant is in the range between about 11 nM to about 20 nM and the serotonin 5-HT7 receptor inhibitory constant is in the range between about 40 nM to about 85 nM.

Embodiment 20

The pharmaceutical composition of embodiment 19, wherein the dopamine D2 receptor inhibitory constant is about 17 nM and the serotonin 5-HT7 receptor inhibitory constant is about 66 nM.

Embodiment 21

The pharmaceutical composition of embodiment 16, wherein the ratio of (R)-(+)-amisulpride to (S)-(−)-amisulpride is in the range between about 80:20 to about 90:10 by weight.

Embodiment 22

The pharmaceutical composition of embodiment 21, wherein the ratio of (R)-(+)-amisulpride to (S)-(−)-amisulpride is 85:15 by weight.

Embodiment 23

The pharmaceutical composition of embodiment 16, wherein the (R)-(+)-amisulpride is crystalline (R)-(+)-amisulpride of crystal Form A; and the (S)-(−)-amisulpride is crystalline (S)-(−)-amisulpride of crystal Form A'.

Embodiment 24

The pharmaceutical composition of embodiment 16, wherein the combined amount of (R)-(+)-amisulpride and (S)-(−)-amisulpride is between about 50 mg and about 1000 mg.

Embodiment 25

The pharmaceutical composition of embodiment 16, wherein the combined amount of (R)-(+)-amisulpride and (S)-(−)-amisulpride is between about 200 mg and about 700 mg.

Embodiment 26

The pharmaceutical composition of embodiment 16, wherein the combined amount of (R)-(+)-amisulpride and (S)-(−)-amisulpride is about 400 mg.

Embodiment 27

The pharmaceutical composition of embodiment 16, wherein the combined amount of (R)-(+)-amisulpride and (S)-(−)-amisulpride is about 500 mg.

Embodiment 28

The pharmaceutical composition of embodiment 16, wherein the combined amount of (R)-(+)-amisulpride and (S)-(−)-amisulpride is about 600 mg.

Embodiment 29

The pharmaceutical composition of embodiment 16, wherein the combined amount of (R)-(+)-amisulpride and (S)-(−)-amisulpride is about 700 mg.

Embodiment 30

The pharmaceutical composition of embodiment 16, wherein the unequal mixture of (R)-(+)-amisulpride and (S)-(−)-amisulpride, or salts thereof, are in amounts effective to provide in a subject after administration:
  an occupancy of dopamine D2 receptors between about 30% and about 50%; and
  a suppression of the time in rapid eye movement (REM) sleep by an amount between about 15 minutes and about 45 minutes.

Embodiment 31

The pharmaceutical composition of embodiment 30, wherein the (R)-(+)-amisulpride is present in an amount between about 300 mg to about 600 mg and the (S)-(−)-amisulpride is present in an amount between about 40 mg to about 105 mg.

Embodiment 32

The pharmaceutical composition of embodiment 16, wherein the composition is provided in a solid oral dosage form comprising one or more pharmaceutically acceptable excipients.

Embodiment 33

A pharmaceutical composition comprising:
a pharmaceutically acceptable excipient; and
a combined amount of (R)-(+)-amisulpride, or a pharmaceutically acceptable salt thereof, and (S)-(−)-amisulpride, or a pharmaceutically acceptable salt thereof, between about 50 mg and about 1000 mg, in the enantiomeric ratio of (R)-(+)-amisulpride to (S)-(−)-amisulpride of about 85:15 by weight.

Embodiment 34

The pharmaceutical composition of embodiment 33, wherein the combined amount of (R)-(+)-amisulpride and (S)-(−)-amisulpride is between about 200 mg and about 700 mg.

Embodiment 35

The pharmaceutical composition of embodiment 33, wherein the combined amount of (R)-(+)-amisulpride and (S)-(−)-amisulpride is about 400 mg.

Embodiment 36

The pharmaceutical composition of embodiment 33, wherein the combined amount of (R)-(+)-amisulpride and (S)-(−)-amisulpride is about 500 mg.

Embodiment 37

The pharmaceutical composition of embodiment 33, wherein the combined amount of (R)-(+)-amisulpride and (S)-(−)-amisulpride is about 600 mg.

Embodiment 38

The pharmaceutical composition of embodiment 33, wherein the combined amount of (R)-(+)-amisulpride and (S)-(−)-amisulpride is about 700 mg.

Embodiment 39

The pharmaceutical composition of embodiment 33, wherein the (R)-(+)-amisulpride is crystalline (R)-(+)-amisulpride of crystal Form A; and the (S)-(−)-amisulpride is crystalline
(S)-(−)-amisulpride of crystal Form A'.

Embodiment 40

The pharmaceutical composition of embodiment 33 wherein the combined amount of (R)-(+)-amisulpride and (S)-(−)-amisulpride is effective to provide in a subject after administration:
an occupancy of dopamine D2 receptors is between about 20% and about 60%; and
a suppression of the time in rapid eye movement (REM) sleep as characterized by one or more of:
a decrease in REM sleep by an amount greater than about 10 minutes,
a latency to REM sleep by an amount greater than about 20 minutes, or
a decrease in total REM sleep time relative to total sleep time by an amount greater than about 5%.

Embodiment 41

The pharmaceutical composition of embodiment 40, wherein the combined amount of (R)-(+)-amisulpride and (S)-(−)-amisulpride is effective to provide in a subject after administration:
an occupancy of dopamine D2 receptors between about 30% and about 50%; and
a suppression of the time in rapid eye movement (REM) sleep by an amount between about 15 minutes and about 45 minutes.

Embodiment 42

The pharmaceutical composition of embodiment 33, wherein the composition is provided in a solid oral dosage form comprising one or more pharmaceutically acceptable excipients.

Embodiment 43

A pharmaceutical composition comprising:
a pharmaceutically acceptable excipient; and
an unequal mixture of (R)-(+)-amisulpride, or a pharmaceutically acceptable salt thereof, and (S)-(−)-amisulpride, or a pharmaceutically acceptable salt thereof, in a combined amount between about 50 mg and about 1000 mg, wherein the amount of (R)-(+)-amisulpride is greater than the amount of (S)-(−)-amisulpride and wherein the combined amount of (R)-(+)-amisulpride and (S)-(−)-amisulpride is present an amount effective to provide in a subject after administration:
an occupancy of dopamine D2 receptors between about 20% and about 60%; and
a suppression of the time in rapid eye movement (REM) sleep as characterized by a decrease in REM sleep by an amount greater than about 10 minutes.

Embodiment 44

The pharmaceutical composition of embodiment 43, wherein the ratio of (R)-(+)-amisulpride to (S)-(−)-amisulpride is in the range between about 80:20 to about 90:10 by weight.

Embodiment 45

The pharmaceutical composition of embodiment 43, wherein the ratio of (R)-(+)-amisulpride to (S)-(−)-amisulpride is 85:15 by weight.

Embodiment 46

The pharmaceutical composition of embodiment 43, wherein the occupancy of dopamine D2 receptors is between about 30% and about 50%.

Embodiment 47

The pharmaceutical composition of embodiment 43, wherein the decrease in REM sleep is between about 15 minutes and about 45 minutes.

Embodiment 48

The pharmaceutical composition of embodiment 43, wherein the (R)-(+)-amisulpride is crystalline (R)-(+)-amisulpride of crystal Form A; and the (S)-(−)-amisulpride is crystalline
(S)-(−)-amisulpride of crystal Form A'.

Embodiment 49

The pharmaceutical composition of embodiment 43, wherein the combined amount of (R)-(+)-amisulpride and (S)-(−)-amisulpride is between about 200 mg and about 700 mg.

Embodiment 50

The pharmaceutical composition of embodiment 43, wherein the combined amount of (R)-(+)-amisulpride and (S)-(−)-amisulpride is about 400 mg.

Embodiment 51

The pharmaceutical composition of embodiment 43, wherein the combined amount of (R)-(+)-amisulpride and (S)-(−)-amisulpride is about 500 mg.

Embodiment 52

The pharmaceutical composition of embodiment 43, wherein the combined amount of (R)-(+)-amisulpride and (S)-(−)-amisulpride is about 600 mg.

Embodiment 53

The pharmaceutical composition of embodiment 43, wherein the combined amount of (R)-(+)-amisulpride and (S)-(−)-amisulpride is about 700 mg.

Embodiment 54

A method of treating a psychiatric disorder in a subject comprising administering a pharmaceutical composition comprising an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride, wherein said unequal mixture is administered in a therapeutically effective amount to provide in a subject after administration:
- an occupancy of dopamine D2 receptors between about 20% and about 60%; and
- a suppression of the time in rapid eye movement (REM) sleep as characterized by one or more of:
- a decrease in REM sleep by an amount greater than about 10 minutes,
- a latency to REM sleep by an amount greater than about 20 minutes, or
- a decrease in total REM sleep time relative to total sleep time by an amount greater than about 5%.

Embodiment 55

The method of embodiment 54 wherein the psychiatric disorder is a depressive disorder.

Embodiment 56

The method of embodiment 55 wherein the psychiatric disorder is major depressive disorder (MDD).

Embodiment 57

The method of embodiment 54 wherein the psychiatric disorder is major depressive disorder with mixed features (MDD-MF).

Embodiment 58

The method of embodiment 54 wherein the psychiatric disorder is treatment resistant depression (TRD).

Embodiment 59

The method of embodiment 54 wherein the psychiatric disorder is one or more of schizophrenia and negative symptoms of schizophrenia.

Embodiment 60

The method of embodiment 54 wherein the psychiatric disorder is schizoaffective disorder.

Embodiment 61

The method of embodiment 54 wherein the psychiatric disorder is bipolar disorder.

Embodiment 62

The method of embodiment 54 wherein the psychiatric disorder is bipolar depression.

Embodiment 63

The method of embodiment 54 wherein method of treatment treats two or more of schizophrenia, negative symptoms of schizophrenia, treatment resistant depression, bipolar disorder and depression.

Embodiment 64

The method of embodiment 54, wherein the occupancy of dopamine D2 receptors is between about 30% and about 50%.

Embodiment 65

The method of embodiment 54, wherein the decrease in REM sleep is between about 15 minutes and about 45 minutes.

Embodiment 66

The method of embodiment 54, wherein the decrease in REM sleep is between about 15 minutes and about 30 minutes.

Embodiment 67

The method of embodiment 54, wherein the decrease in total REM sleep time relative to total sleep time is by an amount greater than about 6.5%.

Embodiment 68

The method of embodiment 54, wherein the ratio of (R)-(+)-amisulpride to (S)-(−)-amisulpride is in the range between about 80:20 to about 90:10 by weight.

Embodiment 69

The method of embodiment 68, wherein the ratio of (R)-(+)-amisulpride to (S)-(−)-amisulpride is 85:15 by weight.

Embodiment 70

The method of embodiment 54, wherein the (R)-(+)-amisulpride is crystalline (R)-(+)-amisulpride of crystal Form A; and the (S)-(−)-amisulpride is crystalline (S)-(−)-amisulpride of crystal Form A'.

Embodiment 71

The method of embodiment 54, wherein the combined amount of (R)-(+)-amisulpride and (S)-(−)-amisulpride is between about 50 mg and about 1000 mg.

Embodiment 72

The method of embodiment 54, wherein the combined amount of (R)-(+)-amisulpride and (S)-(−)-amisulpride is between about 200 mg and about 700 mg.

Embodiment 73

The method of embodiment 54, wherein the combined amount of (R)-(+)-amisulpride and (S)-(−)-amisulpride is about 400 mg.

Embodiment 74

The method of embodiment 54, wherein the combined amount of (R)-(+)-amisulpride and (S)-(−)-amisulpride is about 500 mg.

Embodiment 75

The method of embodiment 54, wherein the combined amount of (R)-(+)-amisulpride and (S)-(−)-amisulpride is about 600 mg.

Embodiment 76

The method of embodiment 54, wherein the combined amount of (R)-(+)-amisulpride and (S)-(−)-amisulpride is about 700 mg.

Embodiment 77

The method of embodiment 54, wherein the composition is provided in a solid oral dosage form comprising one or more pharmaceutically acceptable excipients.

Embodiment 78

A method of treating a psychiatric disorder in a subject comprising administering an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride, in therapeutically effective amounts to provide in a subject after administration:
inhibition of dopamine D2 activity and serotonin 5-HT7 activity in said subject such that the ratio of the serotonin 5-HT7 receptor inhibitory constant to the dopamine D2 receptor inhibitory constant is in the range between about 2 to about 6.

Embodiment 79

The method of embodiment 78 wherein the psychiatric disorder is a depressive disorder.

Embodiment 80

The method of embodiment 79 wherein the psychiatric disorder is major depressive disorder (MDD).

Embodiment 81

The method of embodiment 78 wherein the psychiatric disorder is major depressive disorder with mixed features (MDD-MF).

Embodiment 82

The method of embodiment 78 wherein the psychiatric disorder is treatment resistant depression (TRD).

Embodiment 83

The method of embodiment 78 wherein the psychiatric disorder is one or more of schizophrenia and negative symptoms of schizophrenia.

Embodiment 84

The method of embodiment 78 wherein the psychiatric disorder is schizoaffective disorder.

Embodiment 85

The method of embodiment 78 wherein the psychiatric disorder is bipolar disorder.

Embodiment 86

The method of embodiment 78 wherein the psychiatric disorder is bipolar depression

Embodiment 87

The method of embodiment 78 wherein method of treatment treats two or more of schizophrenia, negative symptoms of schizophrenia, treatment resistant depression, bipolar disorder and depression.

Embodiment 88

The method of embodiment 78, wherein the ratio of the serotonin 5-HT7 receptor inhibitory constant to the dopamine D2 receptor inhibitory constant is about 4.

Embodiment 89

The method of embodiment 78, wherein the dopamine D2 receptor inhibitory constant is in the range between about 11 nM to about 20 nM and the serotonin 5-HT7 receptor inhibitory constant is in the range between about 40 nM to about 60 nM.

Embodiment 90

The method of embodiment 89, wherein the dopamine D2 receptor inhibitory constant is about 17 nM and the serotonin 5-HT7 receptor inhibitory constant is about 66 nM.

Embodiment 91

The method of embodiment 78, wherein the ratio of (R)-(+)-amisulpride to (S)-(−)-amisulpride is in the range between about 80:20 to about 90:10 by weight.

Embodiment 92

The method of embodiment 78, wherein the ratio of (R)-(+)-amisulpride to (S)-(−)-amisulpride is 85:15 by weight.

Embodiment 93

The method of embodiment 78, wherein the (R)-(+)-amisulpride is crystalline (R)-(+)-amisulpride of crystal Form A; and the (S)-(−)-amisulpride is crystalline (S)-(−)-amisulpride of crystal Form A'.

Embodiment 94

The method of embodiment 78, wherein the combined amount of (R)-(+)-amisulpride and (S)-(−)-amisulpride is between about 50 mg and about 1000 mg.

Embodiment 95

The pharmaceutical composition of embodiment 78, wherein the combined amount of (R)-(+)-amisulpride and (S)-(−)-amisulpride is between about 200 mg and about 700 mg.

Embodiment 96

The method of embodiment 78, wherein the combined amount of (R)-(+)-amisulpride and (S)-(−)-amisulpride is about 400 mg.

Embodiment 97

The method of embodiment 78, wherein the combined amount of (R)-(+)-amisulpride and (S)-(−)-amisulpride is about 500 mg.

Embodiment 98

The method of embodiment 78, wherein the combined amount of (R)-(+)-amisulpride and (S)-(−)-amisulpride is about 600 mg.

Embodiment 99

The method of embodiment 78, wherein the combined amount of (R)-(+)-amisulpride and (S)-(−)-amisulpride is about 700 mg.

Embodiment 100

The method of embodiment 78, wherein the unequal mixture of (R)-(+)-amisulpride and (S)-(−)-amisulpride, or salts thereof, are in amounts effective to provide in a subject after administration:

an occupancy of dopamine D2 receptors between about 30% and about 50%; and
a suppression of the time in rapid eye movement (REM) sleep by an amount between about 15 minutes and about 45 minutes.

Embodiment 101

The method of embodiment 100, wherein the (R)-(+)-amisulpride is present in an amount between about 300 mg to about 600 mg and the (S)-(−)-amisulpride is present in an amount between about 40 mg to about 100 mg.

Embodiment 102

The method of embodiment 78, wherein the composition is provided in a solid oral dosage form comprising one or more pharmaceutically acceptable excipients.

Embodiment 103

A method of treating a psychiatric disorder in a subject comprising administering a pharmaceutical composition comprising:
a pharmaceutically acceptable excipient; and
a combined amount of (R)-(+)-amisulpride, or a pharmaceutically acceptable salt thereof, and (S)-(−)-amisulpride, or a pharmaceutically acceptable salt thereof, between about 400 mg and about 700 mg, in the enantiomeric ratio of (R)-(+)-amisulpride to (S)-(−)-amisulpride of about 85:15 by weight.

Embodiment 104

The method of embodiment 103 wherein the psychiatric disorder is a depressive disorder.

Embodiment 105

The method of embodiment 104 wherein the psychiatric disorder is major depressive disorder (MDD).

Embodiment 106

The method of embodiment 103 wherein the psychiatric disorder is major depressive disorder with mixed features (MDD-MF).

Embodiment 107

The method of embodiment 103 wherein the psychiatric disorder is treatment resistant depression (TRD).

Embodiment 108

The method of embodiment 103 wherein the psychiatric disorder is one or more of schizophrenia and negative symptoms of schizophrenia.

Embodiment 109

The method of embodiment 103 wherein the psychiatric disorder is schizoaffective disorder.

Embodiment 110

The method of embodiment 103 wherein the psychiatric disorder is bipolar disorder.

Embodiment 111

The method of embodiment 103 wherein the psychiatric disorder is bipolar depression.

Embodiment 112

The method of embodiment 103 wherein method of treatment treats two or more of schizophrenia, negative symptoms of schizophrenia, treatment resistant depression, bipolar disorder and depression.

Embodiment 113

The method of embodiment 101, wherein the combined amount of (R)-(+)-amisulpride and (S)-(−)-amisulpride is between about 50 mg and about 1000 mg.

Embodiment 114

The method of embodiment 103, wherein the combined amount of (R)-(+)-amisulpride and (S)-(−)-amisulpride is between about 200 mg and about 700 mg.

Embodiment 115

The method of embodiment 103, wherein the combined amount of (R)-(+)-amisulpride and (S)-(−)-amisulpride is about 400 mg.

Embodiment 116

The method of embodiment 103, wherein the combined amount of (R)-(+)-amisulpride and (S)-(−)-amisulpride is about 500 mg.

Embodiment 117

The method of embodiment 103, wherein the combined amount of (R)-(+)-amisulpride and (S)-(−)-amisulpride is about 600 mg.

Embodiment 118

The method of embodiment 103, wherein the combined amount of (R)-(+)-amisulpride and (S)-(−)-amisulpride is about 700 mg.

Embodiment 119

The method of embodiment 103, wherein the (R)-(+)-amisulpride is crystalline (R)-(+)-amisulpride of crystal Form A; and the (S)-(−)-amisulpride is crystalline (S)-(−)-amisulpride of crystal Form A'.

Embodiment 120

The method of embodiment 103, wherein the combined amount of (R)-(+)-amisulpride and (S)-(−)-amisulpride is effective to provide in a subject after administration:
an occupancy of dopamine D2 receptors is between about 20% and about 60%; and
a suppression of the time in rapid eye movement (REM) sleep as characterized by one or more of:
a decrease in REM sleep by an amount greater than about 10 minutes,
a latency to REM sleep by an amount greater than about 20 minutes, or
a decrease in total REM sleep time relative to total sleep time by an amount greater than about 5%.

Embodiment 121

The method of embodiment 120, wherein the combined amount of (R)-(+)-amisulpride and (S)-(−)-amisulpride is effective to provide in a subject after administration:
an occupancy of dopamine D2 receptors between about 30% and about 50%; and
a suppression of the time in rapid eye movement (REM) sleep by an amount between about 15 minutes and about 45 minutes.

Embodiment 122

The method of embodiment 103, wherein the composition is provided in a solid oral dosage form comprising one or more pharmaceutically acceptable excipients.

Embodiment 123

A method of treating a psychiatric disorder in a subject comprising administering a pharmaceutical composition comprising:
a pharmaceutically acceptable excipient; and
an unequal mixture of (R)-(+)-amisulpride, or a pharmaceutically acceptable salt thereof, and (S)-(−)-amisulpride, or a pharmaceutically acceptable salt thereof, in a combined amount between about 50 mg and about 1000 mg, wherein the amount of (R)-(+)-amisulpride is greater than the amount of (S)-(−)-amisulpride and wherein the combined amount of (R)-(+)-amisulpride and (S)-(−)-amisulpride is present an amount effective to provide in a subject after administration:
an occupancy of dopamine D2 receptors between about 20% and about 60%; and
a suppression of the time in rapid eye movement (REM) sleep as characterized by a decrease in REM sleep by an amount greater than about 10 minutes.

Embodiment 124

The method of embodiment 123 wherein the psychiatric disorder is a depressive disorder.

Embodiment 125

The method of embodiment 124 wherein the psychiatric disorder is major depressive disorder (MDD).

Embodiment 126

The method of embodiment 123 wherein the psychiatric disorder is treatment resistant depression (TRD).

Embodiment 127

The method of embodiment 123 wherein the psychiatric disorder is one or more of schizophrenia and negative symptoms of schizophrenia.

Embodiment 128

The method of embodiment 123 wherein the psychiatric disorder is major depressive disorder with mixed features (MDD-MF).

Embodiment 129

The method of embodiment 123 wherein the psychiatric disorder is schizoaffective disorder.

Embodiment 130

The method of embodiment 123 wherein the psychiatric disorder is bipolar disorder.

Embodiment 131

The method of embodiment 123 wherein the psychiatric disorder is bipolar depression

Embodiment 132

The method of embodiment 123 wherein method of treatment treats two or more of schizophrenia, negative symptoms of schizophrenia, treatment resistant depression, bipolar disorder and depression.

Embodiment 133

The method of embodiment 123, wherein the ratio of (R)-(+)-amisulpride to (S)-(−)-amisulpride is in the range between about 80:20 to about 90:10 by weight.

Embodiment 134

The method of embodiment 123, wherein the ratio of (R)-(+)-amisulpride to (S)-(−)-amisulpride is 85:15 by weight.

Embodiment 135

The method of embodiment 123, wherein the occupancy of dopamine D2 receptors is between about 30% and about 50%.

Embodiment 136

The method of embodiment 123, wherein the decrease in REM sleep is between about 15 minutes and about 45 minutes.

Embodiment 137

The method of embodiment 123, wherein the (R)-(+)-amisulpride is crystalline (R)-(+)-amisulpride of crystal Form A; and the (S)-(−)-amisulpride is crystalline (S)-(−)-amisulpride of crystal Form A'.

Embodiment 138

The pharmaceutical composition of embodiment 123, wherein the combined amount of (R)-(+)-amisulpride and (S)-(−)-amisulpride is between about 200 mg and about 700 mg.

Embodiment 139

The method of embodiment 123, wherein the combined amount of (R)-(+)-amisulpride and (S)-(−)-amisulpride is about 400 mg.

Embodiment 140

The method of embodiment 123, wherein the combined amount of (R)-(+)-amisulpride and (S)-(−)-amisulpride is about 500 mg.

Embodiment 141

The method of embodiment 123, wherein the combined amount of (R)-(+)-amisulpride and (S)-(−)-amisulpride is about 600 mg.

Embodiment 142

The method of embodiment 123, wherein the combined amount of (R)-(+)-amisulpride and (S)-(−)-amisulpride is about 700 mg.

Embodiment 143

The method of embodiment 123, wherein the composition is provided in a solid oral dosage form.

Embodiment 144

A method of inhibiting dopamine D2 activity and serotonin 5-HT7 activity in a subject, comprising administering to a subject an effective amount of an unequal mixture of (R)-(+)-amisulpride, or a pharmaceutically acceptable salt thereof, and (S)-(−)-amisulpride, or a pharmaceutically acceptable salt thereof.

Embodiment 145

The method of embodiment 144 wherein the subject is a mammal.

Embodiment 146

The method of embodiment 145 wherein the subject is a human.

Embodiment 147

The method of embodiment 146 wherein the inhibition of dopamine D2 activity and the inhibition serotonin 5-HT7 activity comprises:
   an occupancy of dopamine D2 receptors between about 20% and about 60%; and
   a suppression of the time in rapid eye movement (REM) sleep as characterized by one or more of:
      a decrease in REM sleep by an amount greater than about 10 minutes,
      a latency to REM sleep by an amount greater than about 20 minutes, or a decrease in total REM sleep time relative to total sleep time by an amount greater than about 5%.

Embodiment 148

The method of embodiment 146 wherein the inhibition takes place in a subject suffering from one or more psychiatric disorders.

Embodiment 149

The method of embodiment 148 wherein the psychiatric disorder is a depressive disorder.

Embodiment 150

The method of embodiment 149 wherein the psychiatric disorder is major depressive disorder (MDD).

Embodiment 151

The method of embodiment 148 wherein the psychiatric disorder is treatment resistant depression (TRD).

Embodiment 152

The method of embodiment 148 wherein the psychiatric disorder is one or more of schizophrenia and negative symptoms of schizophrenia.

Embodiment 153

The method of embodiment 148 wherein the psychiatric disorder is major depressive disorder with mixed features (MDD-MF).

Embodiment 154

The method of embodiment 148 wherein the psychiatric disorder is schizoaffective disorder.

Embodiment 155

The method of embodiment 148 wherein the psychiatric disorder is bipolar disorder.

Embodiment 156

The method of embodiment 148 wherein the psychiatric disorder is bipolar depression.

Embodiment 157

The method of embodiment 148 wherein the psychiatric disorders comprise two or more of schizophrenia, negative symptoms of schizophrenia, treatment resistant depression, bipolar disorder and depression.

Embodiment 158

The method of embodiment 147 or 148 wherein the effective amount of an unequal mixture of (R)-(+)-amisulpride, or a salt thereof, and (S)-(−)-amisulpride, or a pharmaceutically acceptable salt thereof is a therapeutically effective amount.

Embodiment 159

The method of embodiment 158 wherein the unequal mixture of (R)-(+)-amisulpride and (S)-(−)-amisulpride comprises: an unequal mixture of (R)-(+)-amisulpride, or a pharmaceutically acceptable salt thereof, and (S)-(−)-amisulpride, or a pharmaceutically acceptable salt thereof, in a combined amount between about 50 mg and about 1000 mg, wherein the amount of (R)-(+)-amisulpride is greater than the amount of (S)-(−)-amisulpride.

Embodiment 160

The method of embodiment 159, wherein the combined amount of (R)-(+)-amisulpride and (S)-(−)-amisulpride is between about 200 mg and about 700 mg.

Embodiment 161

The method of embodiment 159 or embodiment 160 wherein the enantiomeric ratio of (R)-(+)-amisulpride to (S)-(−)-amisulpride is about 85:15 by weight.

Embodiment 162

A method of treating a psychiatric disorder in a human subject, comprising administering on a treatment cycle an amount of (R)-(+)-amisulpride, or a pharmaceutically acceptable salt thereof, and an amount of (S)-(−)-amisulpride, or a pharmaceutically acceptable salt thereof, in a combined amount between about 100 mg and about 1000 mg per treatment cycle to a human subject in need thereof, wherein the amount of (R)-(+)-amisulpride is greater than the amount of (S)-(−)-amisulpride during the treatment cycle.

Embodiment 163

The method of embodiment 162 wherein the treatment cycle is daily.

Embodiment 164

The method of embodiment 163 wherein an amount of (R)-(+)-amisulpride, or a pharmaceutically acceptable salt thereof, and an amount of (S)-(−)-amisulpride, or a pharmaceutically acceptable salt thereof, are provided once per day.

Embodiment 165

The method of embodiment 163 wherein an amount of (R)-(+)-amisulpride, or a pharmaceutically acceptable salt thereof, and an amount of (S)-(−)-amisulpride, or a pharmaceutically acceptable salt thereof, are provided about once every twelve hours.

Embodiment 166

The method of embodiment 162 wherein the treatment cycle is every two days.

Embodiment 167

The method of embodiment 162 wherein the (R)-(+)-amisulpride, or a pharmaceutically acceptable salt thereof, and the (S)-(−)-amisulpride, or a pharmaceutically acceptable salt thereof, are given separately during a treatment cycle.

Embodiment 168

The method of embodiment 162 wherein the enantiomeric ratio of (R)-(+)-amisulpride to (S)-(−)-amisulpride over a treatment cycle is about 85:15 by weight.

Embodiment 169

The method of embodiment 162 wherein the psychiatric disorder is a depressive disorder.

Embodiment 170

The method of embodiment 169 wherein the psychiatric disorder is major depressive disorder (MDD).

Embodiment 171

The method of embodiment 162 wherein the psychiatric disorder is treatment resistant depression (TRD).

Embodiment 172

The method of embodiment 162 wherein the psychiatric disorder is one or more of schizophrenia and negative symptoms of schizophrenia.

Embodiment 173

The method of embodiment 162 wherein the psychiatric disorder is major depressive disorder with mixed features (MDD-MF).

Embodiment 174

The method of embodiment 162 wherein the psychiatric disorder is schizoaffective disorder.

Embodiment 175

The method of embodiment 162 wherein the psychiatric disorder is bipolar disorder.

Embodiment 176

The method of embodiment 162 wherein the psychiatric disorder is bipolar depression.

Embodiment 177

The method of embodiment 162 wherein the psychiatric disorder comprises two or more of schizophrenia, negative symptoms of schizophrenia, treatment resistant depression, bipolar disorder and depression.

Embodiment 178

A pharmaceutical composition comprising:
one or more pharmaceutically acceptable excipients; and
an unequal mixture of (R)-(+)-amisulpride, or a pharmaceutically acceptable salt thereof, and (S)-(−)-amisulpride, or a pharmaceutically acceptable salt thereof, in a combined amount between about 50 mg and about 1000 mg, wherein the ratio of (R)-(+)-amisulpride to (S)-(−)-amisulpride is in the range between about 80:20 to about 90:10 by weight.

Embodiment 179

The pharmaceutical composition of embodiment 178, wherein the ratio of (R)-(+)-amisulpride to (S)-(−)-amisulpride is 85:15 by weight.

Embodiment 180

The pharmaceutical composition of embodiment 178, wherein
the total combined amount of (R)-amisulpride and (S)-amisulpride comprises between about 20% to about 40% of the total weight of the pharmaceutical composition; and
the one or more pharmaceutically acceptable excipients comprise:
a filler comprising between about 30% and about 55% of the total weight of the pharmaceutical composition; and
a disintegrant comprising between about 15% and about 30% of the total weight of the pharmaceutical composition.

Embodiment 181

The pharmaceutical composition of embodiment 180, wherein the filler is D-mannitol.

Embodiment 182

The pharmaceutical composition of embodiment 181, wherein the disintegrant is one or more of pregelatinized starch and croscarmellose sodium.

Embodiment 183

The pharmaceutical composition of embodiment 181, further comprising:
a binder comprising between about 1% and about 3% of the total weight of the pharmaceutical composition; and
a lubricant comprising between about 0.75% and about 3% of the total weight of the pharmaceutical composition.

Embodiment 184

The pharmaceutical composition of embodiment 178 where the pharmaceutical composition comprises a core comprised of the composition of embodiment 178 and a coating about the core.

Embodiment 185

The pharmaceutical composition of embodiment 179 where the pharmaceutical composition comprises a core comprised of the composition of embodiment 179 and a coating about the core.

Embodiment 186

The pharmaceutical composition of embodiment 180 where the pharmaceutical composition comprises a core comprised of the composition of embodiment 180 and a coating about the core.

Embodiment 187

The pharmaceutical composition of embodiment 184, 185 or 186, wherein the coating comprises a film coat comprised of one or more of hydroxypropylmethylcellulose and talc.

Embodiment 188

A liquid pharmaceutical composition comprising:
one or more pharmaceutically acceptable excipients; and
an aqueous solution comprising an unequal mixture of (R)-(+)-amisulpride, or a pharmaceutically acceptable salt thereof, and (S)-(−)-amisulpride, or a pharmaceutically acceptable salt thereof, with a combined amount between about 5 mg/mL and about 200 mg/mL, wherein the ratio of (R)-(+)-amisulpride to (S)-(−)-amisulpride is in the range between about 80:20 to about 90:10 by weight.

Embodiment 189

The pharmaceutical composition of embodiment 188, wherein the ratio of (R)-(+)-amisulpride to (S)-(−)-amisulpride is 85:15 by weight.

Embodiment 190

The pharmaceutical composition of embodiment 188, further comprising
a buffer; and
a sweetener comprising between about 2% and about 60% of the total weight of the aqueous solution.

Embodiment 191

The pharmaceutical composition of embodiment 190, wherein the sweetener comprises one or more of glycerin and sucralose.

Embodiment 192

The pharmaceutical composition of embodiment 190, wherein the buffer comprises citric acid.

Embodiment 193

The pharmaceutical composition of embodiment 192, wherein the buffer comprises citric acid in an amount sufficient to maintain the pH of the aqueous solution between 3 to 5.

Embodiment 194

The pharmaceutical composition of embodiment 190, further comprising a preservative.

Embodiment 195

A pharmaceutical composition comprising an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride, in amounts effective to provide in vitro: inhibition of dopamine D2 activity and serotonin 5-HT7 activity in vitro such that the ratio of the serotonin 5-HT7 receptor inhibitory constant to the dopamine D2 receptor inhibitory constant is in the range between about 2 to about 6.

Embodiment 196

The pharmaceutical composition of embodiment 195, wherein the ratio of the serotonin 5-HT7 receptor inhibitory constant to the dopamine D2 receptor inhibitory constant is in the range between about 3 to about 5.

Embodiment 197

The pharmaceutical composition of embodiment 196, wherein the ratio of the serotonin 5-HT7 receptor inhibitory constant to the dopamine D2 receptor inhibitory constant is about 4.

Embodiment 198

The pharmaceutical composition of embodiment 195, wherein the dopamine D2 receptor inhibitory constant is in the range between about 11 nM to about 20 nM and the serotonin 5-HT7 receptor inhibitory constant is in the range between about 40 nM to about 85 nM.

Embodiment 199

The pharmaceutical composition of embodiment 198, wherein the dopamine D2 receptor inhibitory constant is about 17 nM and the serotonin 5-HT7 receptor inhibitory constant is about 66 nM.

Embodiment 200

The pharmaceutical composition of embodiment 195, wherein the ratio of (R)-(+)-amisulpride to (S)-(−)-amisulpride is in the range between about 80:20 to about 90:10 by weight.

Embodiment 201

The pharmaceutical composition of embodiment 200, wherein the ratio of (R)-(+)-amisulpride to (S)-(−)-amisulpride is 85:15 by weight.

Embodiment 202

The pharmaceutical composition of embodiment 195, wherein the (R)-(+)-amisulpride is crystalline (R)-(+)-amisulpride of crystal Form A; and the (S)-(−)-amisulpride is crystalline (S)-(−)-amisulpride of crystal Form A'.

Embodiment 203

The pharmaceutical composition of embodiment 195, wherein the combined amount of (R)-(+)-amisulpride and (S)-(−)-amisulpride is between about 50 mg and about 1000 mg.

Embodiment 204

The pharmaceutical composition of embodiment 195, wherein the combined amount of (R)-(+)-amisulpride and (S)-(−)-amisulpride is between about 200 mg and about 700 mg.

Embodiment 205

The pharmaceutical composition of embodiment 195, wherein the combined amount of (R)-(+)-amisulpride and (S)-(−)-amisulpride is about 400 mg.

Embodiment 206

The pharmaceutical composition of embodiment 195, wherein the combined amount of (R)-(+)-amisulpride and (S)-(−)-amisulpride is about 500 mg.

Embodiment 207

The pharmaceutical composition of embodiment 195, wherein the combined amount of (R)-(+)-amisulpride and (S)-(−)-amisulpride is about 600 mg.

Embodiment 208

The pharmaceutical composition of embodiment 195, wherein the combined amount of (R)-(+)-amisulpride and (S)-(−)-amisulpride is about 700 mg.

Embodiment 209

The pharmaceutical composition of embodiment 195, wherein the (R)-(+)-amisulpride is present in an amount between about 300 mg to about 600 mg and the (S)-(−)-amisulpride is present in an amount between about 40 mg to about 105 mg.

Embodiment 210

A composition according to any of embodiments 1-53 or embodiments 178-209 used for the treatment of a psychiatric disorder.

Embodiment 211

The composition of embodiment 210 wherein the psychiatric disorder is a depressive disorder.

Embodiment 212

The composition of embodiment 211 wherein the psychiatric disorder is major depressive disorder (MDD).

Embodiment 213

The composition of embodiment 210 wherein the psychiatric disorder is major depressive disorder with mixed features (MDD-MF).

Embodiment 214

The composition of embodiment 210 wherein the psychiatric disorder is treatment resistant depression (TRD).

Embodiment 215

The composition of embodiment 210 wherein the psychiatric disorder is one or more of schizophrenia and negative symptoms of schizophrenia.

Embodiment 216

The composition of embodiment 210 wherein the psychiatric disorder is bipolar disorder.

Embodiment 217

The composition of embodiment 210 wherein the psychiatric disorder is bipolar depression.

Embodiment 218

The composition of embodiment 210 wherein the psychiatric disorder is two or more of schizophrenia, negative symptoms of schizophrenia, treatment resistant depression, bipolar disorder and depression.

Embodiment 219

Use of a composition according to any of embodiments 1-53 or embodiments 178-209 in the manufacture of a medicament for the treatment of a psychiatric disorder.

Embodiment 220

The medicament of embodiment 219 wherein the psychiatric disorder is a depressive disorder.

Embodiment 221

The medicament of embodiment 220 wherein the psychiatric disorder is major depressive disorder (MDD).

Embodiment 222

The medicament of embodiment 219 wherein the psychiatric disorder is major depressive disorder with mixed features (MDD-MF).

Embodiment 223

The medicament of embodiment 219 wherein the psychiatric disorder is treatment resistant depression (TRD).

Embodiment 224

The medicament of embodiment 219 wherein the psychiatric disorder is one or more of schizophrenia and negative symptoms of schizophrenia.

Embodiment 225

The medicament of embodiment 219 wherein the psychiatric disorder is bipolar disorder.

Embodiment 226

The medicament of embodiment 219 wherein the psychiatric disorder is bipolar depression.

Embodiment 227

The medicament of embodiment 219 wherein the psychiatric disorder is two or more of schizophrenia, negative symptoms of schizophrenia, treatment resistant depression, bipolar disorder and depression.

The present disclosure also provides the following embodiments:

Embodiment 1A

A pharmaceutical composition comprising:
an amount between about 85 mg and about 600 mg of (R)-(+)-amisulpride, or a pharmaceutically acceptable salt thereof, by weight of free base; and
an amount between about 15 mg and about 100 mg (S)-(−)-amisulpride, or a pharmaceutically acceptable salt thereof, by weight of free base;
in the enantiomeric ratio of (R)-(+)-amisulpride to (S)-(−)-amisulpride between about 65:35 and about 88:12 by weight of free base.

Embodiment 2A

The pharmaceutical composition of embodiment 1A wherein the ratio of (R)-(+)-amisulpride to (S)-(−)-amisulpride is between about 75:25 to about 88:12 by weight of free base.

Embodiment 3A

The pharmaceutical composition of embodiment 1A or 2A wherein the ratio of (R)-(+)-amisulpride to (S)-(−)-amisulpride is between about 80:20 to about 88:12 by weight of free base.

Embodiment 4A

The pharmaceutical composition of any one of embodiments 1A-3A wherein the ratio of (R)-(+)-amisulpride to (S)-(−)-amisulpride is between about 85:15 by weight of free base.

Embodiment 5A

The pharmaceutical composition of any one of embodiments 1A-4A comprising:
an amount between about 170 mg and about 340 mg of (R)-(+)-amisulpride, or a pharmaceutically acceptable salt thereof, by weight of free base; and
an amount between about 30 mg and about 60 mg (S)-(−)-amisulpride, or a pharmaceutically acceptable salt thereof, by weight of free base.

Embodiment 6A

The pharmaceutical composition of any one of embodiments 1A-5A comprising:
an amount about 170 mg of (R)-(+)-amisulpride, or a pharmaceutically acceptable salt thereof, by weight of free base; and
an amount about 30 mg of (S)-(−)-amisulpride, or a pharmaceutically acceptable salt thereof, by weight of free base.

Embodiment 7A

The pharmaceutical composition of any one of embodiments 1A-5A comprising:
an amount about 340 mg of (R)-(+)-amisulpride, or a pharmaceutically acceptable salt thereof, by weight of free base; and
an amount about 60 mg of (S)-(−)-amisulpride, or a pharmaceutically acceptable salt thereof, by weight of free base.

Embodiment 8A

The pharmaceutical composition of any one of embodiments 1A-4A, wherein the combined amount of (R)-(+)-amisulpride, or a pharmaceutically acceptable salt thereof, and (S)-(−)-amisulpride, or a pharmaceutically acceptable salt thereof, is about 100 mg, 200 mg, 300 mg, 400 mg, 500 mg, 600 mg or 700 mg by weight of free base.

Embodiment 9A

The pharmaceutical composition of any one of embodiments 1A-4A, wherein the combined amount of (R)-(+)-amisulpride, or a pharmaceutically acceptable salt thereof, and (S)-(−)-amisulpride, or a pharmaceutically acceptable salt thereof, is between about 200 mg and about 600 mg by weight of free base.

Embodiment 10A

The pharmaceutical composition of any one of embodiments 1A-4A and 9A, wherein the combined amount of (R)-(+)-amisulpride, or a pharmaceutically acceptable salt thereof, and (S)-(−)-amisulpride, or a pharmaceutically acceptable salt thereof, is between about 200 mg and about 400 mg by weight of free base.

Embodiment 11A

The pharmaceutical composition of any one of embodiments 1A-4A and 8A-10A, wherein the combined amount of (R)-(+)-amisulpride, or a pharmaceutically acceptable salt thereof, and (S)-(−)-amisulpride, or a pharmaceutically acceptable salt thereof, is about 200 mg by weight of free base.

Embodiment 12A

The pharmaceutical composition of any one of embodiments 1A-4A and 8A-10A, wherein the combined amount of (R)-(+)-amisulpride, or a pharmaceutically acceptable salt thereof, and (S)-(−)-amisulpride, or a pharmaceutically acceptable salt thereof, is about 400 mg by weight of free base.

Embodiment 13A

The pharmaceutical composition of any one of embodiments 1A-12A, wherein the (R)-(+)-amisulpride is crystalline (R)-(+)-amisulpride of crystal Form A; and the (S)-(−)-amisulpride is crystalline (S)-(−)-amisulpride of crystal Form A'.

Embodiment 14A

The pharmaceutical composition of any one of embodiments 1A-13A comprising a combined amount of (R)-(+)-amisulpride and (S)-(−)-amisulpride, or pharmaceutically acceptable salts thereof, effective to provide in the subject after administration an occupancy of dopamine D2 receptors between about 20% and about 60%.

Embodiment 15A

The pharmaceutical composition of any one of embodiments 1A-14A comprising a combined amount of (R)-(+)- amisulpride and (S)-(−)-amisulpride, or pharmaceutically acceptable salts thereof, effective to provide in the subject after administration an occupancy of dopamine D2 receptors between about 30% and about 50%.

Embodiment 16A

The pharmaceutical composition of any one of embodiments 1A-15A comprising a combined amount of (R)-(+)-amisulpride and (S)-(−)-amisulpride, or pharmaceutically acceptable salts thereof, effective to provide in the subject after administration a suppression of the time in rapid eye movement (REM) sleep as characterized by a decrease in REM sleep by an amount greater than about 10 minutes.

Embodiment 17A

The pharmaceutical composition of any one of embodiments 1A-16A comprising a combined amount of (R)-(+)-amisulpride and (S)-(−)-amisulpride, or pharmaceutically acceptable salts thereof, effective to provide in the subject after administration a suppression of the time in rapid eye movement (REM) sleep as characterized by a decrease in REM sleep by an amount between about 15 minutes and about 45 minutes.

Embodiment 18A

The pharmaceutical composition of any one of embodiments 1A-17A comprising a combined amount of (R)-(+)-amisulpride and (S)-(−)-amisulpride, or pharmaceutically acceptable salts thereof, effective to provide in the subject after administration a suppression of the time in rapid eye movement (REM) sleep as characterized by a decrease in REM sleep by an amount between about 15 minutes and about 30 minutes.

Embodiment 19A

The pharmaceutical composition of any one of embodiments 1A-18A comprising a combined amount of (R)-(+)-amisulpride and (S)-(−)-amisulpride, or pharmaceutically acceptable salts thereof, effective to provide in the subject after administration a suppression of the time in rapid eye movement (REM) sleep as characterized by a latency to REM sleep by an amount greater than about 20 minutes.

Embodiment 20A

The pharmaceutical composition of any one of embodiments 1A-19A comprising a combined amount of (R)-(+)-amisulpride and (S)-(−)-amisulpride, or pharmaceutically acceptable salts thereof, effective to provide in the subject after administration a suppression of the time in rapid eye movement (REM) sleep as characterized by a latency to REM sleep by an amount greater than about 30 minutes.

Embodiment 21A

The pharmaceutical composition of any one of embodiments 1A-20A comprising a combined amount of (R)-(+)-amisulpride and (S)-(−)-amisulpride, or pharmaceutically acceptable salts thereof, effective to provide in the subject after administration a suppression of the time in rapid eye movement (REM) sleep as characterized by a decrease in total REM sleep time relative to total sleep time by an amount greater than about 5%.

Embodiment 22A

The pharmaceutical composition of any one of embodiments 1A-21A comprising a combined amount of (R)-(+)-amisulpride and (S)-(−)-amisulpride, or pharmaceutically acceptable salts thereof, effective to provide in the subject after administration a suppression of the time in rapid eye movement (REM) sleep as characterized by a decrease in total REM sleep time relative to total sleep time by an amount greater than about 6.5%.

Embodiment 23A

The pharmaceutical composition of any one of embodiments 1A-13A comprising a combined amount of (R)-(+)-amisulpride and (S)-(−)-amisulpride, or pharmaceutically acceptable salts thereof, effective to provide in the subject after administration:
    an occupancy of dopamine D2 receptors between about 30% and about 50%; and
    a suppression of the time in rapid eye movement (REM) sleep by an amount between about 15 minutes and about 45 minutes.

Embodiment 24A

A pharmaceutical composition comprising an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride, and wherein the amount of (R)-(+)-amisulpride and (S)-(−)-amisulpride in the composition is effective to provide in a subject after administration:
    an occupancy of dopamine D2 receptors between about 20% and about 60%; and
    a suppression of time in rapid eye movement (REM) sleep as characterized by one or more of:
    a decrease in REM sleep by an amount greater than about 10 minutes,
    a latency to REM sleep by an amount greater than about 20 minutes, or
    a decrease in total REM sleep time relative to total sleep time by an amount greater than about 5%.

Embodiment 25A

The pharmaceutical composition of embodiment 24A, wherein the occupancy of dopamine D2 receptors is between about 30% and about 50%.

Embodiment 26A

The pharmaceutical composition of embodiment 24A or 25A, wherein the decrease in REM sleep is between about 15 minutes and about 45 minutes.

Embodiment 27A

The pharmaceutical composition of any one of embodiments 24A-26A, wherein the latency to REM sleep is by an amount greater than about 30 minutes.

Embodiment 28A

The pharmaceutical composition of any one of embodiments 24A-27A, wherein the decrease in total REM sleep time relative to total sleep time is by an amount greater than about 6.5%.

Embodiment 29A

The pharmaceutical composition of any one of embodiments 24A-28A wherein the ratio of (R)-(+)-amisulpride to (S)-(−)-amisulpride is between about 85:15 by weight of free base.

Embodiment 30A

The pharmaceutical composition of any one of embodiments 24A-29A, wherein the combined amount of (R)-(+)-amisulpride, or a pharmaceutically acceptable salt thereof, and (S)-(−)-amisulpride, or a pharmaceutically acceptable salt thereof, is between about 100 mg and about 700 mg by weight of free base.

Embodiment 31A

A pharmaceutical composition comprising an unequal mixture of (R)-(+)-amisulpride and (S)-(−)-amisulpride, or pharmaceutically acceptable salts thereof, wherein the amount of (R)-(+)-amisulpride is greater than the amount of (S)-(−)-amisulpride, in amounts effective to provide in a subject after administration:
inhibition of dopamine D2 activity and serotonin 5-HT7 activity in said subject such that the ratio of the serotonin 5-HT7 receptor inhibitory constant to the dopamine D2 receptor inhibitory constant is in the range between about 2 to about 6.

Embodiment 32A

The pharmaceutical composition of embodiment 31A, wherein the ratio of the serotonin 5-HT7 receptor inhibitory constant to the dopamine D2 receptor inhibitory constant is in the range between about 3 to about 5.

Embodiment 33A

The pharmaceutical composition of embodiment 31A or 32A, wherein the ratio of the serotonin 5-HT7 receptor inhibitory constant to the dopamine D2 receptor inhibitory constant is about 4.

Embodiment 34A

The pharmaceutical composition of any one of embodiments 31A-33A, wherein the dopamine D2 receptor inhibitory constant is in the range between about 11 nM to about 20 nM and the serotonin 5-HT7 receptor inhibitory constant is in the range between about 40 nM to about 85 nM.

Embodiment 35A

The pharmaceutical composition of any one of embodiments 31A-34A, wherein the dopamine D2 receptor inhibitory constant is about 17 nM and the serotonin 5-HT7 receptor inhibitory constant is about 66 nM.

Embodiment 36A

The pharmaceutical composition of any one of embodiments 1A-35A, wherein the composition is provided in a solid oral dosage form comprising one or more pharmaceutically acceptable excipients.

Embodiment 37A

The pharmaceutical composition of embodiment 36A, wherein
the total combined amount of (R)-amisulpride and (S)-amisulpride comprises between about 20% to about 40% of the total weight of the pharmaceutical composition; and
the one or more pharmaceutically acceptable excipients comprise:
a filler comprising between about 30% and about 55% of the total weight of the pharmaceutical composition; and
a disintegrant comprising between about 15% and about 30% of the total weight of the pharmaceutical composition.

Embodiment 38A

A liquid pharmaceutical composition comprising: one or more pharmaceutically acceptable excipients; and
an aqueous solution comprising an unequal mixture of (R)-(+)-amisulpride, or a pharmaceutically acceptable salt thereof, and (S)-(−)-amisulpride, or a pharmaceutically acceptable salt thereof, with a combined amount between about 5 mg/mL and about 200 mg/mL, wherein the ratio of (R)-(+)-amisulpride to (S)-(−)-amisulpride is in the range between about 65:35 to about 88:12 by weight of free base.

Embodiment 39A

A method of treating a psychiatric disorder in a subject comprising administering a pharmaceutical composition of any one of embodiments 1A-38A.

Embodiment 40A

The method of embodiment 39A wherein the psychiatric disorder is a depressive disorder.

Embodiment 41A

The method of embodiment 39A wherein the psychiatric disorder is major depressive disorder (MDD).

Embodiment 42A

The method of embodiment 39A wherein the psychiatric disorder is major depressive disorder with mixed features (MDD-MF).

Embodiment 43A

The method of embodiment 39A wherein the psychiatric disorder is treatment resistant depression (TRD).

Embodiment 44A

The method of embodiment 39A wherein the psychiatric disorder is one or more of schizophrenia and negative symptoms of schizophrenia.

Embodiment 45A

The method of embodiment 39A wherein the psychiatric disorder is schizoaffective disorder.

Embodiment 46A

The method of embodiment 39A wherein the psychiatric disorder is bipolar disorder.

Embodiment 47A

The method of embodiment 39A wherein the psychiatric disorder is bipolar depression.

Embodiment 48A

The method of embodiment 39A wherein method of treatment treats two or more of schizophrenia, negative symptoms of schizophrenia, treatment resistant depression, bipolar disorder and depression.

Embodiment 49A

The method of any one of embodiments 39A-48A wherein the composition is administered once daily.

Embodiment 50A

A method of treating bipolar depression comprising administering once daily to a subject in need thereof an effective amount of a composition comprising:
  an amount about 170 mg of (R)-(+)-amisulpride, or a pharmaceutically acceptable salt thereof, by weight of free base; and
  an amount about 30 mg of (S)-(−)-amisulpride, or a pharmaceutically acceptable salt thereof, by weight of free base.

Embodiment 51A

A method of treating bipolar depression comprising administering once daily to a subject in need thereof an effective amount of a composition comprising:
  an amount about 340 mg of (R)-(+)-amisulpride, or a pharmaceutically acceptable salt thereof, by weight of free base; and
  an amount about 60 mg of (S)-(−)-amisulpride, or a pharmaceutically acceptable salt thereof, by weight of free base.

Embodiment 52A

A method of inhibiting dopamine D2 activity and serotonin 5-HT7 activity in a subject, comprising administering to a subject an effective amount of an unequal mixture of (R)-(+)-amisulpride, or a pharmaceutically acceptable salt thereof, and (S)-(−)-amisulpride, or a pharmaceutically acceptable salt thereof.

As used herein the term "polymorph purity" refers to the weight % that is the specified polymorph form. For example, when a crystalline (R)-amisulpride Form A is characterized as having greater than 95% polymorph purity, that means that greater than 95% by weight of the substance is crystalline (R)-amisulpride of Form A and less than 5% by weight of any other polymorph or amorphous form of (R)-amisulpride.

As used herein the terms "chiral purity" and "enantiomeric purity" are used interchangeably and refers to the weight % that is the specified enantiomer. For example, when a (R)-amisulpride containing substance (such as a compound or crystal) is characterized as having greater than 90% chiral purity, that means that greater than 95% by weight of the amisulpride in the substance is the (R)-amisulpride and less than 5% by weight is in any other enantiomeric form of amisulpride.

As used herein the term "chemical purity" refers to the weight % that is the specified chemical entity, including specified polymorph form. For example, when a crystalline amisulpride Form A is characterized as having greater than 95% chemical purity, that means that greater than 95% by weight of the substance is crystalline amisulpride Form A and less than 5% by weight of other compound including other polymorphs.

For example, when a crystalline (R)-amisulpride Form A is characterized as having greater than 99% chemical purity and greater than 97% chiral purity, that means greater than 97% by weight of the substance is of enantiomeric form (R)-amisulpride Form A and less than 3% by weight of any other amisulpride enantiomer, and that greater than 99% by weight of the substance is amisulpride and less than 1% by weight of other compounds. For example, when a crystalline (R)-amisulpride Form A is characterized as having greater than 99% chemical purity, greater than 97% chiral purity and greater than 95% polymorph purity, that means that greater than 95% by weight of the substance is crystalline (R)-amisulpride of Form A and less than 5% by weight of any other polymorph or amorphous form of (R)-amisulpride, greater than 97% by weight of the substance is of enantiomeric form (R)-amisulpride and less than 3% by weight of any other amisulpride enantiomer, and that greater than 99% by weight of the substance is amisulpride and less than 1% by weight of other compounds.

Chemical purity may be characterized using a number of conventional analytical techniques, including but not limited to high performance liquid chromatography (HPLC) and gas chromatography (GC). Chiral purity (also known as enantiomeric purity) may be characterized using a number of conventional analytical techniques, including but not limited to chiral high performance liquid chromatography (HPLC). Water content may be characterized using a number of conventional analytical techniques, including but not limited to coulometric titration.

For example, in various embodiments, crystalline (R)-amisulpride of Form A, crystalline (S)-amisulpride of Form A', or both, are provided as active ingredients that have a greater than about 90% polymorph purity, greater than about 95% polymorph purity, greater than about 97% polymorph purity, greater than about 99% polymorph purity, greater than about 99.5% polymorph purity, greater than about 99.7% polymorph purity, or greater than about 99.9% polymorph purity.

For example, in various embodiments, crystalline (R)-amisulpride of Form A, crystalline (S)-amisulpride of Form A', or both, are provided as active ingredients that have a greater than about 95% chemical purity, greater than about 97% chemical purity, greater than about 99% chemical purity, greater than about 99.5% chemical purity, greater than about 99.7% chemical purity, or greater than about 99.9% chemical purity. In various embodiments, crystalline (R)-amisulpride of Form A, crystalline (S)-amisulpride of Form A', or both, are provided that has less than about 8000 ppm residual solvents, less than about 6000 ppm residual solvents, less than about 4000 ppm residual solvents, less than about 2000 ppm residual solvents, less than about 1000 ppm residual solvents, less than about 800 ppm residual solvents, or less than about 500 ppm residual solvents.

Aspects, embodiments, and features of the inventions may be further understood from the following examples, which should not be construed as limiting the scope of the inventions. Example 1 presents in vitro data, Examples 2 and 3 animal study data, and Examples 4-6 present human clinical data.

Example 1: In Vitro Assays of Dopamine D2 and Serotonin 5-HT7 Affinities

Amisulpride enantiomers and racemic amisulpride were tested for affinity to Dopamine $D_2$s receptors recombinantly expressed in human Chinese Hamster Ovary (CHO) cells by radioligand binding techniques (Eurofins Panlabs, Inc.). The receptors' $B_{max}$ value was 1.6 pmole/mg protein. The radioligand was [3H]Spiperone at 0.16 nM concentration with 0.090 nM dissociation constant (Kd, historical value under identical laboratory conditions). The incubation buffer was 50 mM Tris-HCl, pH 7.4, 1.4 mM ascorbic acid, 0.001% BSA, and 150 mM NaCl. The amisulpride compound under study (e.g., enantiomeric amisulprides and racemic amisulpride) was dissolved in dimethyl sulfoxide (DMSO) and added to the assay wells for a 1% final concentration. Percent inhibition values of specific binding by amisulpride enantiomers and racemic amisulpride were generated with 12 serial dilutions from 10 micromolar down to 3 nM final concentrations. Each concentration was tested in duplicate. Amisulpride enantiomer affinities and racemic amisulpride affinities for dopamine D2 receptors are based on the average of 3 independent experiments. Affinities were calculated with the Cheng-Prusoff equation and the observed IC50 of the tested compound, the concentration of radioligand employed in the assay, and the historical value for the Kd of the ligand (obtained experimentally).

Amisulpride enantiomers and racemic amisulpride were tested for affinity to Serotonin $5\text{-HT}_7$ receptors recombinantly expressed in human CHO-K1 cells by radioligand binding techniques (Eurofins Panlabs, Inc.). The receptors' $B_{max}$ value was 0.95 pmole/mg protein. The radioligand is [3H]Lysergic acid diethylamide (LSD) at 5.5 nM concentration with 7.40 nM dissociation constant (Kd, historical value under identical laboratory conditions). The incubation buffer was 50 mM Tris-HCl, pH 7.4, 10 mM $MgCl_2$, 0.5 mM EDTA. The amisulpride compound under study (e.g., enantiomeric amisulprides and racemic amisulpride) was dissolved in DMSO and added to the assay wells for a 1% final concentration. Percent inhibition values of specific binding by amisulpride enantiomers and racemic amisulpride were generated with 12 serial dilutions from 10 micromolar down to 3 nM final concentrations. Each concentration was tested in duplicate. Amisulpride enantiomer affinities and racemic amisulpride affinities for serotonin 5-HT7 receptors are based on the average of 3 independent experiments. Affinities were calculated with the Cheng-Prusoff equation and the observed IC50 of the tested compound, the concentration of radioligand employed in the assay, and the historical value for the Kd of the ligand (obtained experimentally).

Percent inhibition of specific binding was determined as a function of test drug concentration (i.e., (R)-amisulpride (S)-amisulpride, and racemic amisulpride). It was discovered that there are distinct pharmacological activities with the potential for combined clinical benefit which reside in opposite enantiomers.

Referring to FIG. 1A, depicted is the data on the % inhibition of dopamine D2 binding of Example 1 for (R)-amisulpride (downward triangle), (S)-amisulpride (upward triangle), and racemic amisulpride (circle). The vertical bars represent ±1 standard deviation from the 3 independent determinations. FIG. 1A illustrates that the (S)-enantiomer is the more potent enantiomer for dopamine $D_2$ receptors.

Referring to FIG. 1B, depicted is the data on the % inhibition of serotonin 5-HT7 binding of Example 1 for (R)-amisulpride (downward triangle), (S)-amisulpride (upward triangle), and racemic amisulpride (circle). The vertical bars represent ±1 standard deviation from the 3 independent determinations. FIG. 1B illustrates that the (R)-enantiomer is more potent in inhibiting binding to serotonin $5\text{-HT}_7$ receptors.

Table 4 summarizes inhibitor constant (Ki) values in nM determined in vitro by radioligand binding and compares racemic amisulpride to a mixture of (R)-(+)-amisulpride and (S)-(−)-amisulpride of about 85:15 by weight. Human dopamine $D_2$ receptors or human serotonin $5\text{-HT}_7$ receptors were expressed in CHO cells or CHO-K1 cells, respectively. Standard error of the mean is presented based on multiple, independent determinations.

TABLE 4

|  | Racemic (50:50) | (R)-amisulpride:(S)-amisulpride (85:15) |
|---|---|---|
| Dopamine $D_2$ | 7.1 ± 0.26 | 17 ± 0.62 |
| Serotonin $5\text{-HT}_7$ | 89 ± 2 | 66 ± 16 |
| $5\text{-HT}_7/D_2$ | 13 | 4 |

Example 1 shows that the (R)-enantiomer is highly stereoselective for serotonin 5-HT7 receptors such that the 5-HT7 antagonism of amisulpride resides almost exclusively in the (R)-enantiomer and that the (S)-enantiomer is highly stereoselective for dopamine D2 receptors such that the D2 antagonism of racemic amisulpride resides predominantly in the (S)-enantiomer. Referring to again to FIG. 1A, the D2 antagonism of (S)-amisulpride was determined to be about 20 fold that of the (R)-amisulpride, and referring to again to FIG. 1B, the 5-HT7 antagonism of (R)-amisulpride was determined to be about 300 fold that of the (S)-amisulpride.

Figure 1C:
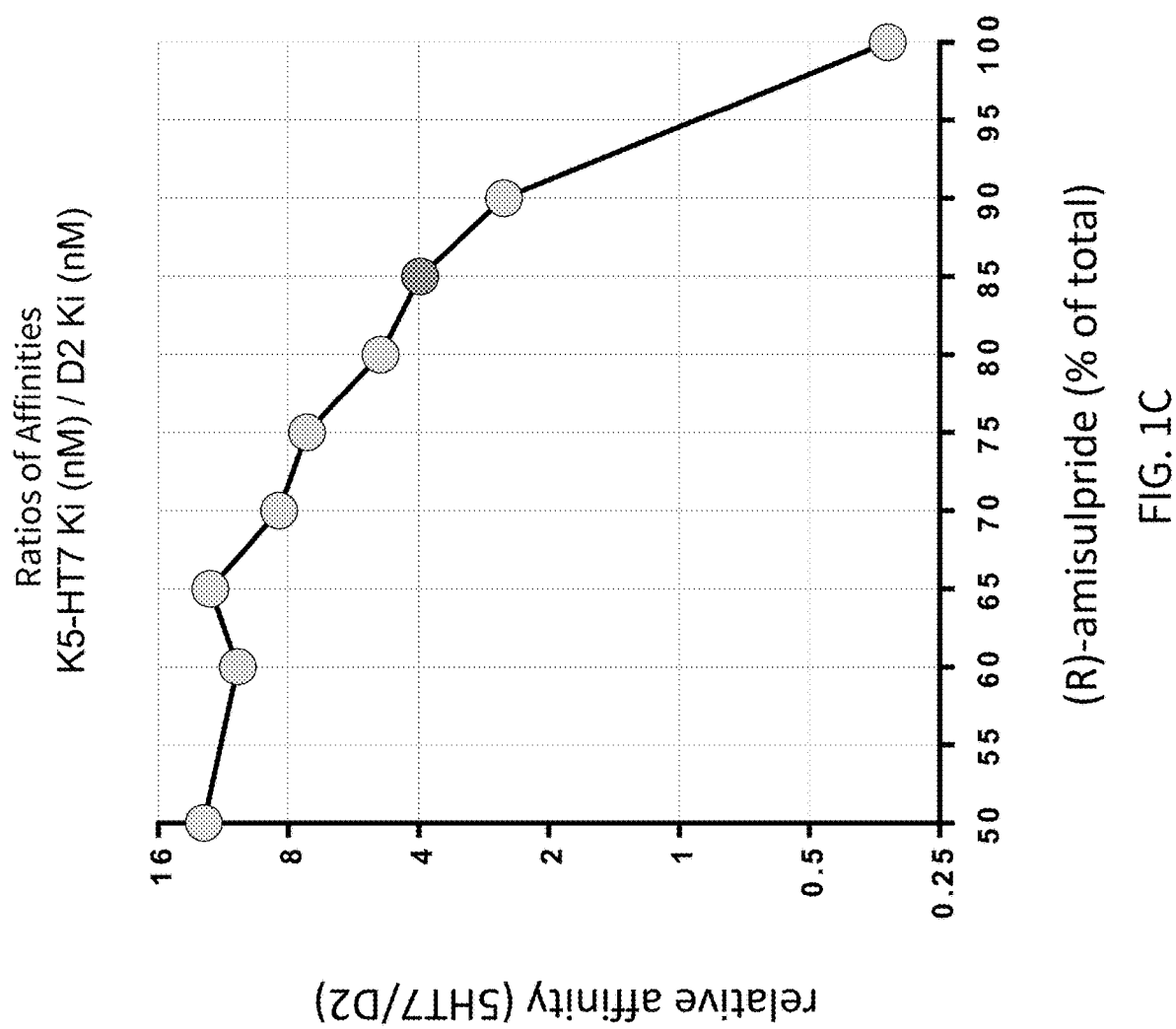

Referring to FIG. 1C, depicted is the data on relative receptor affinity (5-HT7: D2) for various mixtures of (R)-amisulpride and (S)-amisulpride, determined in accordance with the procedures of Example 1, where the x-axis indicates the percentage of the tested drug that was (R)-amisulpride, the remainder percentage being (S)-amisulpride. Table 5 lists for various weight ratios (R)-amisulpride to (S)-amisulpride (first column), from the (S)-enantiomer alone (0:100 ratio) to (R)-enantiomer alone (100:0 ratio), the Ki values (average ±1 standard deviation) in nM for n=3 independent determinations, for dopamine D2 (second column) and serotonin 5-HT7 (third column), and the ratio of 5-HT7 to D2 Ki values (fourth column and plotted in FIG. 1C).

TABLE 5

Ki Values for Enantiomeric Amisulpride and Mixtures of Amisulpride Enantiomers

| Ratio R:S | in vitro Ki values | | Ratio 5-HT7 D2 |
|---|---|---|---|
| | D2 Ki (nM) | 5-HT7 (nM) | |
| 0:100 | 4.43 ± 0.70 | 1,860 ± 260 | 420 |
| 50:50 | 7.10 ± 0.26 | 89 ± 2 | 13 |
| 60:40 | 7.51 ± 0.57 | 79 ± 4 | 11 |
| 65:35 | 6.50 ± 0.64 | 79 ± 9 | 12 |
| 70:30 | 8.54 ± 1.61 | 72 ± 4 | 8 |
| 75:25 | 8.16 ± 0.17 | 59 ± 6 | 7 |
| 80:20 | 12 ± 0.73 | 59 ± 10 | 5 |
| 85:15 | 16 ± 0.62 | 66 ± 16 | 4 |
| 90:10 | 18.9 ± 0.95 | 48 ± 8 | 3 |
| 100:0 | 140 ± 31 | 47 ± 4 | 0.3 |

Examples 2, 3A, and 3B: Animal Studies

A series of animal studies were performed on rats with various doses of (R)-amisulpride.

Example 2: Forced Swim Test

The Forced Swim test (FST) is an indicator of the antidepressant-like activity of a test compound. The rat will swim before "giving up" and becoming immobile. A compound with antidepressant-like activity will decrease the time the rat is immobile.

The animals (n=90) were divided into five groups. Animals in four groups were treated with one of the three doses of (R)-amisulpride or imipramine (control), whereas those in the other group received only vehicle (M phosphoric acid+ 0.1 M NaOH (pH6-7)). In the training session, each animal was gently placed into the plastic cylinder containing 5.8 L of water set at 25±1° C. Fifteen minutes after the beginning of the training session, the animal was removed from the water. The dosing solutions were administered 15 minutes after finishing of the training.

Prior to the swim test, animals were intraperitoneally administered vehicle (1 ml/kg), imipramine (10 mg/kg) or (R)-amisulpride (0.15, 0.5 and 1.5 mg/kg) at 24 hours, 5 hours and 1 hour prior to the swim test. The swim test was performed for 5 minutes in the same manner as the training session. In the swim test, the behavior of each animal was horizontally recorded using a video camera. After the swim test, animals were immediately sacrificed by inhalation of carbon dioxide.

The swim movies were handled in a blind manner to ensure that the person who measured the immobility time had no information on the treatment. An animal was judged to be immobile whenever it remained floating in the water without moving its body or forepaws except for the slight movement to maintain its posture. The total time for which the animal remained immobile was defined as the immobility time. An observer blinded to the doses measured the immobility times. The immobility time of each animal was measured to one decimal place and rounded to a whole number. Immobility time was expressed in units of seconds. In each series the means of immobility time were calculated and rounded to a whole number using. The mean and standard error (SE) for each group were calculated using the data obtained from three experimental series and rounded to a whole number. All results are represented as the mean±SE.

The data of imipramine were analyzed using t-test with a two-sided significance level of 5% ($p<0.05$). In the case imipramine significantly decrease the immobility time compared to control, the data of (R)-amisulpride were then analyzed parametrically using Dunnett's multiple comparison test with a two-sided significance level of 5% ($p<0.05$). The data is presented in FIG. 2.

Figure 2:
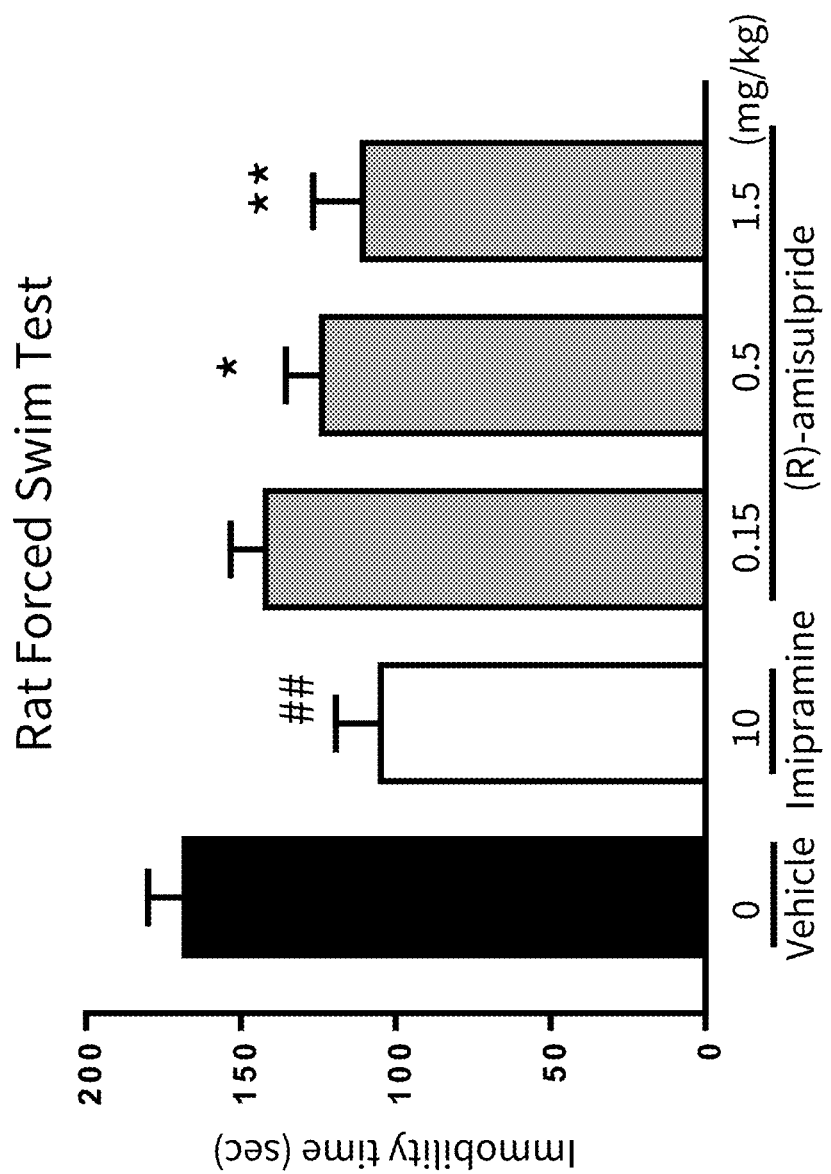
FIG. 2 presents analytical data on the in vivo effects of (R)-amisulpride in a Rat Forced Swim Test, compared to vehicle and imipramine.

Referring to FIG. 2, data is presented for vehicle, imipramine (comparator), and 0.15, 0.5 and 1.5 mg/kg of (R)-amisulpride. The immobility time values are mean±standard error of the mean (SEM). The symbol ## indicates a p-value of $p<0.01$ vs. vehicle (determined using a two-sided t-test); * indicates a p-value of $p<0.05$ and ** indicates a p-value of $p<0.01$ vs. vehicle (determined using a parametric two-sided Dunnett's multiple comparison test).

The immobility time of animals in the vehicle-treated group was 168±12 sec. Imipramine of 10 mg/kg shortened the immobility time by more than 20% in all series and the immobility time average was 105±15 sec, which was significantly shorter than the average of vehicle-treated group. Animals treated with (R)-amisulpride at doses of 0.15, 0.5, and 1.5 mg/kg had immobility times of 142±11, 124±12 and 111±16 sec, respectively. (R)-amisulpride significantly decreased the immobility time at 0.5 and 1.5 mg/kg comparable to imipramine) indicative of antidepressant-like activity for (R)-amisulpride.

Example 3A: Sleep Study of (R)-Amisulpride

In rodents, 5-HT7 receptor blockade has been shown to be effective in models of depression and to increase the latency to REM sleep and decrease REM duration.

In this study, the effect of (R)-amisulpride on sleep architecture in freely moving rats in the light phase was evaluated. Rapid eye movement (REM) sleep time, non-rapid eye movement (NREM) sleep time, WAKE time were measured using electroencephalogram (EEG) and electromyogram (EMG) recordings. (R)-amisulpride (10, 30, 100 mg/kg, p.o.) was administered 10 min before the beginning of recording, during the light phase. EEG and EMG recordings were made for 6 hr starting at the beginning of the light phase. Vehicle (0.05 N HCl/0.5% Methyl Cellulose 400 solution) or dosing suspensions were orally administered 10 min before the beginning of light phase. The volume of administration was 5 mL/kg. The order of drug treatment varied pseudo-randomly and at least 1 week was allowed between the experiments for individual animals.

A radio transmitter (TL 11M2-F40-EET; Data Science International, New Brighton, Minn., USA) was implanted subcutaneously in the back of anesthetized animals, and a pair of electrode wires was stereotaxically implanted into the skull in the following locations: one in the frontoparietal (2 mm anterior to the bregma and 2 mm left to the midline), and the other in parietal (5 mm posterior to the bregma and 2 mm right to the midline) areas. The EEG electrodes were fixed using dental cement. Electromyograms (EMG) were recorded from the dorsal neck muscle. The animals, then, were allowed at least 1 week recovery in individual plastic cages before EEG/EMG recording. EEG/EMG were recorded in the home cages in a soundproof box using Dataquest A.R.T. software (Data Science International, New Brighton, Minn., USA) at a sampling rate of 500 Hz.

Sleep stage analysis was conducted off-line using Sleepsign software (KISSEI COMTEC CO., LTD, Nagano, Japan). Electrographic activity of 10-sec epochs were analyzed and each epoch was automatically assigned as WAKE, REM, and NREM based on the waveforms of EEG and EMG according to the following definitions: WAKE was defined as a condition in which EMG exceeded the individual threshold, NREM was defined as a condition in which the power of delta waves (0.5-4 Hz) exceeded the individual threshold with no EMG activity, and REM was defined as a condition in which the power of theta waves (4-8 Hz) exceeded 40% of the total power of frequencies between 0.5 and 80 Hz in the presence of no EMG activity. The duration of each REM, WAKE, and NREM periods were calculated by summing time spent in each condition during sleep every 2 hours.

Figures 3A, 3B:
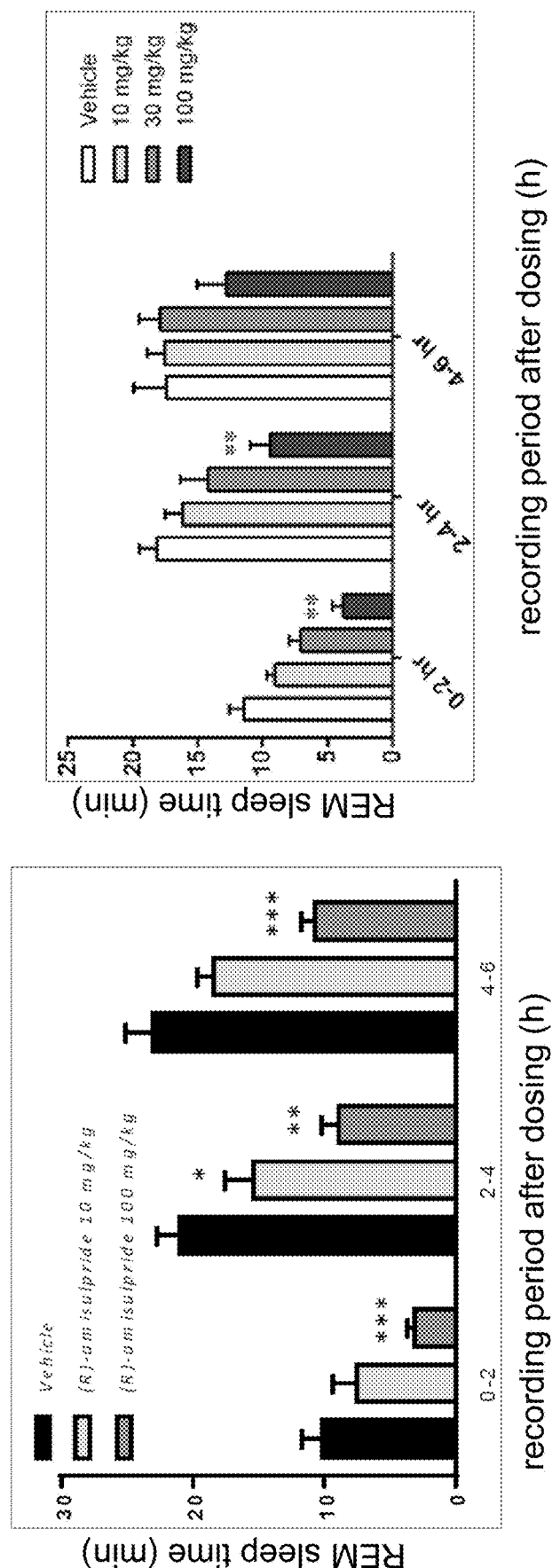
FIGS. 3A and 3B present analytical data on the in vivo effects of (R)-amisulpride on suppression of REM sleep time in rats.

Referring to FIGS. 3A (n=6) and 3B (n=7), data is presented for vehicle and 10 mg/kg, 30 mg/kg and 100 mg/kg of (R)-amisulpride. The y-axis represents the time in minutes that REM sleep was suppressed and these values are mean±standard error of the mean (SEM). The symbol * indicates a p-value of p<0.05,  indicates a p-value of p<0.01; and * indicates a p-value of p<0.001; (determined using a two-way ANOVA followed by post-hoc parametric Dunnett multiple comparison test).

All data are expressed as means±S.E.M. REM sleep, NREM sleep time, and WAKE time each of sequential 2-hr periods were compared statistically using a repeated measures two-way ANOVA, followed by post-hoc Dunnett tests. All statistical analyses were performed using GraphPad Prism 6 software (GraphPad Software, Inc., CA, USA, ver. 6.03J).

It was determined that (R)-amisulpride (10, 30, 100 mg/kg, p.o.) treatment reduced REM sleep duration in dose-dependent manner in freely moving rat, with significant reductions in REM sleep duration following 100 mg/kg in the 0-2 hr and 2-4 hr periods (time after administration). There was no observed effect of (R)-amisulpride on NREM sleep time and WAKE time.

Example 3B: Sleep Study of 85:15 (R:S-Amisulpride) and Racemic Amisulpride

In rodents, 5-HT7 receptor blockade has been shown to be effective in models of depression and to increase the latency to REM sleep and decrease REM duration.

In this study, the effect of 85:15 (R:S-amisulpride) and racemic amisulpride on sleep architecture in freely moving rats in the light phase was evaluated. Groups in this study were as follows. Test compound was administered to rats in a cross-over design.

| Group No. | Fixed ratio amisulpride | Total dose (R/S dose) (mg/kg) | Number of animals |
| --- | --- | --- | --- |
| 1 | Vehicle(*) | | 7 |
| 2 | R/S = 50/50 | 30 (15/15) | |
| 3 | R/S = 85/15 | 30 (25.5/4.5) | |
| 4 | R/S = 50/50 | 100 (50/50) | |
| 5 | R/S = 85/15 | 100 (85/15) | |

(*)0.05N HCl/0.5% MC treatment

Vehicle or fixed ratio amisulpride dosing solutions were orally administered 10 min before the beginning of light phase (light phase: 10:00 AM to 10:00 PM). The individual dosing volume was 4 mL/kg. The individual dosing volume was calculated based on the animals' body weight measured on each experimental day. At least 1-week wash-out period after each treatment was provided.

| Animal No. | Treatments (R/S ratio; Dose mg/kg) | | | | |
| --- | --- | --- | --- | --- | --- |
| | $1^{st}$ | $2^{nd}$ | $3^{rd}$ | $4^{th}$ | $5^{th}$ |
| Rat 1 | Vehicle | 50/50; 100 | 85/15; 100 | 50/50; 30 | 85/15; 30 |
| Rat 2 | 50/50; 100 | Vehicle | 85/15; 100 | 50/50; 30 | 85/15; 30 |
| Rat 3 | Vehicle | 50/50; 100 | 85/15; 100 | 50/50; 30 | 85/15; 30 |
| Rat 4 | 50/50; 100 | Vehicle | 85/15; 100 | 50/50; 30 | 85/15; 30 |
| Rat 5 | Vehicle | 50/50; 100 | 85/15; 100 | 50/50; 30 | 85/15; 30 |
| Rat 6 | Vehicle | 50/50; 100 | 85/15; 100 | 50/50; 30 | 85/15; 30 |
| Rat 7 | 50/50; 100 | Vehicle | 85/15; 100 | 50/50; 30 | 85/15; 30 |

The R-amisulpride and S-amisulpride were separately weighed. The vehicle (0.05 N HCl/0.5% MC solution) was then added to prepare each solution with a concentration of 25 mg/mL (100 mg/kg dosing solution) or 7.5 mg/mL (30 mg/kg dosing solution). Fixed-ratio amisulpride (R/S=85/15 or 50/50) solution (i.e. a dosing formulation) was prepared by mixing R-amisulpride and S-amisulpride solution.

A radio transmitter was implanted intraperitoneally in each anesthetized animal (sodium pentobarbital, 32.4 mg/kg, i.p. and medetomidine hydrochloride, 0.5 mg/kg, i.p.). A pair of electrode wires was stereotaxically implanted into the skull in the following locations: one in the fronto-parietal (2 mm anterior to the bregma and 2 mm left to the midline), and the other in parietal (5 mm posterior to the bregma and 2 mm right to the midline) areas. The electroencephalogram (EEG) electrodes were fixed using dental cement. Electromyograms (EMG) were recorded from the dorsal neck muscle. The animals were allowed at least 2 weeks recovery in individual plastic cages before EEG/EMG recording. EEG/EMG was recorded in the home cages in a soundproof box using Dataquest A.R.T. software (Data Science International, New Brighton, Minn., USA) at a sampling rate of 500 Hz.

Sleep stage analysis was conducted off-line using Sleepsign software (KISSEI COMTEC CO., LTD, Japan). Electrographic activity of 10-sec epochs were analyzed and each epoch was automatically assigned as WAKE, REM, and NREM based on the waveforms of EEG and EMG according to the following definitions: WAKE was defined as a condition in which EMG exceeded the individual threshold, NREM was defined as a condition in which the power of delta waves (0.5-4 Hz) exceeded the individual threshold with no EMG activity, and REM was defined as a condition in which the power of theta waves (4-8 Hz) exceeded 40% of the total power of frequencies between 0.5 and 80 Hz in the presence of no EMG activity. Based on the previous study which demonstrated that R-amisulpride was active 0 to 4 hours after administration (1), durations of REM sleep, NREM sleep, and WAKE were calculated using the data from the first 4 hours after treatment.

All data were expressed as a mean±SEM. Difference between 85/15 and 50/50 amisulpride at each dose in each sleep architecture (i.e. REM sleep duration, NREM sleep duration, and WAKE duration) during the first 4 hours after administration were assessed by a repeated measures one-way ANOVA, followed by post-hoc Bonferroni multiple comparison test. All statistical analyses were performed using GraphPad Prism 6 software (GraphPad Software, Inc., CA, USA, ver. 6.03J). P values less than 0.05 were considered to be statistically significant.

Figure 3C:
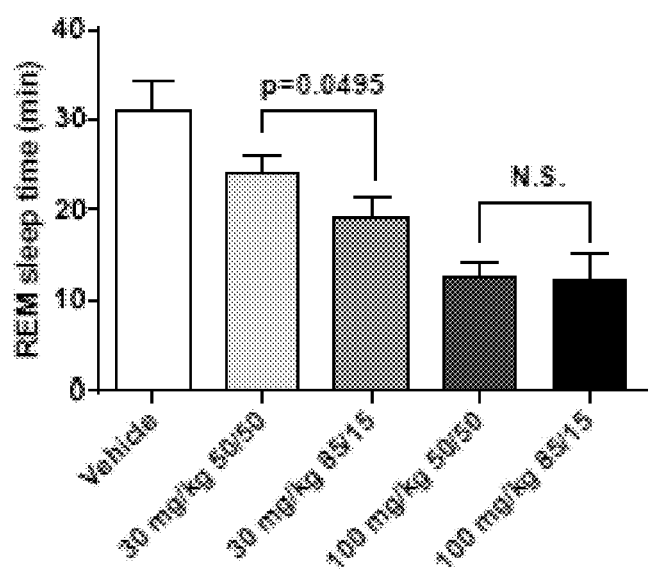
FIGS. 3C, 3D, and 3E present analytical data on the in vivo effects of 85:15 ratio (R:S-amisulpride) and racemic amisulpride (50:50 R:S-amisulpride) on suppression of REM sleep time in rats.
Figure 3D:
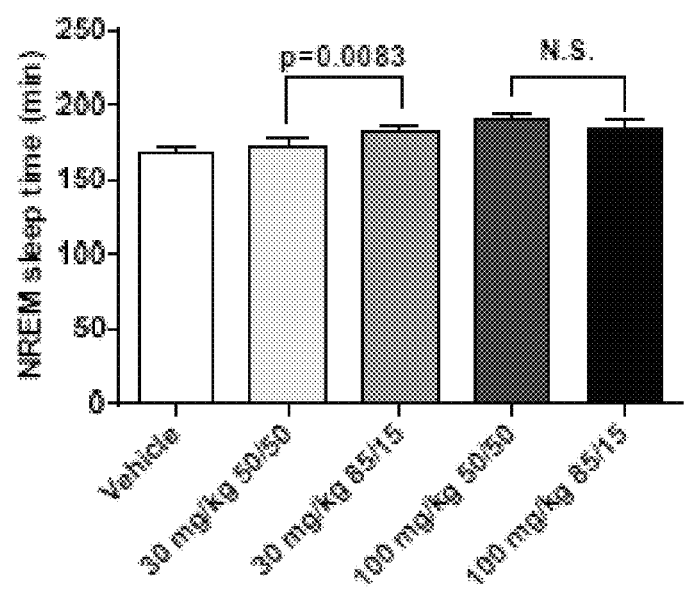
Figure 3E:
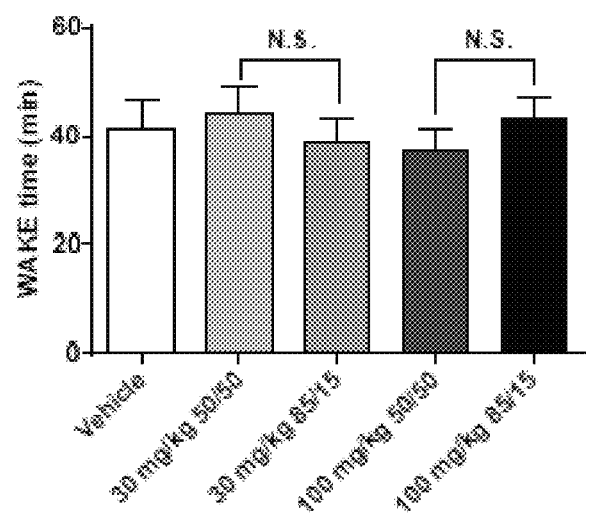

FIG. 3C presents data comparing vehicle to 30 mg/kg and 100 mg/kg of 85:15 ratio (R:S-amisulpride) and racemic amisulpride in REM sleep time (min). FIG. 3D presents data comparing vehicle to 30 mg/kg and 100 mg/kg of 85:15 ratio (R:S-amisulpride) and racemic amisulpride in NREM sleep time (min). FIG. 3E presents data comparing vehicle to 30 mg/kg and 100 mg/kg of 85:15 ratio (R:S-amisulpride) and racemic amisulpride in WAKE time (min).

Results show that at total 30 mg/kg dose of amisulpride, the fixed ratio (R/S=85/15) demonstrated greater REM sleep time reduction (p=0.0495) and NREM sleep time increase (p=0.0083), compared to racemate (R/S=50/50). These differences in REM and NREM sleep times were not observed at total 100 mg/kg dose of amisulpride. There was no difference between 85/15 and 50/50 in WAKE time at any doses tested in this study. The intensity of REM sleep suppression appeared to be dose-dependent on the amount of R-amisulpride in the total dose. Indeed, each treatment, 30 mg/kg (50/50), 30 mg/kg (85/15), 100 mg/kg (50/50), and 100 mg/kg (85/15) contained 15, 25.5, 50, and 85 mg/kg of R-amisulpride, respectively. Greater REM sleep reduction was observed in the treatment group administered higher doses of R-amisulpride. The effect of R-amisulpride on REM sleep suppression was saturated at higher doses (i.e. >50 mg/kg of R-amisulpride). Similar effects were also observed in the NREM sleep time.

In conclusion, the fixed ratio (R/S=85/15) amisulpride exhibits greater REM sleep time reduction and NREM sleep time increase than those of racemate (R/S=50/50) in freely moving rats.

Examples 4-6 Human Studies

A series of human clinical studies were performed with various doses of (R)-amisulpride, (S)-amisulpride, and an 85:15 ratio by weight percentage (w/w %) mixture of (R)-amisulpride to (S)-amisulpride.

Example 4: Dopamine $D_2$ Receptor Occupancy PET Study

In these human clinical studies, each of the enantiomers is administered to healthy human subjects in single doses to determine the maximum tolerated doses.

The minimum dose of (S)-amisulpride able to occupy Dopamine $D_2$ receptors in the brain at a clinically significant threshold for effect was determined by administering single doses of (S)-amisulpride to healthy human volunteers participating in a Positron Emission Tomography (PET) clinical study. The set-point for minimum effective dose of (S)-amisulpride was the lowest dose level able to bind approximately one quarter to one third of brain Dopamine $D_2$ receptors in volunteers.

Dopamine $D_2$ occupancy of (S)-amisulpride following single oral administration was performed in normal healthy volunteers using Positron Emission Tomography (PET) together with a highly selective $D_2$ PET radiotracer. Subjects were enrolled into the study with the aim of having a narrow (<2-fold) prediction interval for $RO_{50}$ (the dose required for 50% D2 receptor occupancy). On day -1 (prior to dose administration), baseline PET scans (2 hours) were performed for each subject and served as a control. On day 1, (S)-amisulpride was orally administered as a 10 ml oral solution prepared at the clinical site pharmacy. The oral solution is a citrate buffer solution at pH 4.5 containing citric acid monohydrate, trisodium citrate dihydrate and water. The concentration can be determined from the amount of (S)-amisulpride and total volume. Dosages of 25 mg, 45 mg, 100 mg and 200 mg were used. The selective D2 PET tracer (11C PHNO) was then administered intravenously prior to PET scans post-dose. At a predetermined time after PET tracer administration, post-dose PET scans (90 minute) were initiated and conducted at approximately 3, 8, and 27 hours post-dose. Plasma samples were collected throughout the course of the PET scan session and were analyzed for (S)-amisulpride levels. The plasma concentrations peaked in a 3 hour time frame and declined several-fold to near baseline levels over the 27 hour time interval. The elimination of (S)-amisulpride was consistent with the biphasic elimination half-life reported for amisulpride, which is characterized by an initial elimination phase of 2 to 5 hours and a terminal plasma half-life of approximately 12 hours. (A. J. Coukell et al, CNS Drugs 6(3), 237-256 (1996))

A Simplified Reference Tissue Model (SRTM) analysis with the caudate and putamen serving as the regions of interest (ROI) and cerebellum as the reference region was employed for estimating $D_2$ occupancy. To more accurately determine the relationship between $D_2$ occupancy and doses of S-amisulpride, the observed $D_2$ occupancy for each dose/subject was plotted against the derived plasma concentration to determine the dose levels associated with occupancies between 30% and 50% of brain Dopamine $D_2$ receptors.

Figure 4:
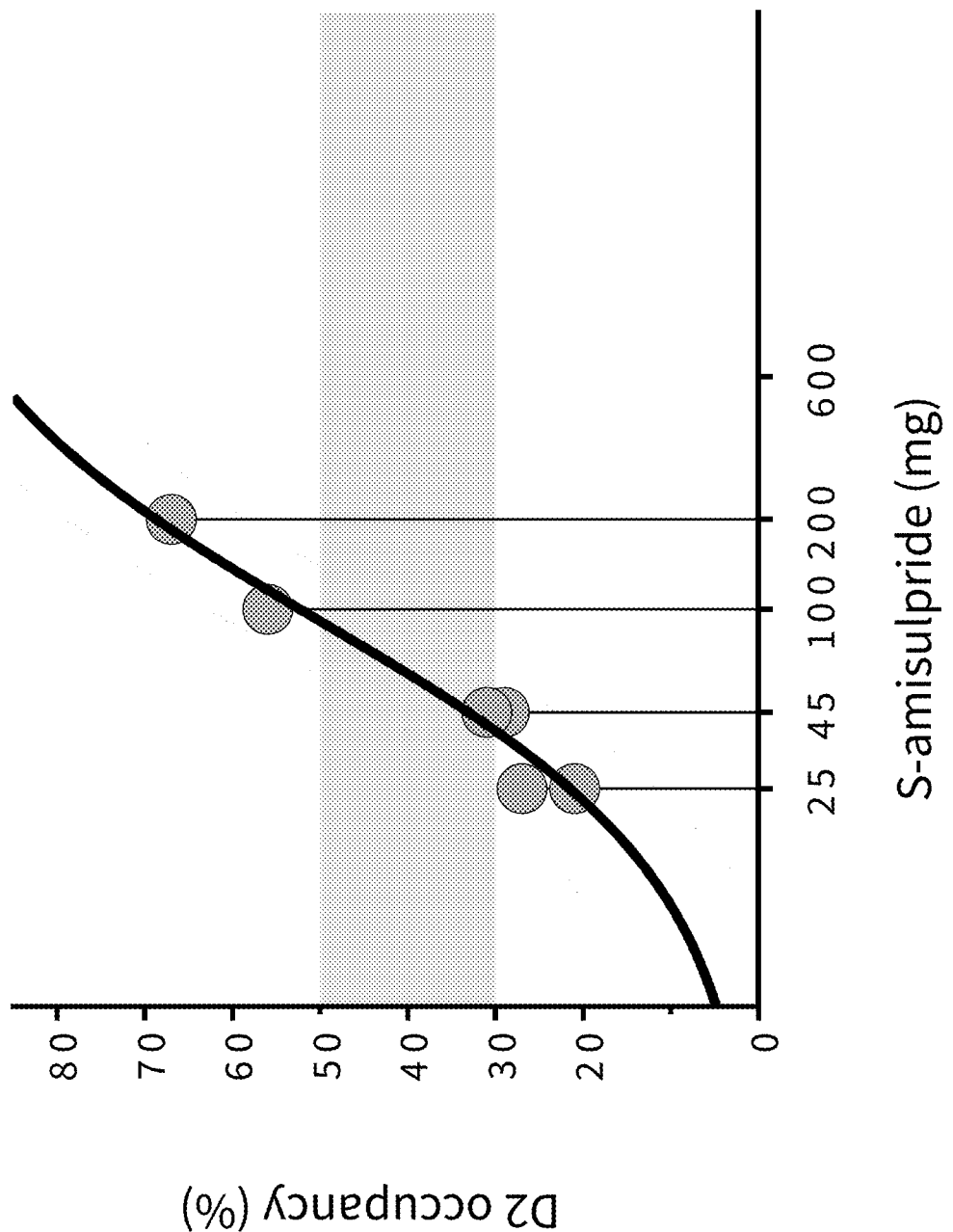
FIG. 4 presents analytical data from human clinical studies on the effects of (S)-amisulpride binding to dopamine D2 receptors in the brain of human volunteers using PET imaging.

FIG. 4 presents analytical data from the human clinical studies (n=6) on the effects of (S)-amisulpride binding to dopamine D2 receptors. The PET scans were conducted 27 hours post-dose, and the amount of (S)-amisulpride resulting in 50% occupancy ($RO_{50}$) was determined to be 92 mg with a ±95% confidence interval of 72 mg to 124 mg.

It was unexpectedly discovered that given the declining plasma concentrations, stable D2 brain occupancies were nevertheless observed out to 27 hours. In comparison, another rapidly eliminated D2 antagonist, quetiapine, has an elimination half-life of about 7 hours and a D2 occupancy trough associated with the plasma concentration trough. (C. L. Delaney and C. B. Nemeroff, Clin. Pharmokinetics, 40 (7), 509-522 (2001); D. C. Mamo et al., J. Clin. Psychiatry, 69:1, 81-86 (2008)). Thus, it was surprisingly discovered that after 27 hours (over two full half-lives) the brain D2 occupancy in the study (Example 6 of the human studies) for subjects administered an 85:15 mixture ((R)-amisulpride:(S)-amisulpride) was still as high as it was at 8 hours post dose.

Example 5: REM Suppression Study

The minimum dose of (R)-amisulpride able to significantly suppress Rapid Eye Movement (REM) sleep in healthy volunteers to a clinically significant effect was determined by administering (R)-amisulpride, as a 20 ml oral solution prepared at the clinical site pharmacy, to volunteers participating in a polysomnography (PSG) clinical study. The oral solution is a citrate buffer solution at pH 4.5 containing citric acid monohydrate, trisodium citrate dihydrate and water. The concentration can be determined from the amount of (S)-amisulpride and total volume. REM suppression was the biomarker used to determine clinically-significant levels of 5-$HT_7$ antagonism and its pharmacodynamics. REM suppression was assessed by total time in minutes spent in REM sleep and by the latency in minutes to REM sleep. It was determined that an example minimum effective dose of (R)-amisulpride was the dose able to inhibit REM sleep by more than about 10 minutes. REM suppression in human volunteers is an established translational biomarker useful to identify doses for antidepressant effects in patients.

The dose of (R)-amisulpride able to suppress Rapid Eye Movement (REM) sleep in humans was identified in healthy subjects in a single-blind, placebo-controlled, randomized, 2-stage, 2-way crossover in-clinic polysomnography (PSG)

study of a single oral dose of (R)-amisulpride. Subjects receive a single dose of either (R)-amisulpride or placebo on each of 2 sequential nights, subjects received drug on one night or the other of the two sequential nights. Two dose-levels of (R)-amisulpride (either 340 mg or 600 mg) were administered in the 2 different stages of the clinical study. The primary endpoint was REM sleep suppression as determined at post dose time points in the measures of latency to REM sleep, REM sleep time in minutes, and percent decrease in REM sleep time relative to total sleep time.

Figure 5:
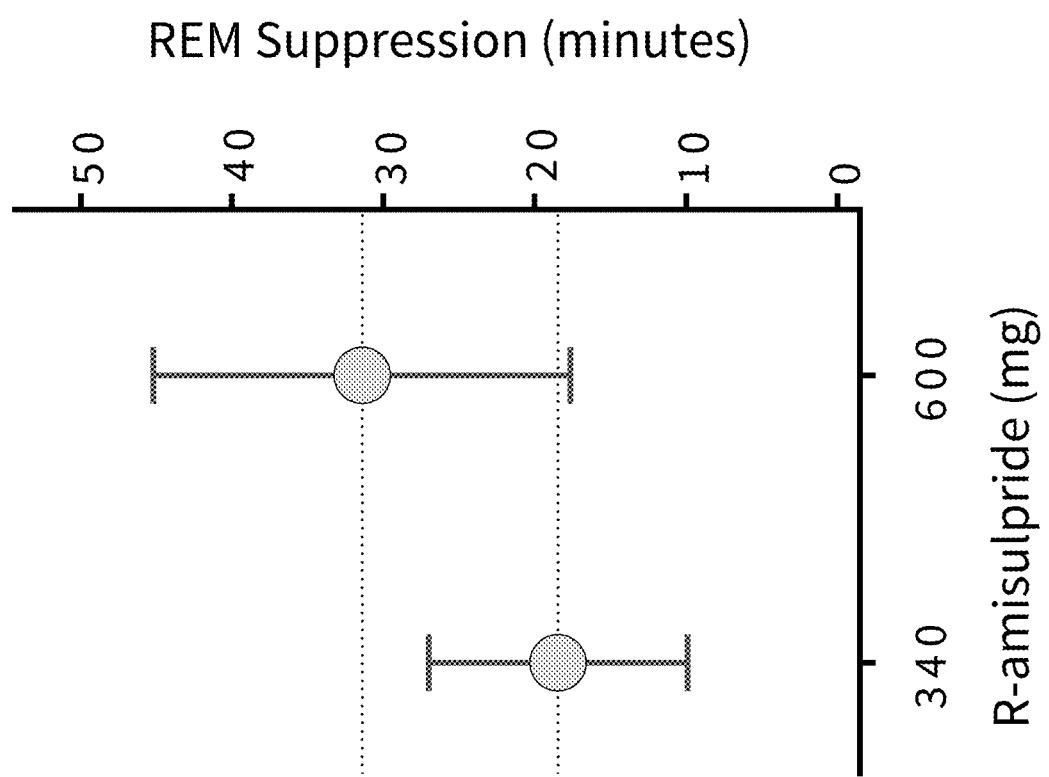
FIG. 5 presents analytical data from human clinical studies on the effects of (R)-amisulpride in suppressing REM sleep in human volunteers using PSG to record sleep stages.

FIG. 5 presents analytical data from the human clinical studies (n=33) on the effects of (R)-amisulpride in suppressing REM sleep. The REM suppression time value is the Least Square Mean differences from placebo, and the error bars represent the 90% confidence interval (CI). Tables 6A-6C present data from this study.

The results presented in Tables 6A-6C were determined from an analysis of the date based on a linear mixed model with terms for treatment, period, and treatment sequence as fixed effects, respective baseline PSG value as a continuous covariate, and treatment-by-baseline PSG interaction, and subject nested within sequence as a random effect, the Kenward and Roger correction for the degrees of freedom and an unstructured covariance structure to model the intra-subject correlation. The abbreviations used in Tables 6A-6C are as follows: PSG=polysomnography; CI=confidence interval; LS=least-squares; REM=rapid eye movement; SE=standard error.

TABLE 6A

REM Suppression and % Decrease in REM Sleep Time

| Primary | | | | | (R)-amisulpride v Placebo | |
|---|---|---|---|---|---|---|
| PSG Endpoint (unit) | Treatment | n | LS Mean (SE) | 90% CI | LS Mean Difference (SE) | 90% CI |
| REM Time (Minutes) | Placebo | 13 | 107.98 (5.65) | (98.23, 117.72) | -31.39 (7.99) | (-45.17, -17.61) |
| | (R)-amisulpride 600 mg | 13 | 76.59 (5.65) | (66.85, 86.33) | | |
| REM Time (Minutes) | Placebo | 20 | 110.05 (4.69) | (102.08, 118.02) | -18.45 (4.91) | (-26.99, -9.91) |
| | (R)-amisulpride 340 mg | 20 | 91.60 (4.69) | (83.63, 99.57) | | |

TABLE 6B

% Decrease in REM Sleep Time

| Primary | | | | | (R)-amisulpride v Placebo | |
|---|---|---|---|---|---|---|
| PSG Endpoint (unit) | Treatment | n | LS Mean (SE) | 90% CI | LS Mean Difference (SE) | 90% CI |
| REM Percent (%) | Placebo | 13 | 24.30 (1.14) | (22.33, 26.27) | -6.24 (1.45) | (-8.87, -13.61) |
| | (R)-amisulpride 600 mg | 13 | 18.06 (1.14) | (16.09, 20.03) | | |
| REM Percent (%) | Placebo | 20 | 25.69 (0.92) | (24.13, 27.25) | -4.15 (1.09) | (-6.04, -2.25) |
| | (R)-amisulpride 340 mg | 20 | 21.55 (0.92) | (19.98, 23.11) | | |

TABLE 6C

Latency to REM Sleep

| Primary | | | | | (R)-amisulpride v Placebo | |
|---|---|---|---|---|---|---|
| PSG Endpoint (unit) | Treatment | n | LS Mean (SE) | 90% CI | LS Mean Difference (SE) | 90% CI |
| Latency to REM Sleep (Minutes) | Placebo | 13 | 89.06 (7.71) | (75.72, 102.40) | 20.30 (9.39) | (3.28, 37.31) |
| | (R)-amisulpride 600 mg | 13 | 109.35 (7.71) | (96.01, 122.69) | | |

TABLE 6C-continued

Latency to REM Sleep

| Primary PSG Endpoint (unit) | Treatment | n | LS Mean (SE) | 90% CI | (R)-amisulpride v Placebo LS Mean Difference (SE) | 90% CI |
|---|---|---|---|---|---|---|
| Latency to REM Sleep (Minutes) | Placebo | 20 | 77.03 (9.42) | (61.01, 93.04) | 28.23 (9.82) | (11.15, 45.30) |
| | (R)-amisulpride 340 mg | 20 | 105.25 (9.42) | (89.23, 121.27) | | |

A single oral dose of 340 mg (R)-amisulpride was observed to result in a decrease in the time spent in REM sleep of 10-27 minutes, reducing the portion of the night spent in REM by 2-6 percentage points, and increasing the latency to first REM by 11 to 45 minutes (ranges are for 90% confidence intervals).

A single oral dose of 600 mg (R)-amisulpride was observed to result in a decrease in the time spent in REM sleep of 18-45 minutes, reducing the portion of the night spent in REM by 4-9 percentage points, and increasing the latency to first REM by 3 to 37 minutes (ranges are for 90% confidence intervals). Further, R-amisulpride was well tolerated in this study. Of the 13 subjects dosed with 600 mg R-amisulpride, 3 subjects reported adverse events. Vital signs and ECGs were normal.

The human clinical trials of Examples 4 and 5 identified distinct pharmacological effects between the R- and S-enantiomers of amisulpride. The dose-occupancy relationship of S-amisulpride identified minimal effective doses of 25 mg to 100 mg for levels of D2 occupancies between 20% to 50%. Additionally, a single dose of R-amisulpride (600 mg) was sufficient to produce clinically meaningful and statistically significant suppression of REM sleep, indicating serotonergic (5-HT7) antagonism for R-amisulpride in humans.

Example 6: Dopamine D$_2$ Receptor Occupancy Study 85:15, R:S Mixture

In these human clinical studies, single oral doses of a fixed ratio composition of (R)-amisulpride to (S)-amisulpride of 85:15 by weight were administered to healthy volunteers at total composition amounts of: 200 mg (170 mg R-amisulpride: 30 mg S-amisulpride); 300 mg (255 mg R-amisulpride:45 mg S-amisulpride); 400 mg (340 mg R-amisulpride:60 mg S-amisulpride); 600 mg (510 mg R-amisulpride:90 mg S-amisulpride); and 700 mg (595 mg R-amisulpride:105 mg S-amisulpride). Doses were administered as a 20 mL oral solution in citrate buffer.

Dopamine D2 occupancy was measured by using Positron Emission Tomography (PET) together with a highly selective D2 and PET radiotracer 11C-PHNO. PET scans were performed prior to and post dosing. Dopamine D2 receptor occupancy was calculated for each postdose PET scan via regional estimate of the binding potential relative to the nondisplaceable component (BPND). These estimates were derived using the simplified reference tissue model (SRTM) with the cerebellum serving as the reference region. Brain regions of interest that were considered include the D2-rich regions such as caudate and putamen. Identification of brain regions was performed using co-registration of PET images with each subject's high-resolution T1-weighted MRI (structural brain) scan.

The primary endpoint of this study was to determine the relationship between the dose (total mg) of the fixed ratio composition and its occupancy of brain dopamine D2 receptors in healthy subjects using PET.

Figure 6A:
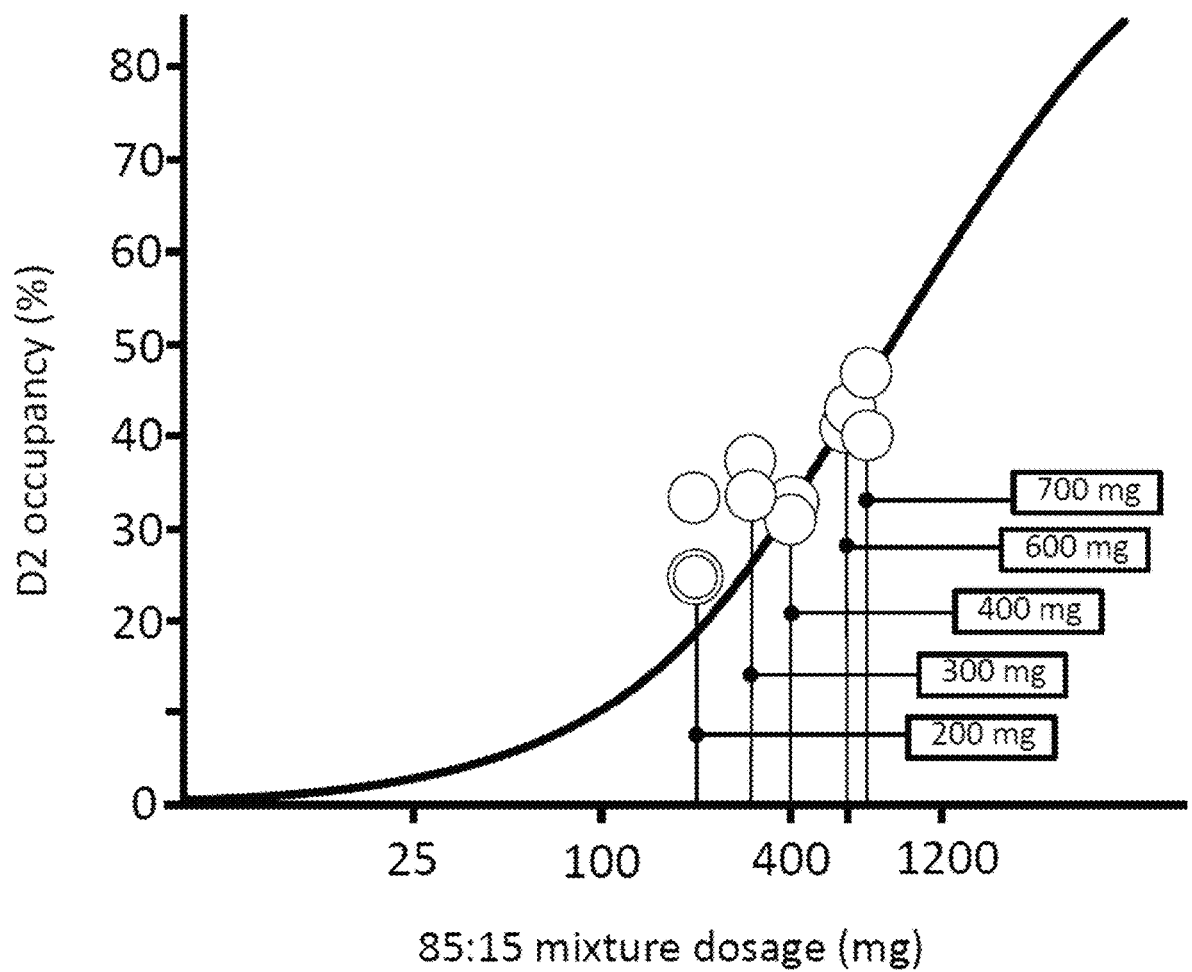
FIGS. 6A, 6B and 6C present analytical data on the effects of mixtures of amisulpride; where

FIG. 6A presents data from the human clinical study (n=11) on the binding to dopamine D2 receptors of the 85:15 ratio by weight percentage (w/w %) composition of (R)-amisulpride to (S)-amisulpride.

The human clinical trials of Examples 4-6 determined that increasing the ratio of (R)-amisulpride relative to (S)-amisulpride changes the pharmacology of the unequal enantiomeric mixtures of amisulpride. Increasing the ratio of (R)-amisulpride relative to (S)-amisulpride changed the balance of clinically-meaningful pharmacological activities from a dopamine D2 receptor-dominating compound (the racemate) into a 5-HT7 pharmacodynamic-preferring composition.

The human clinical trials of Examples 5 and 6 unexpectedly discovered that given the declining plasma concentrations, stable D2 brain occupancies were nevertheless observed out to 27 hours. In comparison, another rapidly eliminated D2 antagonist, quetiapine, has an elimination half-life of about 7 hours and a D2 occupancy trough associated with the plasma concentration trough. (C. L. Delaney and C. B. Nemeroff, Clin. Pharmokinetics, 40 (7), 509-522 (2001); D. C. Mamo et al., J. Clin. Psychiatry, 69:1, 81-86 (2008)). Thus, it was surprisingly discovered that after 27 hours (over two full half-lives) the brain D2 occupancy in the study for subjects administered an 85:15 mixture ((R)-amisulpride:(S)-amisulpride) was still as high as it was at 8 hours post dose.

The human clinical trials of Examples 4 and 5 also determined that the 85:15 fixed ratio composition of (R)-amisulpride to (S)-amisulpride provided the highest ratio of overlap of 5-HT7 effect (required to sustain a decrease in the amount of REM sleep between about 20 to about 45 minutes, a latency to REM sleep of about 15 minutes, and a decrease in total REM sleep time relative to total sleep time of about 5%) with a D2 occupancy in the range between about 30% to about 50%.

Figure 6B:
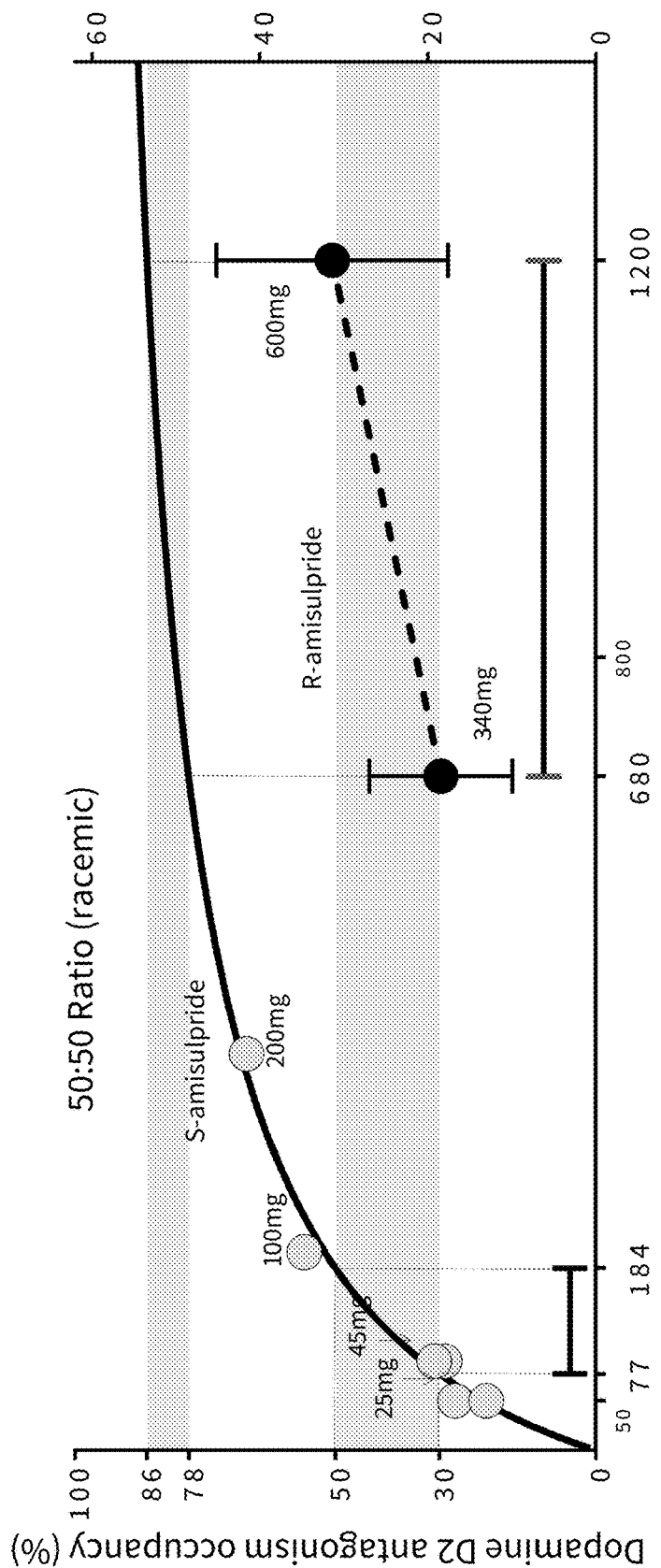
Figure 6C:
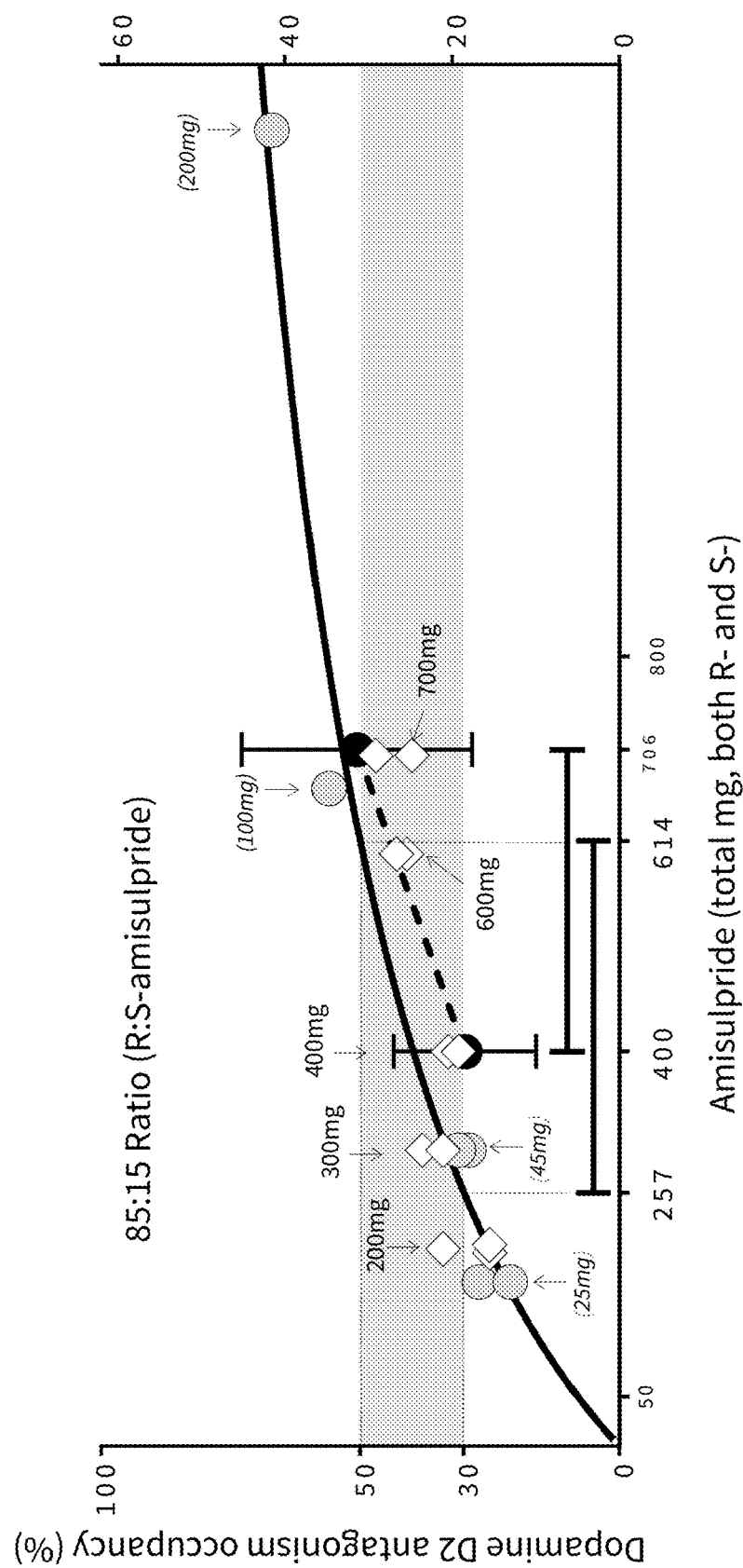

FIGS. 6B and 6C summarize data from Examples 4-6 and illustrates the substantial overlap of the 5-HT$_7$ effect with 30% to 50% D2 receptor occupancy that may be achieved with administration of an 85:15 ratio by weight percentage (w/w %) mixture of (R)-amisulpride to (S)-amisulpride. FIG. 6B presents data on a racemic (50:50 ratio by weight percentage mixture of (R)-amisulpride to (S)-amisulpride) and FIG. 6C presents data on an 85:15 ratio by weight percentage mixture of (R)-amisulpride to (S)-amisulpride.

FIG. 6B illustrates that the desired therapeutic effect attributable to serotonin 5-HT7 antagonism cannot be achieved with a racemic mixture without also resulting in D2 occupancy levels associate with EPS side effects. For example, even for lower 5-HT7 antagonism effects (e.g., decrease in the amount of REM sleep by about 20) the D2 occupancy is about 78%, a level strongly associated with EPS related side effects. Accordingly, racemic amisulpride cannot provide the antidepressant effect of (R)-(+)-amisulpride discovered by the present inventors at dosages that also have less than about 60% D2 receptor occupancy. Correspondingly, dosages of racemic amisulpride that provide less than about 60% D2 receptor occupancy cannot provide sufficient serotonergic antagonism to provide the discovered antidepressant effect of (R)-(+)-amisulpride.

FIG. 6C illustrates a R:S enantiomeric ratio (85:15) ratio discovered by the present inventors that provides both a desirable D2 dopamine effect at D2 occupancy levels not generally associated with EPS side effects and a desirable serotonergic antagonism that provides the discovered antidepressant effect of (R)-(+)-amisulpride. In various embodiments, the present inventors have discovered that between about 200 mg and about 700 mg of total amisulpride, in a R:S ratio of 85:15 by weight, can provide a therapeutic D2 dopamine effect and a therapeutic serotonergic antagonism whilst decreasing and/or eliminating negative side effects generally associated with high D2 occupancy.

Figure 15B:
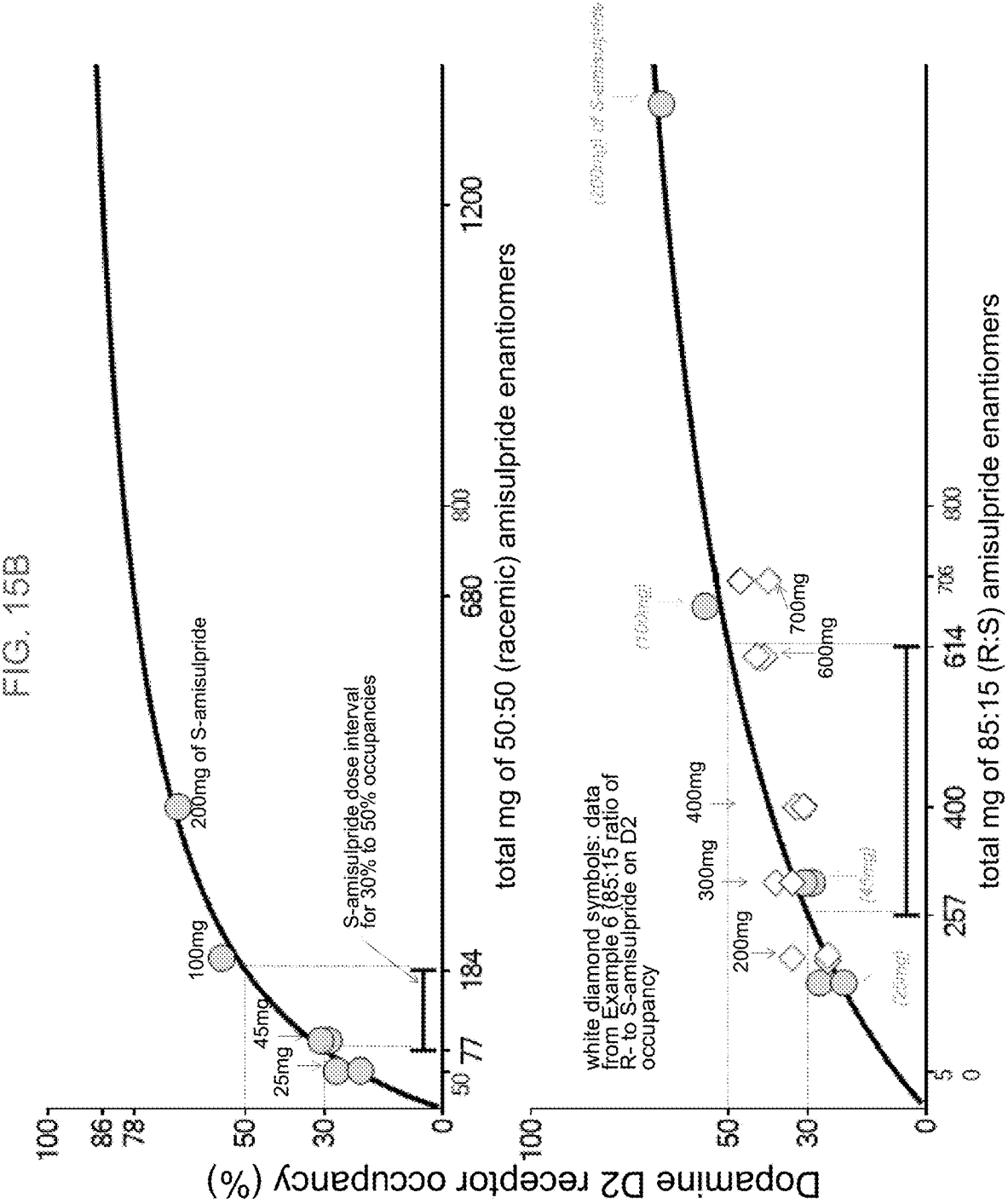
Figure 15C:
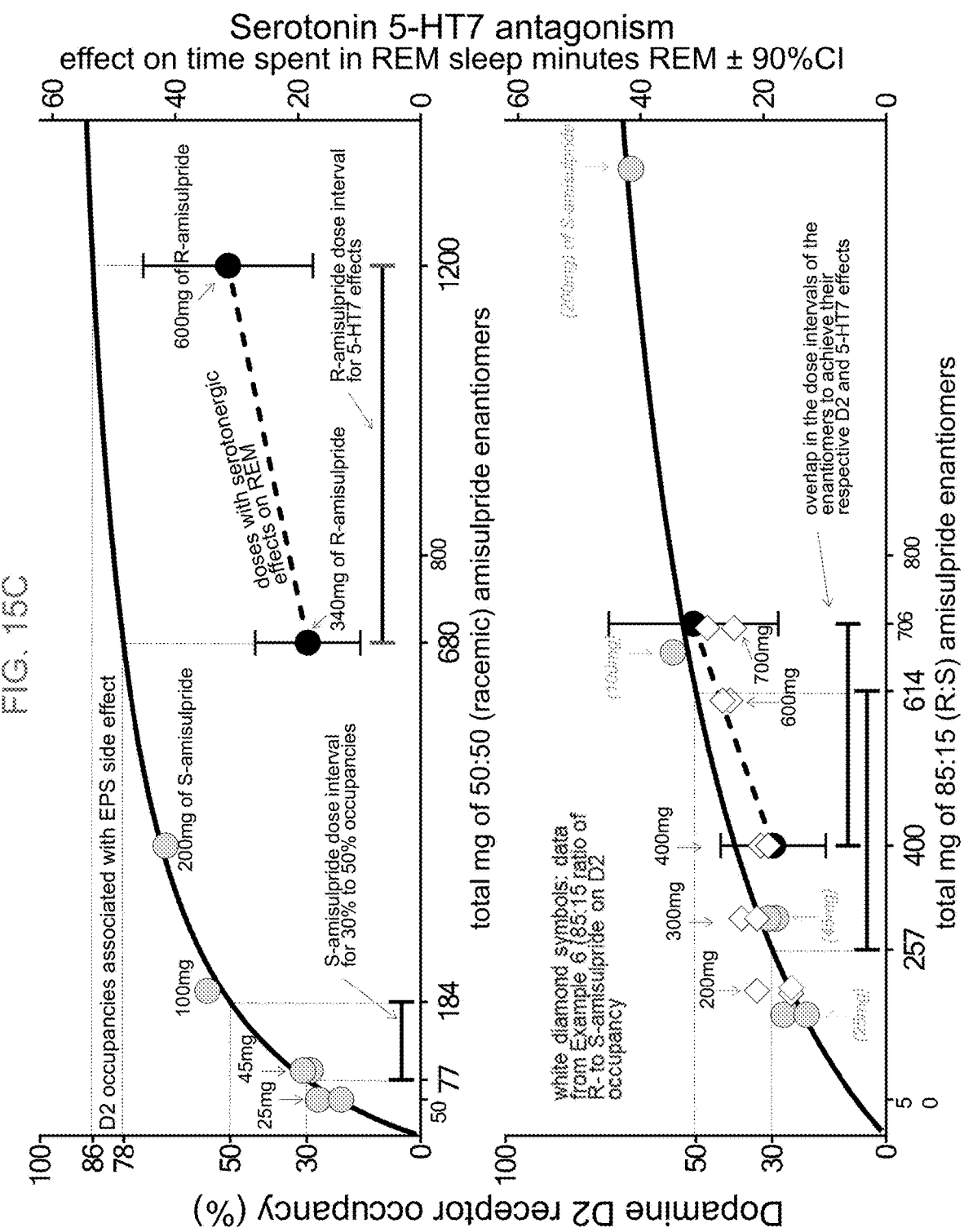

From another perspective, FIGS. 15A, 15B, and 15C present analytical data on the effects of mixtures of amisulpride.

FIG. 15A presents data from human clinical studies on the effects of (R)-amisulpride (dark circles) on 5-HT7 (decrease in the amount of REM sleep minutes) from Example 5, where the x-axis in the top graph is 50:50 racemic amisulpride, and the x-axis in the bottom graph is 85:15 ratio by weight percentage (w/w %) of R:S-amisulpride. The mg designations indicate the amount of the indicted enantiomer in the racemic mixture (top graph) and in the 85:15 ratio of R:S amisulpride. The amount of total amisulpride is reduced by changing the mixture of R:S amisulpride. For example, in a racemic mixture, it would require 680 mg of amisulpride in order to administer 340 mg of (R)-amisulpride. In contrast, in an 85:15 ratio of R:S, 400 mg of amisulpride would provide 340 mg of (R)-amisulpride.

FIG. 15B presents data from human clinical studies on the binding to dopamine D2 receptors of (S)-amisulpride and an 85:15 ratio by weight percentage (w/w %) of (R)-amisulpride to (S)-amisulpride. The x-axis in the top graph is 50:50 racemic amisulpride. The mg designations indicate the amount of the indicted enantiomer in the racemic mixture (top graph). The top graph shows the effect of (S)-amisulpride (grey circles) has on D2 occupancy based on data from Example 4. In the top graph, about 30-50% of D2 occupancy is associated with about 77-184 mg of racemic amisulpride, which corresponds to about 39-92 mg of (S)-amisulpride and about 39-92 mg of (R)-amisulpride. The x-axis in the bottom graph is 85:15 ratio of (R)-amisulpride to (S)-amisulpride. The mg designations indicate the amount of the indicted enantiomer in the 85:15 ratio of R:S-amisulpride (bottom graph). The bottom graph shows the effects of (S)-amisulpride (grey circles) and 85:15 ratio (white diamonds) have on D2 occupancy based on data from Example 4 and Example 6, respectively. The bottom graph shows that about 30-50% of D2 occupancy is associated with about 257-614 mg of 85:15 ratio of R:S-amisulpride, which corresponds to about 39-92 mg of (S)-amisulpride and about 218-522 mg of (R)-amisulpride. As readily apparent, the ratio of 85:15 R:S amisulpride provides a greater amount of R enantiomer than S enantiomer.

FIG. 15C illustrates the substantial overlap of the 5-HT7 effect with 30% to 50% D2 receptor occupancy that can be achieved with administration of an 85:15 ratio of (R)-amisulpride to (S)-amisulpride. The x-axis in the top graph is the total amount of racemic amisulpride. The mg designations indicate the amount of the indicted enantiomer in the racemic mixture. The grey shaded circles are the data for (S)-amisulpride from Example 4, showing the effect of (S)-amisulpride has on D2 occupancy. The dark circles are the data for (R)-amisulpride from Example 5, showing the effect of (R)-amisulpride has on 5-HT$_7$. The x-axis in the bottom graph is the total amount of 85:15 ratio R:S amisulpride. The mg designations indicate the amount of the indicted enantiomer in the 85:15 ratio mixture (bottom graph). The grey shaded circles are the data for (S)-amisulpride from Example 4, showing the effect of (S)-amisulpride has on D2 occupancy. The dark circles are the data for (R)-amisulpride from Example 5, showing the effect of (R)-amisulpride has on 5-HT$_7$. The white diamonds are data for the 85:15 ratio R:S amisulpride from Example 6 (D2 occupancy).

As can be seen in FIG. 15C top graph, about 30-50% of $D_2$ occupancy is associated with about 77-184 mg of racemic amisulpride, which corresponds to about 39-92 mg of (S)-amisulpride and about 39-92 mg of (R)-amisulpride (top graph). However, about 39-92 mg of (R)-amisulpride is not enough to achieve sufficient 5-HT7 effect associated with the discovered antidepressant activity. As shown on the dotted line and solid black circles, 340 mg of (R)-amisulpride provides a decrease in REM sleep by about 20 minutes. 340 mg of (R)-amisulpride projected onto the curve of racemic amisulpride (solid line) shows that the D2 occupancy is 78%, which is in the range that is associated with side effects. Similarly, as shown on the dotted line and solid black circles, 600 mg of (R)-amisulpride provides a decrease in REM sleep by about 30 minutes. 600 mg of (R)-amisulpride projected onto the curve of racemic amisulpride (solid line) shows that the D2 occupancy is 86%, which above the occupancy level associated with significant dopamine D2 receptor occupancy side effects.

Also, as shown in FIG. 15C bottom graph, about 275-614 mg of amisulpride (85:15 ratio of R:S) provides about 30-50% $D_2$ antagonism. The amount of about 257-614 mg (85:15 ratio of R:S) corresponds to about 39-92 mg (S)-amisulpride and about 218-522 mg (R)-amisulpride. The ratio of 85:15 R:S amisulpride provides a greater amount of R enantiomer than the S enantiomer. This in turn allows for administration of greater amount of (R)-amisulpride than (S)-amisulpride in order to avoid side effects associated with $D_2$ occupancy while, as the inventors have discovered, still providing sufficient 5-HT7 effect. A racemic mixture of amisulpride does not and cannot provide this unequal amount of (R) and (S)-amisulpride. The inventors have thus discovered that the ratio of 85:15 R:S amisulpride provides a substantial overlap in the dose intervals of the two enantiomers that achieves their respective D2 and 5-HT7 effects.

The compounds disclosed herein can include isotopes. Isotopes include those atoms having the same atomic number but different mass numbers. For example, isotopes of hydrogen include tritium and deuterium. In some embodiments, one or more atoms of the compounds can be replaced or substituted with isotopes of the atoms in natural or non-natural abundance. In some embodiments, one or more hydrogen atoms in a compound of the present disclosure can be replaced or substituted by deuterium.

As used herein, and unless otherwise specified, the term "about", when used in connection with a numeric value or range of values may vary by 5%, 4%, 3%, 2%, 1%, 0.9%, 0.8%, 0.7%, 0.6%, 0.5%, 0.4%, 0.3%, 0.2% or 0.1% of the recited value or range of values. In some embodiments, the numeric value or range of values vary by 5%.

Crystal Forms of Enantiomeric Amisulpride

In various embodiments, the present inventions make use of a distinct polymorph of (R)-(+)-amisulpride, (S)-(−)-amisulpride, or both, in various embodiments of the compositions, formulations, methods and medicaments of the present inventions.

Polymorphism is the ability of an element or compound to crystallize into distinct crystalline phases. Although the term polymorph implies more than one morphology, the term is still used in the art, and herein, to refer to a crystalline structure of a compound as a polymorph even when only one crystalline phase is currently known. Thus, polymorphs are distinct solids sharing the same molecular formula as other polymorphs and the amorphous (non-crystalline) phase, however since the properties of any solid depends on its structure, polymorphs often exhibit physical properties distinct from each other and the amorphous phase, such as different solubility profiles, different melting points, different dissolution profiles, different thermal stability, different photostability, different hygroscopic properties, different shelf life, different suspension properties and different physiological absorption rates. Inclusion of a solvent in the crystalline solid leads to solvates, and in the case of water as a solvent, hydrates, often leads to a distinct crystalline form with one or more physical properties that are distinctly different from the non-solvated and non-hydrated (e.g., free base) crystalline form. In various embodiments, Form A and A' are anhydrous, e.g., substantially free of water and solvent.

As used herein, the term "polymorph" refers to different crystal structures achieved by a particular chemical entity. As used herein, the term "solvate" refers to a crystal form where a stoichiometric or non-stoichiometric amount of solvent, or mixture of solvents, is incorporated into the crystal structure. Similarly, the term "hydrate" refers to a crystal form where a stoichiometric or non-stoichiometric amount of water is incorporated into the crystal structure.

In various embodiments of the compositions of the present inventions, (R)-amisulpride and (S)-amisulpride are independently provided in a free base crystal form, and thus without any water or solvent incorporated into the crystal structure. It has been found that (R)-amisulpride and (S)-amisulpride can exist in at least one such free base crystal form, or polymorph, which is referred to herein as Form A for crystalline (R)-amisulpride, and Form A' for crystalline (S)-amisulpride.

Form A and Form A' are described herein, and further described in U.S. Provisional Patent Application Ser. No. 62/594,851 filed contemporaneously with the present application; and which is hereby incorporated herein by reference in its entirety. Form A and Form A' are also described U.S. Provisional Patent Application Ser. No. 62/594,851 filed on Mar. 30, 2018, and is hereby incorporated herein by reference in its entirety.

Crystal forms of amisulpride, enantiomeric amisulpride, and crystalline forms of their salts, hydrates and solvates, including those of the present inventions, may be characterized and differentiated using a number of conventional analytical techniques, including but not limited to X-ray powder diffraction (XRPD) patterns, nuclear magnetic resonance (NMR) spectra, Raman spectra, Infrared (IR) absorption spectra, dynamic vapor sorption (DVS), Differential Scanning calorimetry (DSC), and melting point. Chemical purity may be characterized using a number of conventional analytical techniques, including but not limited to high performance liquid chromatography (HPLC) and gas chromatography (GC). For example, one skilled in the art could use a reverse phase gradient HPLC method or a reverse phase isocratic HPLC method to determine organic impurities, a headspace GC method to determine residual solvents, coulometric titration (Karl Fischer) to determine water content, and a reverse phase isocratic HPLC method or a polar organic phase isocratic HPLC method to determine the amount of drug product in a sample. Chiral purity (also known as enantiomeric purity) may be characterized using a number of conventional analytical techniques, including but not limited to chiral high performance liquid chromatography (HPLC).

In various embodiments, the crystal forms of racemic amisulpride, enantiomeric amisulpride, and enantiomeric amisulpride solvates are characterized by X-ray powder diffraction (XRPD). XRPD is a technique of characterizing a powdered sample of a material by measuring the diffraction of X-rays by the material. The result of an XRPD experiment is a diffraction pattern. Each crystalline solid produces a distinctive diffraction pattern containing sharp peaks as a function of the scattering angle 20 (2-theta). Both the positions (corresponding to lattice spacing) and the relative intensity of the peaks in a diffraction pattern are indicative of a particular phase and material. This provides a "fingerprint" for comparison to other materials. In contrast to a crystalline pattern comprising a series of sharp peaks, amorphous materials (liquids, glasses etc.) produce a broad background signal in a diffraction pattern.

It is to be understood that the apparatus employed, humidity, temperature, orientation of the powder crystals, and other parameters involved in obtaining an XRPD pattern may cause some variability in the appearance, intensities, and positions of the lines in the diffraction pattern. An XRPD pattern that is "substantially in accord with" that of a Figure provided herein (e.g., FIG. 7B) is an XRPD pattern that would be considered by one skilled in the art to represent a compound possessing the same crystal form as the compound that provided the XRPD pattern of that Figure. That is, the XRPD pattern may be identical to that of the Figure, or more likely it may be somewhat different. Such an XRPD pattern may not necessarily show each of the lines of the diffraction patterns presented herein, and/or may show a slight change in appearance, intensity, or a shift in position of said lines resulting from differences in the conditions involved in obtaining the data. A person skilled in the art is capable of determining if a sample of a crystalline compound has the same form as, or a different form from, a form disclosed herein by comparison of their XRPD patterns.

Figure 7A:
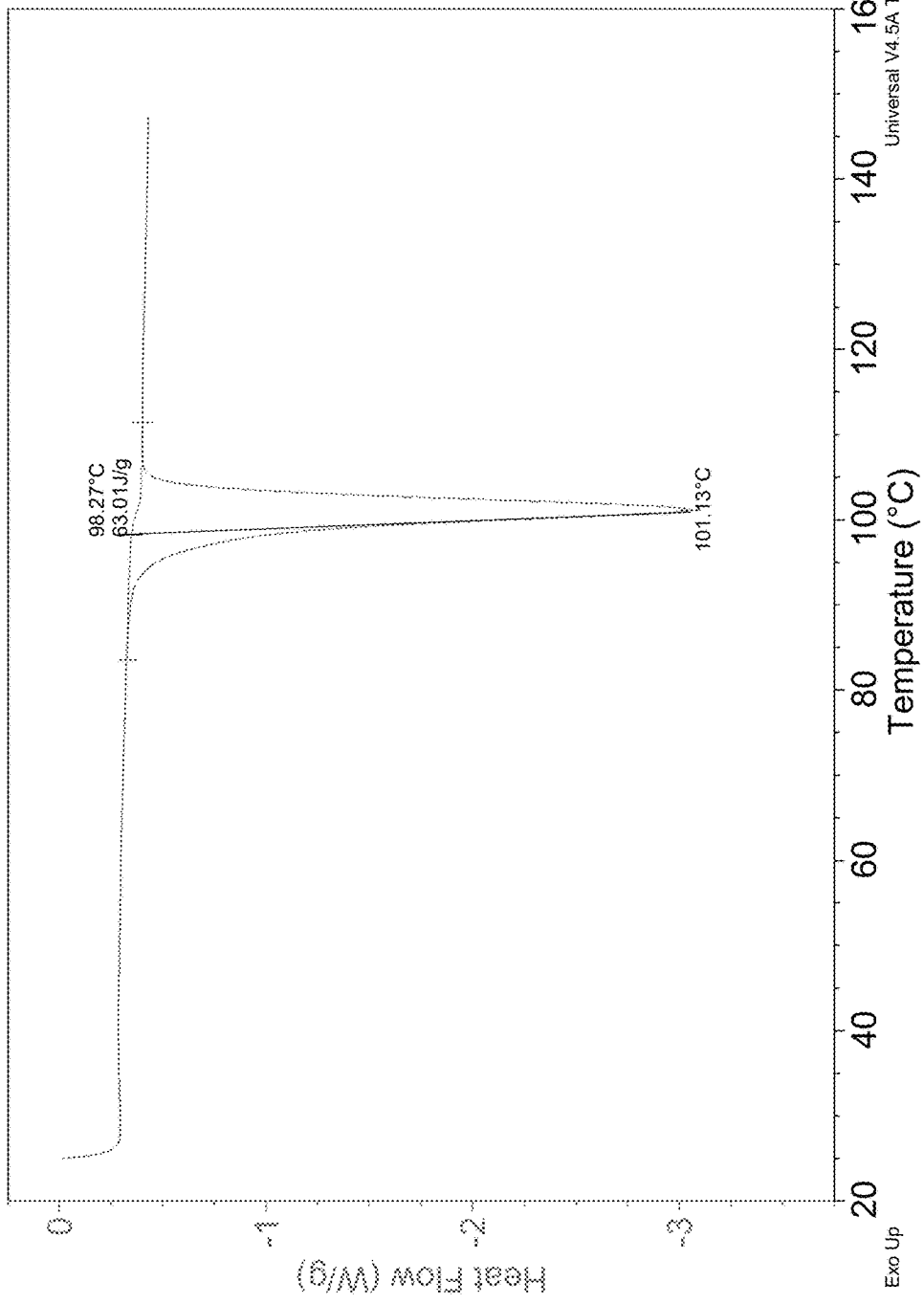
FIGS. 7A-7C present various analytical data and images for Form A crystals of (R)-amisulpride, where
Figure 7B:
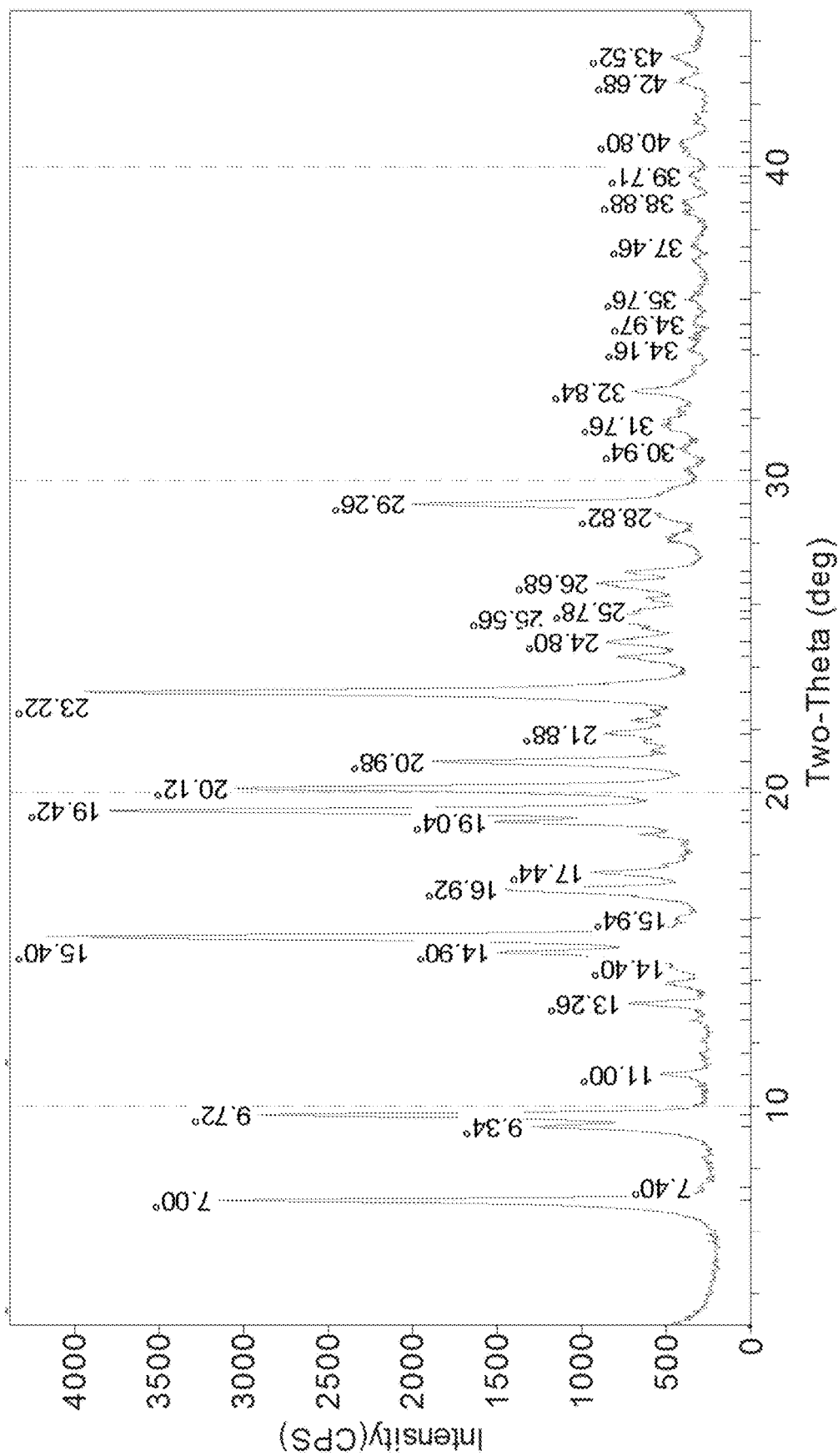
Figure 8A:
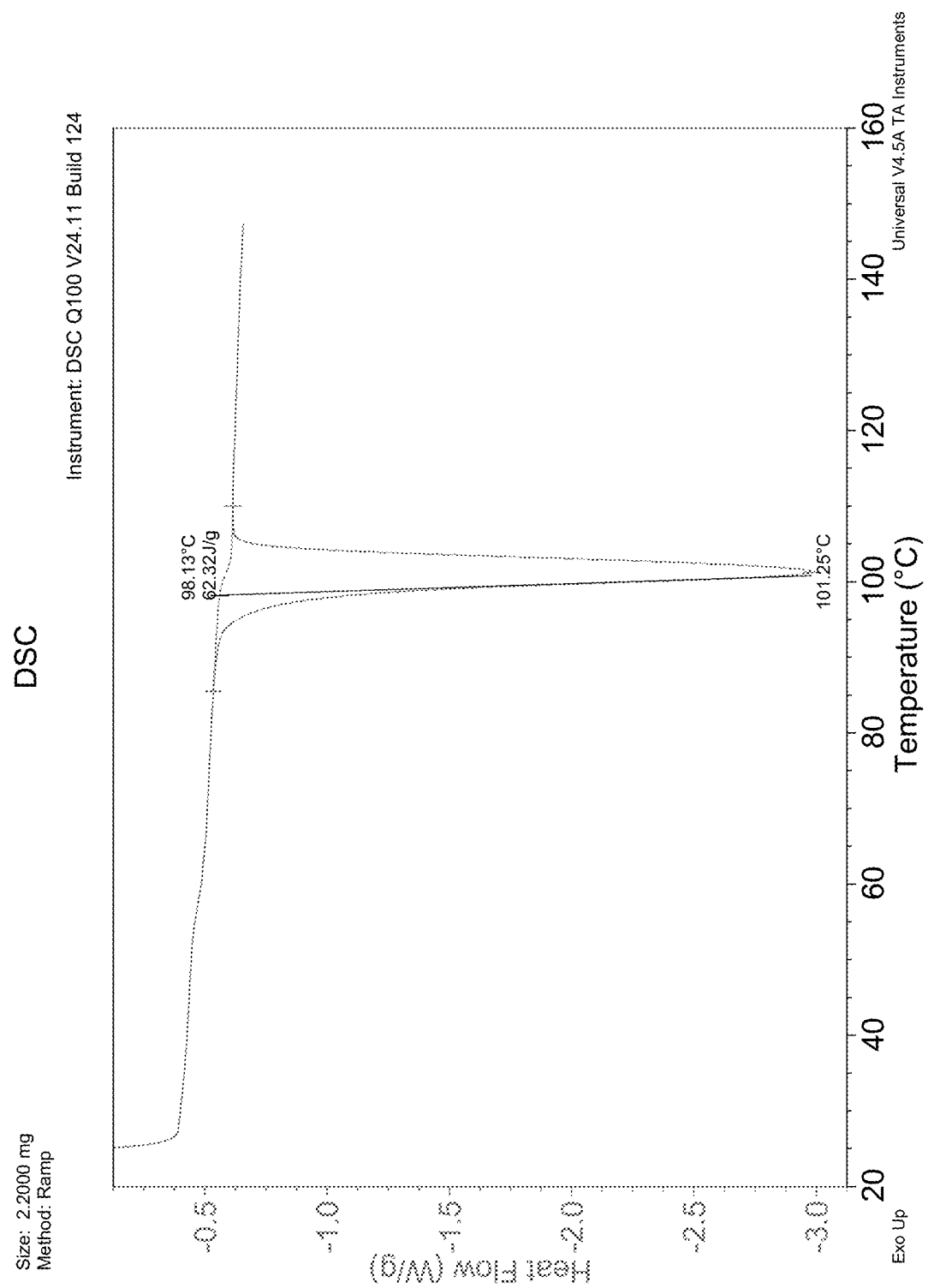
FIGS. 8A-8D present various analytical data and images for Form A' crystals of (S)-amisulpride, where
Figure 8B:
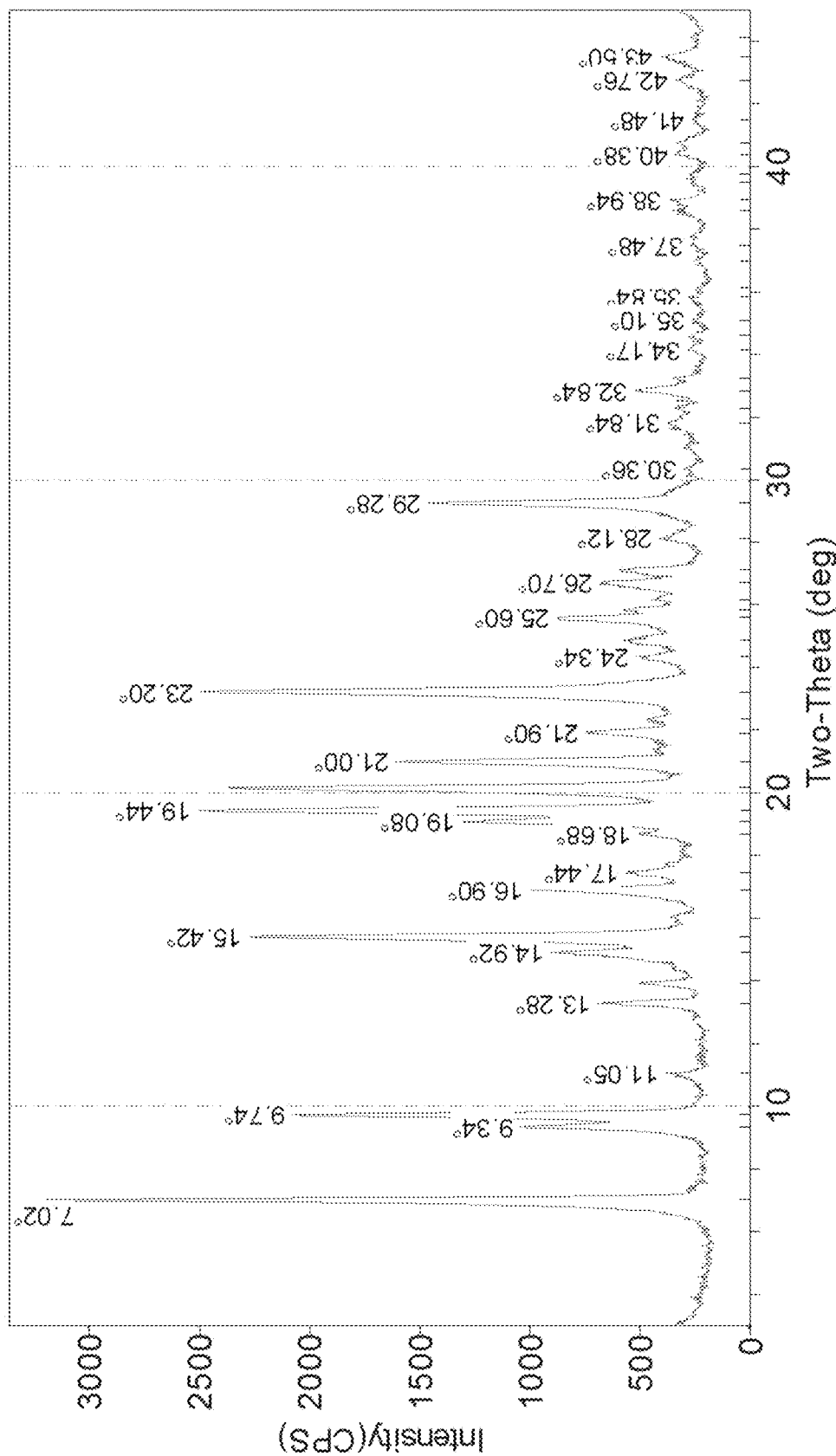

For example, one skilled in the art could use a chiral HPLC method (e.g. polar organic mode isocratic HPLC) to determine the enantiomeric identity of an amisulpride sample and if, for example, the sample is identified as (R)-amisulpride, one skilled in the art can overlay an XRPD pattern of the amisulpride sample with FIG. 7B and/or FIG. 8B, and using expertise and knowledge in the art, readily determine whether the XRPD pattern of the sample is substantially in accordance with the XRPD pattern of crystalline (R)-amisulpride of Form A presented in FIG. 7B. If, for example, HPLC identifies the sample as being (R)-amisulpride and the sample XRPD pattern is substantially in accord with FIG. 7B, the sample can be readily and accurately identified as (R)-amisulpride of Form A.

In various embodiments, the crystal forms of racemic amisulpride, enantiomeric amisulpride, and enantiomeric amisulpride solvates are characterized by melting point. Melting points were determined by conventional methods such as capillary tube and may exhibit a range over which complete melting occurs, or in the case of a single number, a melt point of that temperature ±1° C.

In various embodiments, the crystal forms of racemic amisulpride, enantiomeric amisulpride, and enantiomeric amisulpride solvates are characterized by differential scanning calorimetry (DSC). DSC is a thermoanalytical technique in which the difference in the amount of heat required to increase the temperature of a sample and a reference is measured as a function of temperature. Both the sample and reference are maintained at substantially the same temperature throughout the experiment. The result of a DSC experiment is a curve of heat flow versus temperature, called a DSC thermogram.

In various embodiments, the hygroscopicity of crystal forms of racemic amisulpride, enantiomeric amisulpride, and enantiomeric amisulpride solvates are characterized by dynamic vapor sorption (DVS). DVS is a gravimetric technique that measures how much of a solvent is absorbed by a sample by varying the vapor concentration surrounding the sample (e.g., relative humidity) and measuring the change in mass. In the present application, DVS is used to generate water sorption isotherms, which represent the equilibrium amount of vapor sorbed as a function of steady state relative vapor pressure at a constant temperature.

As used herein, the term "substantially non-hygroscopic" refers to a compound exhibiting less than a 1% maximum mass change in water sorption isotherms, at 25° C. scanned over 0 to 95% relative humidity, as measured by dynamic vapor sorption (DVS).

In various embodiments, the compositions of the present inventions use new crystalline forms of enantiomeric amisulpride, Form A and Form A'. Forms A and A' have been found to be a distinct polymorph, different from the crystalline form of a racemic amisulpride, having a distinctly different structure and XRPD pattern, as well as physical properties. Table 7 compares various properties and data on Form A crystals of (R)-amisulpride and Form A' crystals of (S)-amisulpride where the Figure references are to figures in the present application. The Specific Rotation data was obtained by polarimetry, the subject compound was dissolved in methanol at nominal concentration of c=1 using the 589 nm (Sodium Line). It is to be understood that upon dissolution of the compound it is no longer of a crystalline form, thus one of ordinary skill in the art will understand that the specific rotation in Table 7 refers to that of the non-crystalline compound.

TABLE 7

Figure 7C:
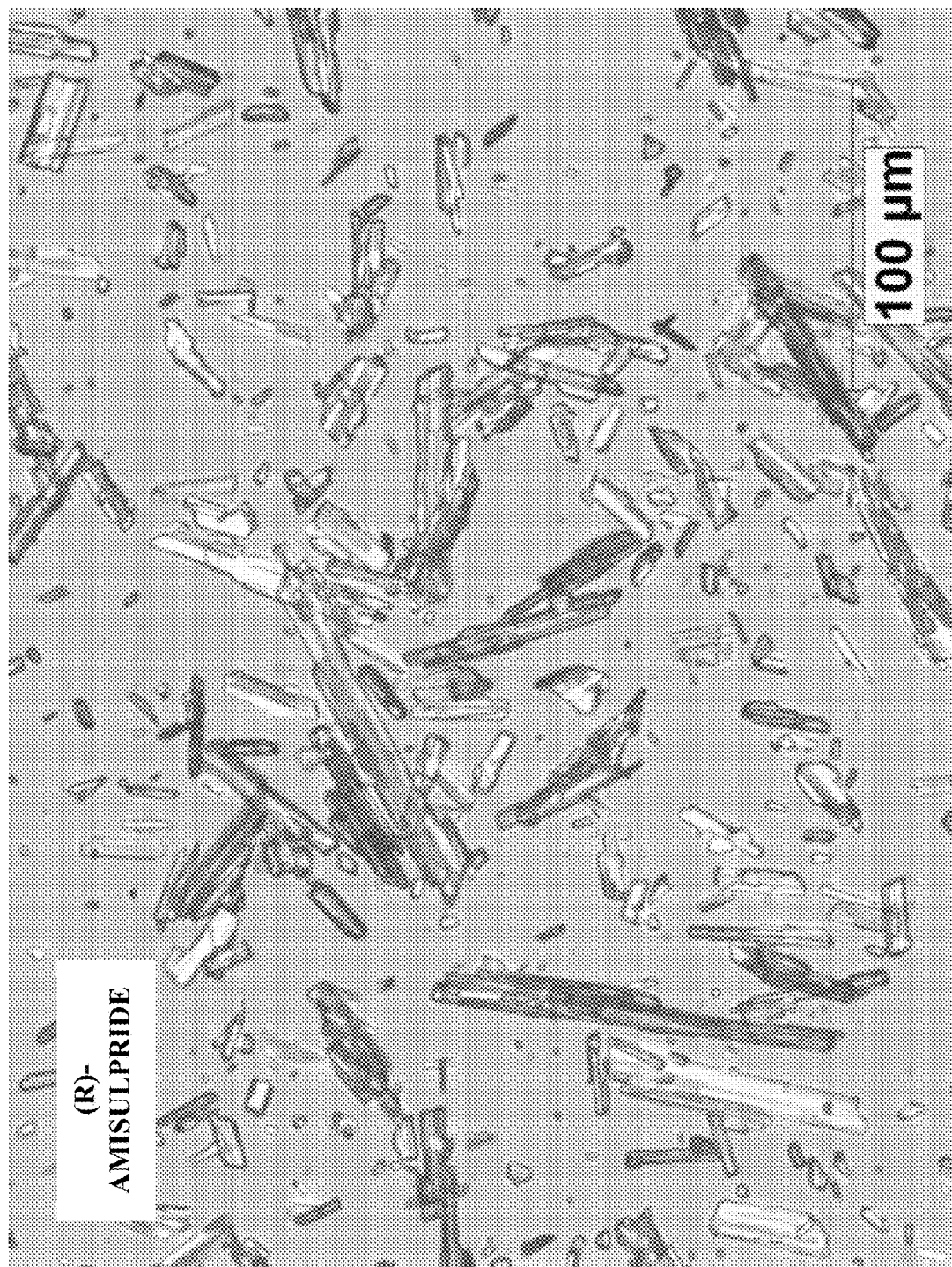
Figure 8C:
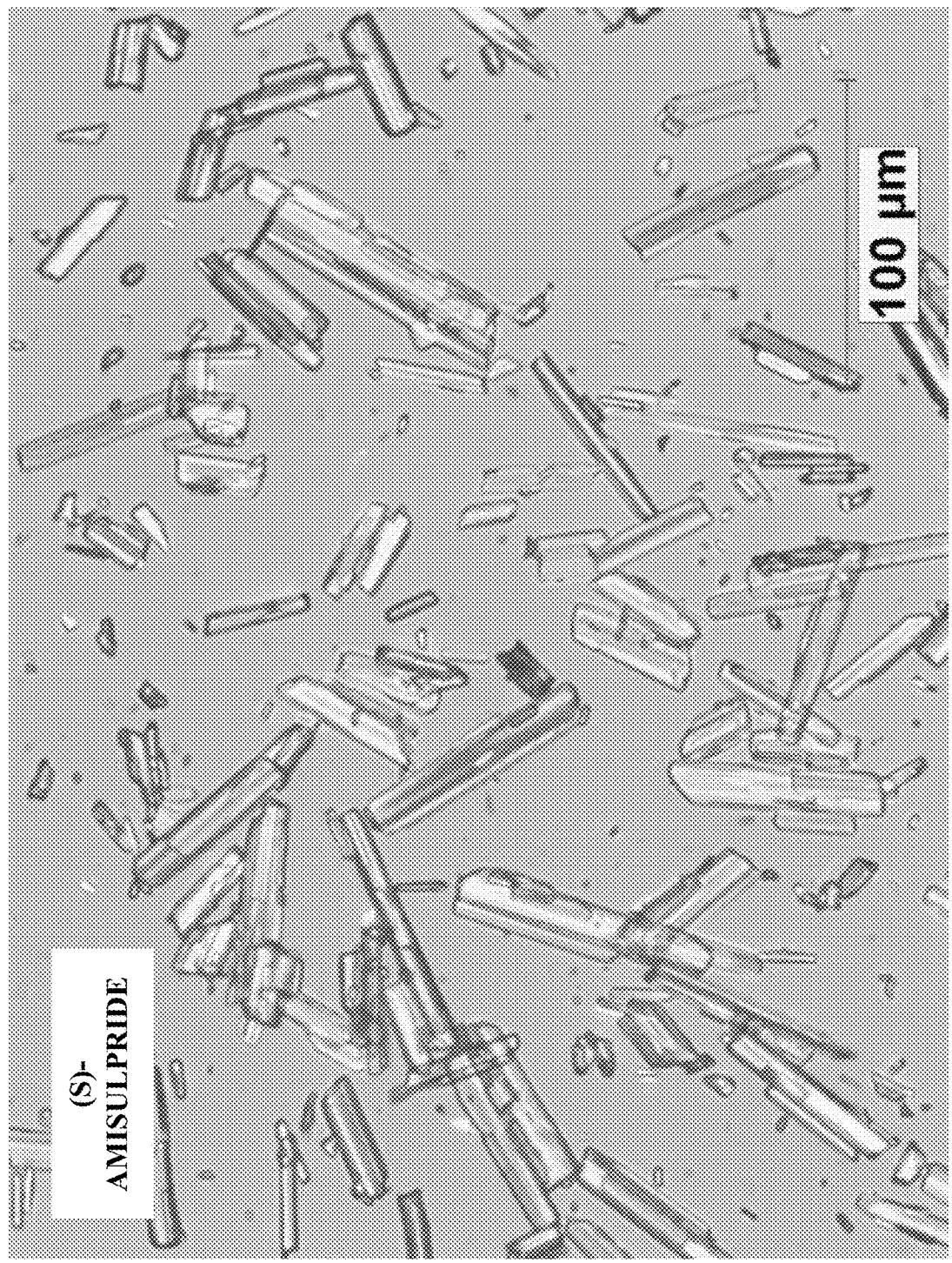

| Physical Property | Compound | |
| --- | --- | --- |
| | (R)-amisulpride Form A | (S)-amisulpride Form A' |
| # of Solid Phases | 1 | 1 |
| Melting Point, ° C. | 102 | 102 |
| DSC Thermograph | FIG. 7A | FIG. 8A |
| XRPD Pattern | FIG. 7B | FIG. 8B |
| Micrograph Image | FIG. 7C | FIG. 8C |
| Specific Rotation | $[\alpha]^{20}_D = 5.1 \cdot 10^1$ (MeOH, c = 1) | $[\alpha]^{20}_D = -5.0 \cdot 10^1$ (MeOH, c = 1) |
| Solubility (mg/mL): | | |
| Water | 2 | 2 |

TABLE 7-continued

| Physical Property | Compound | |
| --- | --- | --- |
| | (R)-amisulpride Form A | (S)-amisulpride Form A' |
| (solution pH) | (10.2) | (10.3) |
| 0.05M Acetate Buffer | >100 | >100 |
| (solution pH) | (4.5) | (4.5) |
| Ethyl Acetate | 3.9 | 3.9 |
| Acetone/MtBE 1:4 | 8 | 8 |
| Acetone/MtBE 1:9 | 2 | 2 |
| Simulated Gastric Fluid (no enzyme) | >100 (pH adjusted to 1.1) | >100 (pH adjusted to 1.2) |
| Simulated Intestinal Fluid (no enzyme) | >100 (pH adjusted to 6.7) | >100 (pH adjusted to 6.9) |

In various embodiments, Form A is a crystalline form of (R)-amisulpride characterized by an XRPD pattern comprising peaks, in terms of 2-theta, at 7.0±0.2°, 9.7±0.2°, and 19.4±0.2°. In various embodiments, the crystalline form of (R)-amisulpride is characterized by three or more peaks in its XRPD pattern selected from those at 7.0±0.2°, 9.7±0.2°, 15.4±0.2°, 19.4±0.2°, 20.1±0.2°, 21.0±0.2°, 23.2±0.2°, and 29.3±0.2°, in terms of 2-theta. In various embodiments, the crystalline form of (R)-amisulpride is characterized by an XRPD pattern substantially in accord with FIG. 7B.

In various embodiments, the crystalline Form A of (R)-amisulpride is characterized by the following properties, an XRPD pattern comprising peaks, in terms of 2-theta, at 7.0±0.2°, 9.7±0.2°, and 19.4±0.2°, a melting point of 102±3° C., a chiral purity of greater than about 99%, a chemical purity greater than about 99%, a residual solvent content of less than about 1000 ppm, and is substantially non-hygroscopic.

In various embodiments, the crystalline Form A of (R)-amisulpride is characterized by the following properties, an XRPD pattern comprising peaks, in terms of 2-theta, at 7.0±0.2°, 9.7±0.2°, and 19.4±0.2° and one or more of the following:
  (a) the powder x-ray diffraction pattern further comprising peaks, in terms of 2-theta, at 15.4±0.2° and 29.3±0.2°;
  (b) the powder x-ray diffraction pattern further comprising peaks, in terms of 2-theta, at 20.1±0.2°, 21.0±0.2°, and 23.2±0.2°;
  (c) a melting point of 102±3° C.;
  (d) a differential scanning calorimetry thermogram comprising a peak at 101±3° C.;
  (e) a differential scanning calorimetry thermogram substantially in accord with FIG. 7A;
  (f) a chiral purity of greater than about: (i) 90%, (ii) 95%, (iii) 97%, (iv) 99%, (v) 99.5%, (vi) 99.7%, or (vii) 99.9%;
  (g) a chemical purity of greater than about: (i) 80%, (ii) 90%, (iii) 95%, (iv) 97%, (v) 99%, (vi) 99.5%, (vii) 99.7%, or (viii) 99.9%;
  (h) residual solvents present in an amount less than about: (i) 8000 ppm, (ii) 6000 ppm, (iii) 4000 ppm, (iv) 2000 ppm, (v) 1000 ppm, (vi) 800 ppm, or 500 ppm; and
  (i) as measured by dynamic vapor sorption (DVS), at 25° C. scanned over 0 to 95% relative humidity, a maximum mass change in water sorption isotherms of less than about (i) 2%, (ii) 1%, (iii) 0.5%, or (iv) 0.4%.

In various embodiments, the crystalline Form A' of (S)-amisulpride is characterized by an XRPD pattern comprising peaks, in terms of 2-theta, at 7.0±0.2°, 9.7±0.2°, and 19.4±0.2°. In various embodiments, the present inventions provide a crystalline form of (S)-amisulpride characterized by three or more peaks in its XRPD pattern selected from those at 7.0±0.2°, 9.7±0.2°, 15.4±0.2°, 19.4±0.2°, 20.1±0.2°, 21.0±0.2°, 23.2±0.2°, and 29.3±0.2°, in terms of 2-theta. In various embodiments, the present inventions provide a crystalline form of (S)-amisulpride characterized by an XRPD pattern substantially in accord with FIG. 8B.

In various embodiments, the crystalline Form A' of (S)-amisulpride is characterized by the following properties, an XRPD pattern comprising peaks, in terms of 2-theta, at 7.0±0.2°, 9.7±0.2°, and 19.4±0.2°, a melting point of 102±3° C., a chiral purity of greater than about 99%, a chemical purity greater than about 99%, a residual solvent content of less than about 1000 ppm, and is substantially non-hygroscopic.

In various embodiments, the crystalline Form A' of (S)-amisulpride is characterized by the following properties, an XRPD pattern comprising peaks, in terms of 2-theta, at 7.0±0.2°, 9.7±0.2°, and 19.4±0.2° and two or more of the following:
  (a) the powder x-ray diffraction pattern further comprising peaks, in terms of 2-theta, at 15.4±0.2° and 29.3±0.2°;
  (b) the powder x-ray diffraction pattern further comprising peaks, in terms of 2-theta, at 20.1±0.2°, 21.0±0.2°, and 23.2±0.2°;
  (c) a melting point of 102±3° C.;
  (d) a differential scanning calorimetry thermogram comprising a peak at 101±3° C.;
  (e) a differential scanning calorimetry thermogram substantially in accord with FIG. 8A;
  (f) a chiral purity of greater than about: (i) 90%, (ii) 95%, (iii) 97%, (iv) 99%, (v) 99.5%, (vi) 99.7%, or (vii) 99.9%;
  (g) a chemical purity of greater than about: (i) 80%, (ii) 90%, (iii) 95%, (iv) 97%, (v) 99%, (vi) 99.5%, (vii) 99.7%, or (viii) 99.9%;
  (h) residual solvents present in an amount less than about: (i) 8000 ppm, (ii) 6000 ppm, (iii) 4000 ppm, (iv) 2000 ppm, (v) 1000 ppm, (vi) 800 ppm, or 500 ppm; and
  (i) as measured by dynamic vapor sorption (DVS), at 25° C. scanned over 0 to 95% relative humidity, a maximum mass change in water sorption isotherms of less than about (i) 2%, (ii) 1%, (iii) 0.5%, or (iv) 0.4%.

In various embodiments, crystalline enantiomeric amisulpride of Form A is characterized at least in part by having an XRPD pattern comprising peaks, in terms of 2-theta, at 7.0±0.2°, 9.7±0.2°, and 19.4±0.2° and not having a peak, in terms of 2-theta, at 6.6±0.3° that has a height greater than about 5% of the highest of the peaks at 7.0±0.2°, 9.7±0.2°, and 19.4±0.2°.

In various embodiments, crystalline enantiomeric amisulpride of Form A' is characterized at least in part by having an XRPD pattern comprising peaks, in terms of 2-theta, at 7.0±0.2°, 9.7±0.2°, and 19.4±0.2° and not having a peak, in terms of 2-theta, at 6.6±0.3° that has a height greater than about 5% of the highest of the peaks at 7.0±0.2°, 9.7±0.2°, and 19.4±0.2°.

In various embodiments, XRPD information and patterns are used to characterize Forms A and A'. FIGS. 7B and 8B XRPD patterns for, respectively, (R)-amisulpride Form A and (S)-amisulpride Form A'. Tables 8-11 present further information and details on XRPD patterns obtained for Forms A and A'.

The XRPD patterns of both (R)-amisulpride Form A (FIG. 7B) and (S)-amisulpride Form A' (FIG. 8B) show prominent peaks, in terms of 2-theta, at 7.0±0.2°, 9.7±0.2°, 15.4±0.2°, 19.4±0.2°, 20.1±0.2°, 21.0±0.2°, 23.2±0.2°, and 29.3±0.2°.

In various embodiments, provided herein is a crystalline form of (R)-(+)-amisulpride characterized by a powder x-ray diffraction pattern comprising peaks, in terms of 2-theta, at 7.0±0.2°, 9.7±0.2°, and 15.4±0.2°. In some embodiment, the crystalline form of (R)-(+)-amisulpride is further characterized by the powder x-ray diffraction pattern further comprising peaks, in terms of 2-theta, at 9.3±0.2°, and 19.4±0.2°. In some embodiment, the crystalline form of (R)-(+)-amisulpride is further characterized by the powder x-ray diffraction pattern further comprising peaks, in terms of 2-theta, at 14.9±0.2°, 16.9±0.2°, and 20.1±0.2°. In some embodiment, the crystalline form of (R)-(+)-amisulpride is further characterized by the powder x-ray diffraction pattern further comprising peaks, in terms of 2-theta, at 19.0±0.2°, 21.0±0.2°, and 23.2±0.2°.

In various embodiments, provided herein is a crystalline form of (S)-(−)-amisulpride characterized by a powder x-ray diffraction pattern comprising peaks, in terms of 2-theta, at 7.0±0.2°, 9.7±0.2°, and 15.4±0.2°. In some embodiments, the crystalline form of (S)-(−)-amisulpride is further characterized by the powder x-ray diffraction pattern further comprising peaks, in terms of 2-theta, at 9.3±0.2°, and 19.4±0.2°. In some embodiments, the crystalline form of (S)-(−)-amisulpride is further characterized by the powder x-ray diffraction pattern further comprising peaks, in terms of 2-theta, at 14.9±0.2°, 16.9±0.2°, and 20.2±0.2°. In some embodiments, the crystalline form of (S)-(−)-amisulpride is further characterized by the powder x-ray diffraction pattern further comprising peaks, in terms of 2-theta, at 19.1±0.2°, 21.0±0.2°, and 23.2±0.2°.

The DSC thermograms of FIGS. 7A and 8A were obtained using TA Instruments Q100 differential scanning calorimeter. Each sample was heated in a sealed pan under a 50 mL/min nitrogen purge at a heating rate of 10° C./min, from a starting temperature of 25° C. up to a final temperature of 150° C. or 200° C.

The micrograph images of FIGS. 7C and 8C were obtained using the Nikon Microphot polarizing light microscope. Samples were prepared in Isopar G/3% Lecithin, and imaged using cross-polarized light with a quarter wave plate.

The XRPD patterns of FIGS. 7B and 8B were performed using a Rigaku MiniFlex II Desktop X-Ray diffractometer using Cu radiation. The tube voltage and amperage were set to 30 kV and 15 mA, respectively. The scattering slit was fixed at 1.25° and the receiving slit was fixed at 0.3 mm. Diffracted radiation was detected by a NaI scintillation detector. A 0-2θ continuous scan at 1.0°/min with a step size of 0.02-0.05° from 3 to 45° 2θ was used. Data were collected and analyzed using Jade 8.5.4. Each sample was prepared for analysis by placing it in a low background, round, 0.1 mm indent sample holder. In FIGS. 7B and 8B, 2-Theta angles in degrees (x-axis) are plotted against peak intensity in terms of the count rate per second (y-axis).

Crystals of (R)-Amisulpride Form A

For single crystal structure determination, a colorless needle having approximate dimensions of 0.25×0.04×0.02 mm$^3$, was mounted on a polymer loop in random orientation. Preliminary examination and data collection were performed on a Rigaku SuperNova diffractometer, equipped with a copper anode microfocus sealed X-ray tube (Cu Kα$\lambda$=1.54184 Å) and a Dectris Pilatus3 R 200K hybrid pixel array detector. Cell constants and an orientation matrix for data collection were obtained from least-squares refinement using the setting angles of 16528 reflections in the range 3.5080°<θ<77.29500. The data was collected to a maximum diffraction angle (2θ) of 155.296°, at a temperature of 100 K. A total of 35826 reflections were collected, of which 12849 were unique. Lorentz and polarization corrections were applied to the data. The linear absorption coefficient is 1.728 mm$^{-1}$ for Cu Kα radiation. An empirical absorption correction using CRYSALISPRO was applied (CrysAlisPro 1.171.38.41r (Rigaku Oxford Diffraction, 2015). Transmission coefficients ranged from 0.659 to 1.000. Intensities of equivalent reflections were averaged. The agreement factor for the averaging was 5.72% based on intensity.

Figure 16:
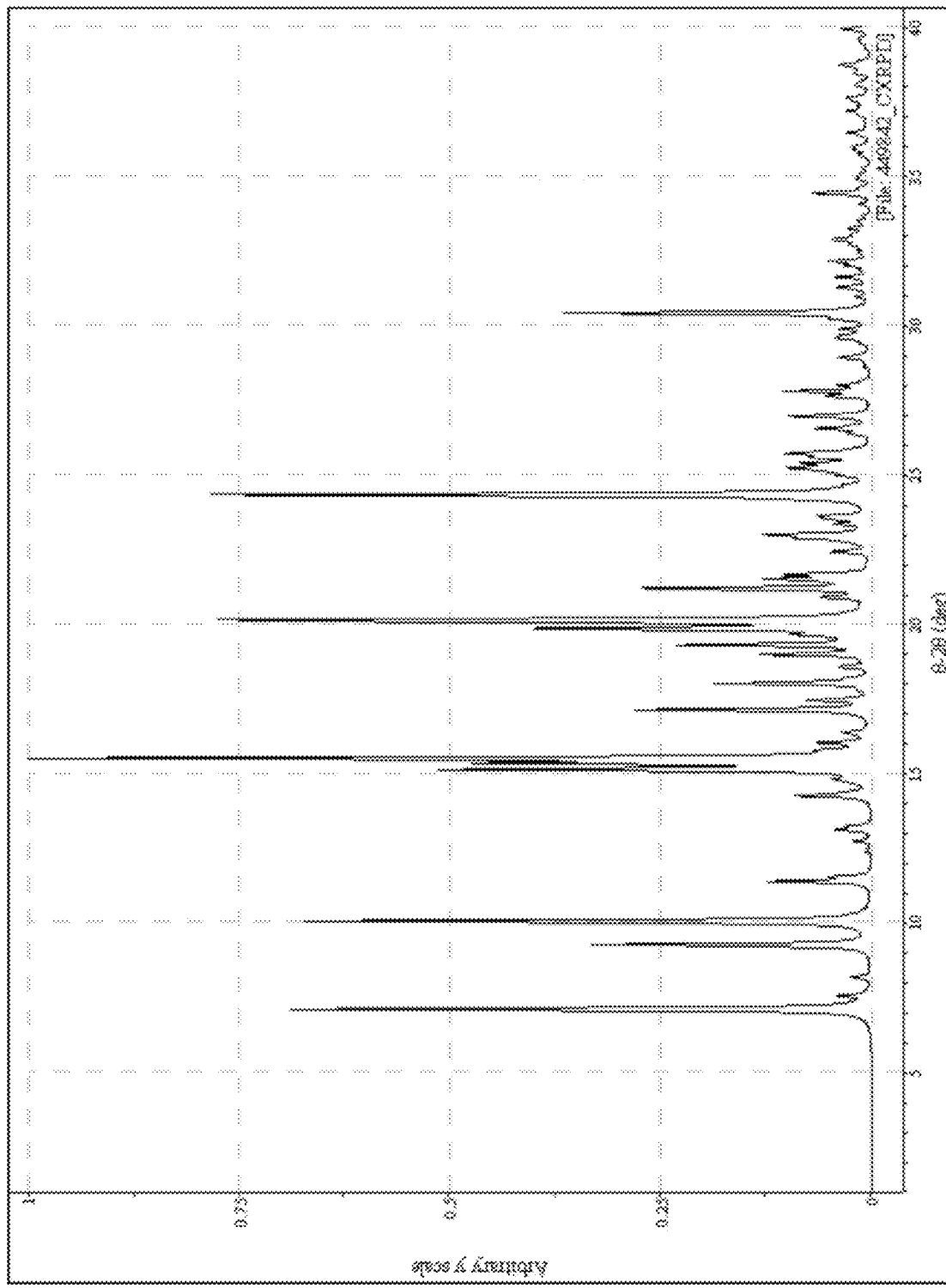
FIG. 16 presents a calculated XRPD based on single crystal structure determination for (R)-amisulpride Form A.

A calculated XRPD pattern was generated for Cu radiation using MERCURY and the atomic coordinates, space group, and unit cell parameters from the single crystal structure (Macrae, C. F. et al., *J. J. Appl. Cryst.*, 2006, 39, 453-457). It is to be understood that because the single crystal data are collected at low temperatures (100 K), peak shifts may be evident between the pattern calculated from low temperature data and room temperature experimental powder diffraction patterns, particularly at high diffraction angles. FIG. 16 shows the calculated XRPD pattern of Form A.

In various embodiments, the crystal system of (R)-amisulpride Form A crystals is triclinic and the space group is P1. Referring to FIG. 7C, by microscopy the solids consisted of birefringent spherulites of long needles. Further details of the crystal data and crystallographic data collection parameters are summarized in Table 8 and a listing of the peaks of the experimental XRPD of FIG. 7B are listed in Table 9. The calculated XRPD pattern of Form A is shown in FIG. 16.

In some embodiment, the crystalline form of (R)-(+)-amisulpride is characterized by single crystal x-ray diffraction having a P1 space group and cell formula units (Z) of 4. In some embodiments, crystalline form of (R)-(+)-amisulpride has unit cell parameters: a is about 12.3 Å, b is about 12.8 Å, c is about 14.1 Å, α is about 64.0°, β is about 73.4°, and γ is about 75.9°.

TABLE 8

| (R)-amisulpride Form A Single Crystal Data and Data Collection Parameters | |
|---|---|
| Empirical formula | $C_{17}H_{27}N_3O_4S$ |
| Molecular weight (g mol$^{-1}$) | 369.47 |
| Temperature (K) | 100 |
| Wavelength (Å) | 1.54184 |
| Crystal system | triclinic |
| Space group | P1 |
| Unit cell parameters | |
| a = 12.3348(4) Å | α = 64.033(4)° |
| b = 12.8343(6) Å | β = 73.431(3)° |
| c = 14.1403(6) Å | γ = 75.881(3)° |
| Unit cell volume (Å$^3$) | 1910.47(15) |
| Cell formula units, Z | 4 |
| Calculated density (g cm$^{-3}$) | 1.285 |
| Absorption coefficient (mm$^{-1}$) | 1.728 |
| F(000) | 792 |
| Crystal size (mm$^3$) | 0.25 × 0.04 × 0.02 |
| Reflections used for cell measurement | 16528 |
| ϑ range for cell measurement | 3.5080°-77.2950° |
| Total reflections collected | 35826 |
| Index ranges | −15 ≤ h ≤ 15; −16 ≤ k ≤ 16; −17 ≤ l ≤ 17 |
| ϑ range for data collection | $\vartheta_{min}$ = 3.552°, $\vartheta_{max}$ = 77.648° |
| Completeness to $\theta_{max}$ | 97.6% |
| Completeness to $\theta_{full}$ = 67.684° | 99.8% |
| Absorption correction | multi-scan |
| Transmission coefficient range | 0.659-1.000 |
| Refinement method | full matrix least-squares on F$^2$ |
| Independent reflections | 12849 [$R_{int}$ = 0.0572, $R_\sigma$ = 0.0533] |
| Reflections [I > 2σ(I)] | 11460 |
| Reflections/restraints/parameters | 12849/3/954 |
| Goodness-of-fit on F$^2$ | S = 1.02 |
| Final residuals [I > 2σ(I)] | R = 0.0607, $R_w$ = 0.1675 |
| Final residuals [all reflections] | R = 0.0658, $R_w$ = 0.1739 |
| Largest diff. peak and hole (e Å$^{-3}$) | 0.640, −0.670 |
| Max/mean shift/standard uncertainty | 0.000/0.000 |
| Absolute structure determination | Flack parameter: 0.009(18) |
| | Hooft parameter: 0.007(12) |
| | Friedel coverage: 60.2% |

TABLE 9

| (R)-amisulpride Form A XRPD (FIG. 7B) Peak List | |
|---|---|
| 2-Theta | Relative Height |
| 7.00 | 75 |
| 7.42 | 1.6 |
| 9.34 | 26.9 |
| 9.72 | 68.3 |
| 9.95 | 1.5 |
| 11.00 | 6.7 |
| 11.66 | 1.2 |
| 12.72 | 2.3 |
| 13.26 | 11.3 |
| 13.90 | 5.2 |
| 14.41 | 4.8 |
| 14.72 | 13.5 |
| 14.90 | 31 |
| 15.40 | 100 |
| 15.94 | 4 |
| 16.64 | 7.9 |
| 16.92 | 28 |
| 17.44 | 14.8 |
| 17.70 | 4 |
| 18.66 | 7.5 |

TABLE 9-continued (R)-amisulpride Form A XRPD (FIG. 7B) Peak List

| 2-Theta | Relative Height |
|---|---|
| 19.04 | 29.3 |
| 19.42 | 87 |
| 20.12 | 63.7 |
| 20.98 | 34.8 |
| 21.62 | 3.5 |
| 21.88 | 7.8 |
| 22.32 | 3.8 |
| 22.61 | 2.5 |
| 23.22 | 89.3 |
| 24.34 | 8.1 |
| 24.80 | 8.7 |
| 25.26 | 3 |
| 25.56 | 17 |
| 25.78 | 4.3 |
| 26.20 | 3.2 |
| 26.68 | 15.8 |
| 27.10 | 11.3 |
| 28.12 | 3.5 |
| 28.28 | 2.6 |
| 28.82 | 5.2 |
| 29.26 | 42.2 |
| 29.56 | 5.9 |
| 29.76 | 3.7 |
| 30.32 | 1.9 |
| 30.92 | 1.7 |
| 31.02 | 2.6 |
| 31.70 | 4.3 |
| 31.94 | 3.8 |
| 32.26 | 2.2 |
| 32.84 | 8.9 |
| 33.22 | 2.7 |
| 34.16 | 2.7 |
| 34.55 | 2.2 |
| 34.97 | 1.7 |
| 35.24 | 1.1 |
| 35.48 | 0.9 |
| 35.76 | 2.9 |
| 37.00 | 1.9 |
| 37.44 | 1.3 |
| 38.58 | 3.2 |
| 38.88 | 3.4 |
| 39.50 | 1.6 |
| 39.76 | 2.1 |
| 40.38 | 2.5 |
| 40.80 | 3.7 |
| 41.39 | 1.4 |
| 41.68 | 1.5 |
| 42.68 | 3.7 |
| 43.28 | 2.8 |
| 43.52 | 4.7 |

Crystals of (S)-Amisulpride Form A'

For single crystal structure determination, a colorless needle having approximate dimensions of 0.20×0.04×0.02 mm³, was mounted on a polymer loop in random orientation. Preliminary examination and data collection were performed on a Rigaku SuperNova diffractometer, equipped with a copper anode microfocus sealed X-ray tube (Cu Kα λ=1.54184 Å) and a Dectris Pilatus3 R 200K hybrid pixel array detector. Cell constants and an orientation matrix for data collection were obtained from least-squares refinement using the setting angles of 14943 reflections in the range 3.51700<θ<77.97400. The data was collected to a maximum diffraction angle (2θ) of 156.71°, at a temperature of 100 K. A total of 36278 reflections were collected, of which 12840 were unique. Lorentz and polarization corrections were applied to the data. The linear absorption coefficient is 1.728 mm-1 for Cu Kα radiation. An empirical absorption correction using CRYSALISPRO was applied (CrysAlisPro 1.171.38.41r (Rigaku Oxford Diffraction, 2015). Transmission coefficients ranged from 0.791 to 1.000. Intensities of equivalent reflections were averaged. The agreement factor for the averaging was 5.83% based on intensity.

Figure 17:
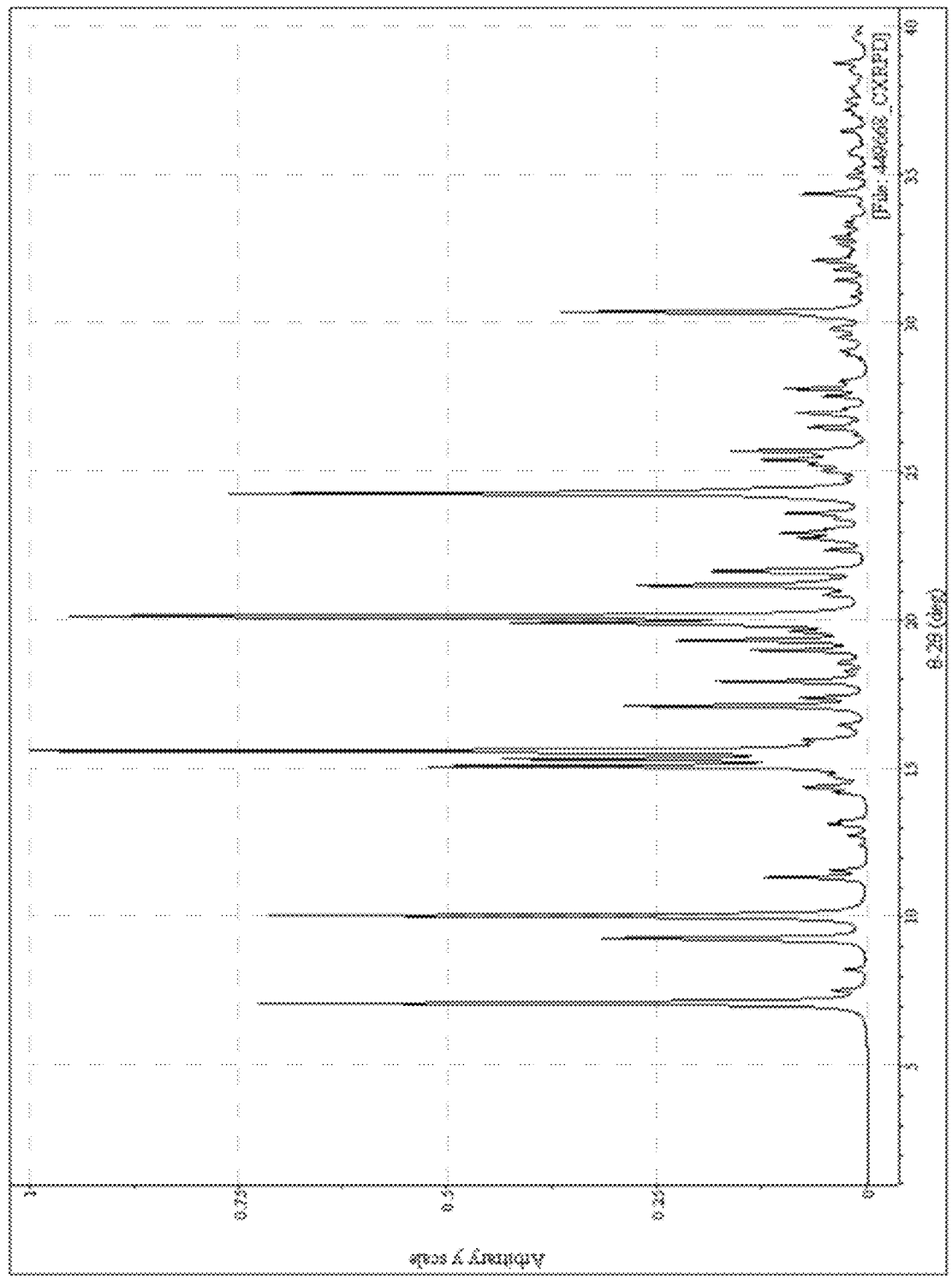
FIG. 17 presents a calculated XRPD based on single crystal structure determination for (S)-amisulpride Form A'.

A calculated XRPD pattern was generated for Cu radiation using MERCURY and the atomic coordinates, space group, and unit cell parameters from the single crystal structure (Macrae, C. F. et a., J. J. Appl. Cryst., 2006, 39, 453-457). It is to be understood that because the single crystal data are collected at low temperatures (100 K), peak shifts may be evident between the pattern calculated from low temperature data and room temperature experimental powder diffraction patterns, particularly at high diffraction angles. FIG. 17 shows the calculated XRPD pattern of Form A'.

In various embodiments, the crystal system of (S)-amisulpride Form A' crystals is triclinic and the space group is P1. Referring to FIG. 8C, by microscopy the solids consisted of birefringent spherulites of long needles. Further details of the crystal data and crystallographic data collection parameters are summarized in Table 10 and a listing of the peaks of the experimental XRPD of FIG. 8B are listed in Table 11. The calculated XRPD pattern of Form A' is shown in FIG. 17.

In some embodiments, the crystalline form of (S)-(−)-amisulpride is characterized by single crystal x-ray diffraction having a P1 space group and cell formula units (Z) of 4. In some embodiments, the crystalline form of (S)-(−)-amisulpride has unit cell parameters: a is about 12.4 Å, b is about 12.8 Å, c is about 14.1 Å, α is about 64.2°, β is about 73.6°, and γ is about 75.8°.

TABLE 10

(S)-amisulpride Form A' Single Crystal Data and Data Collection Parameters

| | |
|---|---|
| Empirical formula | $C_{17}H_{27}N_3O_4S$ |
| Formula weight (g mol$^{-1}$) | 369.47 |
| Temperature (K) | 100 |
| Wavelength (Å) | 1.54184 |
| Crystal system | triclinic |
| Space group | P1 |
| Unit cell parameters | |
| a = 12.3795(4) Å | α = 64.246(3)° |
| b = 12.7526(4) Å | β = 73.598(3)° |
| c = 14.1438(4) Å | γ = 75.797(3)° |
| Unit cell volume (Å³) | 1909.71(11) |
| Cell formula units, Z | 4 |
| Calculated density (g cm$^{-3}$) | 1.285 |
| Absorption coefficient (mm$^{-1}$) | 1.728 |
| F(000) | 792 |
| Crystal size (mm³) | 0.2 × 0.04 × 0.02 |

TABLE 10-continued (S)-amisulpride Form A' Single Crystal Data and Data Collection Parameters

| | |
|---|---|
| Reflections used for cell measurement | 14943 |
| ϑ range for cell measurement | 3.5170°-77.9740° |
| Total reflections collected | 36278 |
| Index ranges | $-15 \leq h \leq 14; -16 \leq k \leq 16; -17 \leq l \leq 17$ |
| ϑ range for data collection | $\vartheta_{min} = 3.542°, \vartheta_{max} = 78.355°$ |
| Completeness to $\theta_{max}$ | 97.6% |
| Completeness to $\theta_{full} = 67.684°$ | 99.9% |
| Absorption correction | multi-scan |
| Transmission coefficient range | 0.791-1.000 |
| Refinement method | full matrix least-squares on $F^2$ |
| Independent reflections | 12840 [$R_{int}$= 0.0583, $R_G$ = 0.0539] |
| Reflections [I > 2σ(I)] | 11066 |
| Reflections/restraints/parameters | 12840/3/956 |
| Goodness-of-fit on $F^2$ | S = 1.08 |
| Final residuals [I > 2σ(I)] | R = 0.0613, $R_w$ = 0.1732 |
| Final residuals [all reflections] | R = 0.0694, $R_w$ = 0.1817 |
| Largest diff. peak and hole (e Å$^{-3}$) | 0.470, -0.468 |
| Max/mean shift/standard uncertainty | 0.000/0.000 |
| Absolute structure determination | Flack parameter: 0.008(18) |
| | Hooft parameter: 0.019(12) |
| | Friedel coverage: 58.8% |

TABLE 11

(S)-amisulpride Form A' XRPD (FIG. 8B) Peak List

| 2-Theta | Relative Height |
|---|---|
| 7.02 | 100 |
| 9.34 | 28 |
| 9.74 | 62 |
| 11.05 | 5.6 |
| 13.28 | 15.2 |
| 13.94 | 7.8 |
| 14.92 | 20 |
| 15.42 | 66.2 |
| 16.90 | 23.9 |
| 17.44 | 8.9 |
| 18.68 | 7.4 |
| 19.08 | 34.2 |
| 19.44 | 74.4 |
| 20.16 | 70 |
| 21.00 | 41.2 |
| 21.9 | 12 |
| 22.36 | 3.1 |
| 23.20 | 72.1 |
| 24.34 | 5.7 |
| 24.87 | 7 |
| 25.60 | 16.9 |
| 25.84 | 6.2 |
| 26.17 | 2.3 |
| 26.70 | 14.8 |
| 27.12 | 12.1 |
| 28.12 | 5.2 |
| 29.28 | 40.4 |
| 30.36 | 2.2 |
| 31.84 | 3.8 |
| 32.30 | 2.4 |
| 32.84 | 9 |
| 33.26 | 3.7 |
| 34.17 | 2.5 |
| 34.64 | 2 |
| 35.10 | 1.8 |
| 35.84 | 2.8 |
| 36.14 | 1.6 |
| 37.00 | 1.6 |
| 37.48 | 2.1 |
| 38.60 | 4.8 |
| 38.94 | 5.2 |
| 39.52 | 1.6 |
| 39.75 | 2.1 |
| 40.38 | 4.1 |
| 40.76 | 4.2 |
| 41.48 | 1.8 |
| 42.76 | 3.6 |
| 43.50 | 5.7 |
| 44.12 | 1.1 |

In various embodiments, the crystalline Form A of (R)-amisulpride is characterized by an XRPD pattern comprising peaks, in terms of 2-theta, at two or more of 7.0±0.2°, 9.7±0.2°, and 19.4±0.2°, and a DSC thermogram having a peak at 101±3° C. In various preferred embodiments, the DSC thermogram has a single peak at 101±3° C.

In various embodiments, the a crystalline Form A of (R)-amisulpride is characterized by an XRPD pattern comprising peaks, in terms of 2-theta, at two or more of 7.0±0.2°, 9.7±0.2°, and 19.4±0.2°, and a differential scanning calorimetry thermogram substantially in accord with FIG. 7A.

In various embodiments, the crystalline Form A' of (S)-amisulpride is characterized by an XRPD pattern comprising peaks, in terms of 2-theta, at two or more of 7.0±0.2°, 9.7±0.2°, and 19.4±0.2°, and a DSC thermogram having a peak at 101±3° C. In various preferred embodiments, the DSC thermogram has a single peak at 101±3° C.

In various embodiments, the crystalline Form A' of (S)-amisulpride is characterized by an XRPD pattern comprising peaks, in terms of 2-theta, at two or more of 7.0±0.2°, 9.7±0.2°, and 19.4±0.2°, and a differential scanning calorimetry thermogram substantially in accord with FIG. 8A.

In various embodiments, the crystalline Forms A and A' of enantiomeric amisulpride is substantially non-hygroscopic. In various embodiments, crystalline (R)-amisulpride of Form A has a maximum mass change of less than about 2%, less than about 1%, or less than about 0.5%, in water sorption isotherms as measured by dynamic vapor sorption (DVS), at 25° C. scanned over 0 to 95% relative humidity. In various embodiments, crystalline (S)-amisulpride of Form A' has a maximum mass change of less than about 2%, less than about 1%, or less than about 0.5%, in water sorption isotherms as measured by dynamic vapor sorption (DVS), at 25° C. scanned over 0 to 95% relative humidity.

Figure 8D:
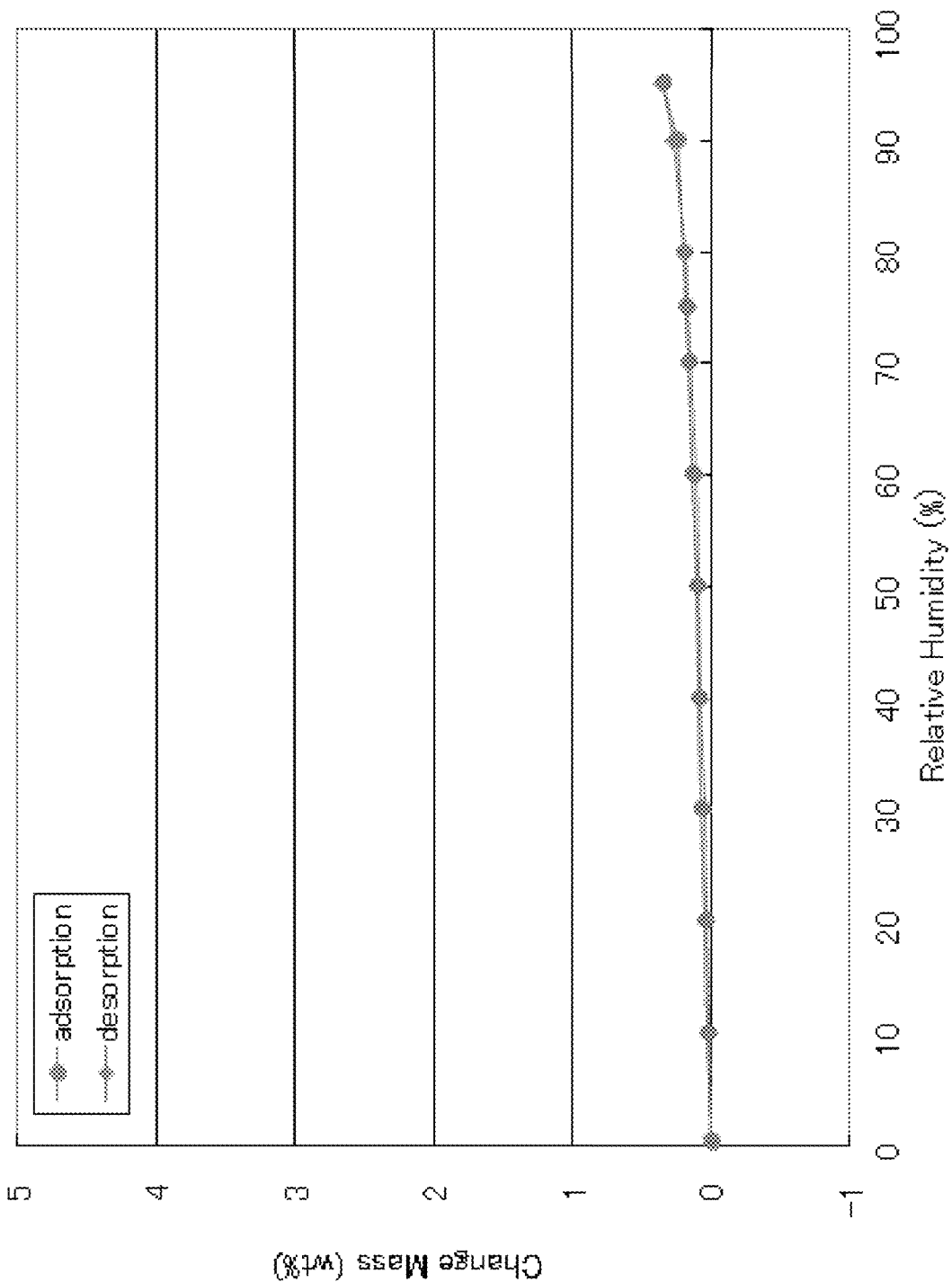

FIG. 8D shows a DVS water sorption isotherm for 19.077 mg of (S)-amisulpride crystal Form A' and Table 12 lists the data plotted in FIG. 8D. As can be seen, crystalline (S)-amisulpride Form A' is substantially non-hygroscopic, exhibiting a maximum mass change of only 0.35%.

TABLE 12

(S)-amisulpride Form A' DVS Water Sorption Isotherm of FIG. 8D

| Relative Humidity % | Change Mass (wt %) | Time/step (min) |
|---|---|---|
| 0 | 0.00 | 60.72 |
| 10 | 0.03 | 33.25 |
| 20 | 0.05 | 31.89 |
| 30 | 0.07 | 32.20 |
| 40 | 0.09 | 31.53 |
| 50 | 0.11 | 31.95 |
| 60 | 0.13 | 31.87 |
| 70 | 0.16 | 31.10 |
| 75 | 0.18 | 31.28 |
| 80 | 0.19 | 31.43 |
| 90 | 0.25 | 31.97 |
| 95 | 0.34 | 32.77 |
| 95 | 0.35 | 36.47 |
| 90 | 0.28 | 31.35 |
| 80 | 0.17 | 32.11 |
| 75 | 0.16 | 31.01 |
| 70 | 0.14 | 31.50 |
| 60 | 0.11 | 32.10 |
| 50 | 0.08 | 32.12 |
| 40 | 0.07 | 31.41 |
| 30 | 0.05 | 62.67 |
| 20 | 0.03 | 32.05 |
| 10 | 0.01 | 31.00 |
| 1 | −0.01 | 32.02 |

In various aspects, provided are methods of making enantiomeric amisulpride crystalline polymorphs of Form A and Form A'. Various embodiments of the methods described below produce novel crystal forms and various embodiments of these methods are in themselves novel.

As used in the context of the methods of the present inventions, the term "Form A" or "Form A'" refers to a method that produces a crystalline form of enantiomeric amisulpride having a powder x-ray crystal pattern comprising peaks, in terms of 2-theta, at least at 7.0±0.2°, 9.7±0.2°, and 19.4±0.2°; and preferably with additional peaks, in terms of 2-theta, at two or more of: 15.4±0.2°, 20.1±0.2°, 21.0±0.2°, 23.2±0.2°, and 29.3±0.2°; and in various preferred embodiments an powder x-ray crystal pattern substantially in accord with FIG. 7B, in the case of (R)-amisulpride, and FIG. 8B in the case of (S)-amisulpride.

Producing high yields of a specific crystalline form, and thus high purity of that crystalline form, is often limited by the formation of amorphous products and other crystalline forms that may, for example, be kinetically favored. It has been discovered through experimentation that making crystalline enantiomeric amisulpride is complicated by the fact that traditional methods result in non-crystalline (amorphous) enantiomeric amisulpride, including methods that produce crystalline racemic amisulpride.

It has been discovered that formation of certain enantiomeric amisulpride solvates as intermediates followed by conversion to the free base allows for isolation of a crystalline form of enantiomeric amisulpride (having a powder x-ray crystal pattern comprising peaks, in terms of 2-theta, at least at 7.0±0.2°, 9.7±0.2°, and 19.4±0.2°) that is greater than 90% by weight, greater than 95% by weight, greater than 97% by weight, greater than 99% by weight; or greater than 99.5% by weight of the enantiomeric amisulpride starting material.

In various embodiments, methods of making crystalline enantiomeric amisulpride, characterized by an XRPD pattern comprising peaks, in terms of 2-theta, at least at 7.0±0.2°, 9.7±0.2°, and 19.4±0.2°, comprise: (a) providing either (R)-amisulpride or (S)-amisulpride as a starting material, where (R)-amisulpride is provided as the starting material when crystalline (R)-amisulpride is the desired product and (S)-amisulpride is provided as the starting material when crystalline (S)-amisulpride is the desired product; (b) solvating the starting material with a first solvent where the first solvent is a carbonyl containing compound having 5 carbons or less; (c) freeing the solvated starting material from the first solvent by adding a second solvent other than water to form a mixture with a starting material solubility of less than about 20 wt/wt %; and then (d) isolating the crystalline form of the starting material having a powder x-ray crystal pattern comprising peaks, in terms of 2-theta, at least at 7.0±0.2°, 9.7±0.2°, and 19.4±0.2°.

In various embodiments, the methods start with the provision of either (R)-amisulpride or (S)-amisulpride to make, respectively, crystalline (R)-amisulpride or crystalline (S)-amisulpride. It is to be understood that there are many acceptable ways to separate the enantiomers of amisulpride to provide an enantiomeric starting material for the methods of the present inventions. Examples 7 and 9 provide an in situ method for making enantiomerically enriched amisulpride starting material.

It is to be understood that the enantiomeric amisulpride starting materials of the present invention are not necessarily crystalline, and often are amorphous or a mixture of amorphous and crystalline form. In addition to separation of enantiomers from a racemic starting material, suitable enantiomeric starting materials for the methods of the present inventions can also be directly synthesized.

It is to be understood that the ultimate chiral purity of the crystalline form of the starting material is limited by the chiral purity of the starting material. However, in various embodiments, it has been found that the methods produce the crystalline form of the starting material that has a chiral purity that is no less than the chiral purity of the starting material. Thus, in various embodiments, the present methods of making crystalline enantiomeric amisulpride (characterized by an XRPD pattern comprising peaks, in terms of 2-theta, at least at 7.0±0.2°, 9.7±0.2°, and 19.4±0.2°) provide said crystalline enantiomeric amisulpride having one or more of: a greater than about 90% chiral purity where the starting material has a greater than about 90% chiral purity; a greater than about 95% chiral purity where the starting material has a greater than about 95% chiral purity; a greater than about 97% chiral purity where the starting material has a greater than about 97% chiral purity; a greater than about 99% chiral purity where the starting material has a greater than about 99% chiral purity.

It has been unexpectedly found that by proper selection of the first solvent, an intermediate solvate can be formed that upon subsequent conversion to the free base can provide an amisulpride product where greater than 90% by weight, greater than 95% by weight, greater than 97% by weight, greater than 99% by weight; or greater than 99.5% by weight of amisulpride product is in the form of crystalline enantiomeric amisulpride of starting material, characterized by an XRPD pattern comprising peaks, in terms of 2-theta, at least at 7.0±0.2°, 9.7±0.2°, and 19.4±0.2°.

The first solvent is a carbonyl containing compound having 5 carbons or less. Preferably, the first solvent has a water content of less than 3% by weight, more preferably less than 1% by weight, and more preferably less than 0.5% by weight. It has been found that excess water in the first solvent interferes with, and can even prohibit, proper crystallization. Examples of such larger carbonyl containing solvent include cyclohexanone. In various embodiments, the first solvent is an aldehyde, ketone or ester. In various embodiments, the first solvent is ethyl acetate, propyl acetate, or methyl ethyl ketone; and in various preferred embodiments the first solvent is ethyl acetate.

In various embodiments, the step of solvating includes basifying; for example, by addition of a basic aqueous solution. In various embodiments, a basic solution sufficient to raise the pH to greater than 9.5, preferably to about 10, and in various embodiments between about 9.5 and about 11, is added. In various embodiments, aqueous solutions of potassium carbonate are employed. It is to be understood that a variety of basic solutions can be used to basify including, but not limited to, potassium carbonate, sodium carbonate, sodium hydroxide, and the like.

In various embodiments, the solvating step comprises multiple separations between any aqueous phase and organic phase of the solvent system of the solvating step, as may result, for example, from basifying; the desired products being preferentially partitioned into the organic phase. In various embodiments, the aqueous/organic solvent system is heated to 30-40° C. to facilitate separation.

In various embodiments, subsequent to basifying, the organic phase is concentrated and a stoichiometric excess of the first solvent is added one or more times to facilitate complete conversion to the solvate. In addition, in various embodiments, repeated concentration and addition of the first solvent facilitates producing a concentrated solvate solution having less than about 1 wt % water, less than about 0.7 wt % water, or less than about 0.4 wt % water, as determined by Karl Fischer titration.

In various embodiments, the reaction mixture is seeded with the desired crystalline form, (for example, seeding with crystalline (S)-amisulpride of Form A' where the desired product is crystalline (S)-amisulpride of Form A') prior to addition of the second solvent. In various embodiments, the step of solvating includes formation of a slurry by, for example, seeding the reaction mixture the desired crystalline form and cooling the reaction mixture below about 40° C., in various embodiments below about 30° C., and preferably below about 20° C.

Following formation of the enantiomeric starting material solvate, (i.e., (R)-amisulpride solvate with the first solvent or a (S)-amisulpride solvate with the first solvent) the solvate is freed from the enantiomeric starting material to form the free base of the enantiomeric starting material under conditions that allow for the isolation of crystalline enantiomeric amisulpride characterized by an XRPD pattern comprising peaks, in terms of 2-theta, at least at 7.0±0.2°, 9.7±0.2°, and 19.4±0.2°. In various embodiments, the reaction mixture is seeded with the desired crystalline form, (for example, seeding with crystalline (S)-amisulpride of Form A' where the desired product is crystalline (S)-amisulpride of Form A') prior to addition of the second solvent. In various embodiments, the step of freeing comprises cooling the reaction mixture to below about 40° C.

As used herein, the term "solvating" refers to the combination of (R)-amisulpride or (S)-amisulpride with a solvent.

As used herein, the terms "isolating" and "freeing" refer to separating the desired product from the environment in which it was formed or detected. For example, separation can include compositions containing at least about 50%, at least about 60%, at least about 70%, at least about 80%, at least about 90%, at least about 95%, at least about 97%, or at least about 99% by weight of the desired product.

In various embodiments, a second solvent (other than water) is added to form a mixture with a starting material solubility of less than about 20 wt/wt %; less than about 10 wt/wt %; or less than about 5 wt/wt %. One of skill in the art will understand that in various embodiments the second solvent can be considered an anti-solvent as it lowers the solubility of the mixture with respect to the desired product. It is to be understood that a variety of compounds can be used as a second solvent including, but not limited to, methyl t-butyl ether, toluene, heptane, isopropanol, and the like. In various embodiments the second solvent is methyl t-butyl ether (MtBE).

A variety of procedures can be used to isolate the desired enantiomeric crystalline form of the starting material. In various embodiments, the step of isolating comprises one or more of: (a) adding an anti-solvent; (b) cooling the mixture to below about 30° C., and in various embodiments between about 10° C. and about 20° C.; and (c) adding seed crystal of the R-enantiomer or S-enantiomer. In various embodiments, the step of isolating comprises adding an anti-solvent and/or cooling the reaction mixture. In various embodiments use is made of seed crystals of the crystalline formed desired, and seed crystals can be obtained by one of skill in the art using the teachings provided herein.

For example, Example 11 teaches methods of producing crystalline (R)-amisulpride ethyl acetate solvate. The product of these examples upon drying above about 30° C., desolvates and converts to crystals of crystalline (R)-amisulpride free base of Form A and amorphous. Similarly, for example, Example 13 teaches a method producing crystalline (S)-amisulpride ethyl acetate solvate. The product of these examples upon drying above about 30° C., desolvates and converts to crystals of crystalline (S)-amisulpride free base of Form A' and amorphous. Although the fraction of the solvate that converts to Form A or Form A' in the above examples is low, it is sufficient for obtaining seed crystals.

In various embodiments, the step of isolating the crystalline form comprises seeding the reaction mixture with the desired crystalline form, (for example, seeding with crystalline (S)-amisulpride of Form A' where the desired product is crystalline (S)-amisulpride of Form A') prior to addition of the second solvent, and, in various embodiments, a slurry is then formed by cooling the reaction mixture below about 40° C., in various embodiments below about 30° C., and preferably below about 20° C.

In various embodiments, the step of isolating comprises filtering a slurry comprising the desired crystalline form of the enantiomeric amisulpride free base, washing the solid residue with a solvent system comprising the second solvent and the first solvent, and drying the residue. In various embodiments, the wt/wt ratio of the second solvent to first solvent (second solvent:first solvent) is greater than about 1:9, and in various embodiments between about 1:9 to about 4:1. In various embodiments where the second solvent is MtBE and the first solvent ethyl acetate, the MtBe:ethyl acetate ratio is preferably about 3:1.

In various embodiments, the methods of the present inventions for making crystalline enantiomeric amisulpride, characterized by an XRPD pattern comprising peaks, in terms of 2-theta, at least at 7.0±0.2°, 9.7±0.2°, and 19.4±0.2°, comprise recrystallization. In the Examples, example methods that do not show a recrystallization step are noted as forming a "crude freebase," however it is to be understood that this nomenclature is used only for distinguishing the examples.

Recrystallization can be performed by a variety of techniques. In various embodiments, a step of recrystallization comprises (a) dissolving the crystalline enantiomeric amisulpride material in a solvent/anti-solvent solution; (b) cooling the solution comprising the starting material and the solvent/anti-solvent solution; and (c) adding a seed crystal of the R or S enantiomeric amisulpride material. In various embodiments the step of dissolving includes heating of the solution, to a temperature greater than 40° C. and below about 70° C., and preferably between about 50° C. and about 65° C., and preferably about 60° C.

A variety of solvent/anti-solvent systems can be used. For example, in various embodiments the solvent is acetone and the anti-solvent is methyl t-butyl ether. In various embodiments, the solvent is isopropanol (IPA) and the anti-solvent is heptane. As understood by those of skill in the art, care must be taken in selection of the solvent/anti-solvent system. For example, the inventors have found that in the IPA/heptane system a second liquid phase can form before seeding if the heptane to IPA ratio is greater than 1:1, that if a large excess of IPA is added the seeds will dissolve then crystallize upon addition of heptane antisolvent and cooling, and that a preferred IPA:heptane:product ratio is 36:32:32.

Non-limiting examples of various embodiments of making crystalline enantiomeric amisulpride of Forms A and A', or characterized by an XRPD pattern comprising peaks, in terms of 2-theta, at least at 7.0±0.2°, 9.7±0.2°, and 19.4±0.2°, are further illustrated and described in Examples 7, 8, 9 and 10.

Aspects, embodiments, and features of the preparation and characterization of crystal forms of enantiomeric amisulpride may be further understood from the following examples, which should not be construed as limiting the scope of the present inventions.

Crystal Forms of Enantiomeric Amisulpride Examples

It is to be understood that the enantiomeric amisulpride starting materials of the present invention are not necessarily crystalline, and often are amorphous or a mixture of amorphous and crystalline form. In addition to separation of enantiomers from a racemic starting material, suitable enantiomeric starting materials for the methods of the present inventions can also be directly synthesized.

Example 7: Synthesis of R-4-Amino-N-[(1-ethyl-2-pyrrolidinyl)methyl]-5-(ethylsulfonyl)-2-methoxybenzamide (Crude Freebase)

150 g of 4-amino-5-(ethylsulfonyl)-2-methoxybenzoic acid and 2000 g of acetone were placed in a flask. The solution was cooled to −9° C., and 74.3 mL of ethyl chloroformate was added to the flask. Then 88.9 mL of 4-methyl morpholine was added over 1 hour. 81.4 g of (R)-(1-ethylpyrrolidin-2-yl)methanamine was added and the mixture stirred for 16h. The reaction was then concentrated and 800 g of water and 300 g of ethyl acetate were added. The mixture was agitated and the organic layer removed, which contained the R-4-Amino-N-[(1-ethyl-2-pyrrolidinyl)methyl]-5-(ethylsulfonyl)-2-methoxybenzamide starting material. The solution containing the starting material was basified by the addition of aqueous 20 wt % potassium carbonate and 2.5 L of ethyl acetate was added. The aqueous layer was removed. The organic layer was washed twice with water and concentrated to dryness. Then 800 g of ethyl acetate was added and the mixture was concentrated. This was repeated once. The resulting oil was dissolved into 800 g of ethyl acetate and concentrated to 600 mL. The solution was stirred at 30° C. and a slurry formed. The resulting slurry was cooled to 20° C. and agitated. 600 g of methyl t-butyl ether was added and the mixture stirred. The slurry was then filtered, washed with 3:1 wt/wt methyl t-butyl ether:ethyl acetate and dried. 165 g of R-4-Amino-N-[(1-ethyl-2-pyrrolidinyl)methyl]-5-(ethylsulfonyl)-2-methoxybenzamide was obtained as a crystalline solid.

Example 8: Recrystallization of R-4-Amino-N-[(1-ethyl-2-pyrrolidinyl)methyl]-5-(ethylsulfonyl)-2-methoxybenzamide (Freebase Crystal Form A)

603.05 g of R-4-Amino-N-[(1-ethyl-2-pyrrolidinyl)methyl]-5-(ethylsulfonyl)-2-methoxybenzamide (prepared substantially according to Example 7) and 500.3 g of isopropanol were added to a flask with a stir bar and stopper. The flask was heated to 40° C. to form a solution. The solution was then polish filtered and transferred to a reactor at 40° C. with agitator, nitrogen line, thermocouple and cooling water, using 122.81 g of isopropanol to rinse the flask and polish filter. 603.2 g of heptane was added and the solution was agitated. The reactor was cooled to a jacket temperature of 35° C. and 6.91 g of isopropanol was added to the reactor drop wise to create a clear solution. The solution was agitated and then seeded with 972 mg of R-4-Amino-N-[(1-ethyl-2-pyrrolidinyl)methyl]-5-(ethylsulfonyl)-2-methoxybenzamide (Form A) and then agitated. The reactor was then cooled to 20° C. and then agitated. 1889.24 g of heptane was added using an external pump. Following agitation, the slurry was filtered, washed with 15:85 wt/wt isopropanol:heptane and dried. 531.7 g of R-4-Amino-N-[(1-ethyl-2-pyrrolidinyl)methyl]-5-(ethylsulfonyl)-2-methoxybenzamide of crystal Form A, having greater than 97% chiral purity, and greater than 99% chemical purity, was obtained, representing a yield of about 88%.

Figure 9:
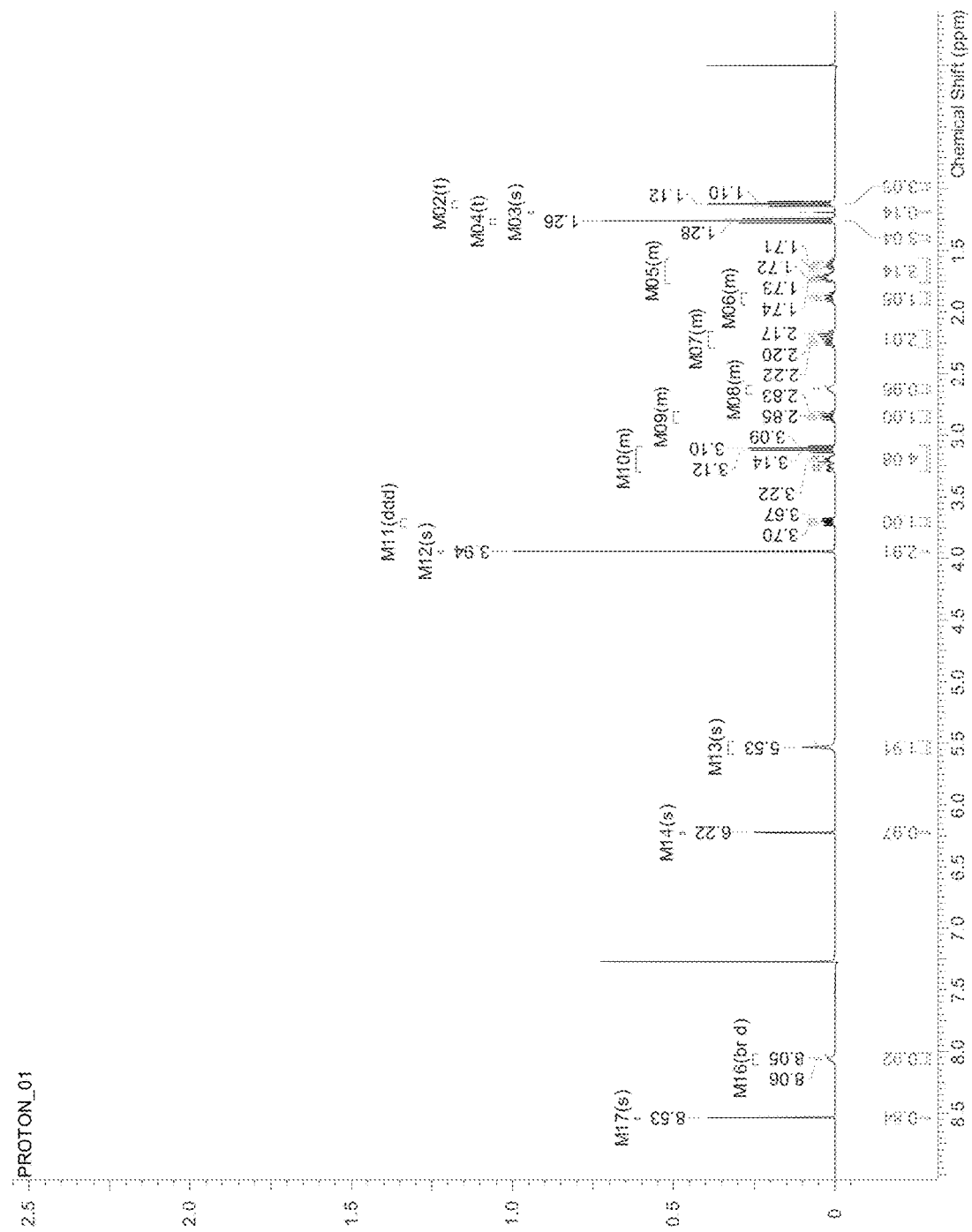
FIG. 9 is an NMR spectrum of an R-4-Amino-N-[(1-ethyl-2-pyrrolidinyl)methyl]-5-(ethylsulfonyl)-2-methoxybenzamide freebase of crystal Form A.

An NMR spectrum of the R-4-Amino-N-[(1-ethyl-2-pyrrolidinyl)methyl]-5-(ethylsulfonyl)-2-methoxybenzamide obtained in Example 8 is illustrated in FIG. 9, having the following characteristics: $^1$H NMR (400 MHz, CHLOROFORM-d) δ ppm 1.12 (t, J=7.24 Hz, 3H) 1.26 (t, J=7.43 Hz, 3H) 1.56-1.76 (m, 3H) 1.84-1.94 (m, 1H) 2.15-2.29 (m, 2H) 2.59-2.66 (m, 1H) 2.81-2.90 (m, 1H) 3.08-3.29 (m, 4H) 3.70 (ddd, J=13.69, 7.24, 2.93 Hz, 1H) 3.94 (s, 3H) 5.53 (s, 2H) 6.22 (s, 1H) 8.06 (br d, J=4.70 Hz, 1H) 8.53 (s, 1H).

Referring to FIGS. 7A-7C, FIGS. 7A-7C present data on the R-4-Amino-N-[(1-ethyl-2-pyrrolidinyl)methyl]-5-(ethylsulfonyl)-2-methoxybenzamide, (R)-amisulpride, of crystal Form A obtained in Example 8. FIG. 7A is a DSC thermogram for crystal Form A of (R)-amisulpride obtained in Example 8; FIG. 7B a XRPD pattern for crystal Form A of (R)-amisulpride obtained in Example 8; and FIG. 7C a micrograph image crystals of crystal Form A of the (R)-amisulpride obtained in Example 7.

Example 9: Synthesis of S-4-Amino-N-[(1-ethyl-2-pyrrolidinyl)methyl]-5-(ethylsulfonyl)-2-methoxybenzamide (Crude Freebase)

153 g of 4-amino-5-(ethylsulfonyl)-2-methoxybenzoic acid and 789 g of acetone were placed in a flask fitted with a stir bar, a thermocouple and a nitrogen line. The solution was cooled to −8° C., and then 70.4 g of ethyl chloroformate was added to the flask. An addition funnel was fitted to the flask and 79.3 g of 4-methyl morpholine was added drop wise, maintaining the temperature below 0° C. The mixture was agitated at −8° C. and then 55 g of (S)-(1-ethylpyrrolidin-2-yl)methanamine was added drop wise. The mixture was agitated at 0° C. for 1 hour, warmed to ambient temperature and then further agitated at ambient temperature to provide S-4-Amino-N-[(1-ethyl-2-pyrrolidinyl)methyl]-5-(ethylsulfonyl)-2-methoxybenzamide starting material. The reaction was then concentrated to minimum volume and 822 g of water, followed by 311 g of ethyl acetate, was added. The mixture was agitated and the organic layer removed. The solution was heated to 35° C. and 755 g of ethyl acetate and 326 g of 40 wt % potassium carbonate (aq) were added. The mixture was agitated, the phases allowed to separate, and the aqueous layer removed. Then 296 g of water of water was added, the mixture agitated, the phases allowed to separate and the aqueous layer removed. 302 g of water was added, the mixture agitated, the phases allowed to separate and the aqueous layer removed. The organic layer was transferred to a flask with a mechanical stirrer, a thermocouple and a nitrogen line. The organic layer was concentrated to dryness and 531 g of ethyl acetate was added. After agitation, the solution was concentrated to 400 mL. Then 305 g of ethyl acetate was added and the solution was concentrated to 400 mL and was 0.35 wt % water by Karl Fischer titration. The solution was then cooled to 30° C. and seeded with 300 mg of S-4-Amino-N-[(1-ethyl-2-pyrrolidinyl)methyl]-5-(ethylsulfonyl)-2-methoxybenzamide and a slurry formed. The solution was then cooled to 20° C. and agitated, and 495 g of methyl t-butyl ether was added. The slurry was then filtered, washed with 3:1 wt/wt methyl t-butyl ether:ethyl acetate and dried. 160.7 g of S-4-Amino-N-[(1-ethyl-2-pyrrolidinyl)methyl]-5-(ethylsulfonyl)-2-methoxybenzamide was obtained as a crystalline solid, representing a yield of about 74%.

Example 10: Recrystallization of: S-4-Amino-N-[(1-ethyl-2-pyrrolidinyl)methyl]-5-(ethylsulfonyl)-2-methoxybenzamide (Freebase Crystal Form A')

300.19 g of S-4-Amino-N-[(1-ethyl-2-pyrrolidinyl)methyl]-5-(ethylsulfonyl)-2-methoxybenzamide (prepared substantially according to Example 9) and 240.2 g of isopropanol were added to a flask with a stir bar and stopper. The flask was heated to 40° C. to form a solution. The solution was then polish filtered and transferred to a reactor at 40° C. with agitator, nitrogen line, thermocouple and cooling water, using 59.8 g of isopropanol to rinse the flask and polish filter. 300.4 g of heptane was added and the solution agitated. The reactor was cooled to a jacket temperature of 35° C. and 6.91 g of isopropanol was added to the reactor drop wise to create a clear solution. The solution was agitated and then seeded with 602 mg of S-4-Amino-N-[(1-ethyl-2-pyrrolidinyl)methyl]-5-(ethylsulfonyl)-2-methoxybenzamide (Form A') and then agitated. The reactor was then cooled to 20° C. and agitated. 1399.86 g of heptane was added using an external pump. Following agitation, the slurry was filtered, washed with 15:85 isopropanol:heptane and dried. 281.03 g of S-4-Amino-N-[(1-ethyl-2-pyrrolidinyl)methyl]-5-(ethylsulfonyl)-2-methoxybenzamide of crystal Form A' having greater than 97% chiral purity, and greater than 98% chemical purity, was obtained, representing a yield of about 91%.

Figure 10:
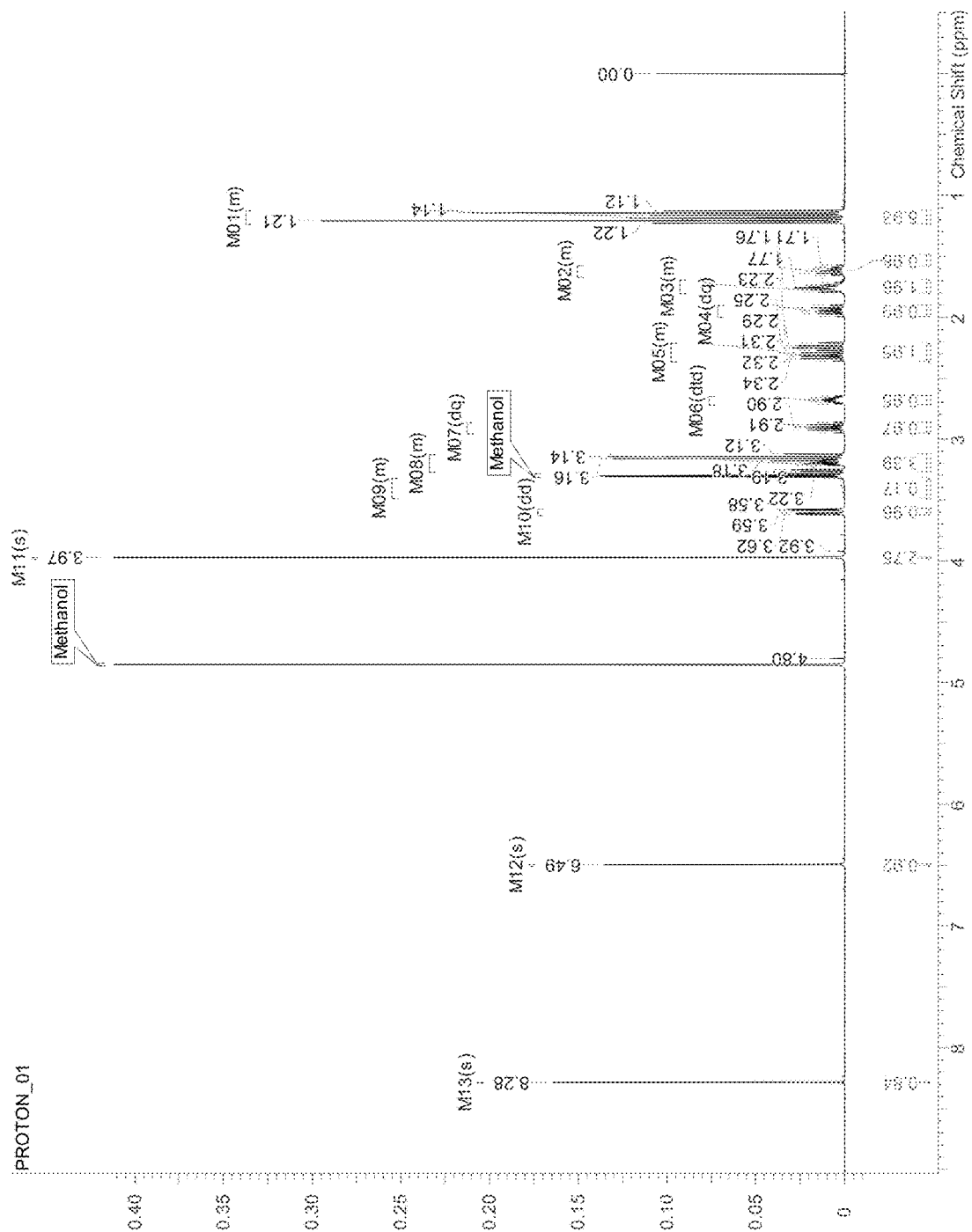
FIG. 10 is an NMR spectrum of an S-4-Amino-N-[(1-ethyl-2-pyrrolidinyl)methyl]-5-(ethylsulfonyl)-2-methoxybenzamide freebase of crystal Form A'.

An NMR spectrum of the S-4-Amino-N-[(1-ethyl-2-pyrrolidinyl)methyl]-5-(ethylsulfonyl)-2-methoxybenzamide obtained in Example 10 is illustrated in FIG. 10, having the following characteristics: $^1$H NMR (400 MHz, METHANOL-$d_4$) δ ppm 1.12-1.23 (m, 6H) 1.57-1.66 (m, 1H) 1.68-1.80 (m, 2H) 1.95 (dq, J=12.18, 8.33 Hz, 1H) 2.20-2.36 (m, 2H) 2.68 (dtd, J=8.61, 6.26, 6.26, 3.91 Hz, 1H) 2.91 (dq, J=12.08, 7.32 Hz, 1H) 3.12-3.27 (m, 3H) 3.32-3.48 (m, 1H) 3.60 (dd, J=13.30, 3.91 Hz, 1H) 3.97 (s, 3H) 6.49 (s, 1H) 8.28 (s, 1H).

Referring to FIGS. 8A-8C, FIGS. 8A-8C present data on the S-4-Amino-N-[(1-ethyl-2-pyrrolidinyl)methyl]-5-(ethylsulfonyl)-2-methoxybenzamide, (S)-amisulpride, of crystal Form A' obtained in Example 10. FIG. 8A is a DSC thermogram for crystal Form A' of(S)-amisulpride obtained in Example 10; FIG. 8B a XRPD pattern for crystal Form A' of(S)-amisulpride obtained in Example 10; and FIG. 8C a micrograph image showing crystals of crystal Form A' of the (S)-amisulpride obtained in Example 10.

Example 11: General Overview of Preparation of R-4-Amino-N-[(1-ethyl-2-pyrrolidinyl)methyl]-5-(ethylsulfonyl)-2-methoxybenzamide In overview, R-4-Amino-N-[(1-ethyl-2-pyrrolidinyl)methyl]-5-(ethylsulfonyl)-2-methoxybenzamide of Form A can be prepared in two steps: Step 1 Preparation of Crude (R)-amisulpride; and Step 2 Recrystallization of the Crude (R)-amisulpride to crystalline (R)-amisulpride of Form A.

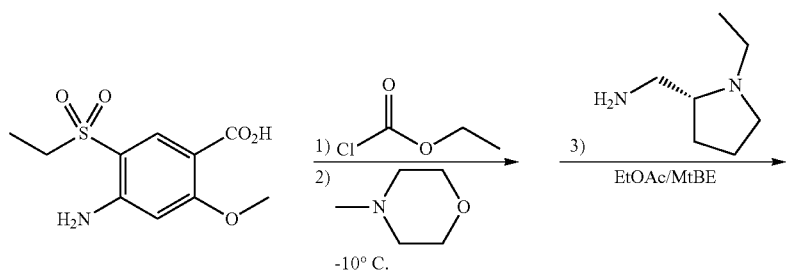

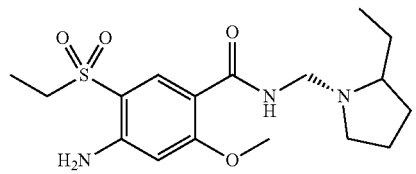

Step 1, Examples 11 and 12

Step 1 in general comprises mixing 4-Amino-5-(ethylsulfonyl)-2-methoxybenzoic acid with ethyl chloroformate and then reacting with (R)-(1-ethyl pyrrolidin-2-yl)methanamine to form R-4-Amino-N-[(1-ethyl-2-pyrrolidinyl)methyl]-5-(ethylsulfonyl)-2-methoxybenzamide hydrochloride. Other coupling reagents such as methyl, isopropyl and isobutyl chloroformates and dimethoxytriazinechloride are also suitable for carrying out the coupling reaction. The resulting product is extracted into water and washed with ethyl acetate. The R-4-Amino-N-[(1-ethyl-2-pyrrolidinyl)methyl]-5-(ethylsulfonyl)-2-methoxybenzamide hydrochloride is converted to freebase, dissolved into ethyl acetate and washed with base and water. The ethyl acetate solution is then dried and concentrated. The ethyl acetate solvate of R-4-Amino-N-[(1-ethyl-2-pyrrolidinyl)methyl]-5-(ethylsulfonyl)-2-methoxybenzamide crystallizes and is converted to R-4-Amino-N-[(1-ethyl-2-pyrrolidinyl)methyl]-5-(ethylsulfonyl)-2-methoxybenzamide (crude freebase) by the addition of methyl-tert butyl ether. The R-4-Amino-N-[(1-ethyl-2-pyrrolidinyl)methyl]-5-(ethylsulfonyl)-2-methoxybenzamide (crude freebase) is then isolated by filtration.

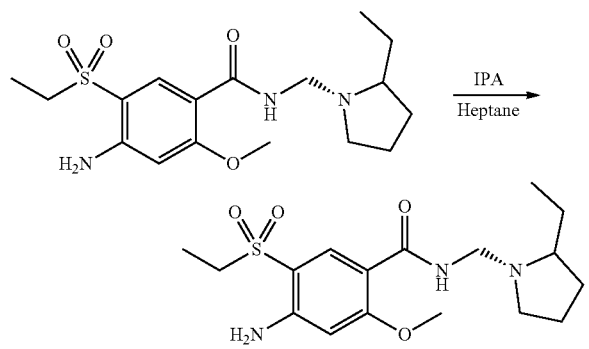

Step 2, Examples 11 and 12

Step 2 in general comprises dissolving the R-4-Amino-N-[(1-ethyl-2-pyrrolidinyl)methyl]-5-(ethylsulfonyl)-2-methoxybenzamide (crude freebase) of Step 1 into isopropanol and polish filtering. The isopropanol solution is concentrated, diluted with n-heptane and seeded with Form A to yield R-4-Amino-N-[(1-ethyl-2-pyrrolidinyl)methyl]-5-(ethylsulfonyl)-2-methoxybenzamide freebase crystals. The mixture is then cooled and filtered to yield crystalline R-4-Amino-N-[(1-ethyl-2-pyrrolidinyl)methyl]-5-(ethylsulfonyl)-2-methoxybenzamide substantially of Form A.

It is to be understood that during the crystallization of R-4-Amino-N-[(1-ethyl-2-pyrrolidinyl)methyl]-5-(ethylsulfonyl)-2-methoxybenzamide (crude freebase) the amount of water in the ethyl acetate solvent affects the crystallization and is preferably less than 0.5%. Accordingly the water content is preferably monitored during the distillation of the ethyl acetate solution, such as for example by coulometric titration (Karl Fischer). For example, in various embodiments coulometric titration (Karl Fischer) was performed by non-aqueous, perchloric acid titration where approximately 300 mg of sample, accurately weighed, was dissolved in about 50 mL of glacial acetic acid and titrated with 0.1 N perchloric acid and the end-point determined potentiometrically. The weight of sample was corrected for water content and residual solvent content prior to assay calculation. The drying of the isolated solid is also preferably monitored. In various embodiments, the reaction of Step 1 is considered complete when the amount of 4-amino-5-(ethylsulfonyl)-2-methoxybenzoic acid in the reaction mixture is less than or equal to 10 A % (where A % refers to Area % by HPLC) and/or when the amount of 4-amino-5-(ethylsulfonyl)-2-methoxybenzoic acid in the reaction mixture is less than or equal to 10 mol %.

Example 12: Detailed Overview of Preparation of R-4-Amino-N-[(1-ethyl-2-pyrrolidinyl)methyl]-5-(ethylsulfonyl)-2-methoxybenzamide of Form A: Step 1

To a mixture of 4-amino-5-(ethylsulfonyl)-2-methoxybenzoic acid in acetone at −10° C. and ethyl chloroformate, 4-methylmorpholine is added at a rate (exothermic) so as to maintain the internal temperature below −5° C. The reaction is stirred for 1 hour at −10° C. and then (R)-(1-ethyl pyrrolidin-2-yl)methanamine is added. After stirring for 2 hours the reaction mixture is concentrated and diluted with water and ethyl acetate. The ethyl acetate layer is removed and the aqueous layer is basified with potassium carbonate. Ethyl acetate is added and the aqueous layer removed. The organic layer is washed with water twice and concentrated. The mixture is diluted with ethyl acetate and concentrated until water content of the ethyl acetate solution is below 0.5%. The solution is seeded at 31° C. with 1 wt % Form A and stirred at the nucleation temperature for 2 h. The mixture is cooled to 20° C. and stirred for 1 h. The slurry is diluted with methyl tert butylether (MtBE) and stirred for 2 h at 20 C. The suspension is filtered and the product cake is washed with MtBE/ethyl acetate. The wet-cake is dried under vacuum at 40° C.±5° C. to constant weight to yield R-4-Amino-N-[(1-ethyl-2-pyrrolidinyl)methyl]-5-(ethylsulfonyl)-2-methoxybenzamide (crude).

Step 2: Isopropanol and R-4-Amino-N-[(1-ethyl-2-pyrrolidinyl)methyl]-5-(ethylsulfonyl)-2-methoxybenzamide (crude) are mixed together. The mixture is heated to 50° C. to achieve dissolution and then passed through a filter. The filtrate is concentrated and cooled to 40° C. n-Heptane is added and the resulting solution is cooled to 28° C. and seeded with Form A. The resulting slurry is cooled to 23° C. and stirred for 1.5 h at this temperature. More n-heptane is added and the slurry is stirred at 22° C. for 13h. The suspension is filtered and the product cake is washed with isopropanol/N-heptane. The wet-cake is dried under vacuum at 40° C.±5° C. to constant weight to yield R-4-Amino-N-[(1-ethyl-2-pyrrolidinyl)methyl]-5-(ethylsulfonyl)-2-methoxybenzamide of Form A.

Figure 11A:
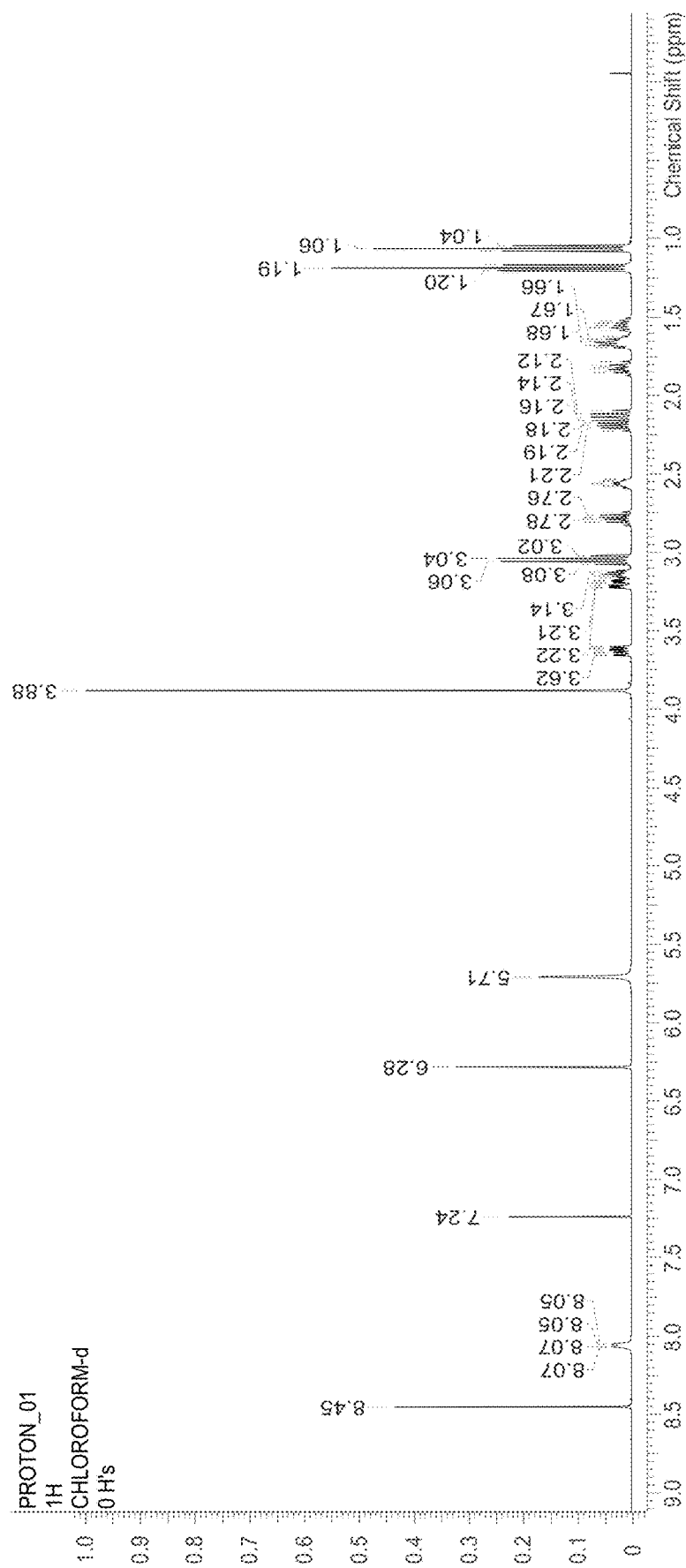
FIG. 11A is an NMR spectrum of an R-4-Amino-N-[(1-ethyl-2-pyrrolidinyl)methyl]-5-(ethylsulfonyl)-2-methoxybenzamide freebase of crystal Form A.
Figure 11B:
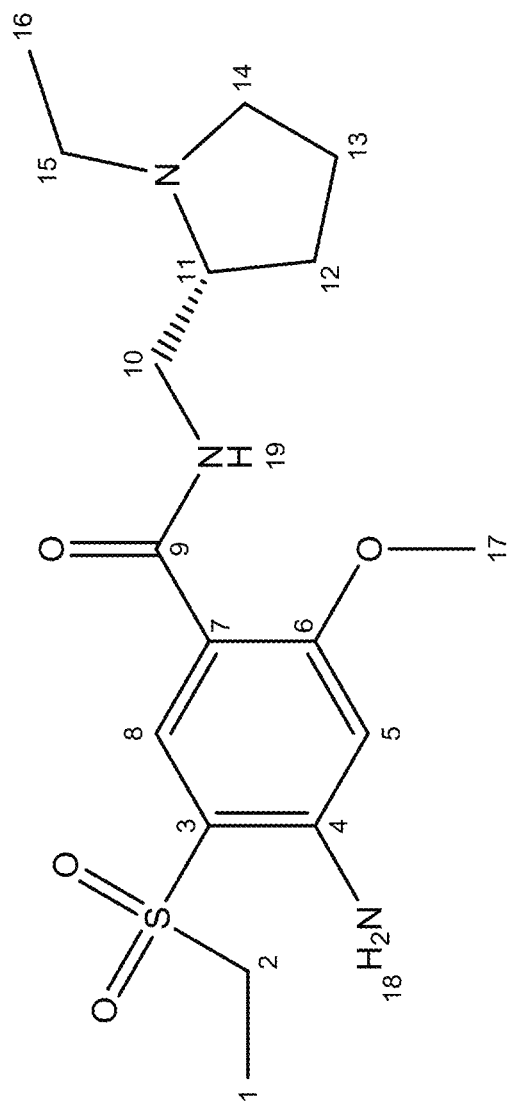
FIG. 11B illustrates the number sequence used for the assignment of peaks in FIG. 11A.

An NMR spectrum of the R-4-Amino-N-[(1-ethyl-2-pyrrolidinyl)methyl]-5-(ethylsulfonyl)-2-methoxybenzamide of Form A obtained by the methods of Examples 11 and 12 is illustrated in FIG. 11A, and FIG. 11B provides the number scheme used for the assignments of Table 13 based on the NMR spectrum of FIG. 11A, where the following notation is used in Table 13: s: singlet, d: doublet, br s: broad singlet, br d broad doublet, ddd: doublet of doublets of doublets, t: triplet, q: quadruplet; m: multiplet, tt: triplet of triplets; dq: doublet of quadruplets.

TABLE 13

Assignment of $^1$H NMR Spectrum of FIG. 11A

| Carbon (see FIG. 11B) | Chemical Shift | Details |
|---|---|---|
| 1 | 1.19-1.20 | t, J = 7.24 Hz, 3 H |
| 2 | 3.02-3.08 | q, J = 7.43 Hz, 2 H |
| 5 | 6.28 | s, 1 H |
| 8 | 8.45 | s, 1 H |
| 10a, b | 3.18-3.23 | ddd, J = 13.50, 4.89, 2.74 Hz, 1 H |
|  | 3.60-3.66 | ddd, J = 13.69, 7.04, 2.74 Hz, 1 H |
| 11 | 2.53-2.64 | m, 1 H |
| 12a, b | 1.52-1.59 | m, 1 H |
|  | 1.79-1.85 | m, 1 H |
| 13 | 1.64-1.69 | m, 2 H |
| 14a, b | 2.09-2.15 | m, 1 H |
|  | 3.12-3.17 | m, 1 H |
| 15a, b | 2.18-2.21 | m, 1 H |
|  | 2.74-2.81 | dq, J = 11.93, 7.37 Hz, 1 H |
| 16 | 1.04-1.06 | t, J = 7.04 Hz, 3 H |
| 17 | 3.88 | s, 3 H |
| 18 | 5.71 | s, 2 H |
| 19 | 8.05-8.07 | br dd, J = 7.04, 2.35 Hz, 1 H |

Figure 12A:
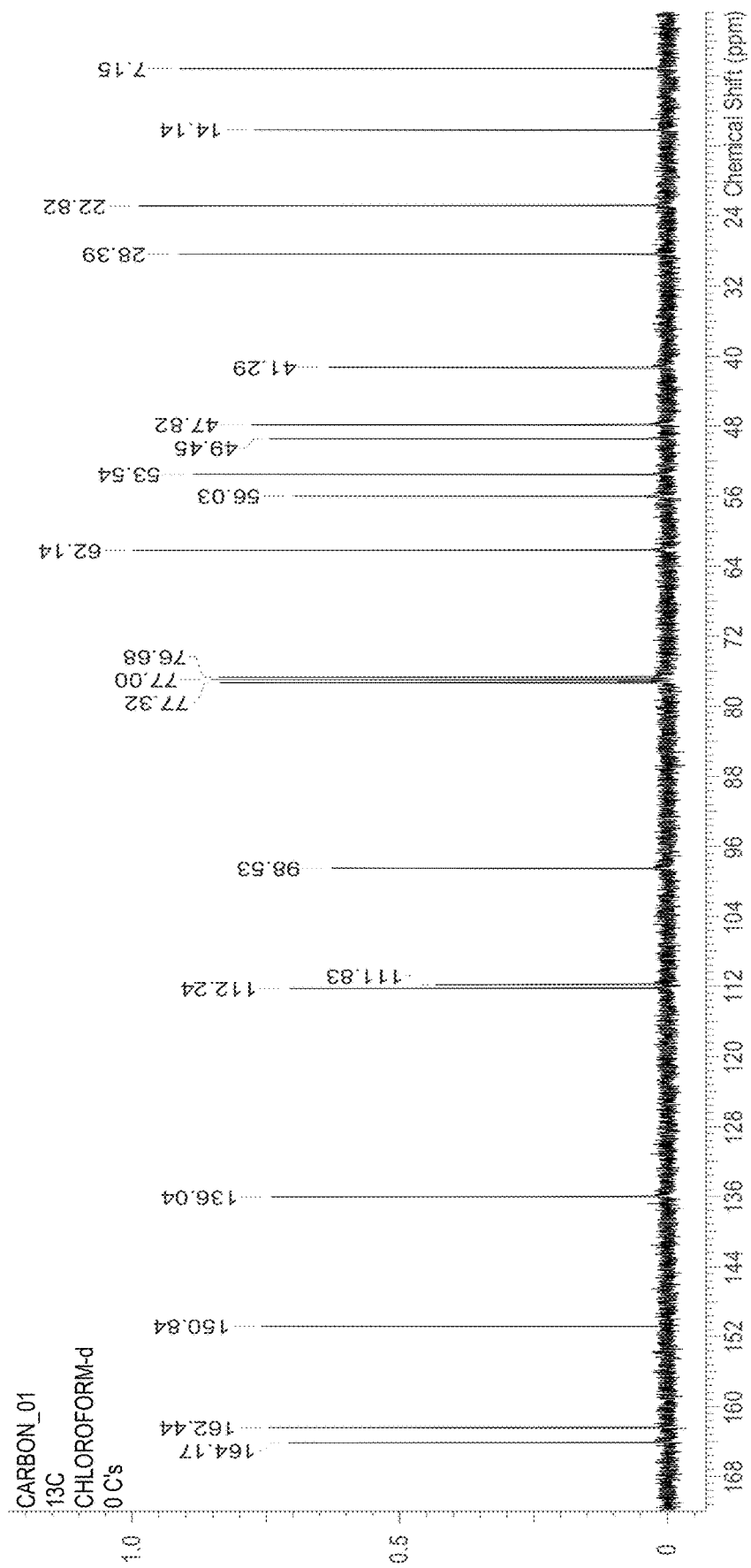
FIG. 12A is an $^{13}C$ NMR spectrum of an R-4-Amino-N-[(1-ethyl-2-pyrrolidinyl)methyl]-5-(ethylsulfonyl)-2-methoxybenzamide freebase of crystal Form A.
Figure 12B:
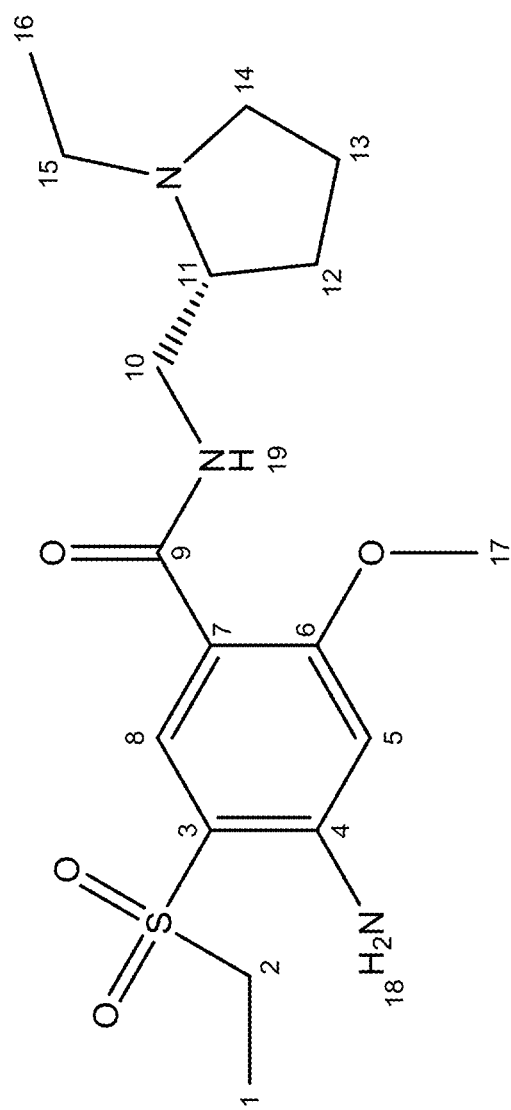
FIG. 12B illustrates the number scheme used for the assignment of peaks in FIG. 12A.

A $^{13}$C NMR spectrum of the R-4-Amino-N-[(1-ethyl-2-pyrrolidinyl)methyl]-5-(ethylsulfonyl)-2-methoxybenzamide of Form A obtained by the methods of Examples 11 and 12 is illustrated in FIG. 12A, and FIG. 12B provides the number scheme used for the assignments of Table 14 based on the $^{13}$C NMR spectrum of FIG. 12A.

TABLE 14

Assignment of $^{13}$C NMR Spectrum of FIG. 12A

| Chemical Shift (ppm) | Assignment (see FIG. 12B) |
|---|---|
| 7.15 | 1 |
| 49.45 | 2 |
| 112.24 | 3 |
| 111.83 | 4 |
| 98.53 | 5 |
| 162.44 | 6 |
| 150.84 | 7 |
| 136.04 | 8 |
| 164.17 | 9 |
| 41.29 | 10 |
| 62.14 | 11 |
| 28.39 | 12 |
| 22.82 | 13 |
| 53.54 | 14 |

TABLE 14-continued

Assignment of $^{13}$C NMR Spectrum of FIG. 12A

| Chemical Shift (ppm) | Assignment (see FIG. 12B) |
|---|---|
| 47.82 | 15 |
| 14.14 | 16 |
| 56.03 | 17 |

Example 13: General Overview of Preparation of S-4-Amino-N-[(1-ethyl-2-pyrrolidinyl)methyl]-5-(ethylsulfonyl)-2-methoxybenzamide In overview, S-4-Amino-N-[(1-ethyl-2-pyrrolidinyl)methyl]-5-(ethylsulfonyl)-2-methoxybenzamide of Form A' can be prepared in two steps: Step 1 Preparation of Crude (S)-amisulpride; and Step 2 Recrystallization of the Crude (S)-amisulpride to crystalline (S)-amisulpride of Form A'.

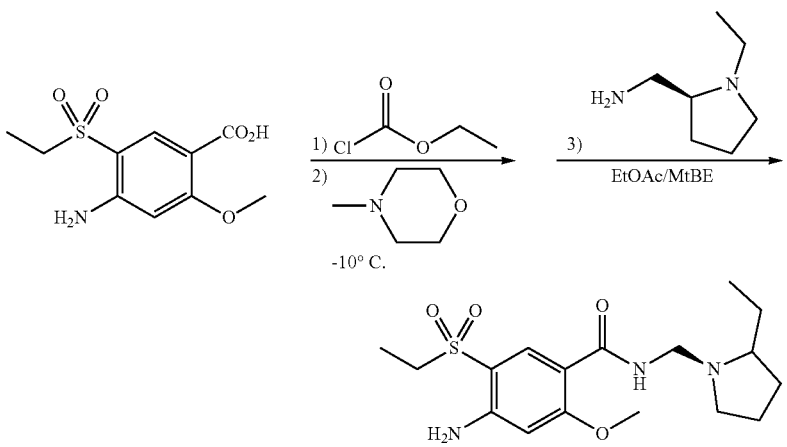

Step 1, Examples 13 and 14

Step 1 in general comprises reacting 4-Amino-5-(ethylsulfonyl)-2-methoxybenzoic acid with ethyl chloroformate and then adding (S)-(1-ethyl pyrrolidin-2-yl)methanamine to form S-4-Amino-N-[(1-ethyl-2-pyrrolidinyl)methyl]-5-(ethylsulfonyl)-2-methoxybenzamide hydrochloride. The resulting product is extracted into water and washed with ethyl acetate. S-4-Amino-N-[(1-ethyl-2-pyrrolidinyl)methyl]-5-(ethylsulfonyl)-2-methoxybenzamide hydrochloride is converted to freebase by the addition of aqueous potassium carbonate, dissolved into ethyl acetate and washed with water. The ethyl acetate solution is dried and concentrated. The ethyl acetate solvate of S-4-Amino-N-[(1-ethyl-2-pyrrolidinyl)methyl]-5-(ethylsulfonyl)-2-methoxybenzamide crystallizes and is desolvated by the addition of methyl-tert butyl ether. The S-4-Amino-N-[(1-ethyl-2-pyrrolidinyl)methyl]-5-(ethylsulfonyl)-2-methoxybenzamide (crude freebase) is isolated by filtration.

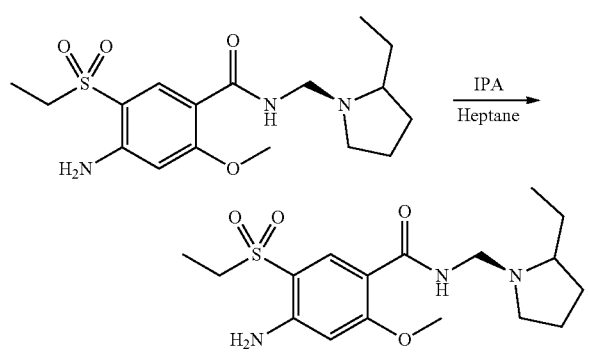

Step 2, Examples 13 and 14

Step 2 in general comprises dissolving the S-4-Amino-N-[(1-ethyl-2-pyrrolidinyl)methyl]-5-(ethylsulfonyl)-2-methoxybenzamide (crude freebase) of into isopropanol and polish filtering. The isopropanol solution is concentrated, diluted with n-heptane and seeded with Form A' to yield a slurry of S-4-Amino-N-[(1-ethyl-2-pyrrolidinyl)methyl]-5-(ethylsulfonyl)-2-methoxybenzamide. The mixture is cooled and filtered to yield crystalline S-4-Amino-N-[(1-ethyl-2-pyrrolidinyl)methyl]-5-(ethylsulfonyl)-2-methoxybenzamide substantially of Form A'.

It is to be understood that during the crystallization of S-4-Amino-N-[(1-ethyl-2-pyrrolidinyl)methyl]-5-(ethylsulfonyl)-2-methoxybenzamide (crude freebase) the amount of water in the ethyl acetate solvent affects the crystallization and is preferably less than 0.5%. Accordingly the water content is preferably monitored during the distillation of the ethyl acetate solution, such as for example by coulometric titration (Karl Fischer). For example, in various embodiments coulometric titration (Karl Fischer) was performed by non-aqueous, perchloric acid titration where approximately 300 mg of sample, accurately weighed, was dissolved in about 50 mL of glacial acetic acid and titrated with 0.1 N perchloric acid and the end-point determined potentiometrically. The weight of sample was corrected for water content and residual solvent content prior to assay calculation. The drying of the isolated solid is also preferably monitored. In various embodiments, the reaction of Step 1 is considered complete when the amount of 4-amino-5-(ethylsulfonyl)-2-methoxybenzoic acid in the reaction mixture is less than or equal to 10 A % (where A % refers to Area % by HPLC) and/or when the amount of 4-amino-5-(ethylsulfonyl)-2-methoxybenzoic acid in the reaction mixture is less than or equal to 10 mol %.

Example 14: Detailed Overview of Preparation of S-4-Amino-N-[(1-ethyl-2-pyrrolidinyl)methyl]-5-(ethylsulfonyl)-2-methoxybenzamide of Form A'

Step 1: To a solution of 4-amino-5-(ethylsulfonyl)-2-methoxybenzoic acid in acetone at −10° C. is added ethyl chloroformate. 4-Methylmorpholine is added at a rate (exothermic) so as to maintain the internal temperature below −5° C. The reaction is stirred for 1 hour at −10° C. and then (S)-(1-ethyl pyrrolidin-2-yl)methanamine is added. After stirring for 2 hours the reaction mixture is concentrated and diluted with water and ethyl acetate. The ethyl acetate layer is removed and the aqueous layer is basified with potassium carbonate. Ethyl acetate is then added and the aqueous layer removed. The organic layer is washed with water twice and concentrated. The mixture is diluted with ethyl acetate and concentrated until the water content of the ethyl acetate solution is below 0.5%. The solution is seeded at 31° C. with 1 wt % S-4-Amino-N-[(1-ethyl-2-pyrrolidinyl)methyl]-5-(ethylsulfonyl)-2-methoxybenzamide of Form A' and stirred at the nucleation temperature for 2 h. The mixture is cooled to 20° C. and stirred for 1 h. The slurry is then diluted with methyl tert butylether (MtBE) and stirred for 2 h at 20° C. The suspension is then filtered and the product cake is washed with MtBE/ethyl acetate. The wet-cake is dried under vacuum at 40° C.±5° C. to constant weight to yield S-4-Amino-N-[(1-ethyl-2-pyrrolidinyl)methyl]-5-(ethylsulfonyl)-2-methoxybenzamide (crude).

Step 2: Isopropanol is added to S-4-Amino-N-[(1-ethyl-2-pyrrolidinyl)methyl]-5-(ethylsulfonyl)-2-methoxybenzamide (crude) and the mixture is heated to 50° C. to achieve dissolution. The resulting solution is then passed through a filter. The filtrate is concentrated and cooled to 40° C. n-Heptane is then added and the resulting solution is cooled to 28° C. and seeded. The resulting slurry is cooled to 23° C. and stirred for 1.5 h at this temperature. More n-heptane is added and the slurry is stirred at 22° C. for 13h. The suspension is then filtered and the product cake is washed with isopropanol/n-heptane. The wet-cake is dried under vacuum at 40° C.±5° C. to constant weight to yield S-4-Amino-N-[(1-ethyl-2-pyrrolidinyl)methyl]-5-(ethylsulfonyl)-2-methoxybenzamide substantially of Form A'.

Figure 13A:
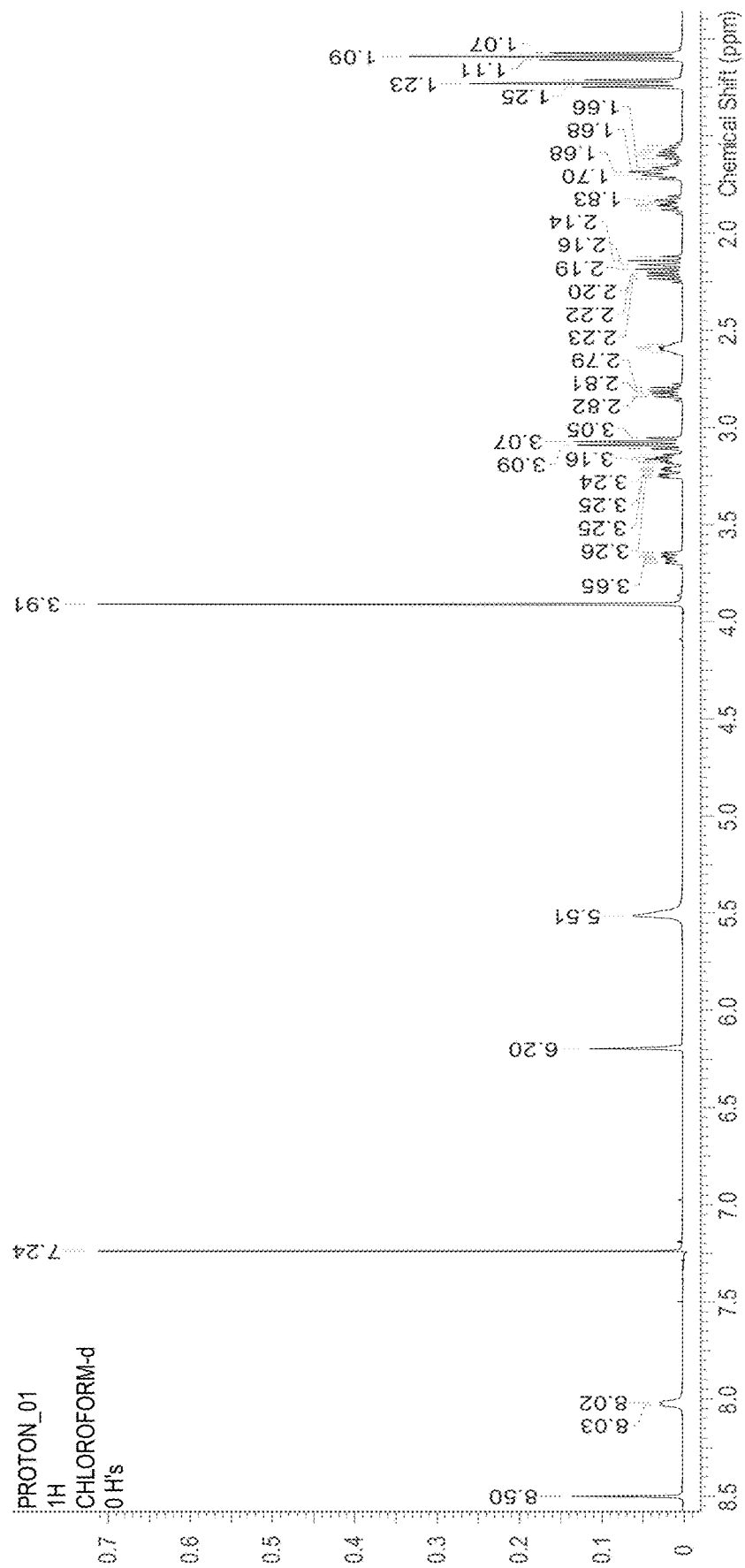
FIG. 13A is an NMR spectrum of an S-4-Amino-N-[(1-ethyl-2-pyrrolidinyl)methyl]-5-(ethylsulfonyl)-2-methoxybenzamide freebase of crystal Form A'.
Figure 13B:
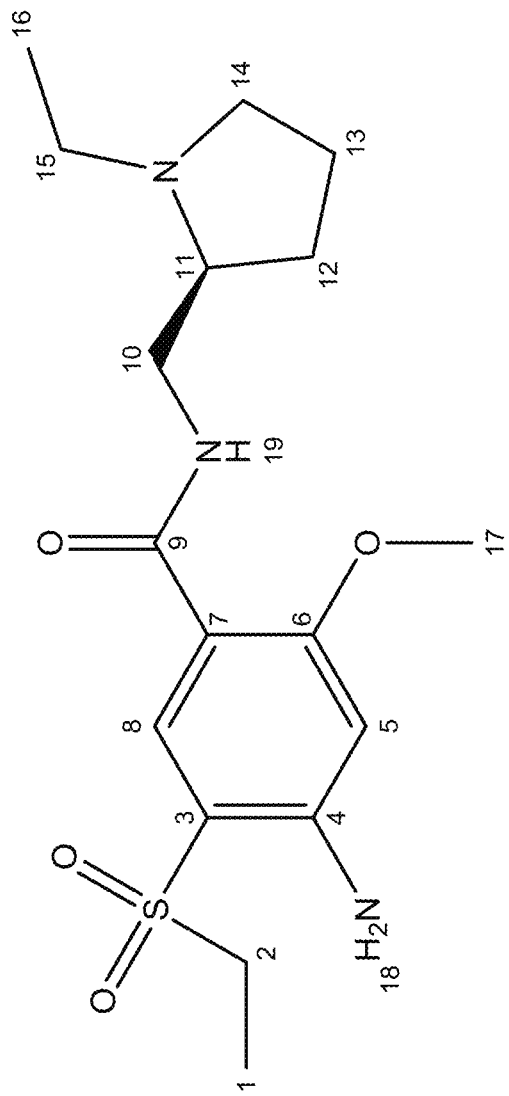
FIG. 13B illustrates the number sequence used for the assignment of peaks in FIG. 13A.

An NMR spectrum of the S-4-Amino-N-[(1-ethyl-2-pyrrolidinyl)methyl]-5-(ethylsulfonyl)-2-methoxybenzamide of Form A' obtained by the methods of Examples 13 and 14 is illustrated in FIG. 13A, and FIG. 13B provides the number scheme used for the assignments of Table 15 based on the NMR spectrum of FIG. 13A, where the following notation is used in Table 15: s: singlet, d: doublet, br s: broad singlet, br d broad doublet, ddd: doublet of doublets of doublets, t: triplet, q: quadruplet; m: multiplet, tt: triplet of triplets; dq: doublet of quadruplets.

TABLE 15

Assignment of $^1$H NMR Spectrum of FIG. 13A

| Carbon (see FIG. 13B) | Chemical Shift | Details |
|---|---|---|
| 1 | 1.21-1.25 | t, 7 = 7.43 Hz, 3 H |
| 2 | 3.05-3.11 | q, J = 7.30 Hz, 2 H |
| 5 | 6.20 | s, 1 H |
| 8 | 8.50 | s, 1 H |
| 10a, b | 3.22-3.26 | ddd, J = 13.69, 4.89, 2.93 Hz, 1 H |
|  | 3.64-3.70 | ddd, J = 13.69, 7.04, 2.74 Hz, 1 H |
| 11 | 2.57-2.61 | m, 1 H |
| 12a, b | 1.57-1.64 | m, 1 H |
|  | 1.83-1.88 | m, 1 H |
| 13 | 1.66-1.72 | m, 2 H |
| 14a, b | 2.12-2.16 | m, 1 H |
|  | 3.13-3.18 | m, 1 H |
| 15a, b | 2.19-2.23 | m, 1 H |
|  | 2.79-2.84 | dq, J = 12.13, 7.43 Hz, 1 H |
| 16 | 1.07-1.11 | t, J = 7.24 Hz, 3 H |
| 17 | 3.91 | s, 3 H |
| 18 | 5.51 | br s, 2 H |
| 19 | 8.02-8.03 | br d, 7 = 5.1 Hz, 1 H |

Figure 14A:
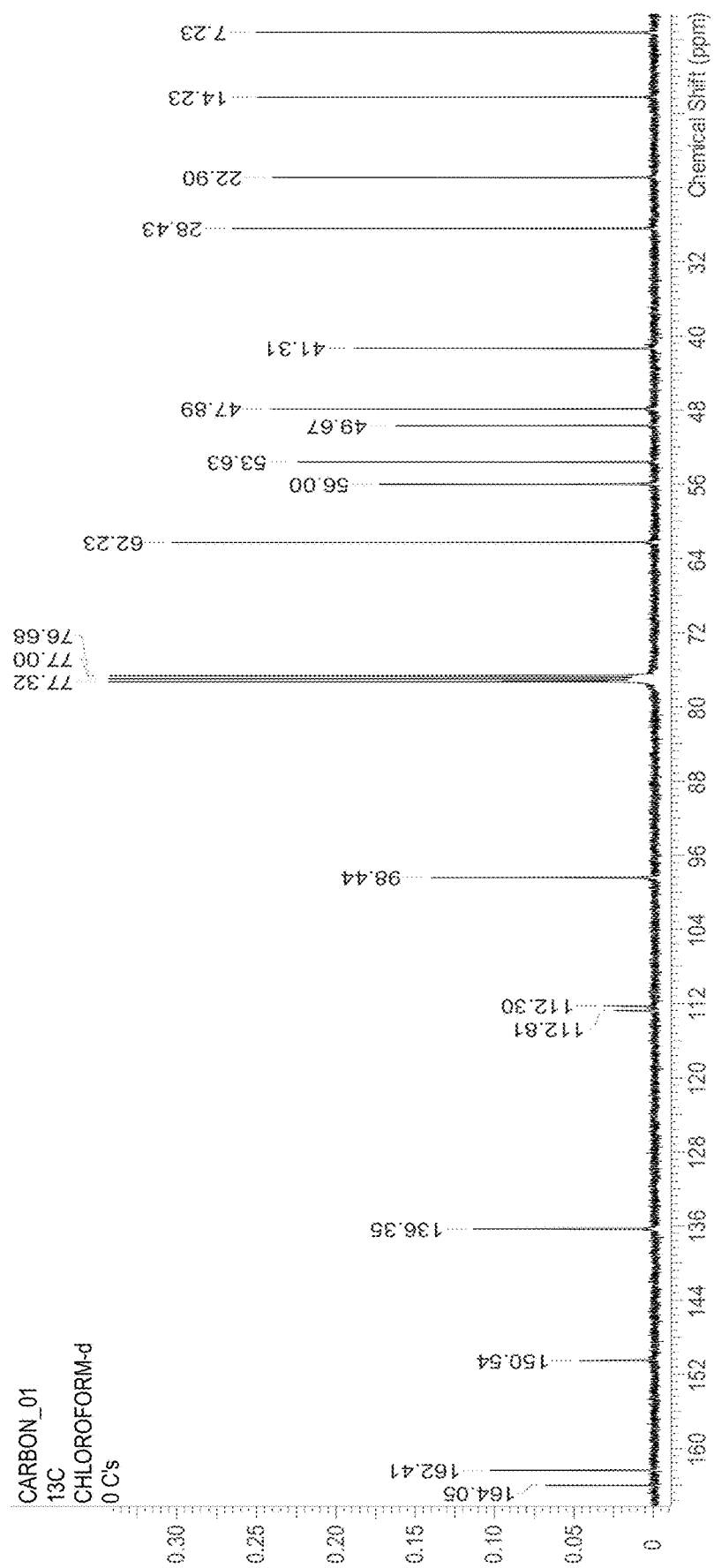
FIG. 14A is an $^{13}C$ NMR spectrum of an S-4-Amino-N-[(1-ethyl-2-pyrrolidinyl)methyl]-5-(ethylsulfonyl)-2-methoxybenzamide freebase of crystal Form A'.
Figure 14B:
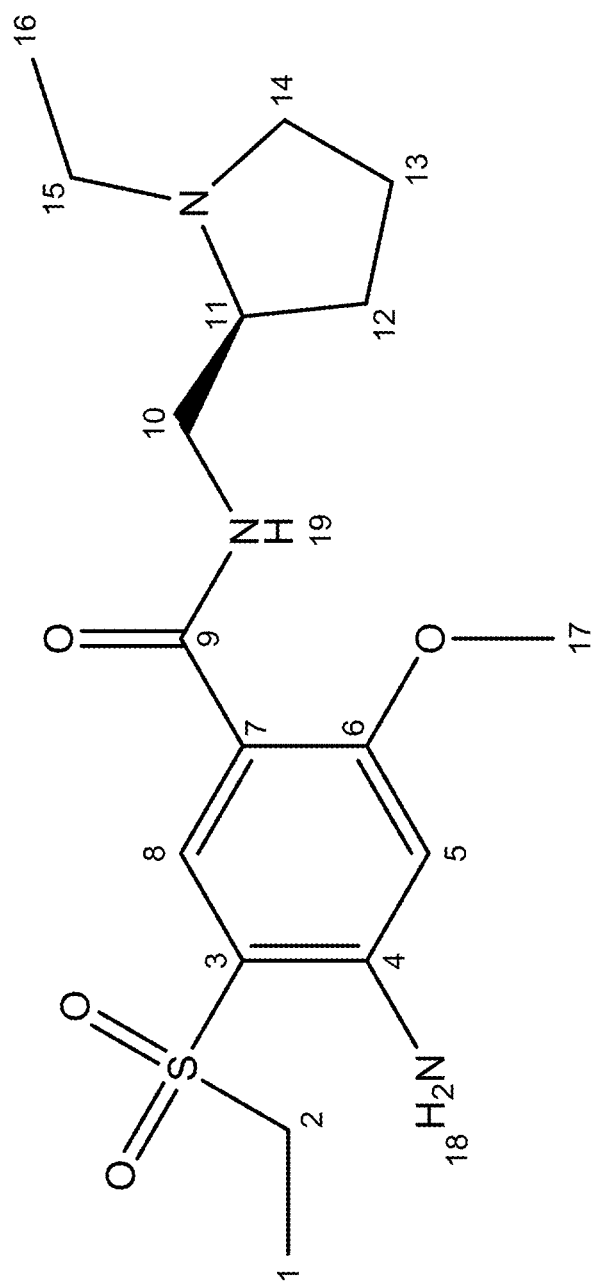
FIG. 14B illustrates the number scheme used for the assignment of peaks in FIG. 14A.

A $^{13}$C NMR spectrum of the S-4-Amino-N-[(1-ethyl-2-pyrrolidinyl)methyl]-5-(ethylsulfonyl)-2-methoxybenzamide of Form A' obtained by the methods of Examples 13 and 14 is illustrated in FIG. 14A, and FIG. 14B provides the number scheme used for the assignments of Table 16 based on the $^{13}$C NMR spectrum of FIG. 14A.

TABLE 16

Assignment of ¹³C NMR Spectrum of FIG. 14A

| Chemical Shift (ppm) | Assignment (see FIG. 14 B) |
|---|---|
| 7.23 | 1 |
| 49.67 | 2 |
| 112.81 | 3 |
| 112.30 | 4 |
| 98.44 | 5 |
| 162.41 | 6 |
| 150.54 | 7 |
| 136.35 | 8 |
| 164.05 | 9 |
| 41.31 | 10 |
| 62.23 | 11 |
| 28.43 | 12 |
| 22.90 | 13 |
| 53.63 | 14 |
| 47.89 | 15 |
| 14.23 | 16 |
| 56.00 | 17 |

Although the invention has been described with reference to a specific embodiment this description is not meant to be construed in a limiting sense. The invention being thus described, it is apparent that the same can be varied in many ways. Such variations are not to be regarded as a departure from the spirit and scope of the present invention, and all such modifications, alternatives, and equivalents as would be obvious to one skilled in the art are intended to be included within the scope of the following claims.

What is claimed is:

1. A composition comprising:
   (R)-(+)-amisulpride, or a pharmaceutically acceptable salt thereof; and
   (S)-(−)-amisulpride, or a pharmaceutically acceptable salt thereof;
   wherein the combined amount of (R)-(+)-amisulpride and (S)-(−)-amisulpride, or pharmaceutically acceptable salts thereof, is about 100 mg to about 600 mg by weight of free base; and
   wherein the enantiomeric ratio of (R)-(+)-amisulpride to (S)-(−)-amisulpride in the composition is 65:35 to 88:12 by weight of free base.

2. The composition of claim 1, wherein the combined amount of (R)-(+)-amisulpride and (S)-(−)-amisulpride, or pharmaceutically acceptable salts thereof, is about 100 mg to about 400 mg by weight of free base.

3. The composition of claim 1, wherein the combined amount of (R)-(+)-amisulpride and (S)-(−)-amisulpride, or pharmaceutically acceptable salts thereof, is about 100 mg by weight of free base.

4. The composition of claim 1, wherein the combined amount of (R)-(+)-amisulpride and (S)-(−)-amisulpride, or pharmaceutically acceptable salts thereof, is about 300 mg by weight of free base.

5. The composition of claim 1, wherein the composition is a tablet comprising about 100 mg, about 200 mg, about 300 mg, or about 400 mg of a combined amount of (R)-(+)-amisulpride and (S)-(−)-amisulpride, or pharmaceutically acceptable salts thereof, by weight of free base.

6. The composition of claim 1, wherein the (R)-(+)-amisulpride is crystalline (R)-(+)-amisulpride of crystal Form A; and the (S)-(−)-amisulpride is crystalline (S)-(−)-amisulpride of crystal Form A';
   wherein Form A is characterized by a powder x-ray diffraction pattern comprising peaks, in terms of 2-theta, at 7.0±0.2°, 9.7±0.2°, and 15.4±0.2°; and
   Form A' is characterized by a powder x-ray diffraction pattern comprising peaks, in terms of 2-theta, at 7.0±0.2°, 9.7±0.2°, and 15.4±0.2°.

7. The composition of claim 1, wherein the enantiomeric ratio of (R)-(+)-amisulpride to (S)-(−)-amisulpride in the composition is 75:25 to 88:12 by weight of free base.

8. The composition of claim 1, wherein the enantiomeric ratio of (R)-(+)-amisulpride to (S)-(−)-amisulpride in the composition is 80:20 to 88:12 by weight of free base.

9. The composition of claim 1, wherein the enantiomeric ratio of (R)-(+)-amisulpride to (S)-(−)-amisulpride in the composition is 85:15 by weight of free base.

10. The composition of claim 9, wherein the combined amount of (R)-(+)-amisulpride and (S)-(−)-amisulpride, or pharmaceutically acceptable salts thereof, is about 100 mg by weight of free base.

11. The composition of claim 9, wherein the combined amount of (R)-(+)-amisulpride and (S)-(−)-amisulpride, or pharmaceutically acceptable salts thereof, is about 300 mg by weight of free base.

12. The composition of claim 9, wherein the (R)-(+)-amisulpride is crystalline (R)-(+)-amisulpride of crystal Form A; and the (S)-(−)-amisulpride is crystalline (S)-(−)-amisulpride of crystal Form A';
   wherein Form A is characterized by a powder x-ray diffraction pattern comprising peaks, in terms of 2-theta, at 7.0±0.2°, 9.7±0.2°, and 15.4±0.2°; and
   Form A' is characterized by a powder x-ray diffraction pattern comprising peaks, in terms of 2-theta, at 7.0±0.2°, 9.7±0.2°, and 15.4±0.2°.

13. The composition of claim 9, wherein the composition is a tablet comprising about 100 mg of a combined amount of (R)-(+)-amisulpride and (S)-(−)-amisulpride, or pharmaceutically acceptable salts thereof, by weight of free base.

14. The composition of claim 9, wherein the composition is a tablet comprising about 200 mg of a combined amount of (R)-(+)-amisulpride and (S)-(−)-amisulpride, or pharmaceutically acceptable salts thereof, by weight of free base.

15. A method of alleviating bipolar disorder comprising administering to a subject in need thereof a composition comprising:
   (R)-(+)-amisulpride, or a pharmaceutically acceptable salt thereof; and
   (S)-(−)-amisulpride, or a pharmaceutically acceptable salt thereof;
   wherein the total daily combined amount of (R)-(+)-amisulpride and (S)-(−)-amisulpride, or pharmaceutically acceptable salts thereof, is about 100 mg to about 600 mg by weight of free base;
   wherein the enantiomeric ratio of (R)-(+)-amisulpride to (S)-(−)-amisulpride in the composition is 65:35 to 88:12 by weight of free base; and
   wherein the composition is administered to the subject as a dosage unit form comprising about 100 mg, about 200 mg, about 300 mg, or about 400 mg of a combined amount of (R)-(+)-amisulpride and (S)-(−)-amisulpride, or pharmaceutically acceptable salts thereof, by weight of free base.

16. The method of claim 15, wherein the total daily combined amount of (R)-(+)-amisulpride and (S)-(−)-amisulpride, or pharmaceutically acceptable salts thereof, is about 100 mg to about 600 mg by weight of free base administered once daily or twice daily.

17. The method of claim 15, wherein the total daily combined amount of (R)-(+)-amisulpride and (S)-(−)- amisulpride, or pharmaceutically acceptable salts thereof, is about 200 mg by weight of free base administered once daily.

18. The method of claim 15, wherein the total daily combined amount of (R)-(+)-amisulpride and (S)-(−)-amisulpride, or pharmaceutically acceptable salts thereof, is about 400 mg by weight of free base administered once daily.

19. The method of claim 15, wherein the enantiomeric ratio of (R)-(+)-amisulpride to (S)-(−)-amisulpride is about 80:20 to about 88:12 by weight of free base.

20. The method of claim 15, wherein the enantiomeric ratio of (R)-(+)-amisulpride to (S)-(−)-amisulpride is about 85:15 by weight of free base.

21. The method of claim 15, wherein the bipolar disorder is bipolar depression.

22. The method of claim 15, wherein the (R)-(+)-amisulpride is crystalline (R)-(+)-amisulpride of crystal Form A; and the (S)-(−)-amisulpride is crystalline (S)-(−)-amisulpride of crystal Form A';
   wherein Form A is characterized by a powder x-ray diffraction pattern comprising peaks, in terms of 2-theta, at 7.0±0.2°, 9.7±0.2°, and 15.4±0.2°; and
   Form A' is characterized by a powder x-ray diffraction pattern comprising peaks, in terms of 2-theta, at 7.0±0.2°, 9.7±0.2°, and 15.4±0.2°.

23. A method of alleviating bipolar depression comprising administering to a subject in need thereof a composition comprising:
   (R)-(+)-amisulpride, or a pharmaceutically acceptable salt thereof; and
   (S)-(−)-amisulpride, or a pharmaceutically acceptable salt thereof;
   wherein the total daily combined amount of (R)-(+)-amisulpride and (S)-(−)-amisulpride, or pharmaceutically acceptable salts thereof, is about 200 mg by weight of free base;
   wherein the enantiomeric ratio of (R)-(+)-amisulpride to (S)-(−)-amisulpride in the composition is 85:15 by weight of free base; and
   wherein the composition is administered once daily to the subject as a dosage unit form comprising about 100 mg or about 200 mg of a combined amount of (R)-(+)-amisulpride and (S)-(−)-amisulpride, or pharmaceutically acceptable salts thereof, by weight of free base.

24. The method of claim 23, wherein the dosage unit form comprises about 100 mg of a combined amount of (R)-(+)-amisulpride and (S)-(−)-amisulpride, or pharmaceutically acceptable salts thereof, by weight of free base.

25. The method of claim 23, wherein the dosage unit form comprises about 200 mg of a combined amount of (R)-(+)-amisulpride and (S)-(−)-amisulpride, or pharmaceutically acceptable salts thereof, by weight of free base.

26. The method of claim 23, wherein the total daily dose of about 200 mg is administered as multiple dosage unit forms once daily.

27. A method of alleviating bipolar depression comprising administering to a subject in need thereof a composition comprising:
   (R)-(+)-amisulpride, or a pharmaceutically acceptable salt thereof; and
   (S)-(−)-amisulpride, or a pharmaceutically acceptable salt thereof;
   wherein the total daily combined amount of (R)-(+)-amisulpride and (S)-(−)-amisulpride, or pharmaceutically acceptable salts thereof, is about 400 mg by weight of free base;
   wherein the enantiomeric ratio of (R)-(+)-amisulpride to (S)-(−)-amisulpride in the composition is 85:15 by weight of free base; and
   wherein the composition is administered once daily to the subject as a dosage unit form comprising about 100 mg or about 200 mg of a combined amount of (R)-(+)-amisulpride and (S)-(−)-amisulpride, or pharmaceutically acceptable salts thereof, by weight of free base.

28. The method of claim 27, wherein the dosage unit form comprises about 100 mg of a combined amount of (R)-(+)-amisulpride and (S)-(−)-amisulpride, or pharmaceutically acceptable salts thereof, by weight of free base.

29. The method of claim 27, wherein the dosage unit form comprises about 200 mg of a combined amount of (R)-(+)-amisulpride and (S)-(−)-amisulpride, or pharmaceutically acceptable salts thereof, by weight of free base.

30. The method of claim 27, wherein the total daily dose of about 400 mg is administered as multiple dosage unit forms once daily.

\* \* \* \* \*